(12) United States Patent
Endo

(10) Patent No.: US 9,808,511 B2
(45) Date of Patent: Nov. 7, 2017

(54) METHOD FOR TREATING ALOPECIA WITH B-TYPE NATRIURETIC PEPTIDE

(71) Applicants: IGISU Co., Ltd., Tokyo (JP); Yori Endo, Sendai-shi, Miyagi (JP); Kyoko Endo, Sendai-shi, Miyagi (JP)

(72) Inventor: Kyoko Endo, Sendai (JP)

(73) Assignees: IGISU Co., Ltd., Tokyo (JP); Yori Endo, Sendai-shi (JP)

( * ) Notice: Subject to any disclaimer, the term of this patent is extended or adjusted under 35 U.S.C. 154(b) by 0 days.

(21) Appl. No.: 15/270,350

(22) Filed: Sep. 20, 2016

(65) Prior Publication Data

US 2017/0065680 A1    Mar. 9, 2017

Related U.S. Application Data

(63) Continuation of application No. 14/254,938, filed on Apr. 17, 2014, now Pat. No. 9,480,728, which is a continuation of application No. 13/355,484, filed on Jan. 21, 2012, now abandoned.

(60) Provisional application No. 61/437,032, filed on Jan. 28, 2011.

(30) Foreign Application Priority Data

Jan. 21, 2011 (JP) .................................. 2011-11437

(51) Int. Cl.

| | |
|---|---|
| *A61K 38/22* | (2006.01) |
| *A61K 8/64* | (2006.01) |
| *A61K 9/00* | (2006.01) |
| *A61Q 7/00* | (2006.01) |
| *A61K 31/14* | (2006.01) |
| *A61K 31/506* | (2006.01) |
| *A61K 31/573* | (2006.01) |
| *A61K 31/7036* | (2006.01) |
| *A61K 45/06* | (2006.01) |

(52) U.S. Cl.
CPC ............... *A61K 38/22* (2013.01); *A61K 8/64* (2013.01); *A61K 9/0014* (2013.01); *A61K 31/14* (2013.01); *A61K 31/506* (2013.01); *A61K 31/573* (2013.01); *A61K 31/7036* (2013.01); *A61K 45/06* (2013.01); *A61Q 7/00* (2013.01)

(58) Field of Classification Search
None
See application file for complete search history.

(56) References Cited

U.S. PATENT DOCUMENTS

| | | |
|---|---|---|
| 5,114,923 A | 5/1992 | Seilhamer et al. |
| 5,583,108 A | 12/1996 | Wei et al. |
| 6,028,055 A | 2/2000 | Lowe et al. |
| 6,818,619 B2 | 11/2004 | Burnett, Jr. et al. |
| 7,276,481 B2 | 10/2007 | Golembo et al. |
| 9,480,728 B2 | 11/2016 | Endo |
| 2006/0034903 A1 | 2/2006 | Maa et al. |
| 2008/0070858 A1 | 3/2008 | Mohapatra |
| 2009/0104295 A1 | 4/2009 | Kohno |
| 2011/0014180 A1* | 1/2011 | Koide ................ A61K 38/2242 424/130.1 |
| 2012/0238498 A1 | 9/2012 | Endo |

FOREIGN PATENT DOCUMENTS

| | | |
|---|---|---|
| EP | 0497368 A1 | 8/1992 |
| EP | 1810716 | 7/2007 |
| EP | 2308889 | 4/2011 |
| JP | HE-05207891 | 8/1993 |
| JP | HE-06009688 | 1/1994 |
| JP | 2000-169387 | 6/2000 |
| JP | 2000-516836 | 12/2000 |
| JP | 2007-70336 | 3/2007 |
| JP | 2007-525213 | 9/2007 |
| JP | 2007-525957 | 9/2007 |

(Continued)

OTHER PUBLICATIONS

Sawaya et al. Why steroids may not always work in alopecia areata: elevated unoccupied glucocorticoid receptors and decreased levels of thioredoxin. Dermatol. Ther., 14, 317-321, 2001.*
NCBI Search results for C-type natriuretic peptide. Feb. 25, 2015.
WIPO, ISR and IPRP of international application Ser. No. PCT/JP2012/051272, dated Apr. 24, 2012.
[No Author Listed] Peptide Institute, Inc. CNP-22 (Human). 2015.
Agoston et al., Dexamethasone stimulates expression of C-type Natriuretic Peptide in chondrocytes, BMC Musculoskeletal Disorders, Nov. 20, 2006, p. 1-7, vol. 7, No. 87.
Arase, Japanese Dermatological Association alopecia areata diagnosis and treatment guidelines 2010, The Japanese Journal of Dermatology, Apr. 21, 2011, p. 1841-1859, vol. 120, No. 9.

(Continued)

*Primary Examiner* — Elly-Gerald Stoica
(74) *Attorney, Agent, or Firm* — Wolf, Greenfield & Sacks, P.C.

(57) ABSTRACT

It is an object of the present invention to provide a new agent for the treatment of alopecia, the agent being not only effective and safe for, in particular, alopecia areata, androgenetic alopecia in a male, androgenetic alopecia in a female, female pattern alopecia, postpartum alopecia, seborrheic alopecia, alopecia pityroides, senile alopecia, cancer chemotherapy drug-induced alopecia, and alopecia due to radiation exposure, but also effective for a target having resistance to treatment with minoxidil or finasteride, there being no side effects such as an itching sensation, irritation, or feminization, and no contraindications, the agent suppressing dandruff or having a therapeutic effect for white hair, and the therapeutic effect for alopecia being maintained for a long period even when use of the agent is stopped.
The solution means of the present invention is an agent for the treatment of alopecia containing as an active ingredient a C-type natriuretic peptide (CNP), a B-type natriuretic peptide (BNP), a derivative of these NPs, a chimeric peptide of these NPs, or a derivative of a chimeric peptide of these NPs.

15 Claims, 63 Drawing Sheets

(56) References Cited

FOREIGN PATENT DOCUMENTS

| | | | |
|---|---|---|---|
| JP | 2008-509746 | | 4/2008 |
| JP | 2008-162987 | * | 7/2008 ............ A61K 38/00 |
| JP | 2008-540509 | | 11/2008 |
| JP | 2009-13122 | | 1/2009 |
| JP | 2010-500032 | | 1/2010 |
| JP | 2010-168283 | | 8/2010 |
| JP | 2010-280696 | | 12/2010 |
| JP | 2010-539022 | | 12/2010 |
| WO | WO 98-052599 | | 11/1998 |
| WO | WO 2004-022003 | | 3/2004 |
| WO | WO 2004-071469 | | 8/2004 |
| WO | WO 2004-110489 | | 12/2004 |
| WO | WO 2005-003764 A2 | | 1/2005 |
| WO | WO 2005-072055 | | 8/2005 |
| WO | WO 2005-094889 | | 10/2005 |
| WO | WO 2005-094890 | | 10/2005 |
| WO | WO 2006-020841 | | 2/2006 |
| WO | WO 2007-023396 | | 3/2007 |
| WO | WO 2008-021872 | | 2/2008 |
| WO | WO 2008-032450 | | 3/2008 |
| WO | WO 2008-140125 | | 11/2008 |
| WO | WO 2009-033724 | | 3/2009 |
| WO | WO 2009-033807 | | 3/2009 |
| WO | WO 2009-046861 | | 4/2009 |
| WO | WO 2010-078325 A2 | | 7/2010 |
| WO | WO 2011-010732 A1 | | 1/2011 |
| WO | WO 2011-024973 A1 | | 3/2011 |

OTHER PUBLICATIONS

Betz et al., Loss-of-function mutations in the filaggrin gene and alopecia areata: strong risk factor for a severe course of disease in patients comorbid for atopic disease, J Invest Dermatol., Jun. 21, 2007, p. 2539-2543, vol. 127.
Cao et al., Natriuretic peptides inhibit DNA synthesis in cardiac fibroblasts. Hypertension. Feb. 1995;25(2):227-34.
Chiurchiu V et al., Brain Natriuretic Peptide (BNP) regulates the production of inflammatory mediators in human THP-1 macrophages, Regulatory Peptides, Mar. 10, 2008, p. 26-32, vol. 148.
Chrisman et al., Seminal plasma factors that cause large elevations in cellular cyclic GMP are C-type natriuretic peptides. J Biol Chem. Feb. 15, 1993;268(5):3698-703.
Chusho H et al., Dwarfism and early death in mice lacking C-type natriuretic peptide, Proceedings of the National Academy of Sciences of the United States of America, Mar. 27, 2001, p. 4016-421, vol. 98, No. 7.
Currie et al., Bioactive cardiac substances: potent vasorelaxant activity in mammalian atria. Science. Jul. 1, 1983;221(4605):71-3.
De Bold M et al., Cardiac hormones ANF and BNP modulate proliferation in the unidirectional mixed lymphocyte reaction, the Journal of Heart and Lung Transplantation, Mar. 2010, p. 323-326, vol. 29, No. 3.
Drewett et al., Natriuretic peptide receptor-B (guanylyl cyclase-B) mediates C-type natriuretic peptide relaxation of precontracted rat aorta. J Biol Chem. Mar. 3, 1995;270(9):4668-74.
Gilhar A et al., Autoimmune hair loss (alopecia areata) transferred by T lymphocytes to human scalp explants on SCID mice, The Journal of Clinical Investigation, Jan., 1998, p. 62-67, vol. 101.
He et al., Structural determinants of natriuretic peptide receptor specificity and degeneracy. J Mol Biol. Aug. 25, 2006;361(4):698-714. Epub Jul. 10, 2006.
Ikeda T, A new classification of alopecia areata, Dermatologica, 1965, p. 421-445, vol. 131.
Itami S, Hair survey (male pattern hair loss) Japanese adult males, The Japan Medical Journal, Dec. 25, 2004, p. 27-29, No. 4209.
Katsuoka K, Atopic disease and alopecia areata—atopic alopecia areata-, MB Derma, 1999, p. 9-12, vol. 23.
Kenny et al., Hydrolysis of human and pig brain natriuretic peptides, urodilatin, C-type natriuretic peptide and some C-receptor ligands by endopeptidase-24.11. Biochem J. Apr. 1, 1993;291 ( Pt 1):83-8.
Kiemer A et al., The atrial natriuretic peptide regulates the production of inflammatory mediators in macrophages, Annals of the Rheumatic Disease, Jun. 28, 2001, vol. 60.
Koller et al., Molecular biology of the natriuretic peptides and their receptors. Circulation. Oct. 1992;86(4):1081-8.
Kubo A et al, C-type natriuretic peptide is synthesized and secreted from leukemia cell lines, peripheral blood cells, and peritoneal macrophages, Experimental Hematology, Jan. 4, 2001, p. 609-615, vol. 29.
Kumar M et al., Atrial natriuretic peptide gene transfer by means of interanasal administration attenuates ailway reactivity in a mouse model of allergic sensitization, J Allergy Clin Immunol., Dec. 2002, p. 879-882, vol. 110, No. 6.
Lopez et al., Salt-resistant hypertension in mice lacking the guanylyl cyclase—A receptor for atrial natriuretic peptide. Nature. Nov. 2, 1995;378(6552):65-8.
Lowe et al., Human atrial natriuretic peptide receptor defines a new paradigm for second messenger signal transduction. EMBO J. May 1989;8(5):1377-84.
MacDonal Hull S et al., Guidelines for the management of alopecia areata, Br J Dermatol., Apr. 17, 2003, p. 692-699, vol. 149.
Marin-Grez et al., Atrial natriuretic peptide causes pre-glomerular vasodilatation and post-glomerular vasoconstriction in rat kidney. Nature. Dec. 4-10, 1986;324(6096):473-6.
Marinissen et al., G-protein-coupled receptors and signaling networks: emerging paradigms. Trends Pharmacol Sci. Jul. 2001;22(7):368-76.
Meirovich Y et al., Relationship between natriuretic peptides and inflammation: proteomic evidence obtained during acute cellular cardiac allograft rejection in humans, the Journal of Heart and Lung Transplantation, Jan. 2008, p. 31-37, vol. 27, No. 1.
Mohapatra S et al., Intranasal atrial natriuretic peptide (ANP) gene transfer attenuates airway reactivity in a mouse model of allergic asthma, J Allergy Clin Immunol., Feb. 2003, p. S309, vol. 111, No. 2.
MSD Kabushiki Kaisha, Drug Interview Form Propecia tablets, MSD K.K., Jan. 2012, p. 1-41.
Nagase et al., Tissue distribution and localization of natriuretic peptide receptor subtypes in stroke-prone spontaneously hypertensive rats. J Hypertens. Nov. 1997;15(11):1235-43.
Neves et al., G protein pathways. Science. May 31, 2002;296(5573):1636-9.
Norwood O., Male pattern baldness: Classification and incidence, South Med. J., Nov. 1975, p. 1359-1365, vol. 68, No. 11.
Obata H et al., CNP infusion attenuates cardiac dysfunction and inflammation in myocarditis, Biochemical and Biophysical Research Communications, Feb. 26, 2007, p. 60-66, vol. 356.
Oliver et al., Hypertension, cardiac hypertrophy, and sudden death in mice lacking natriuretic peptide receptor A. Proc Natl Acad Sci U S A. Dec. 23, 1997;94(26):14730-5.
Olsen E et al., Alopecia areata investigational assessment guidelines, Journal of American Academy of Dermatology, Feb. 1999, p. 242-246, vol. 40, No. 2, Part 1.
Olsen E, Current and novel methods for assessing efficacy of hair growth promotors in pattern hair loss, J Am Acad Dermatol., Feb. 2003, p. 253-262, vol. 48.
Pfeifer et al., Defective smooth muscle regulation in cGMP kinase I-deficient mice. EMBO J. Jun. 1, 1998;17(11):3045-51.
Potter et al., Natriuretic peptides, their receptors, and cyclic guanosine monophosphate-dependent signaling functions. Endocr Rev. Feb. 2006;27(1):47-72. Epub Nov. 16, 2005.
Potter et al., Natriuretic peptides: their structures, receptors, physiologic functions and therapeutic applications. Handb Exp Pharmacol. 2009;(191):341-66. doi: 10.1007/978-3-540-68964-5_15.
Reichert S et al., Molecular and physiological effects of nesiritide, The Canadian Journal of Cardiology, Jul. 2008, p. 15B-18B, vol. 24.
Schulz et al., The primary structure of a plasma membrane guanylate cyclase demonstrates diversity within this new receptor family. Cell. Sep. 22, 1989;58(6):1155-62.
Scotland R et al., C-type natriuretic peptide inhibits leukocyte recruitment and platelet-leukocyte interactions via suppression of

(56) References Cited

OTHER PUBLICATIONS

P-selectin expression, Proceedings of the National Academy of Sciences, Oct. 4, 2005, p. 14452-14457, vol. 102, No. 40.
Serarslan G. et al., Is atopy and autoimmunity more prevalent in patients with alopecia areata? A comparative study, J Eur Acad Dermatol Venereol., May 31, 2011, p. 720-723, vol. 26.
Shellow W et al., Profile of alopecia areata: a questionnaire analysis of patient and family, Int J dermatol, Mar. 1992, p. 186-189, vol. 31, No. 3.
Suga et al. Receptor selectivity of natriuretic peptide family, atrial natriuretic peptide, brain natriuretic peptide, and C-type natriuretic peptide. Endocrinology. Jan. 1992;130(1):229-39.
Tamura et al., Cardiac fibrosis in mice lacking brain natriuretic peptide. Proc Natl Acad Sci U S A. Apr. 11, 2000;97(8):4239-44.
Tosti A et al., Alopecia areata: A long term follow-up study of 191 patients, J Am Acad Dermatol., Jun. 30, 2006, p. 438-441, vol. 55, No. 3.
Tsuboi R et al., Androgenetic alopecia diagnosis and treatment guidelines (2010 edition), The Japanese Journal of Dermatology, 2010, p. 997-986, vol. 120, No. 5 (English version also provided, Guidelines for the management of androgenetic alopecia (2010), The Journal of Dermatology, Jun. 28, 2011, p. 113-120, vol. 39).
Tsuji et al., A loss-of-function mutation in natriuretic peptide receptor 2 (Npr2) gene is responsible for disproportionate dwarfism in cn/cn mouse. J Biol Chem. Apr. 8, 2005;280(14):14288-92. Epub Feb. 18, 2005.
Yoshibayashi M et al., Brain natriuretic peptide versus atrial natriuretic peptide—physiological and pathophysiological significance in children and adults: a review, Eur J Endocrinol., May 20, 1996, p. 265-268, vol. 135.

\* cited by examiner

[Fig. 1]
[Fig. 2]
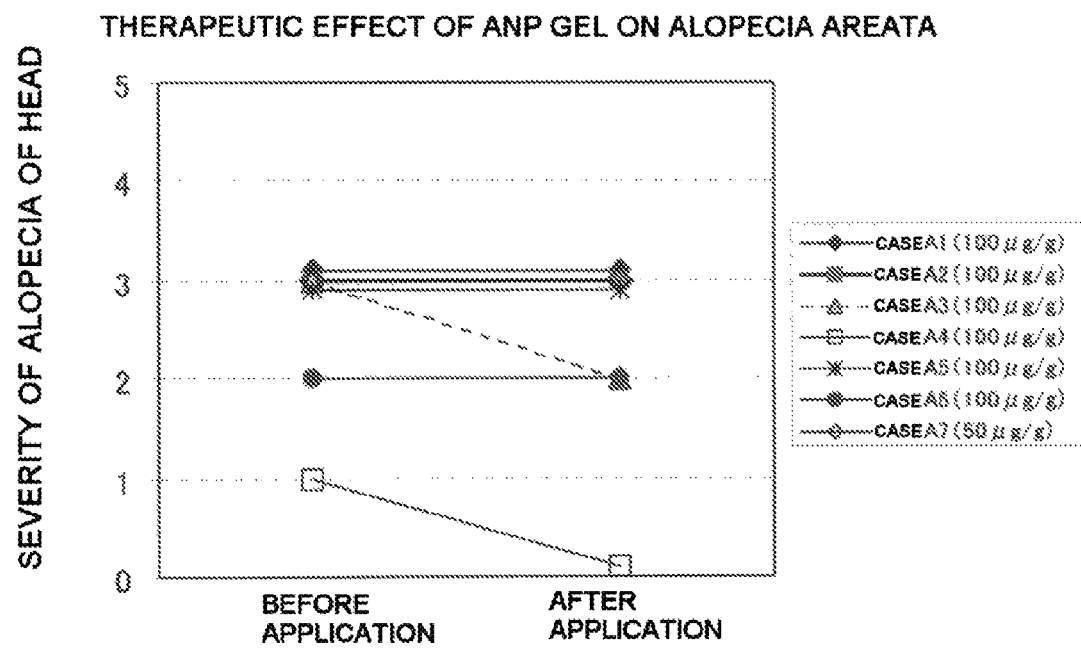

[Fig. 3]
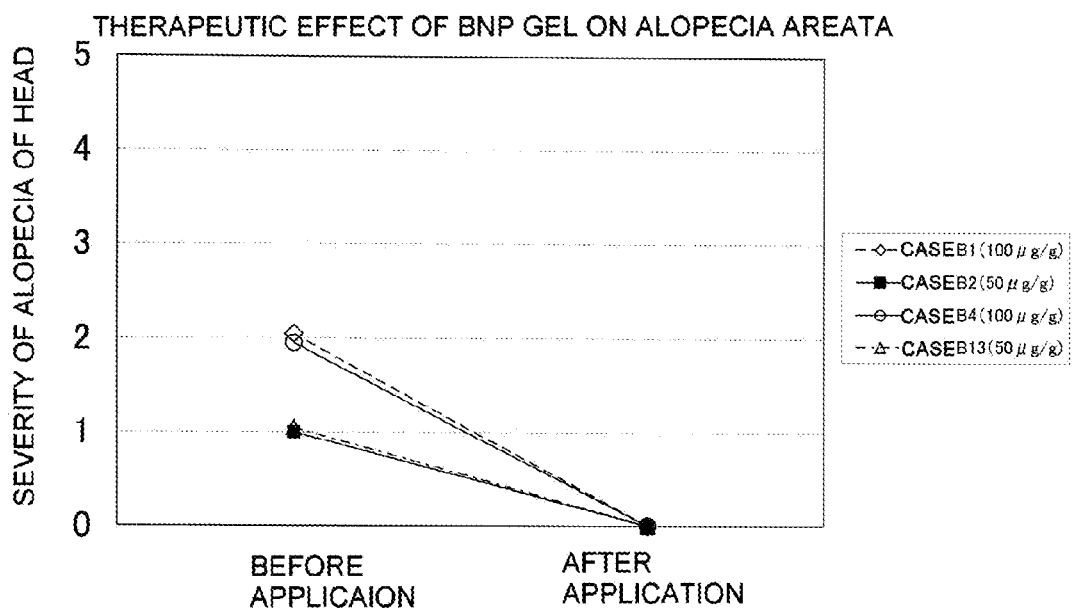
[Fig. 4]
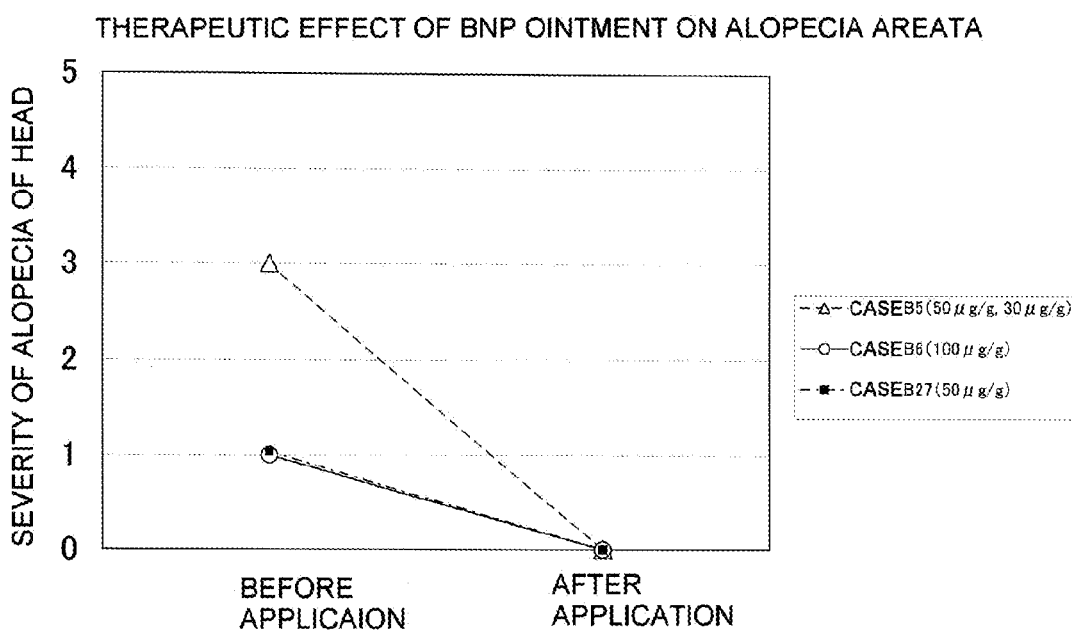

[Fig. 5]
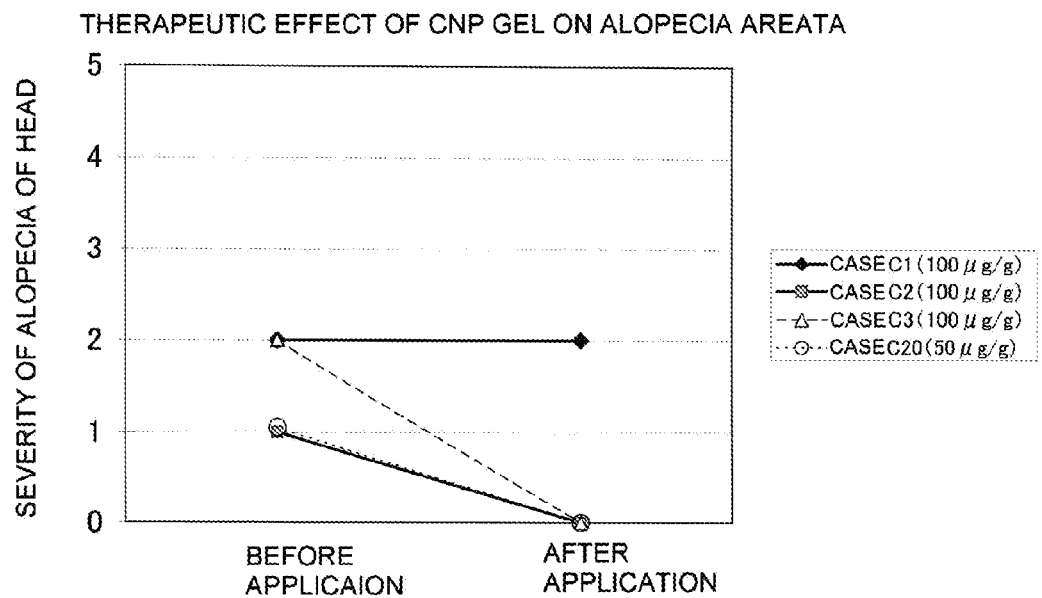
[Fig. 6]
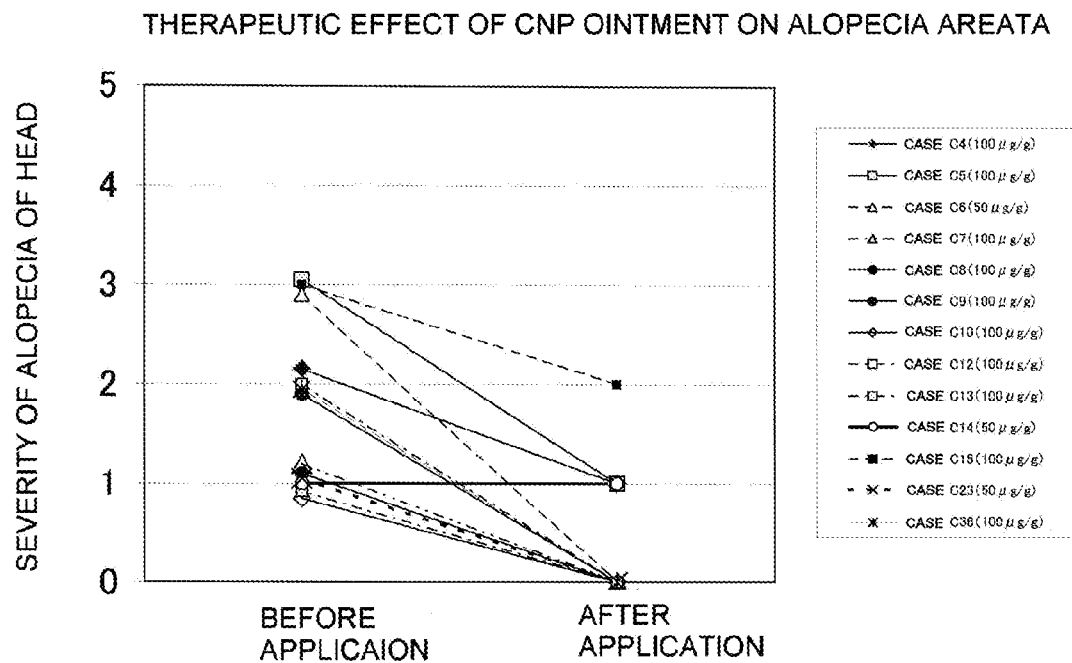

[Fig. 7]
P
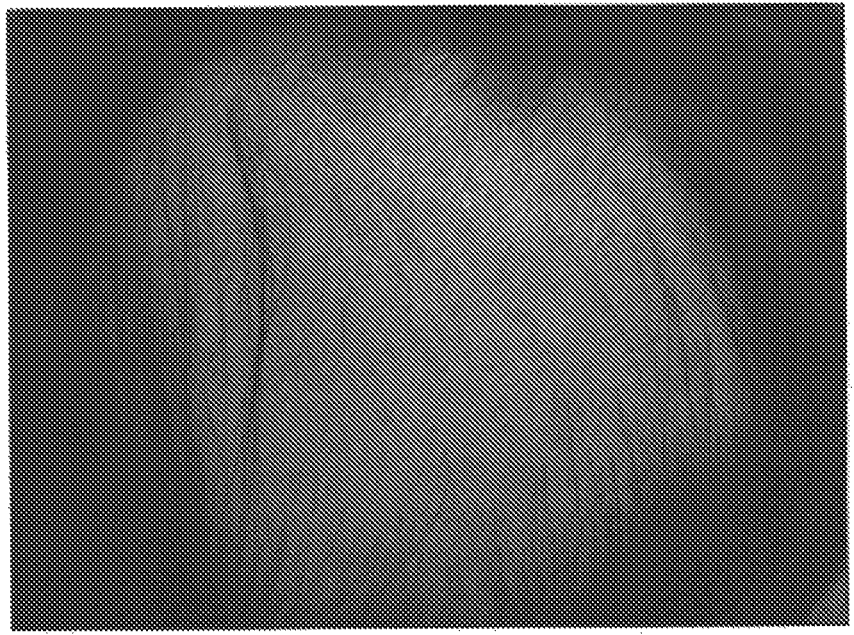
T
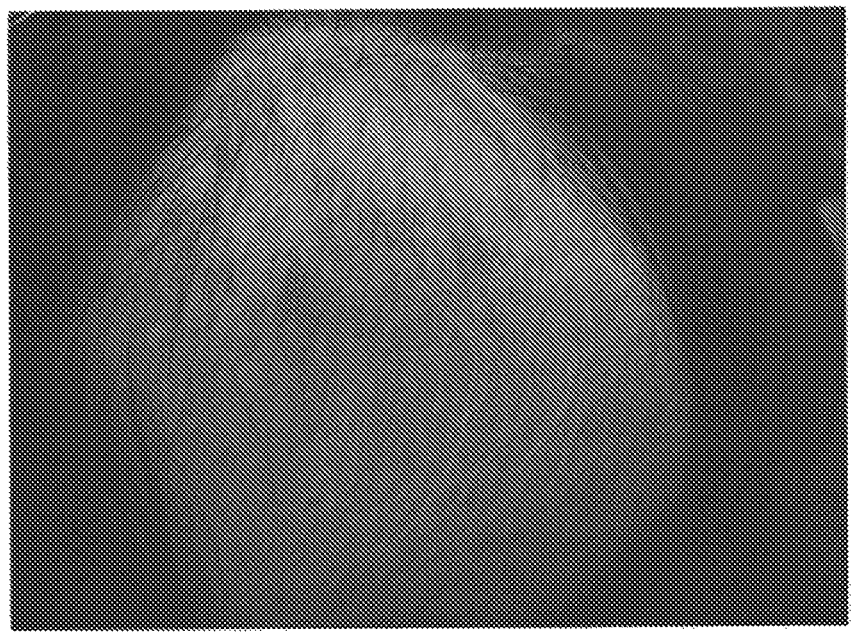

[Fig. 8-1]

[Fig. 8-2]
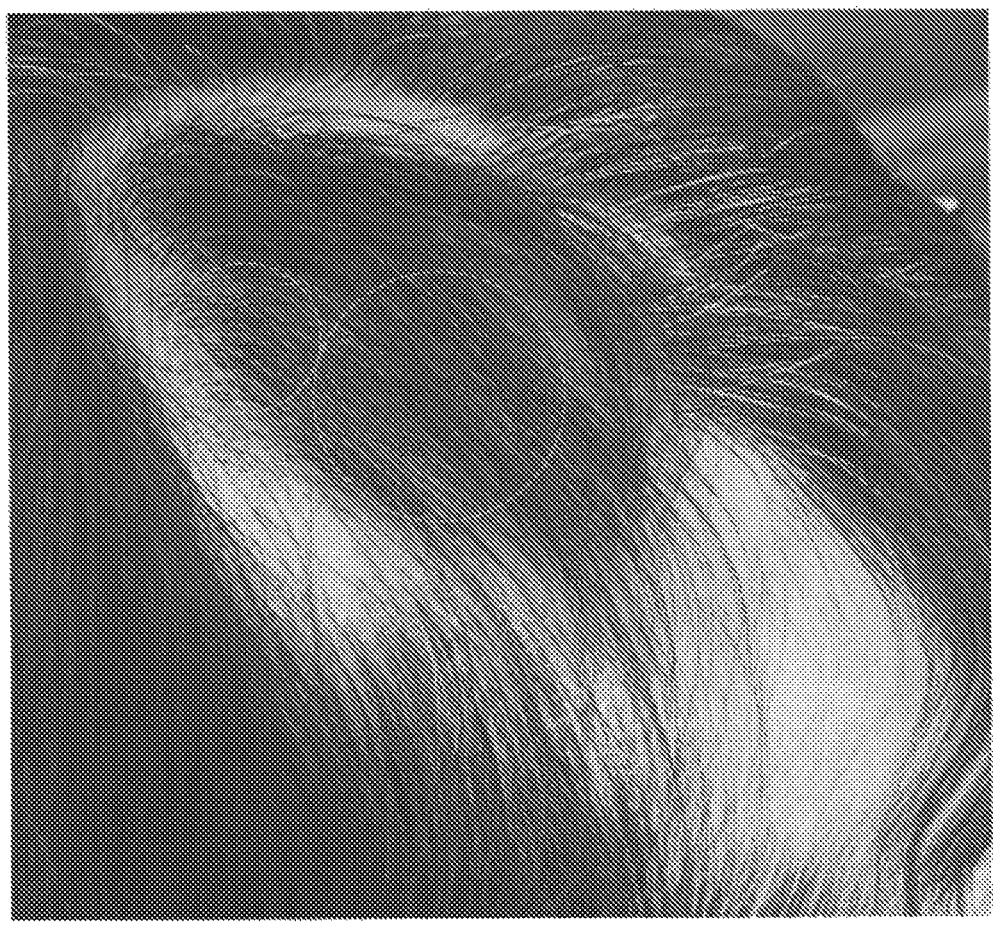

[Fig. 9]
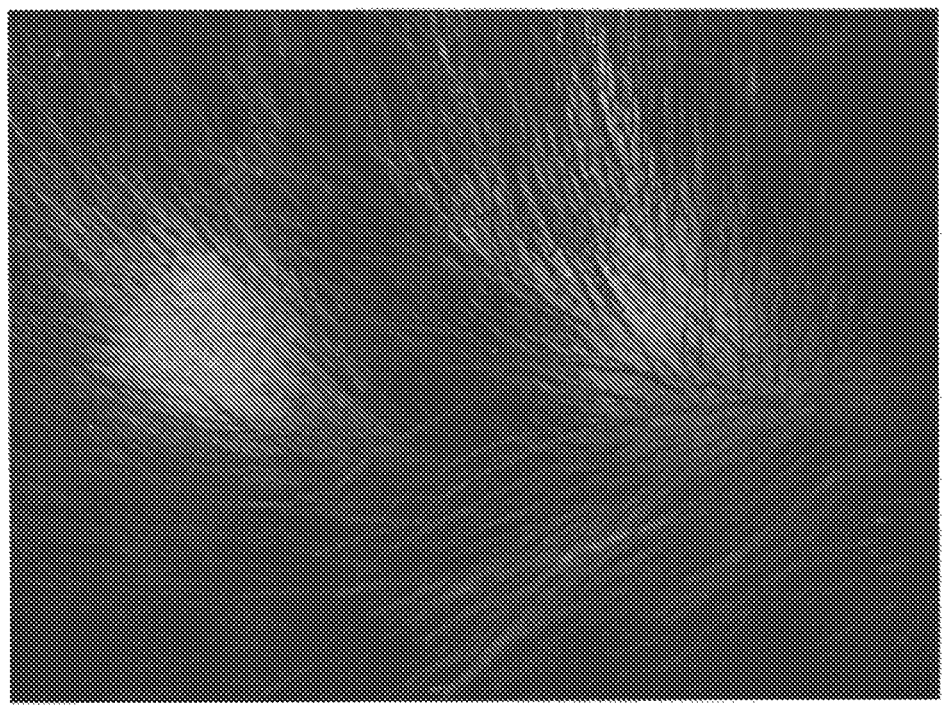
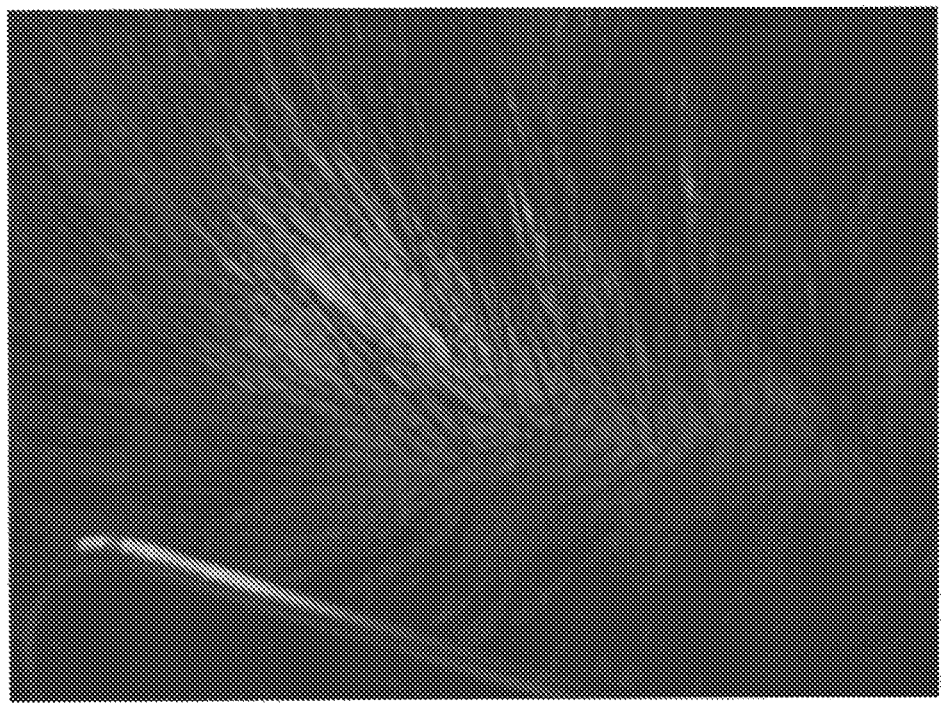

[Fig. 10]
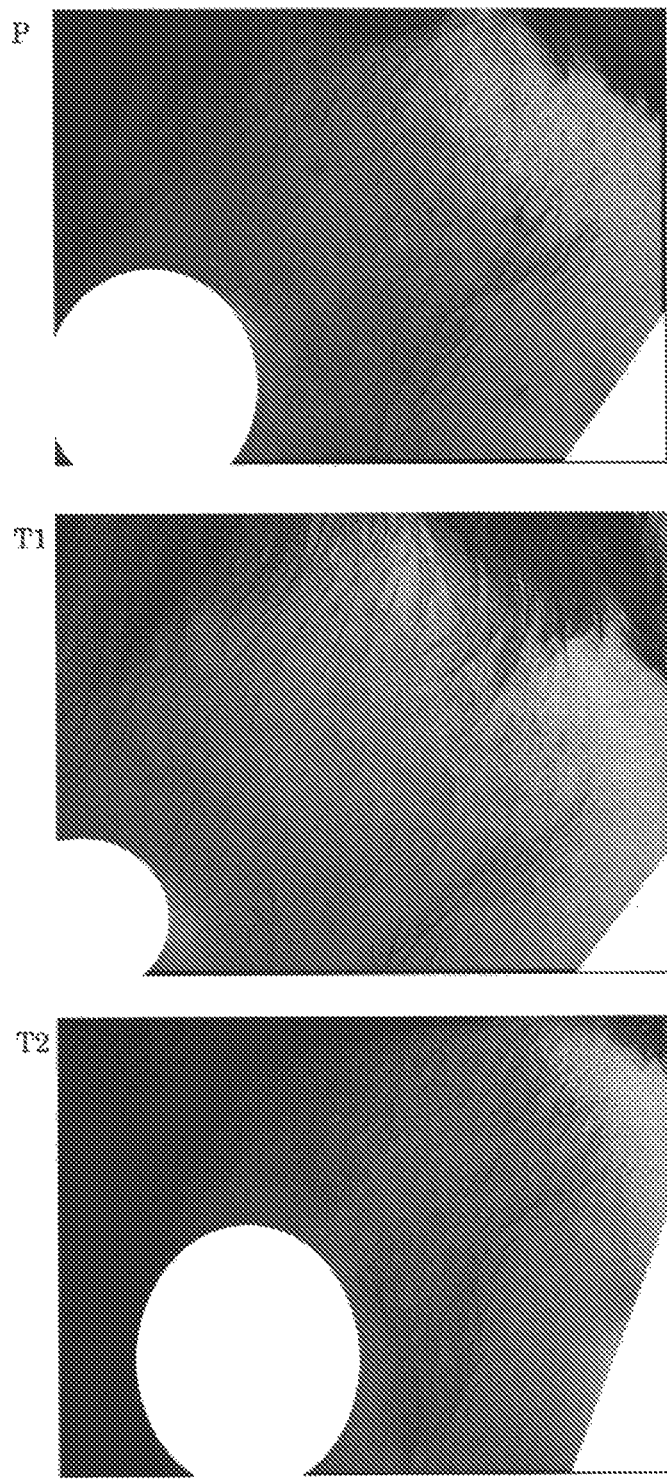

[Fig. 11]
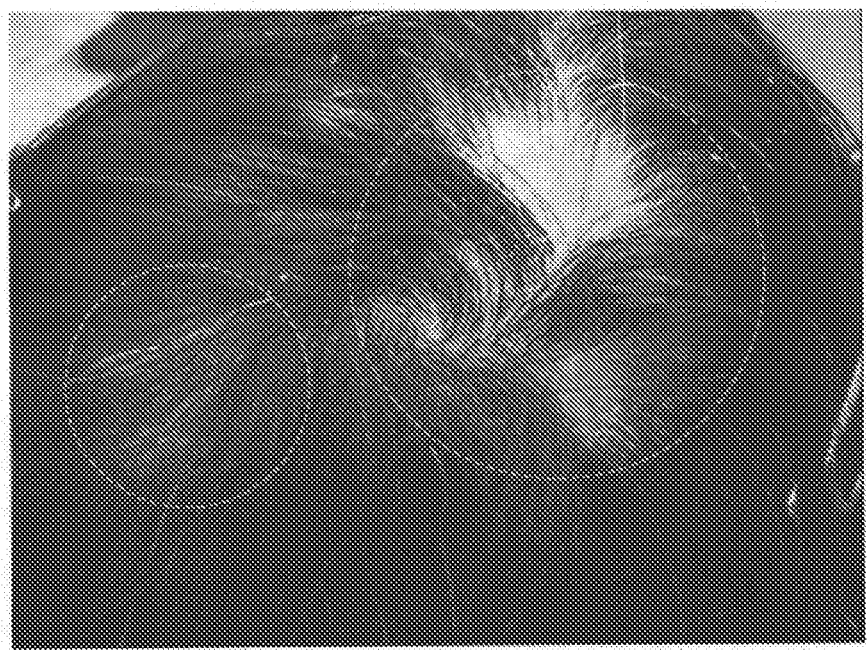
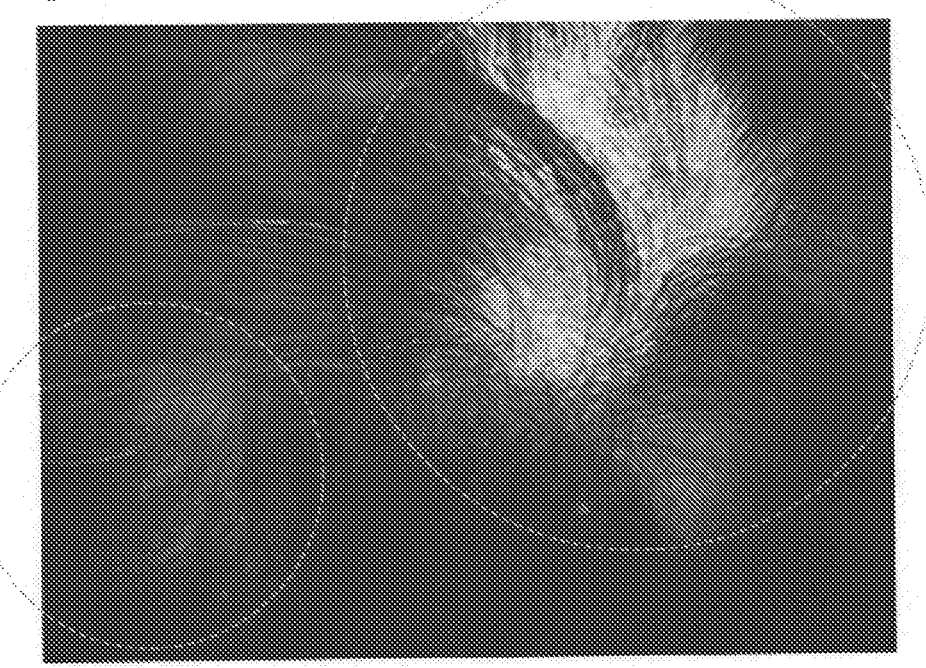

[Fig. 12-1]
P
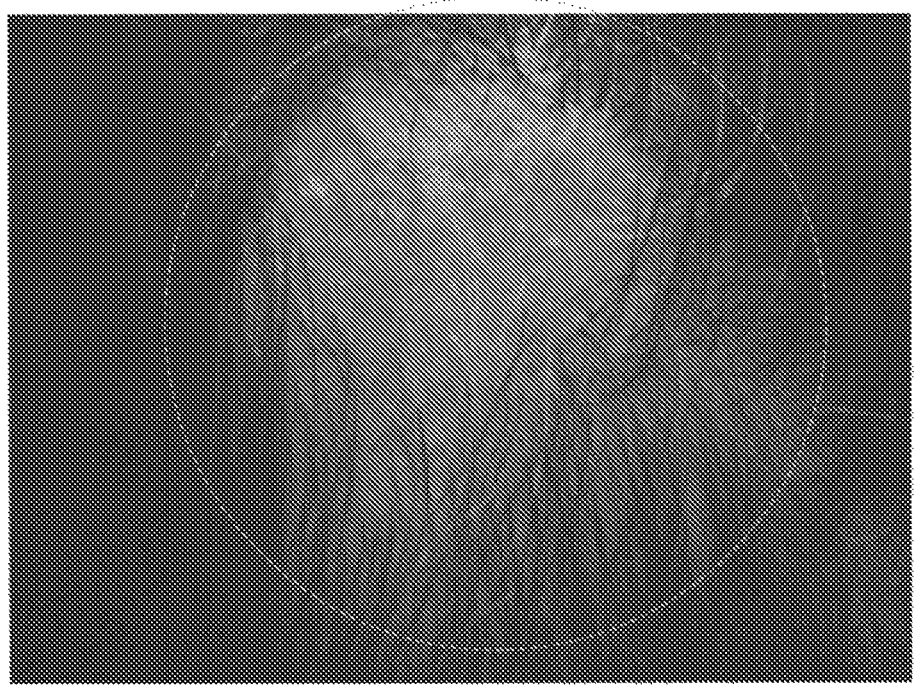
T1
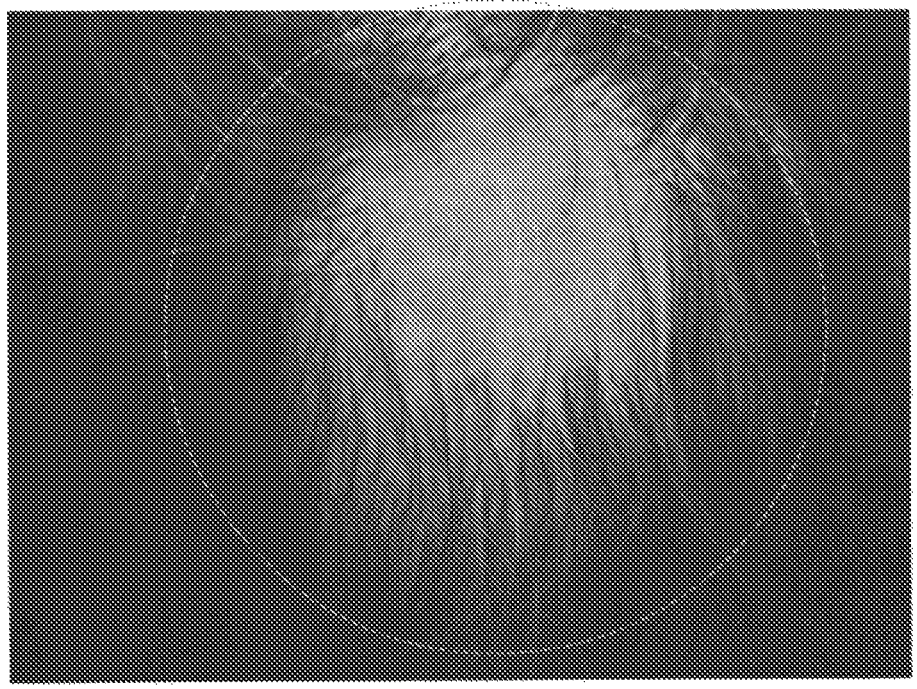

[Fig. 12-2]

[Fig. 13]

[Fig. 14]
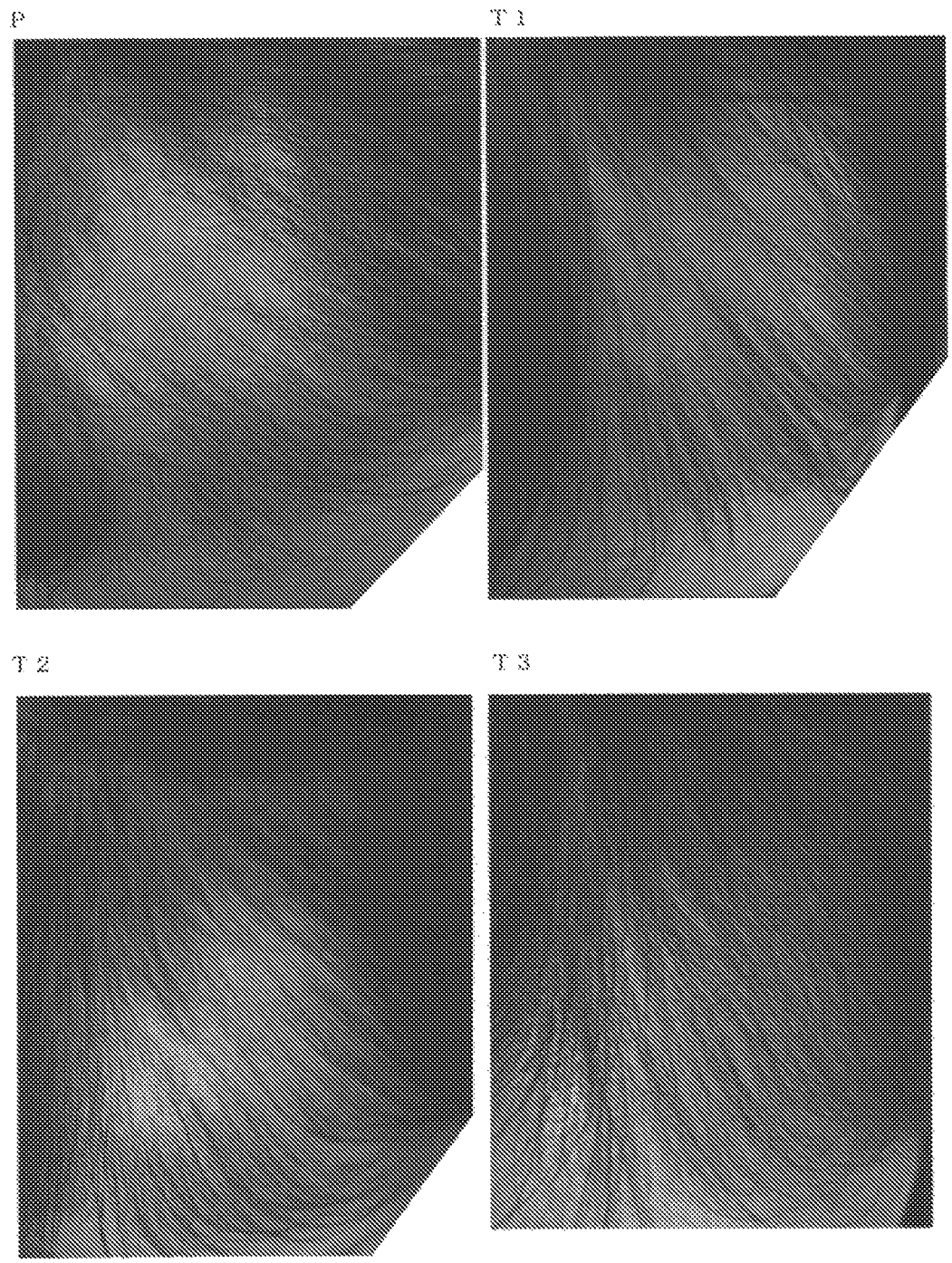

[Fig. 15-1]
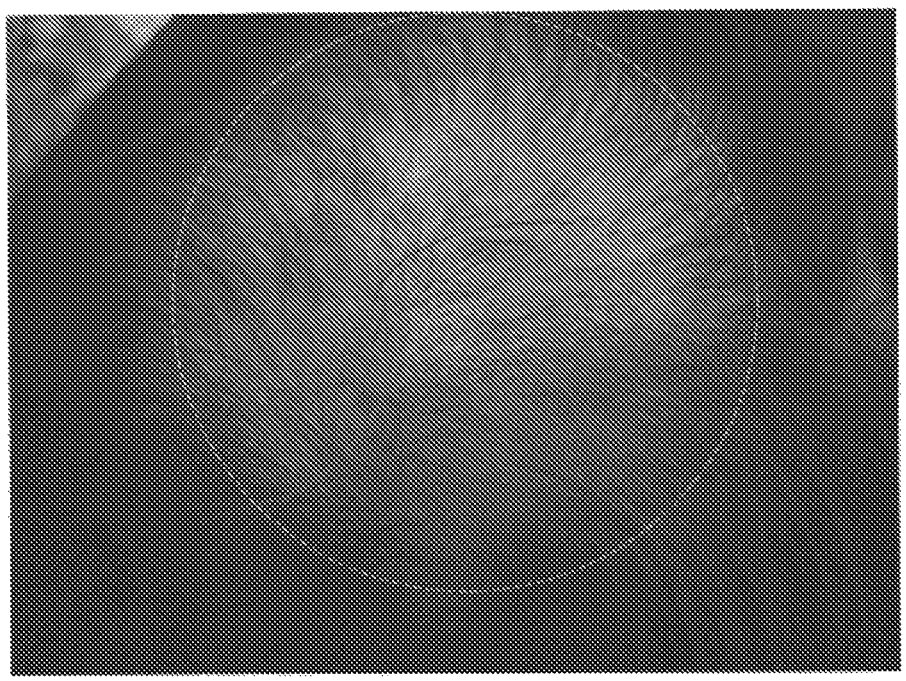
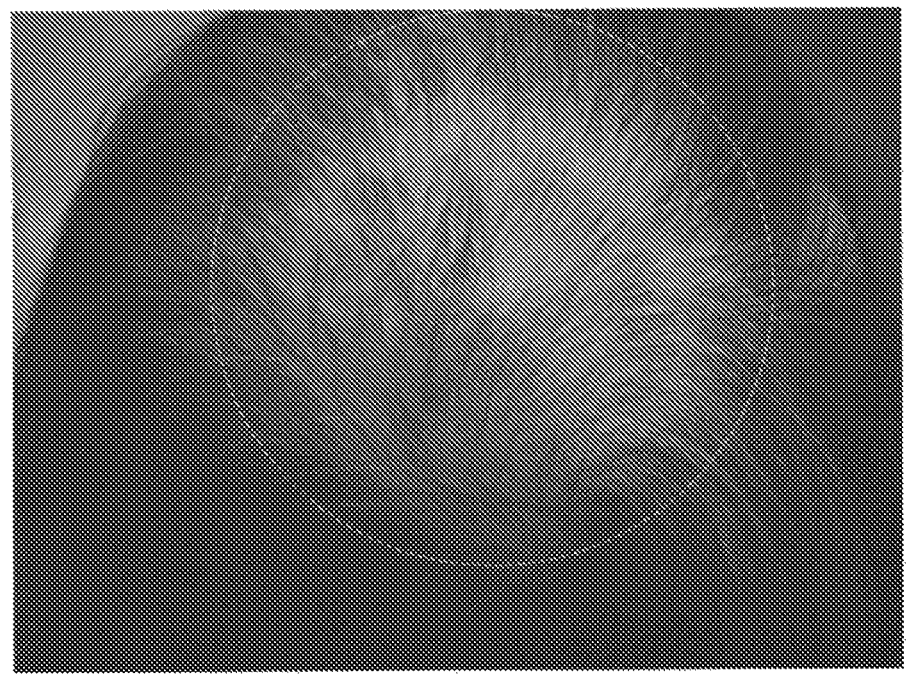

[Fig. 15-2]
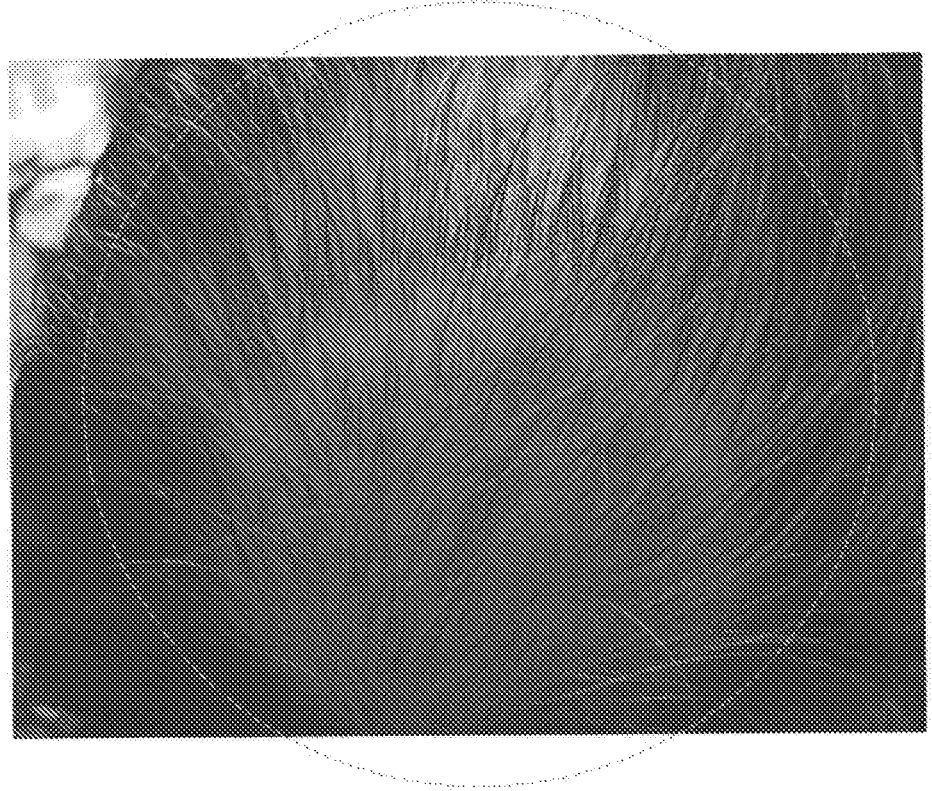

[Fig. 16]
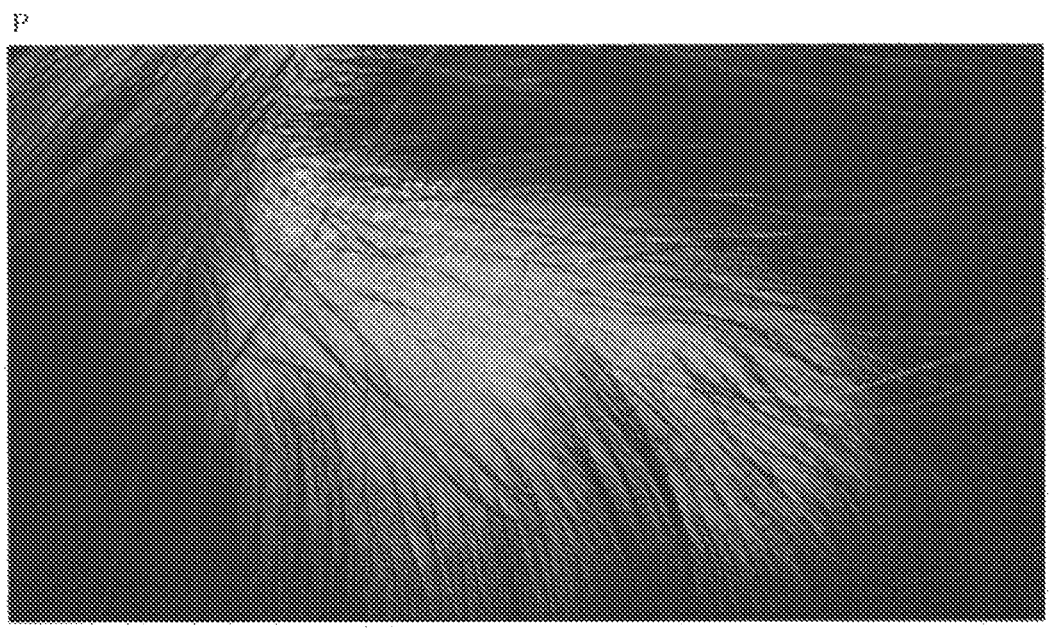

[Fig. 17]
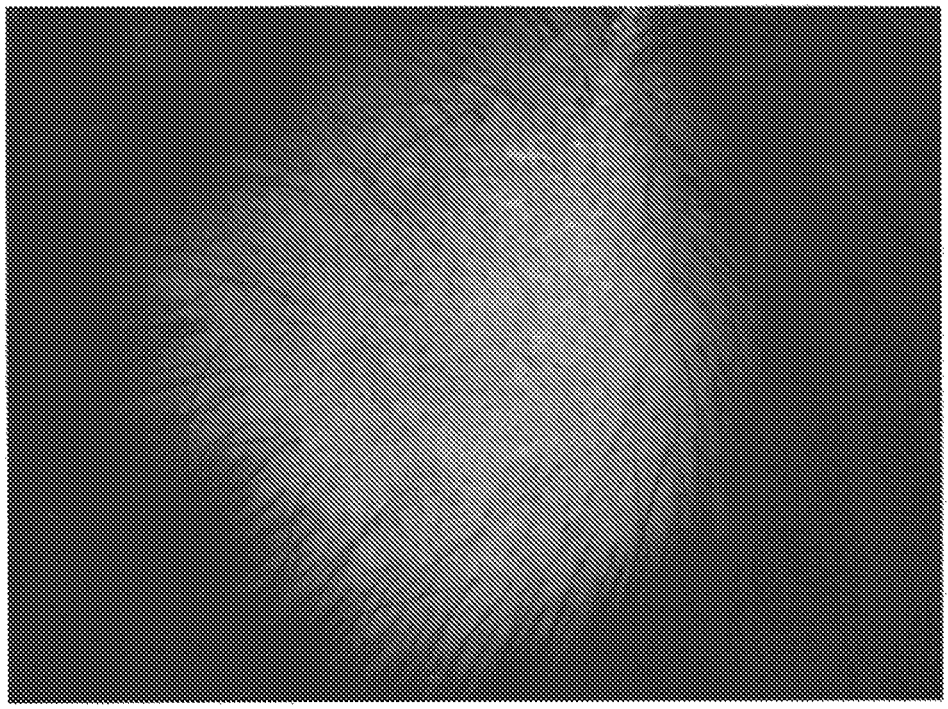
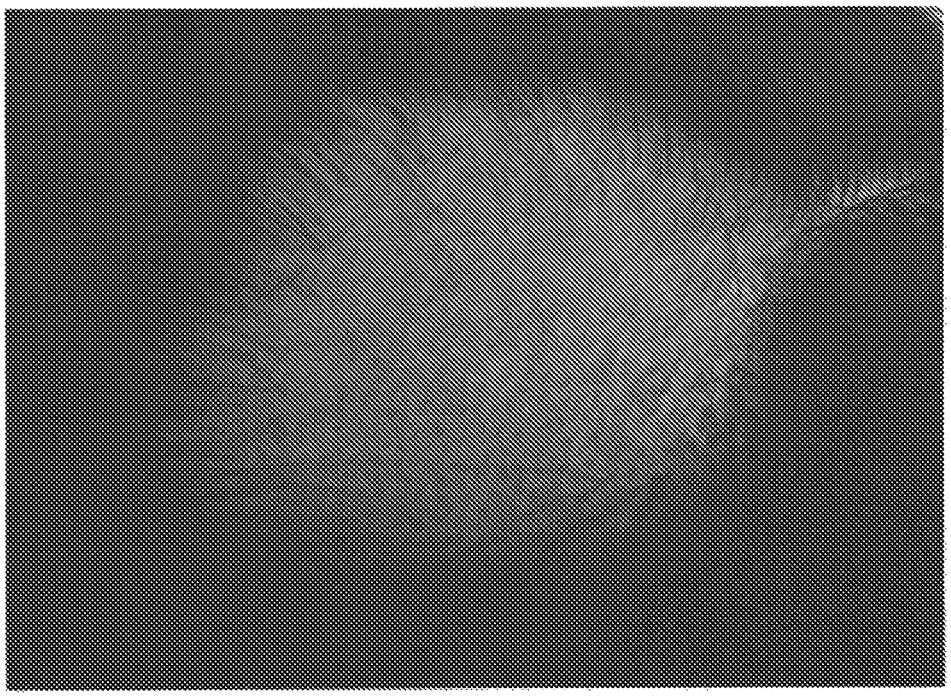

[Fig. 18-1]
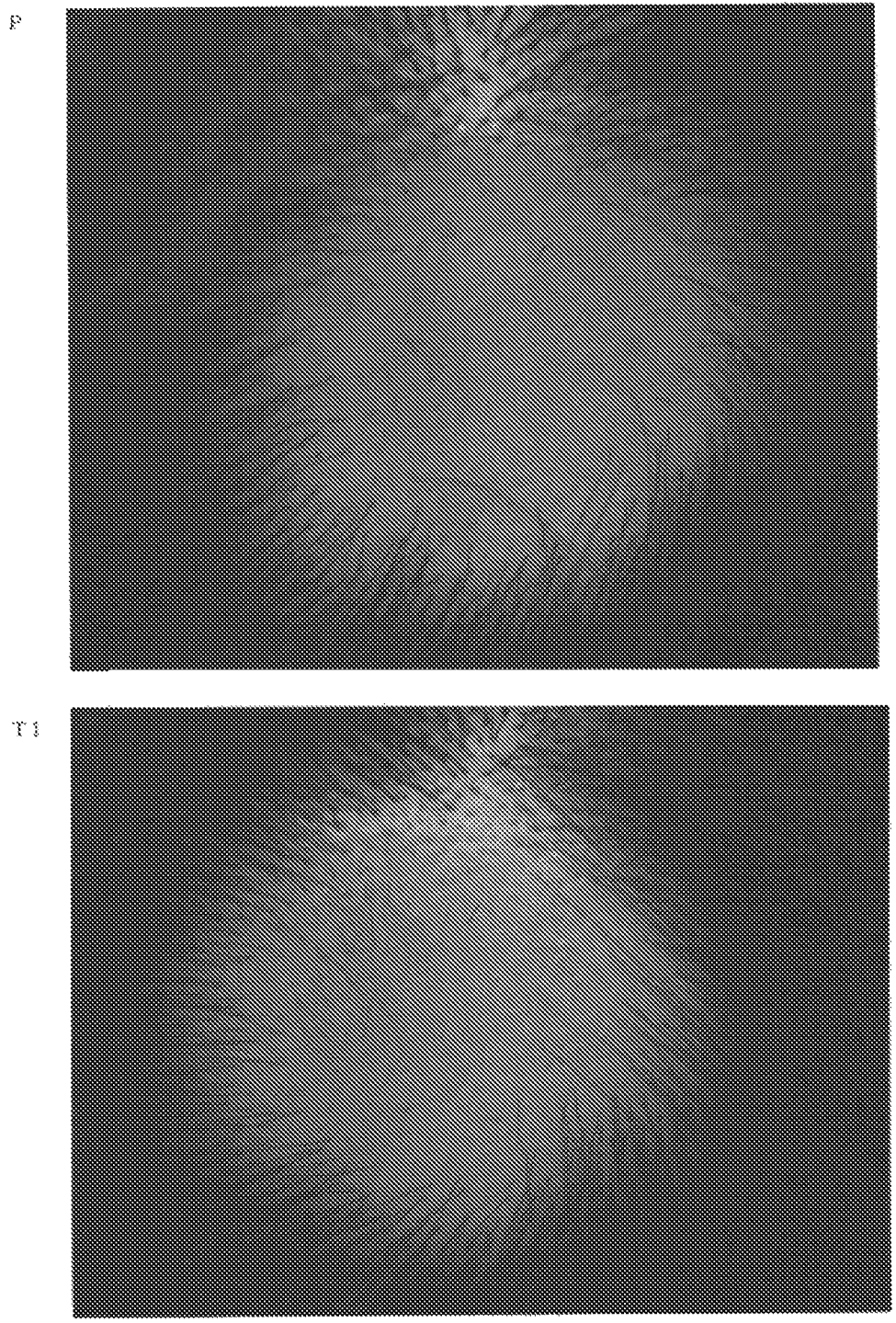

[Fig. 18-2]
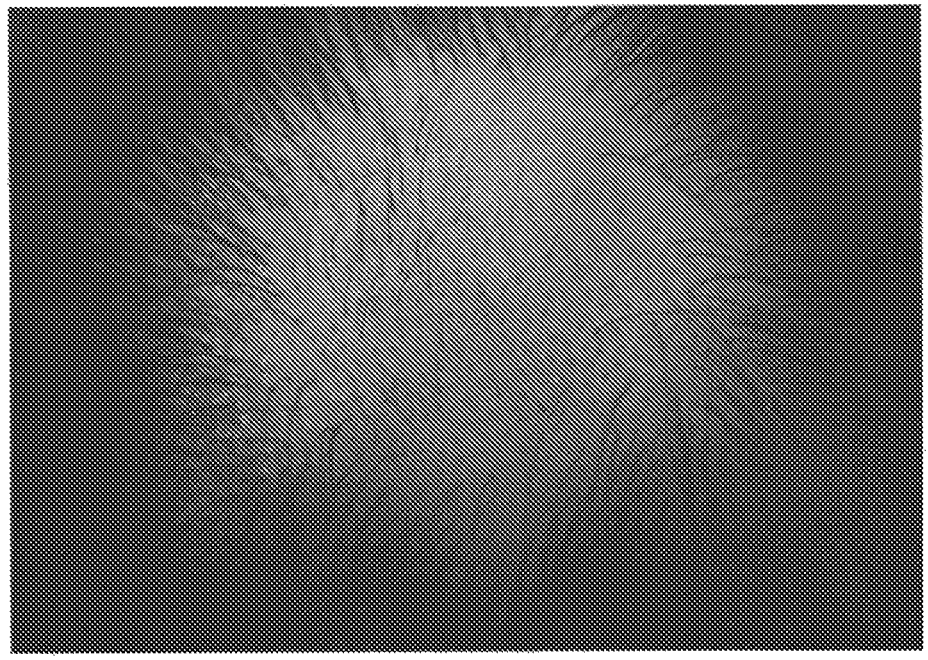
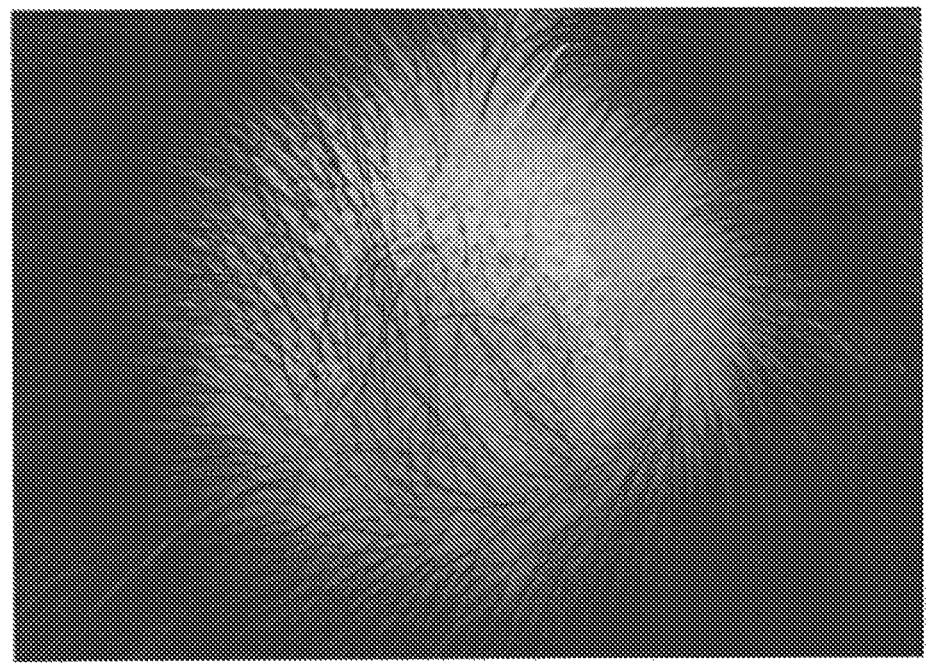

[Fig. 19-1]
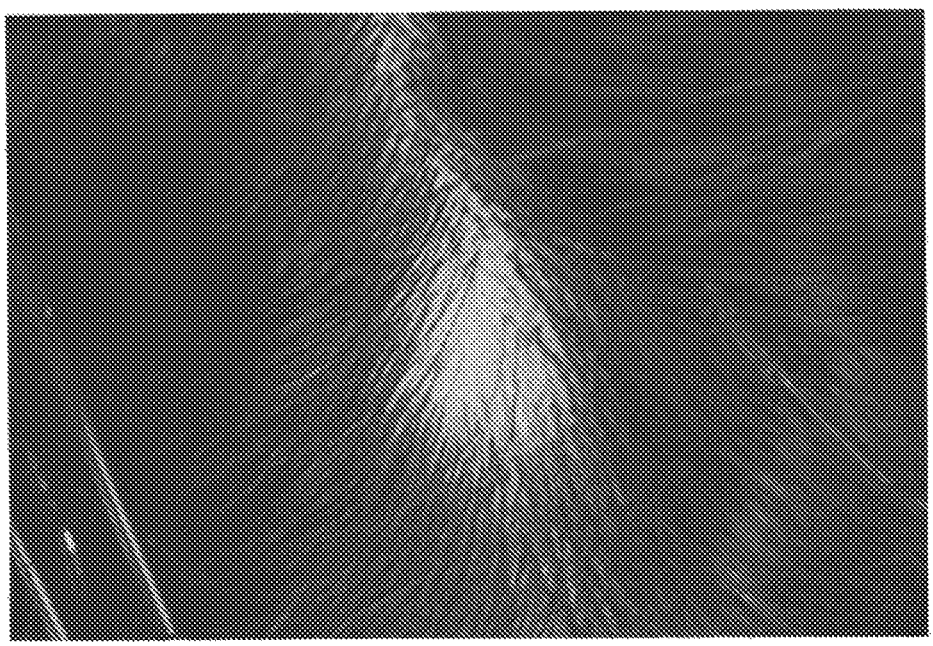
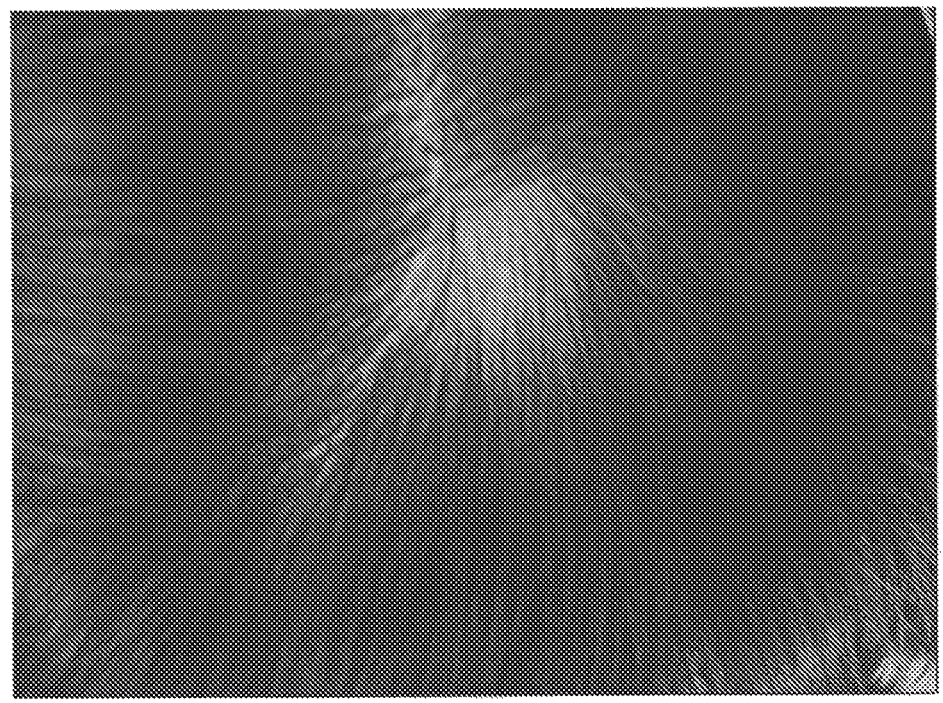

[Fig. 19-2]
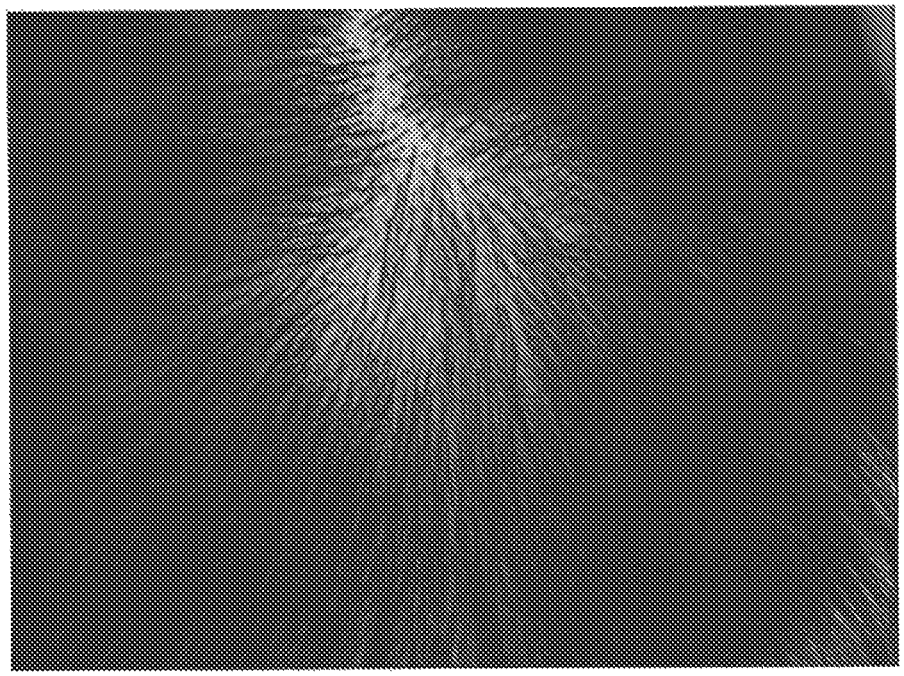

[Fig. 20]
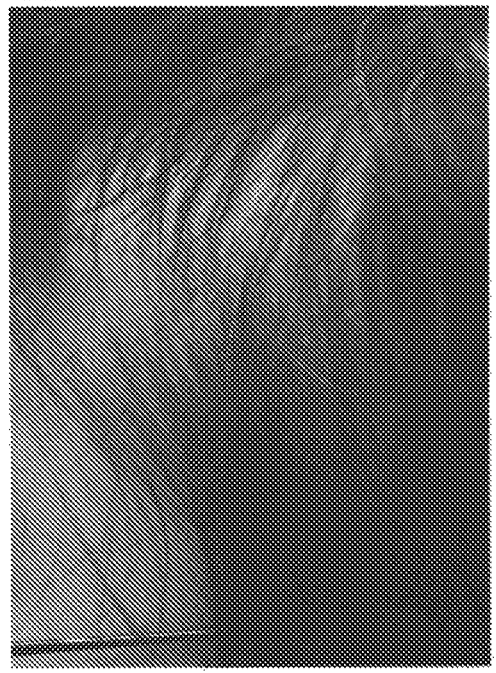

[Fig. 21]
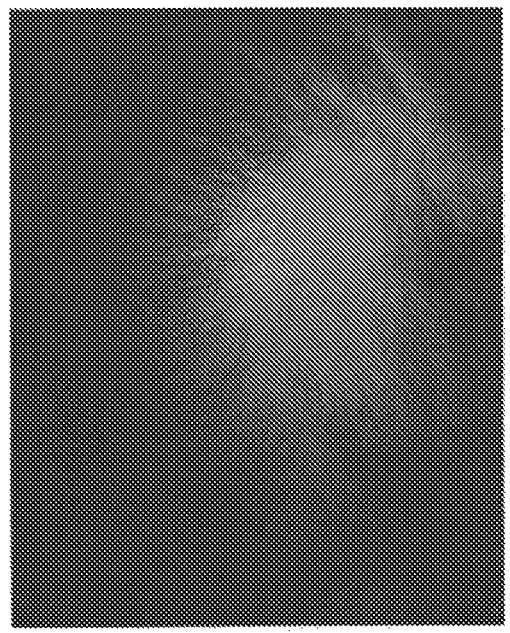
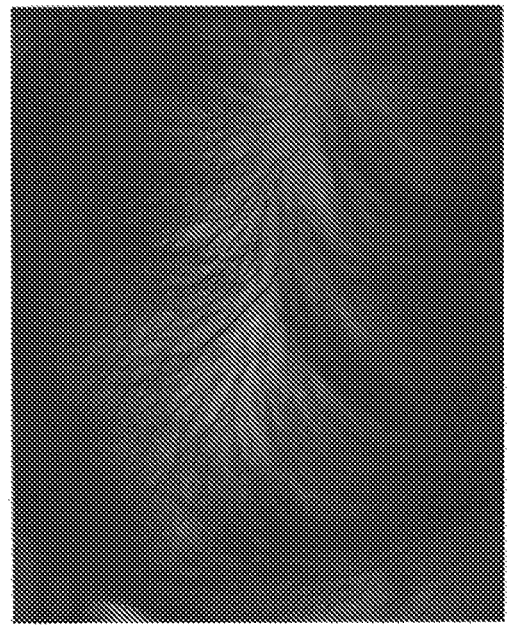

[Fig. 22]
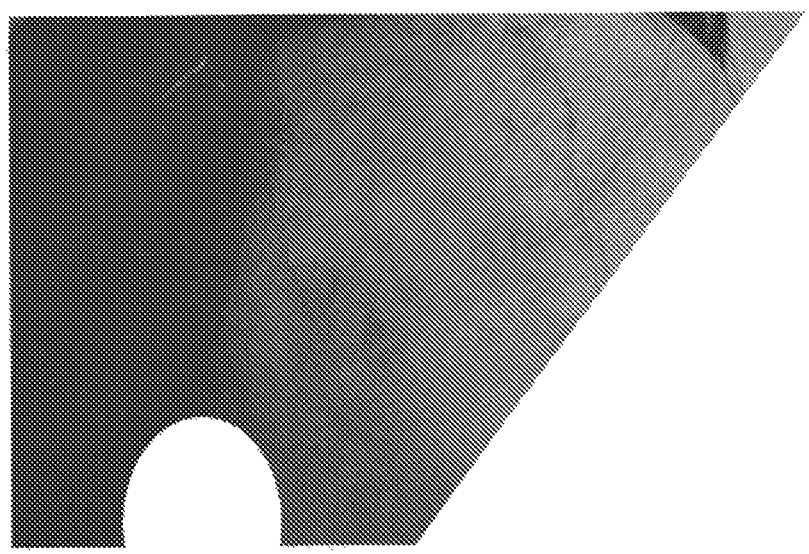
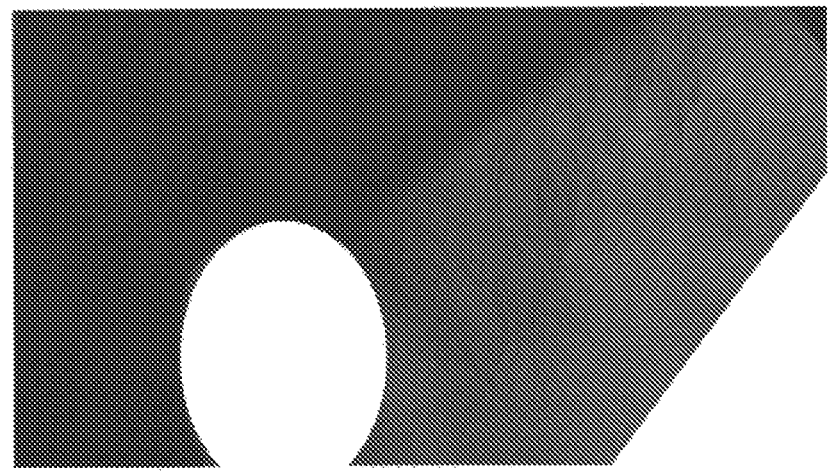

[Fig. 23]
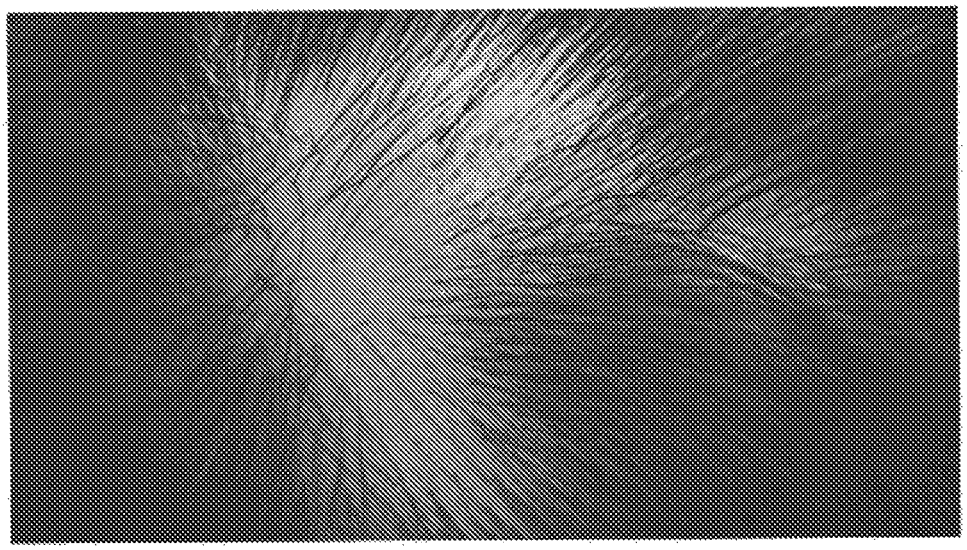
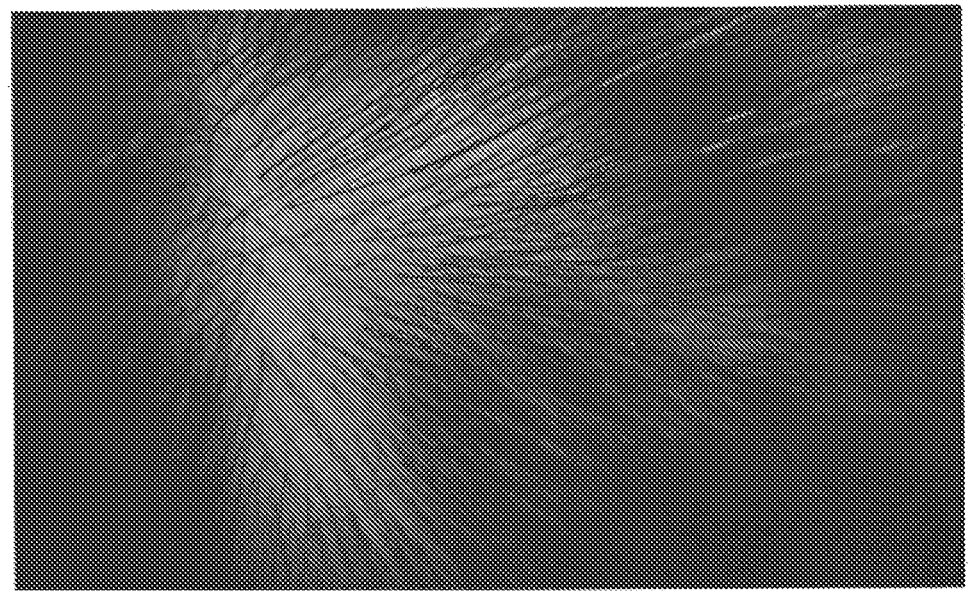

[Fig. 24-1]
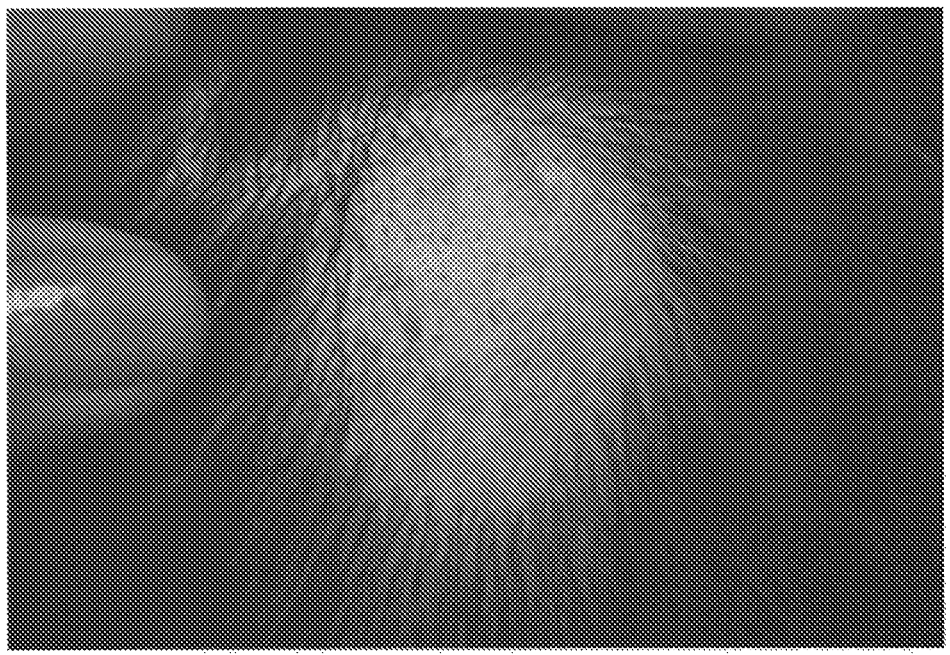
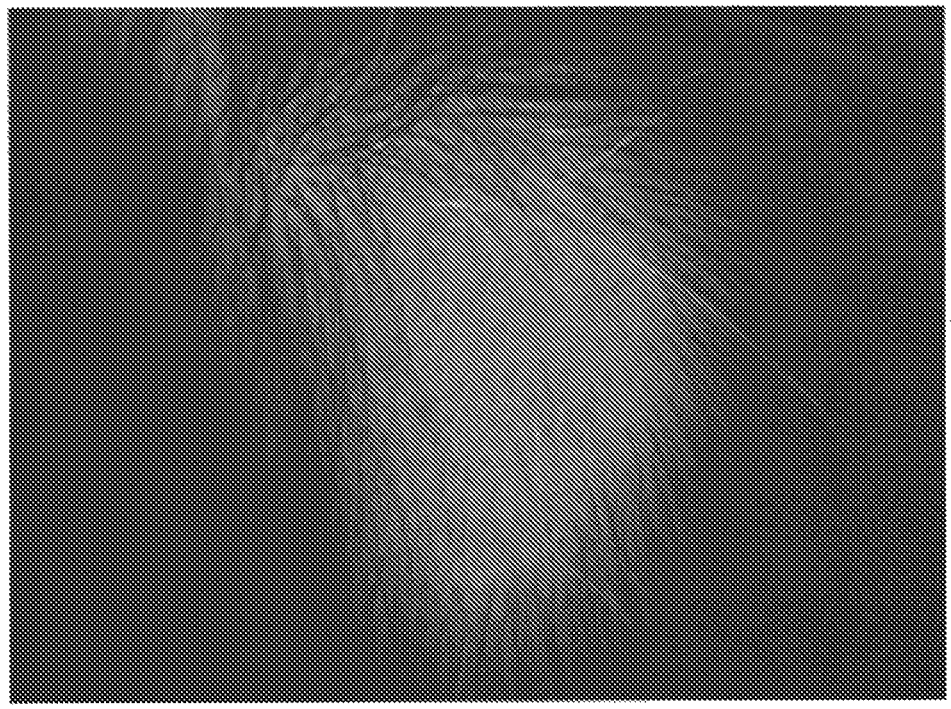

[Fig. 24-2]
T2

[Fig. 25]
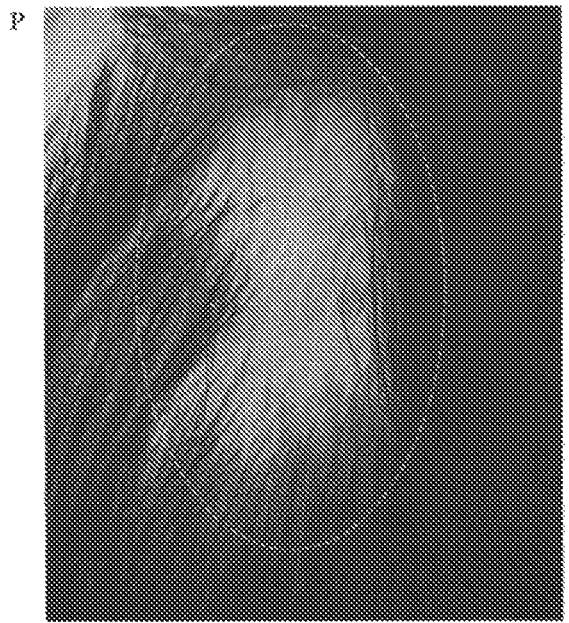
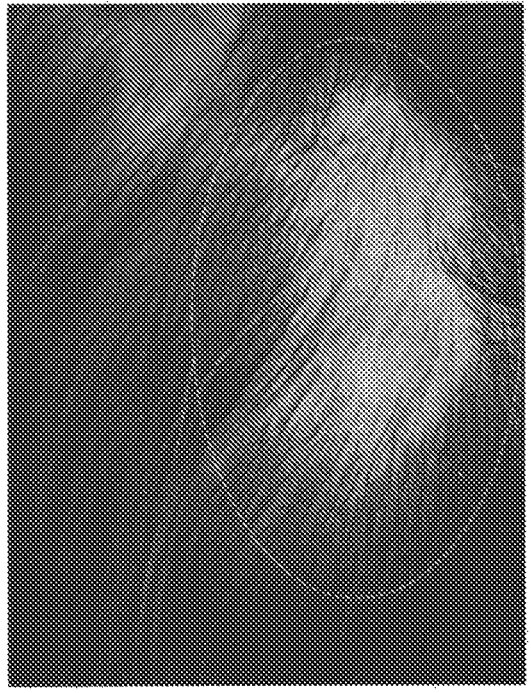
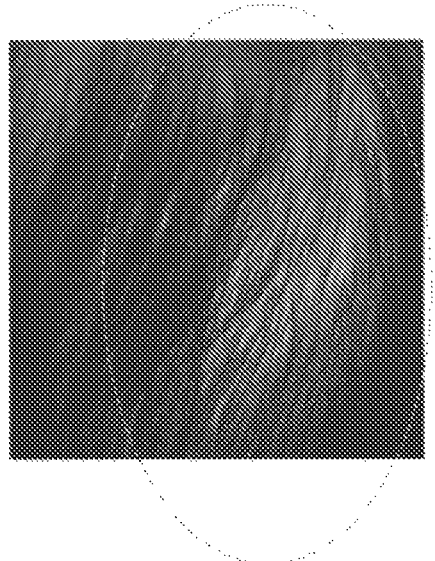

[Fig. 26]
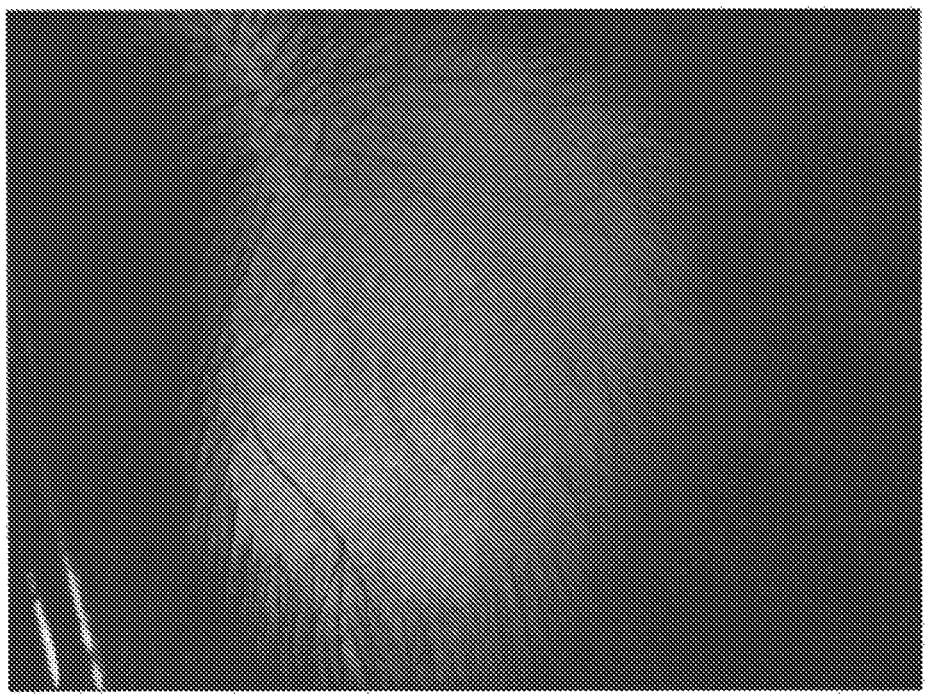
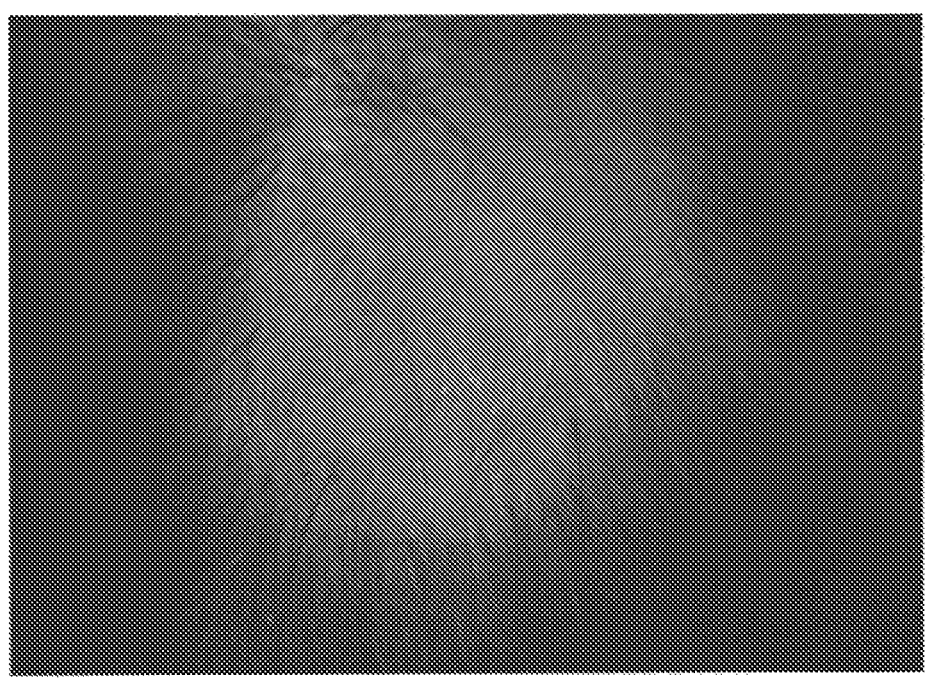

[Fig. 27]
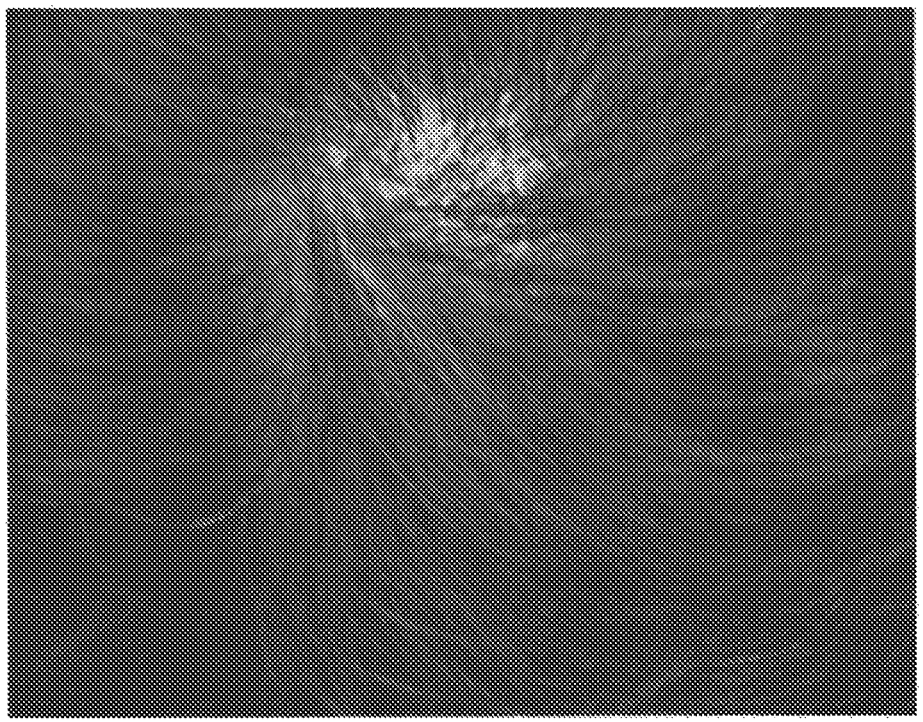
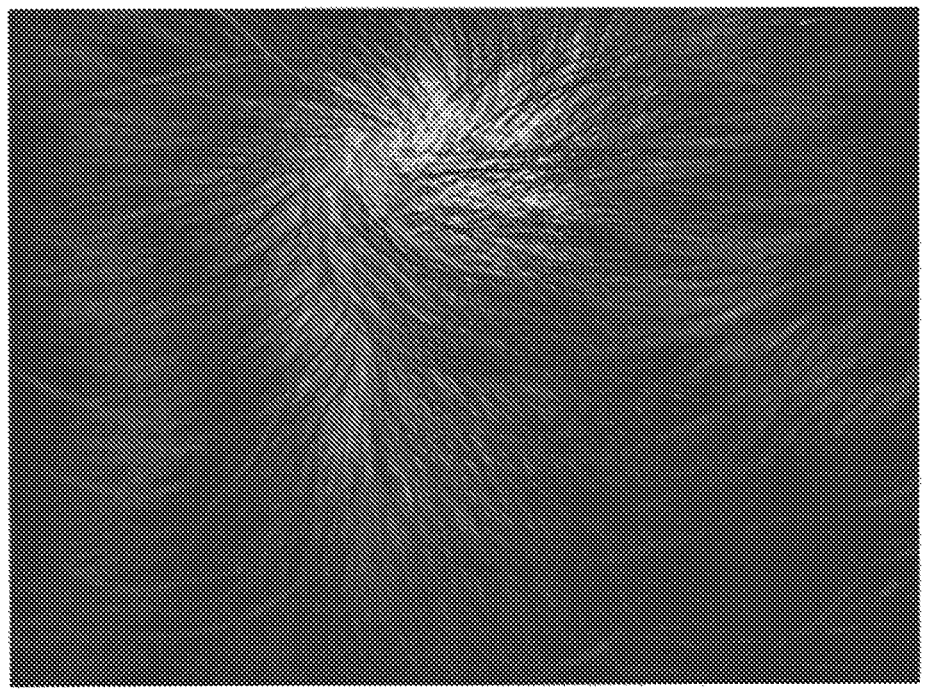

[Fig. 28-1]
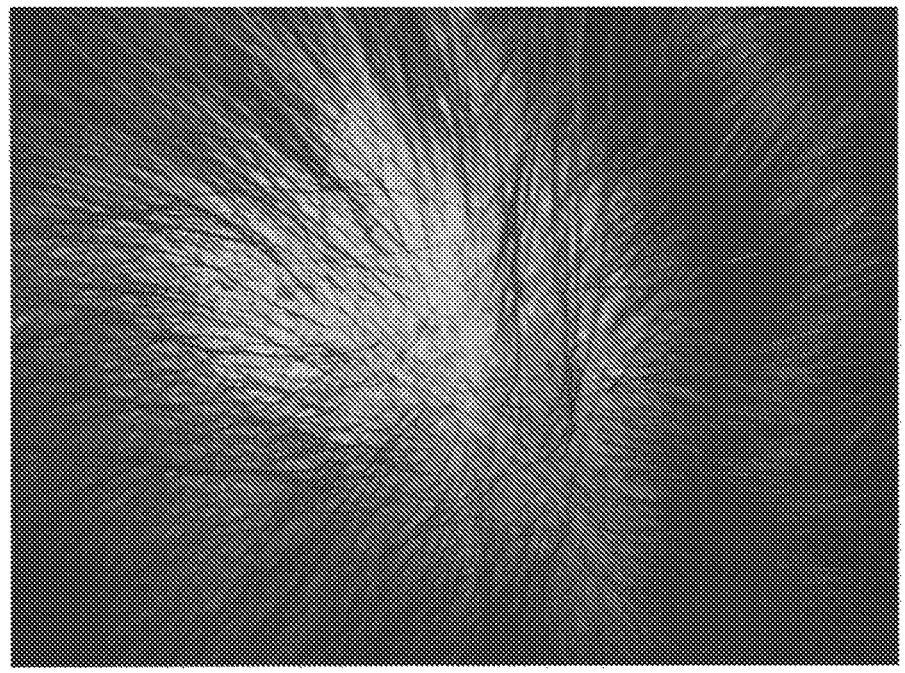
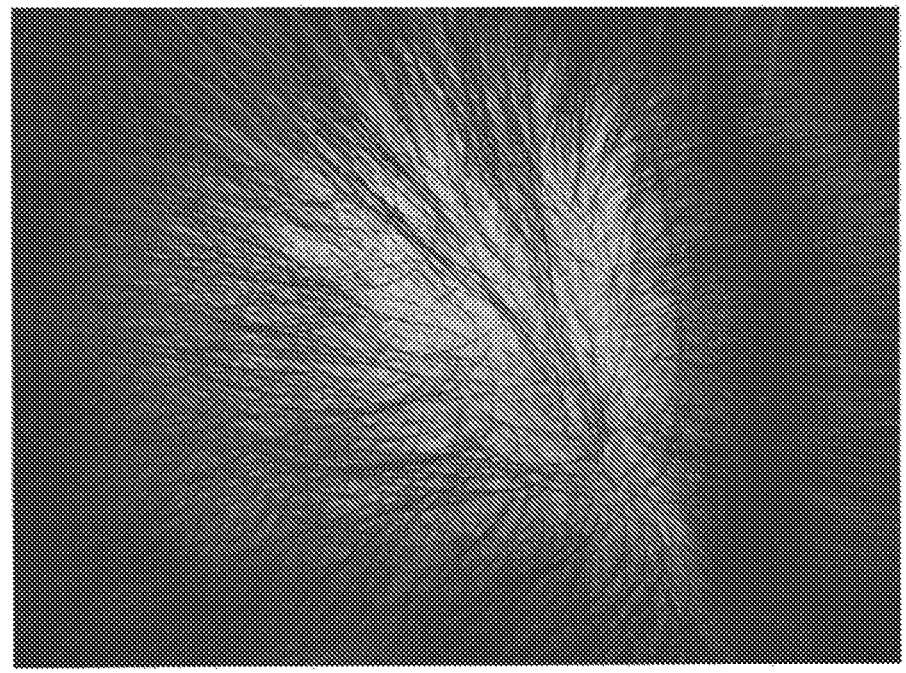

[Fig. 28-2]
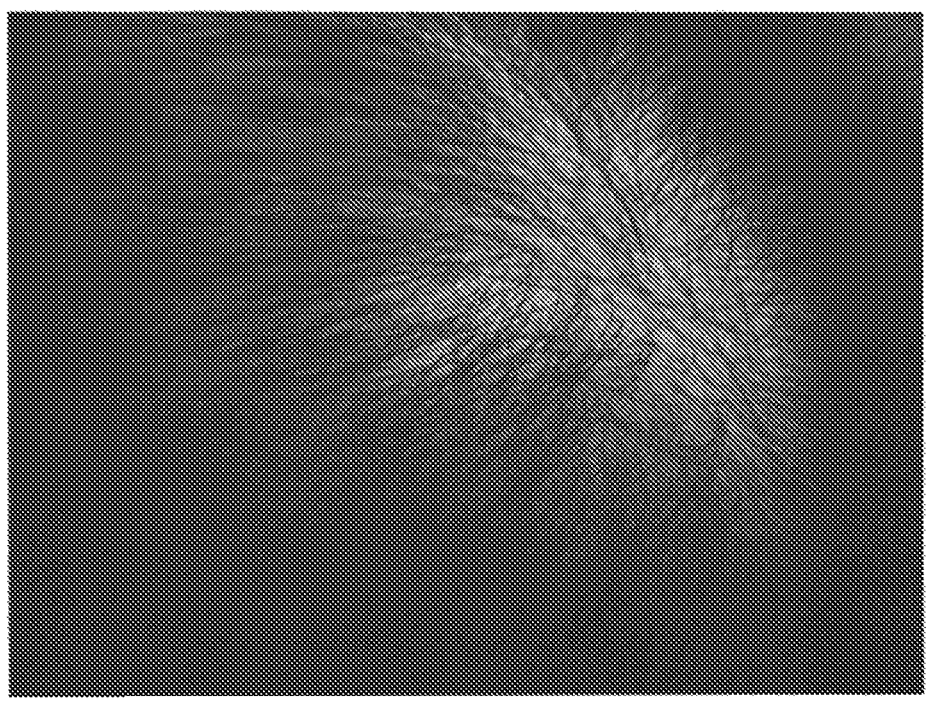

[Fig. 29]
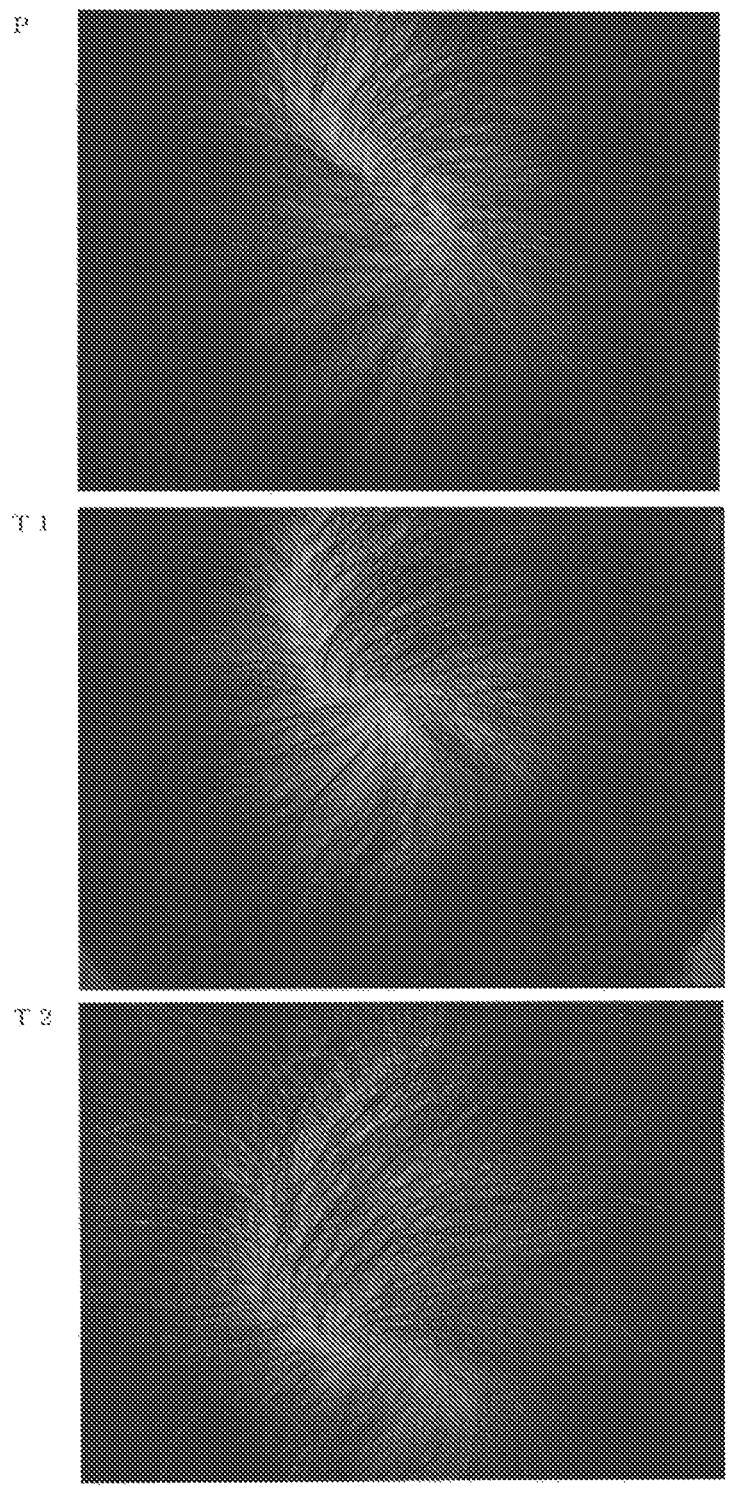

[Fig. 30-1]
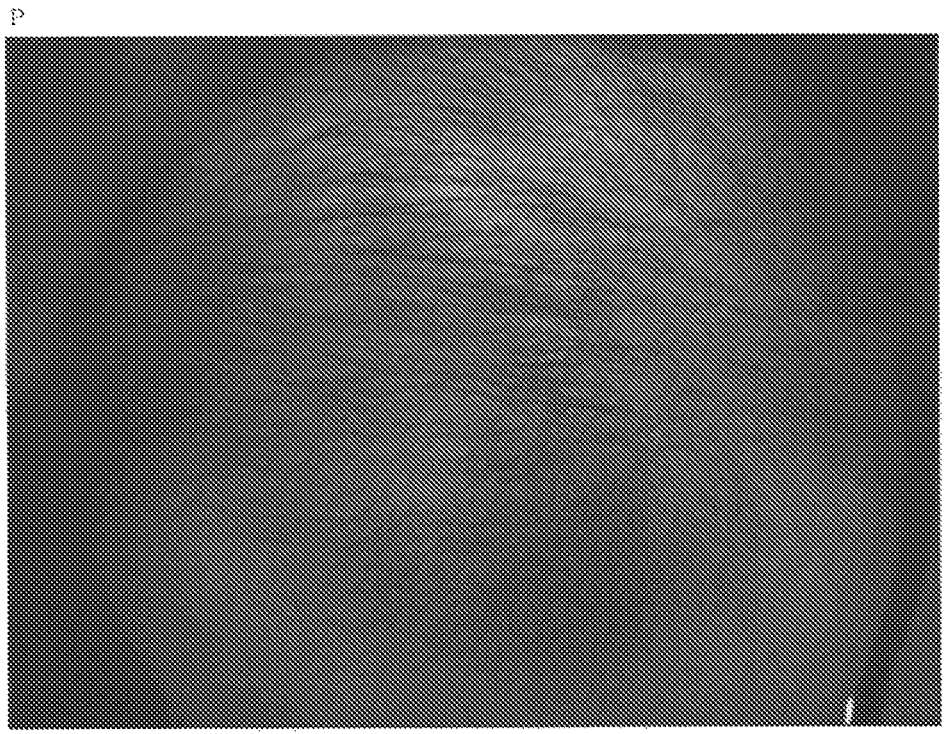

[Fig. 30-2]
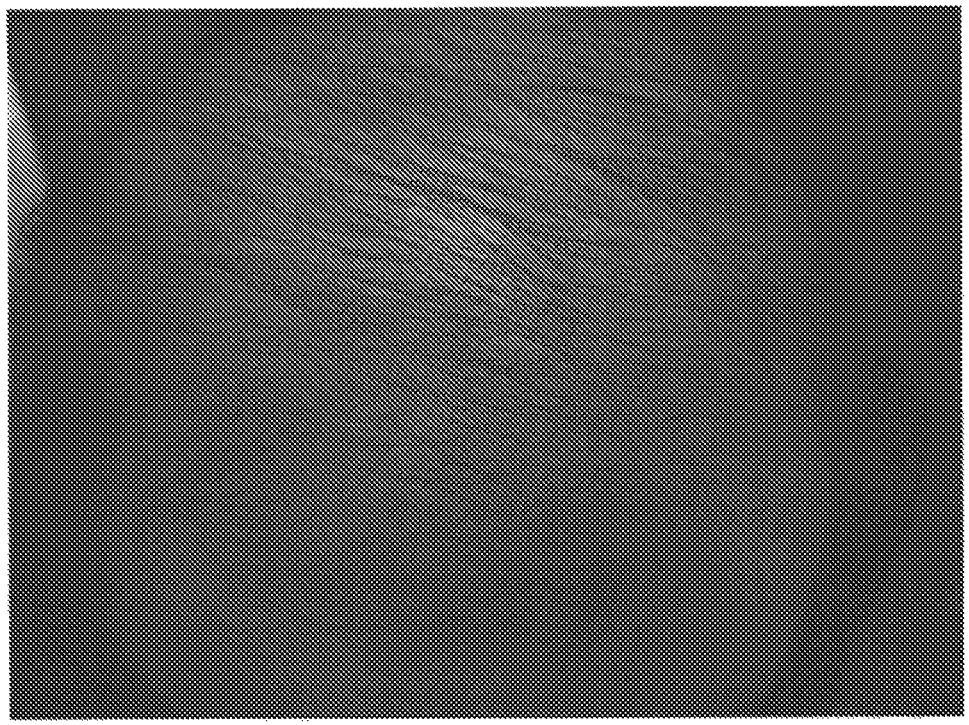

[Fig. 31]
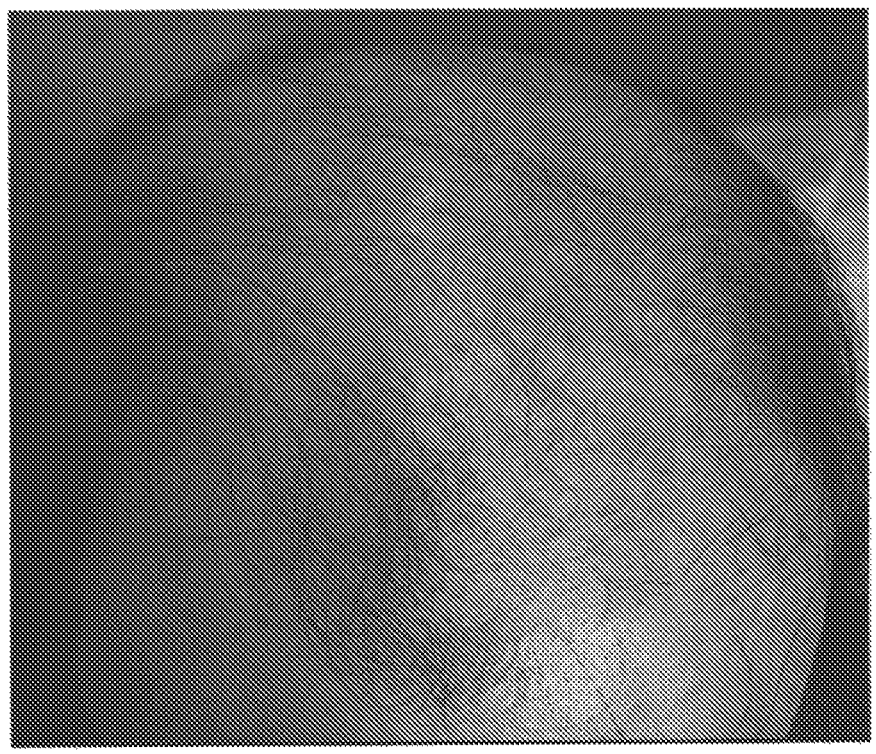

[Fig. 32]
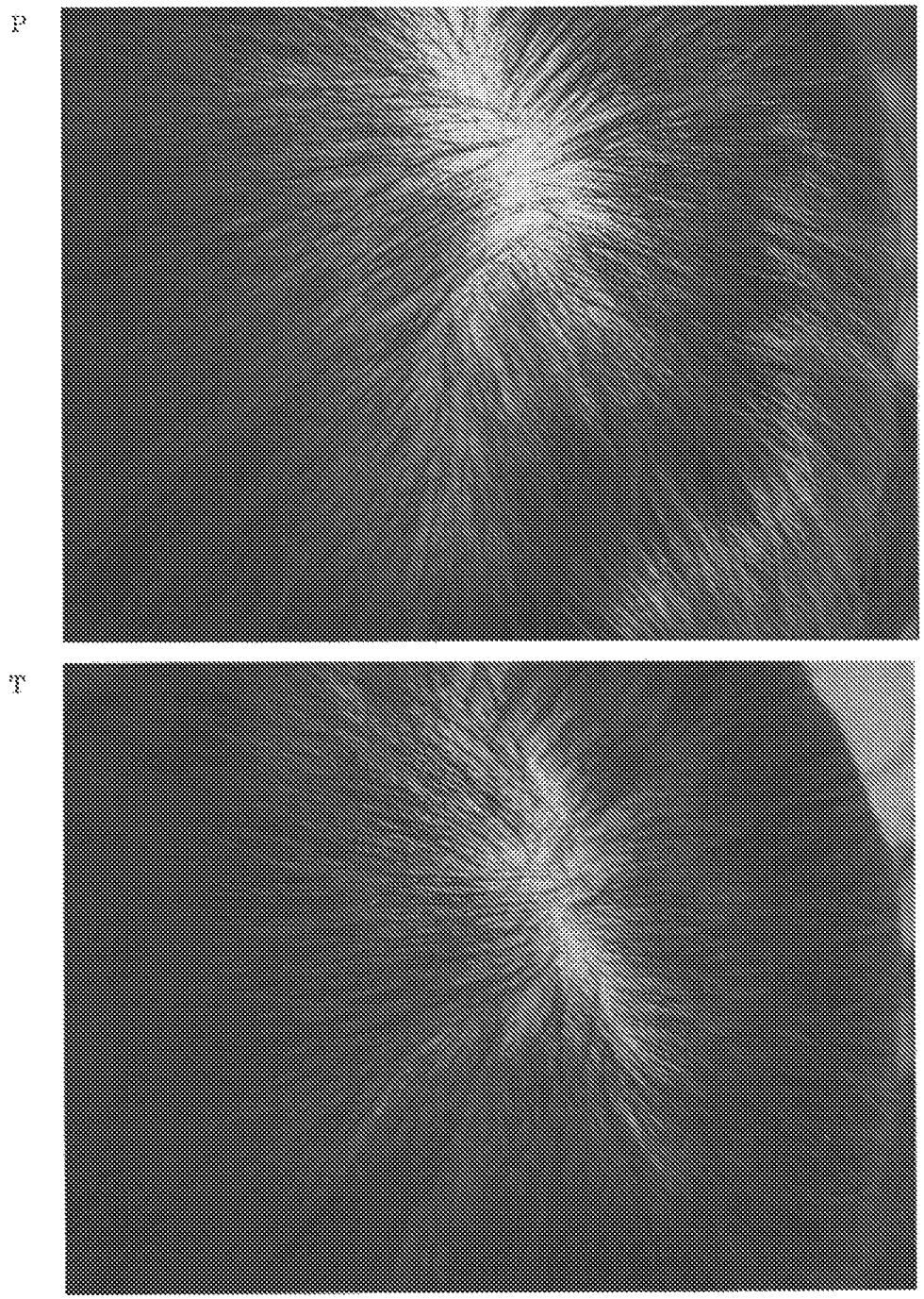

[Fig. 33]
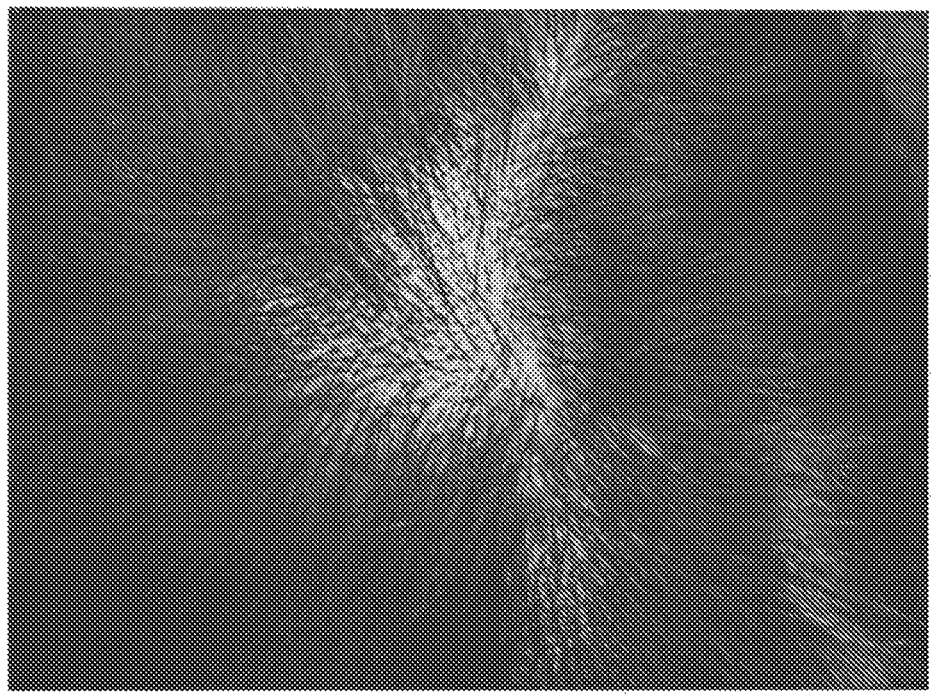
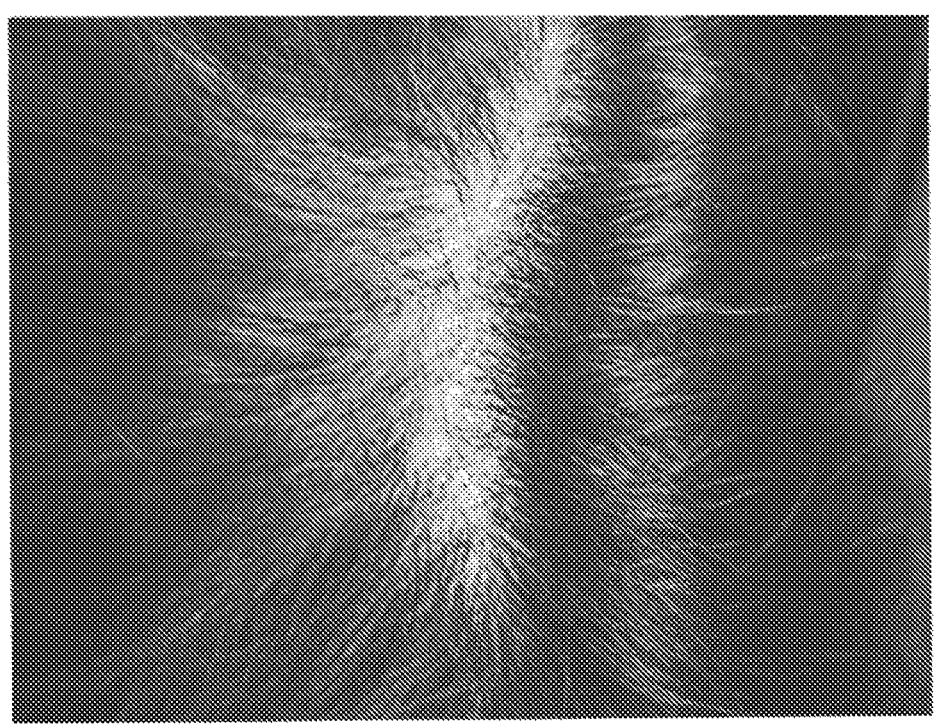

[Fig. 34]
P
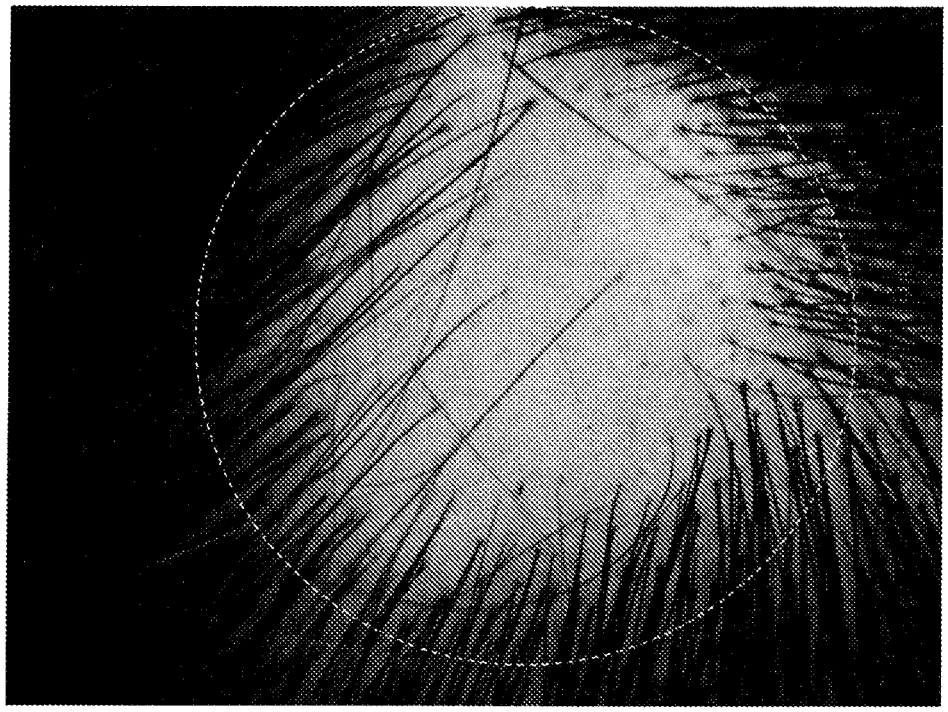
T
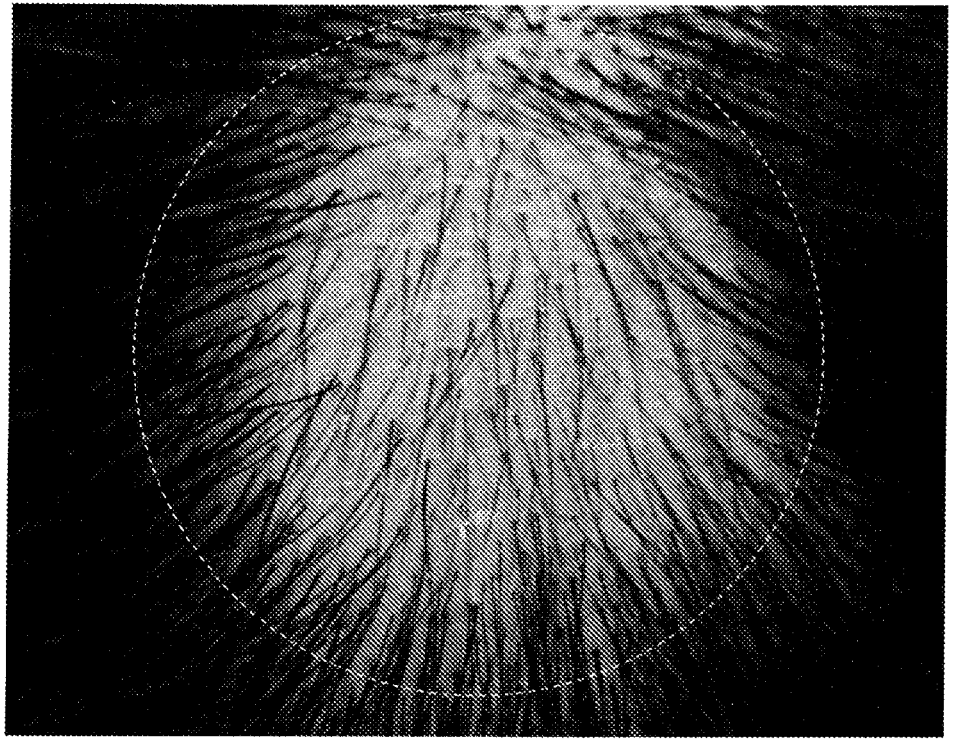

[Fig. 35]
P2
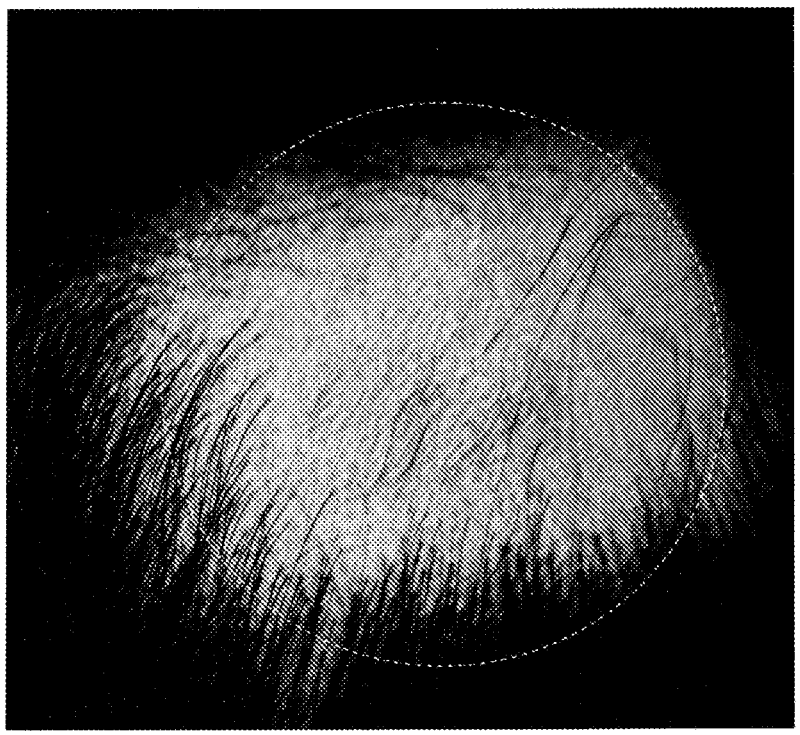
T2
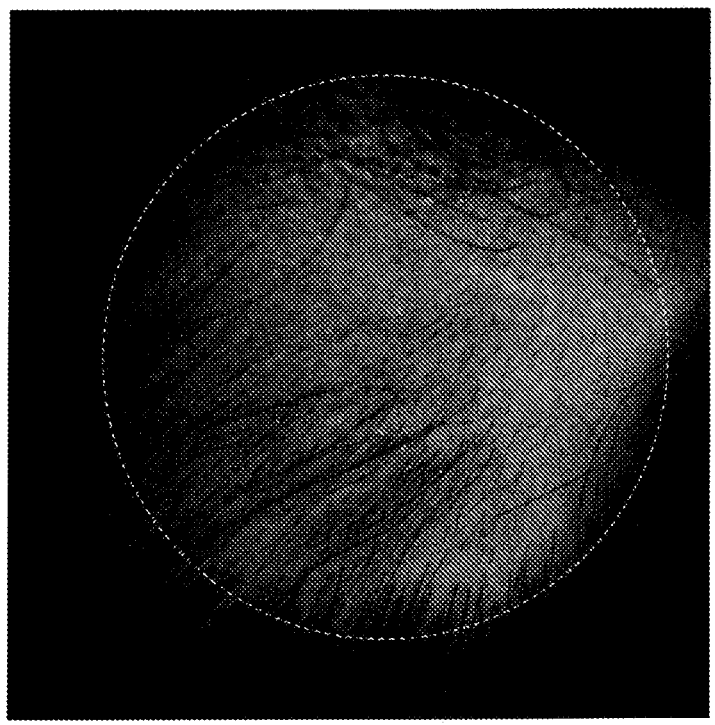

[Fig. 36]
P
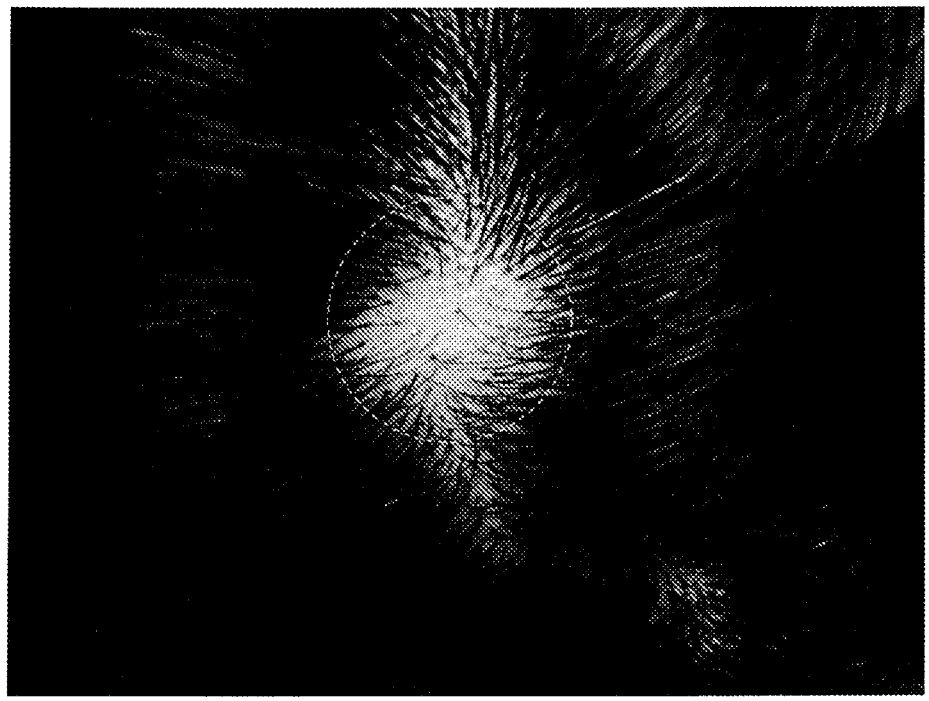
T
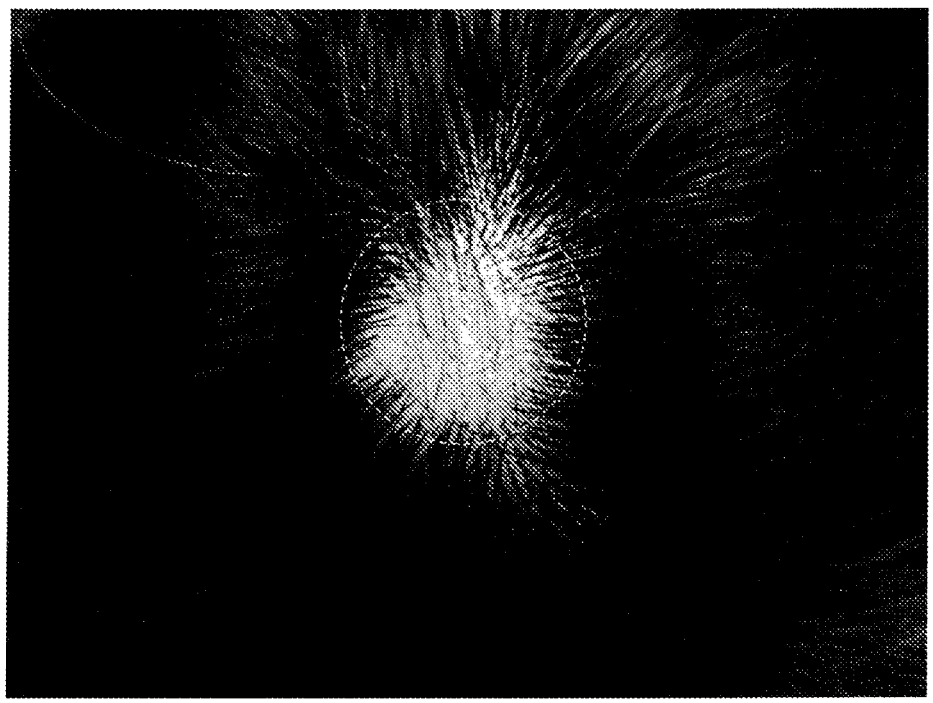

[Fig. 37]
P
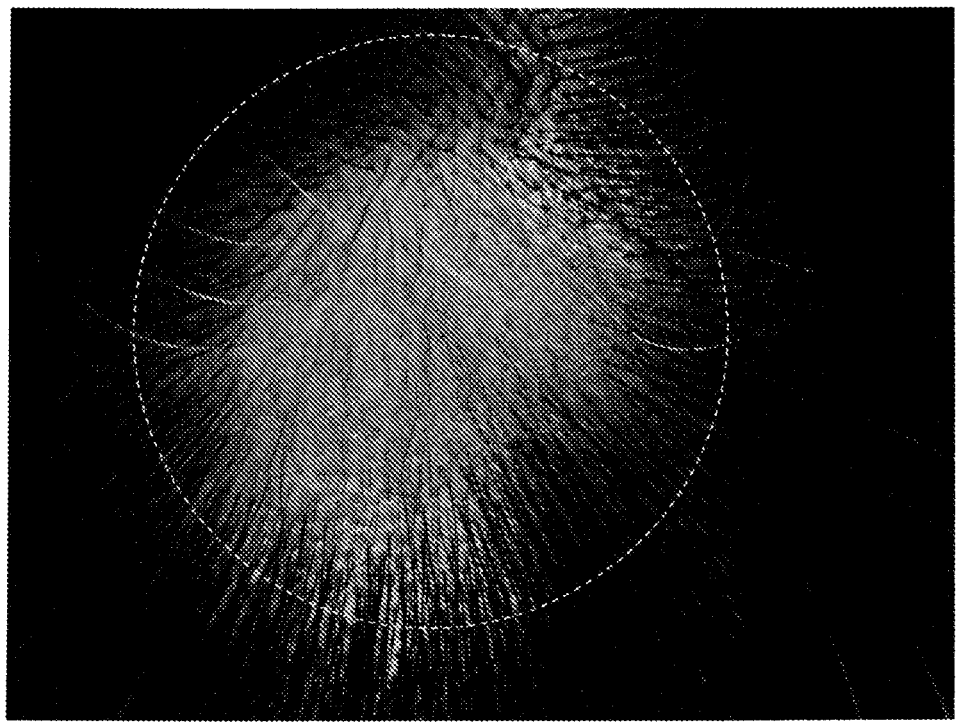
T
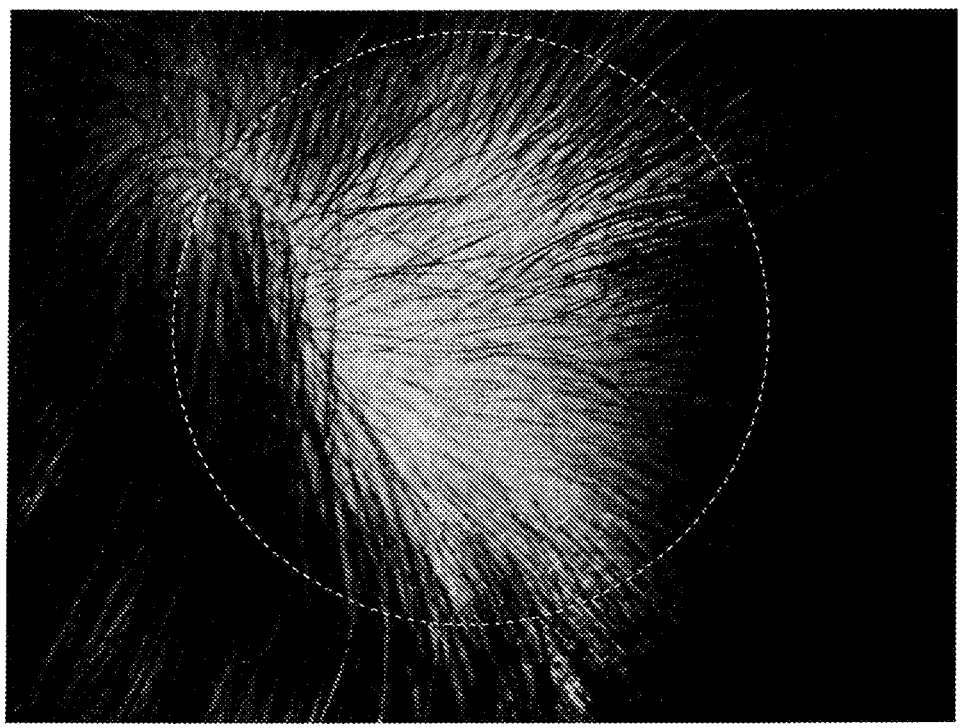

[Fig. 38]
P
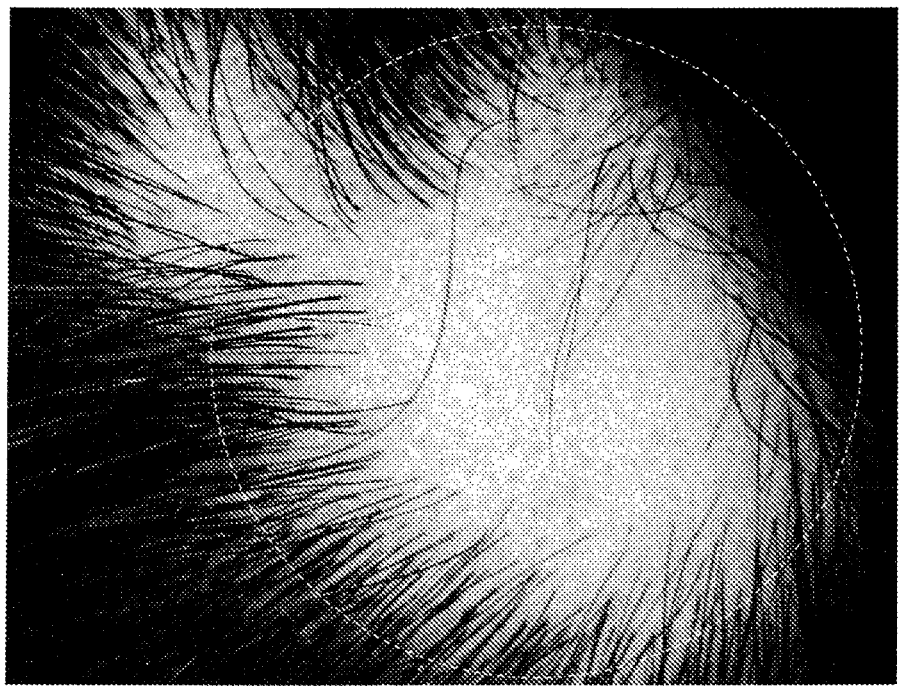
T
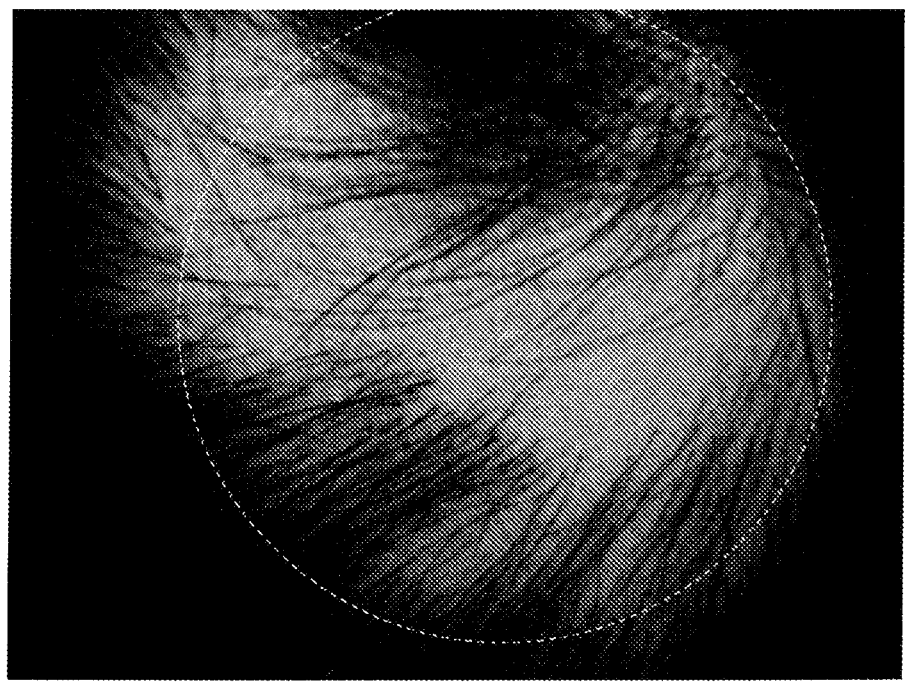

[Fig. 39]
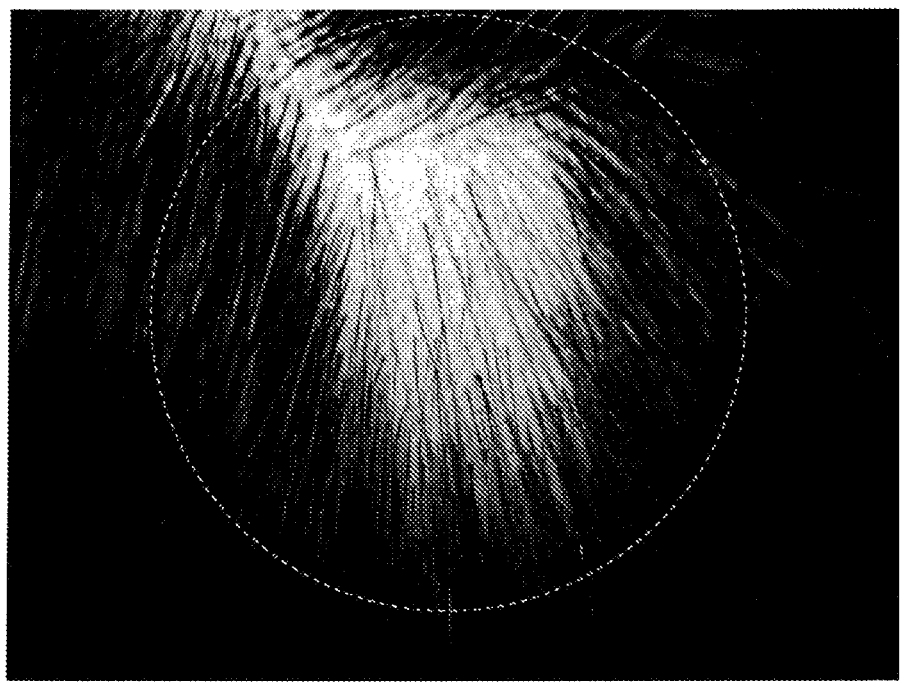
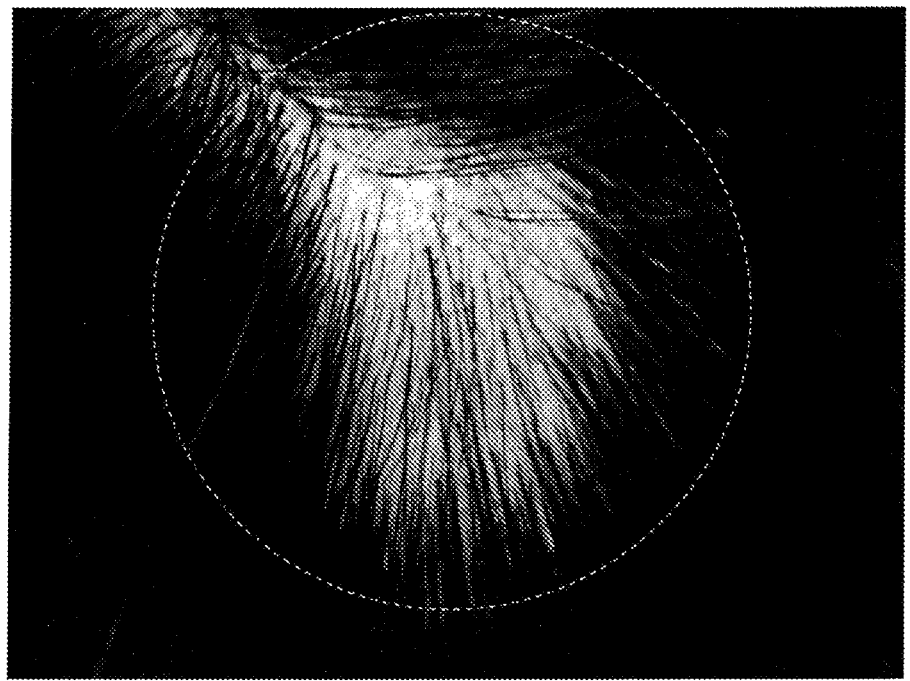

[Fig. 40]
P
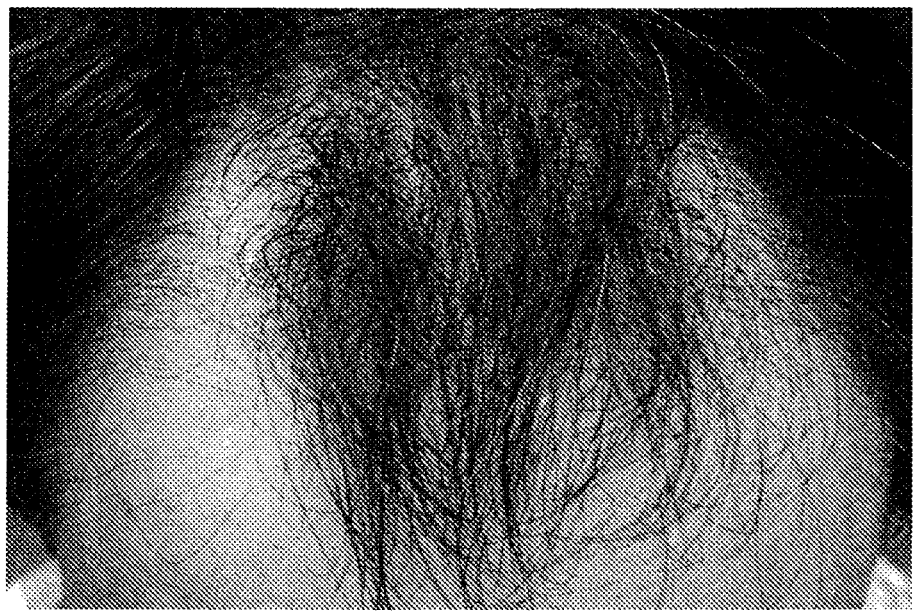
T

[Fig. 41]
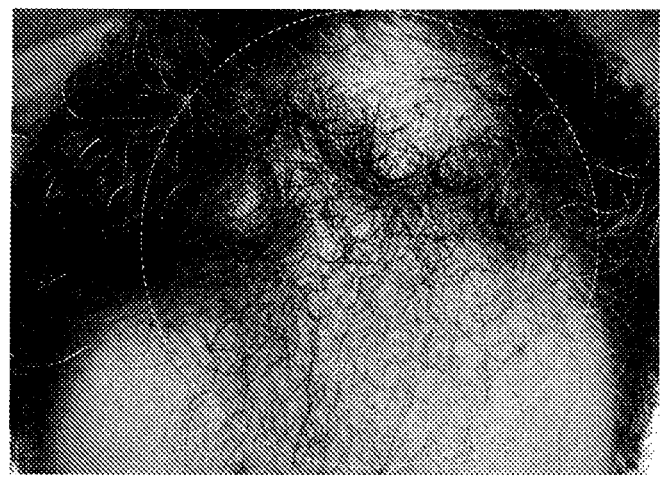
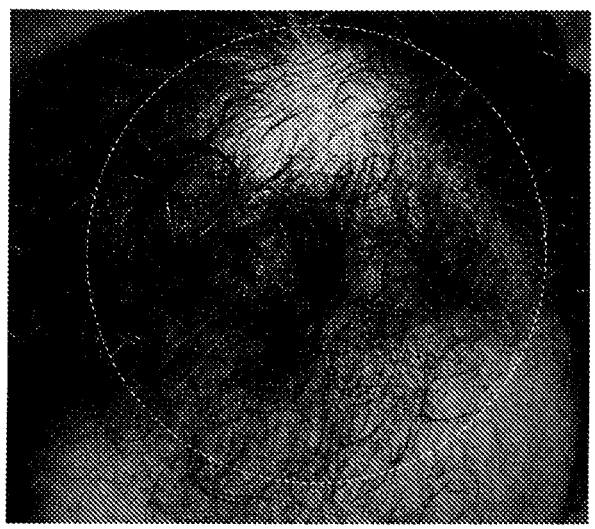
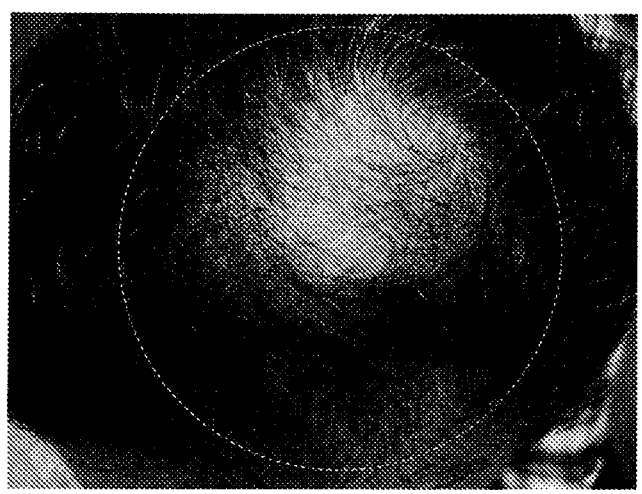

[Fig. 42]
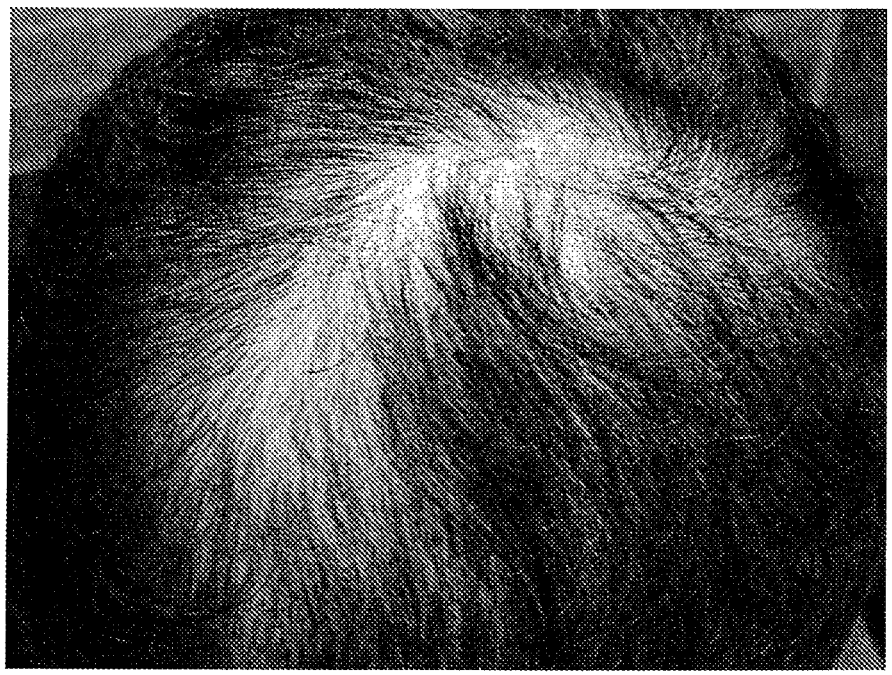
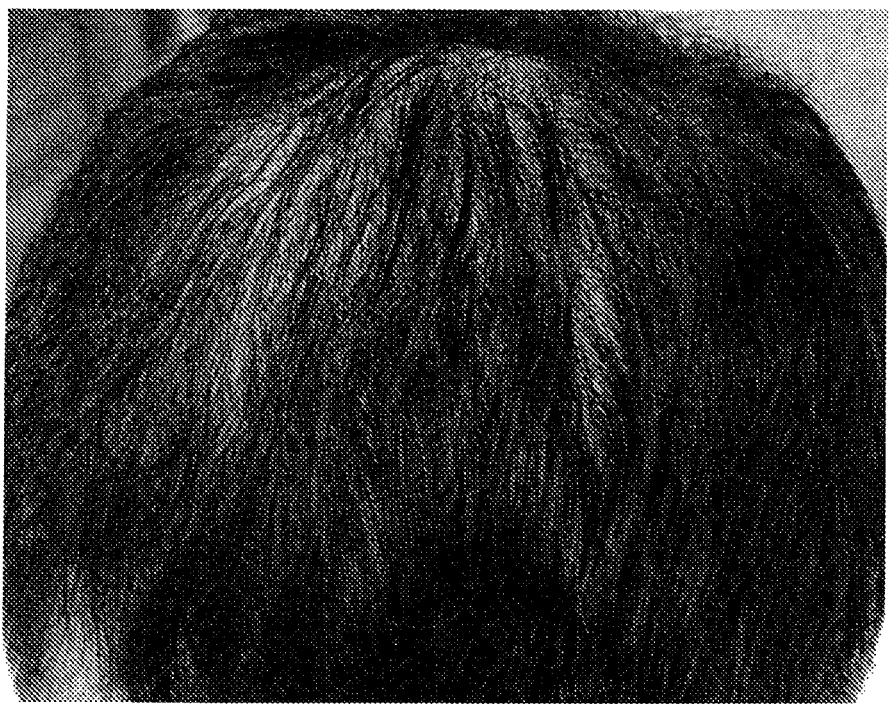

[Fig. 43]
P1
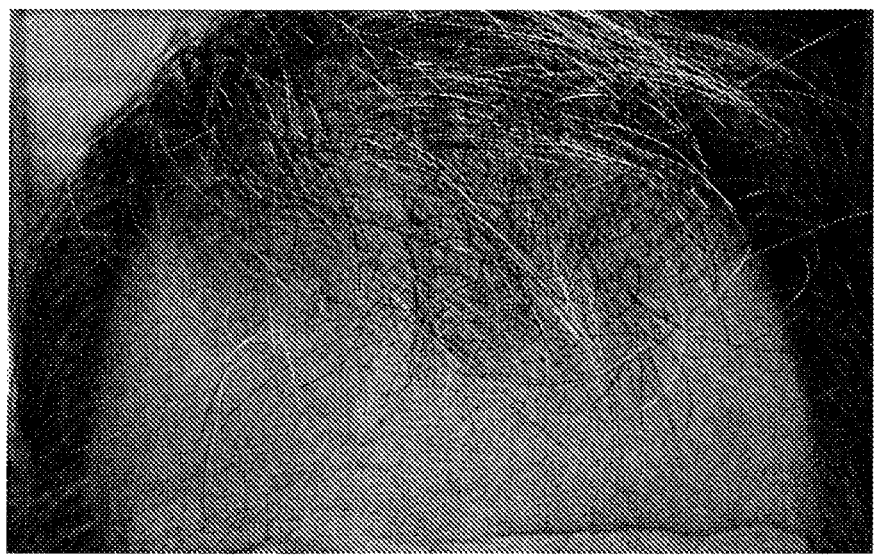
T1
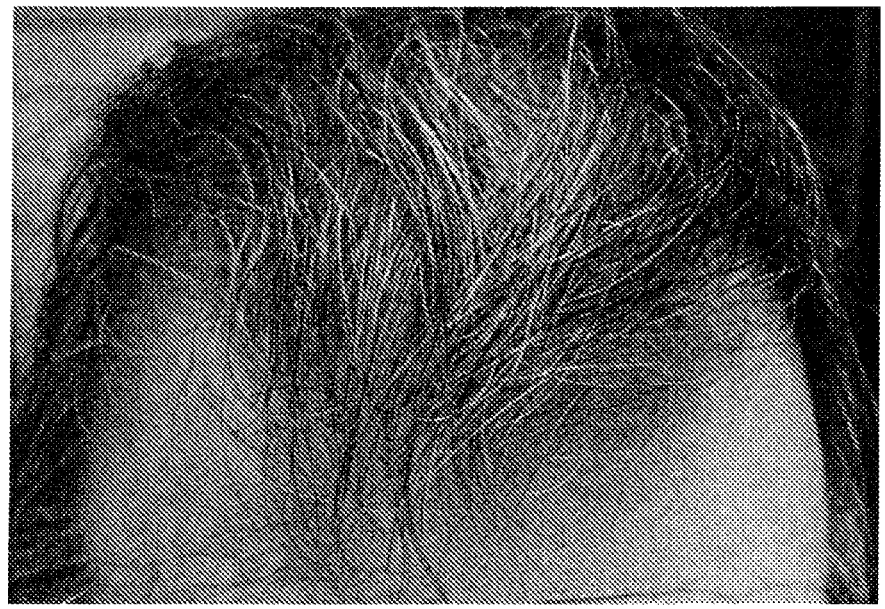

[Fig. 44]
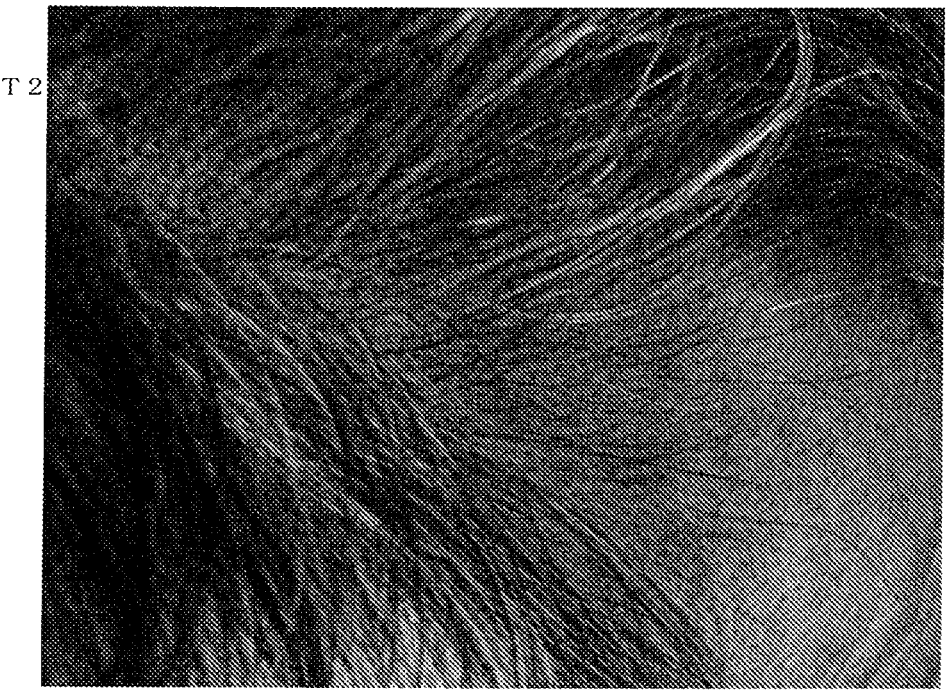

[Fig. 45]
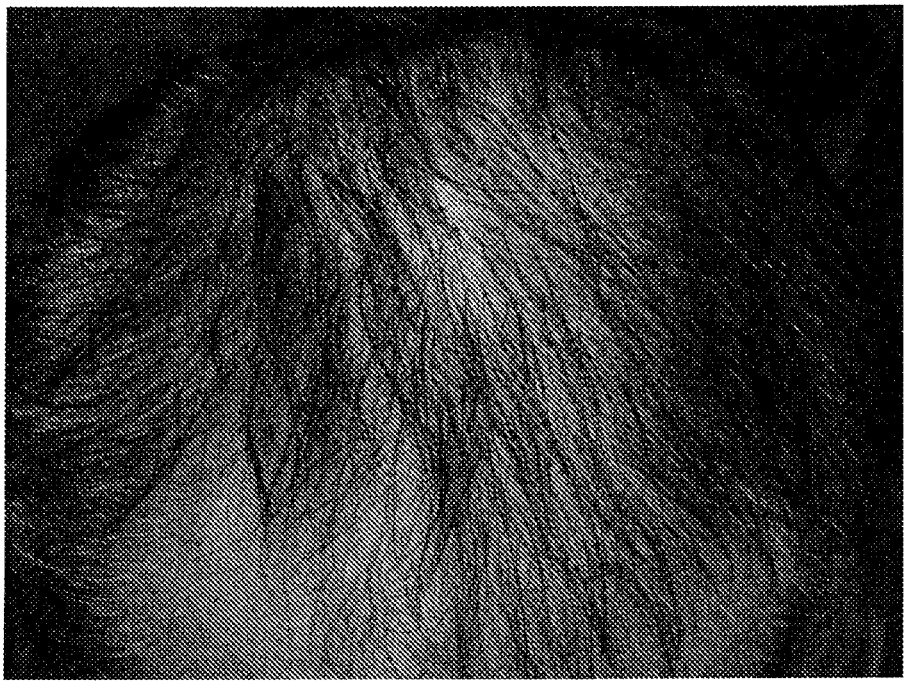

[Fig. 46]
P
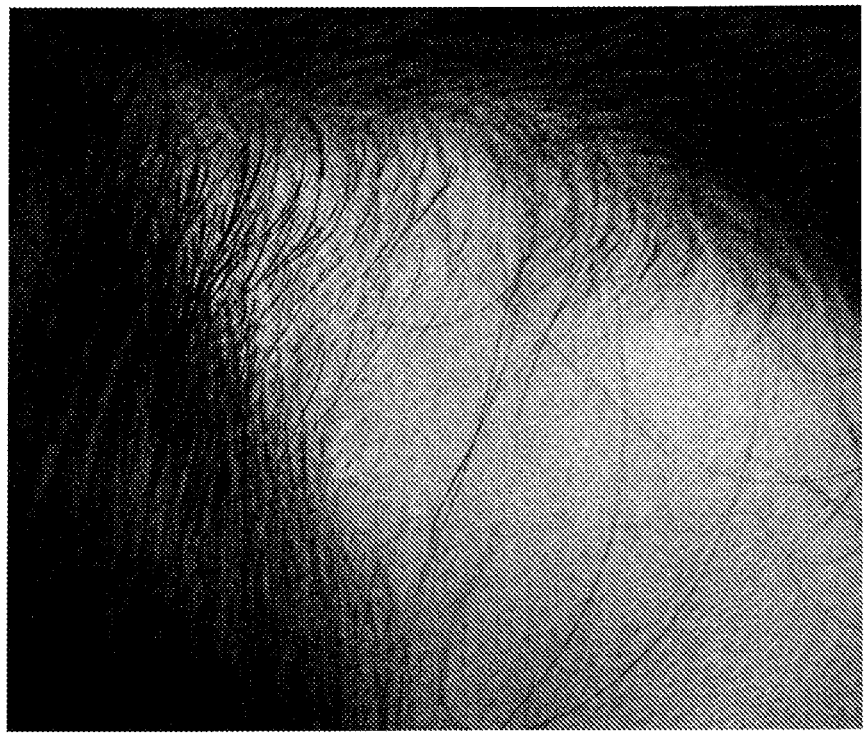
T
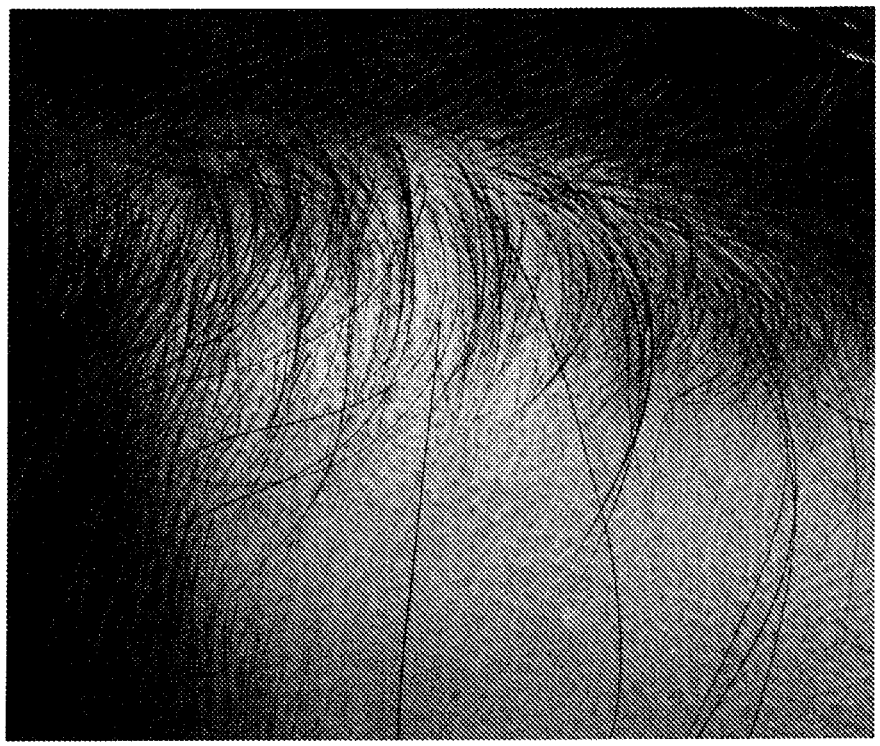

[Fig. 47]
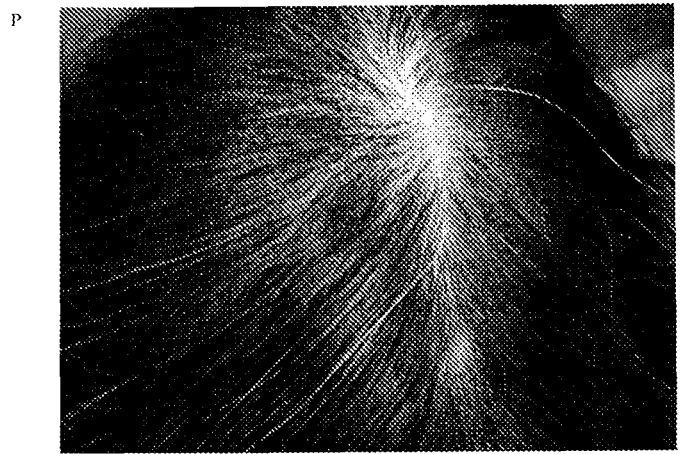
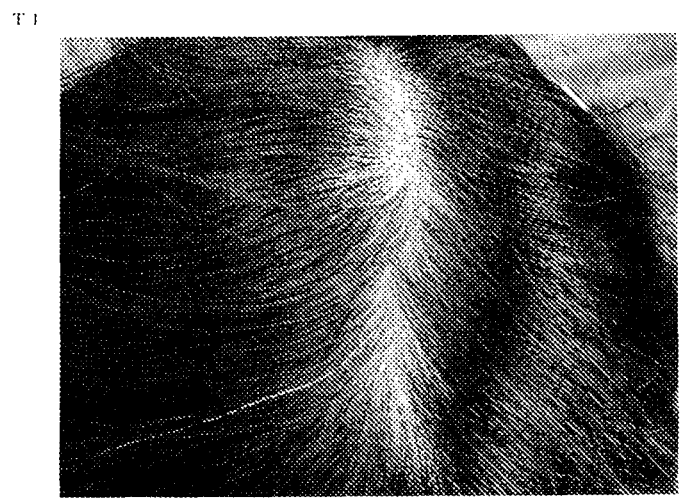
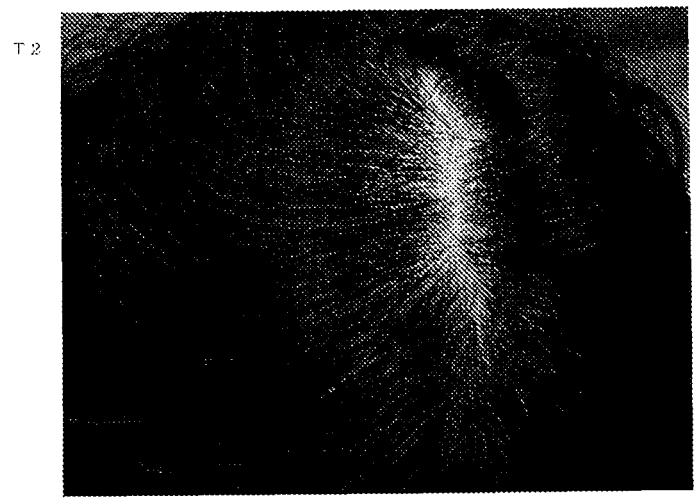

[Fig. 48]
P
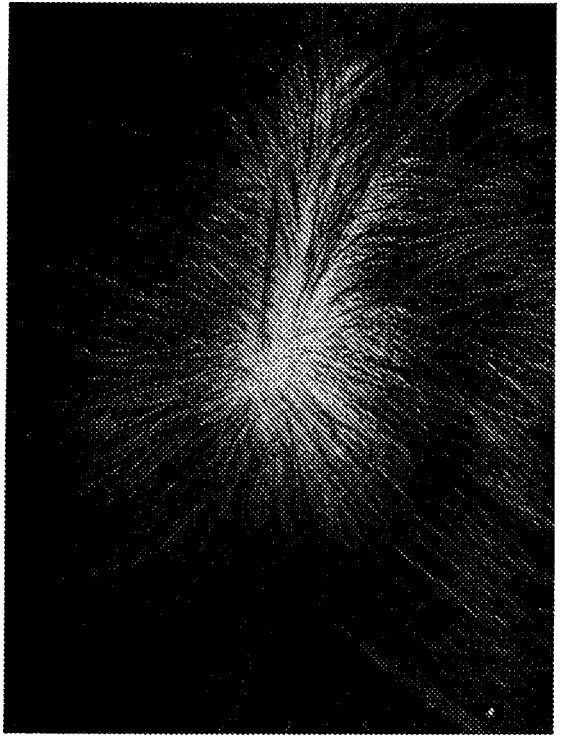
T
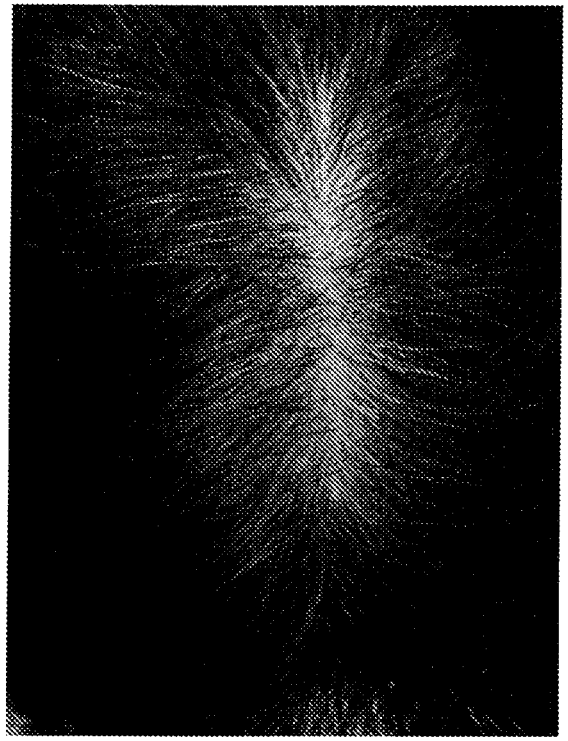

[Fig. 49]
P
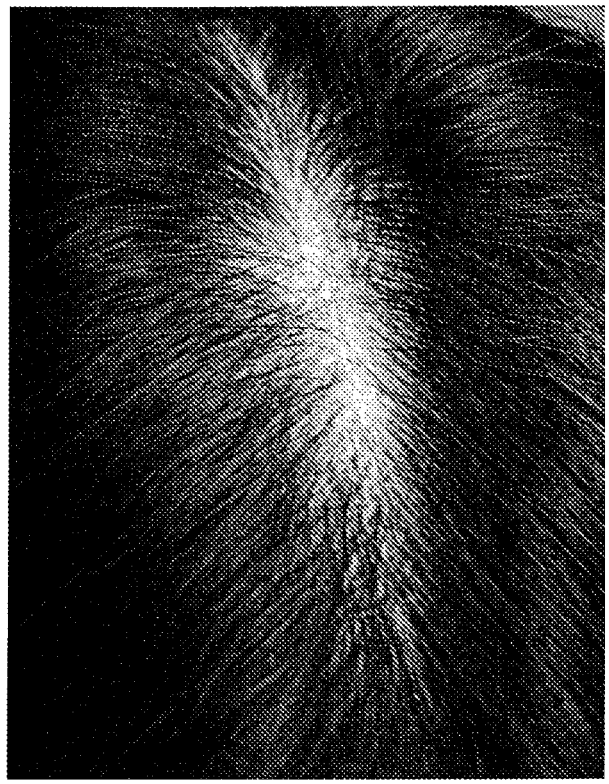
T
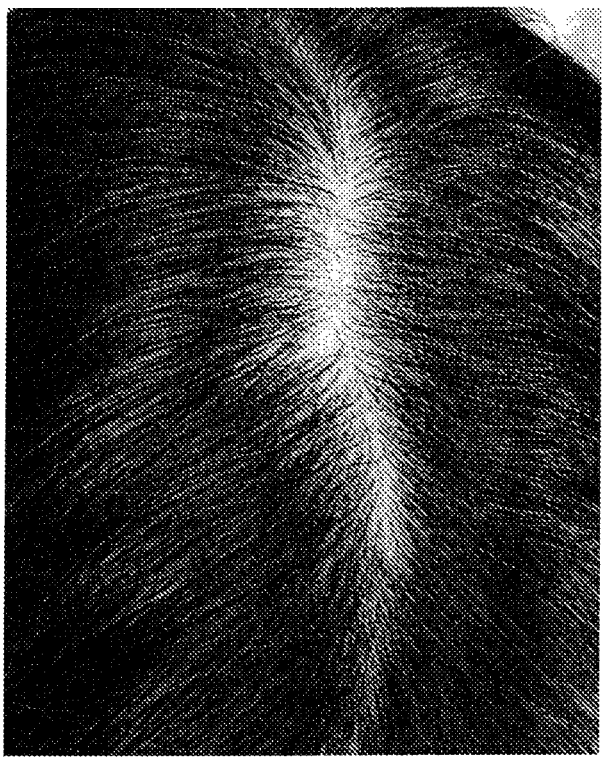

[Fig. 50]

[Fig. 51]
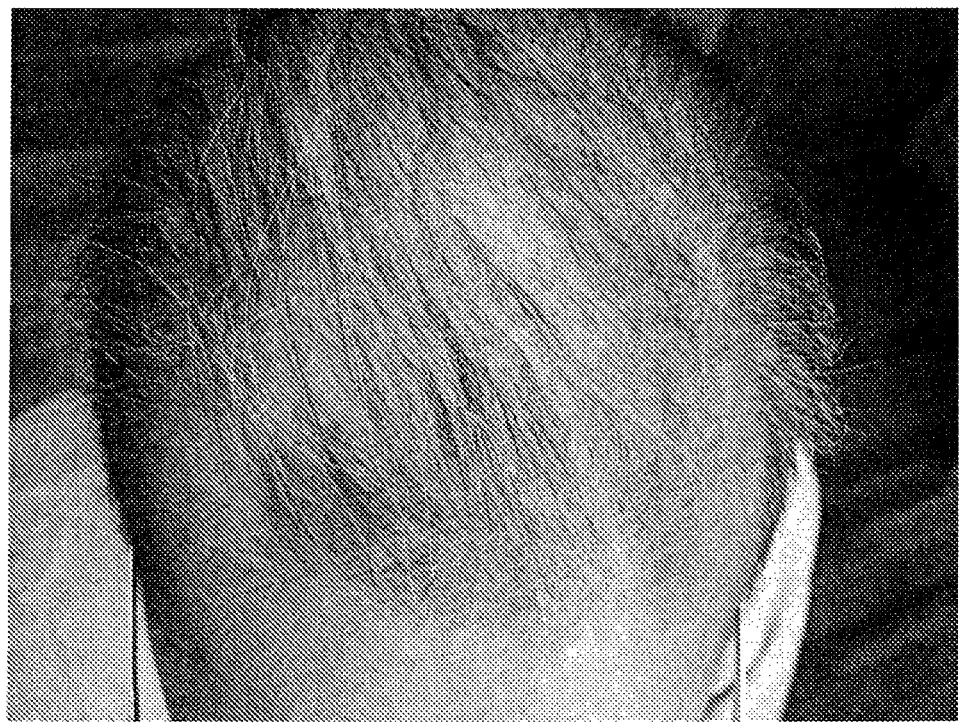
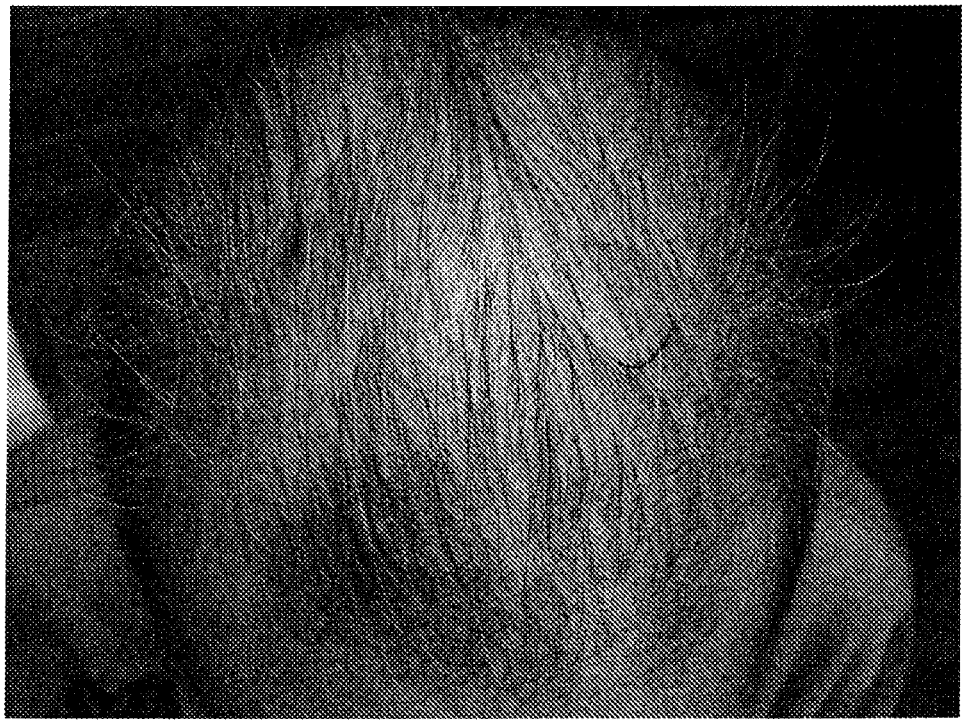

[Fig. 52]
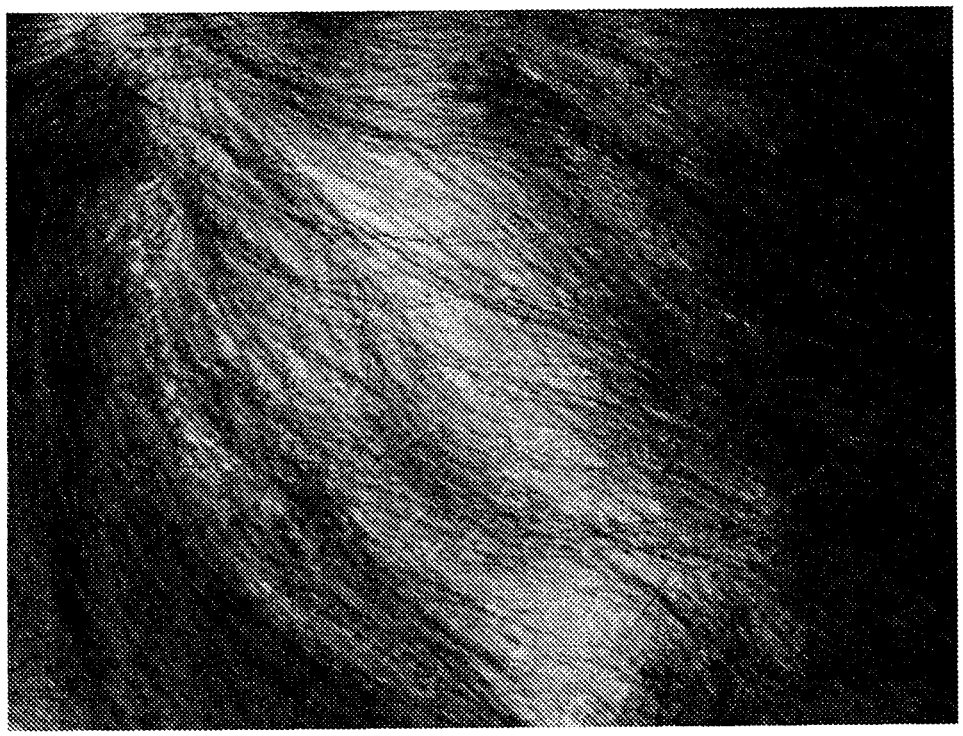
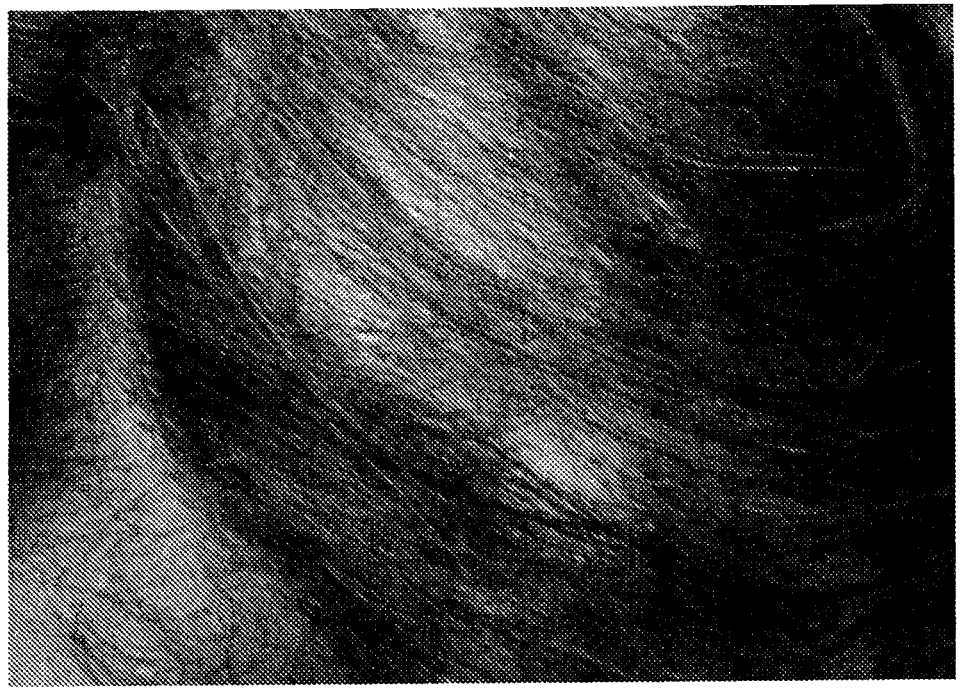

[Fig. 53]
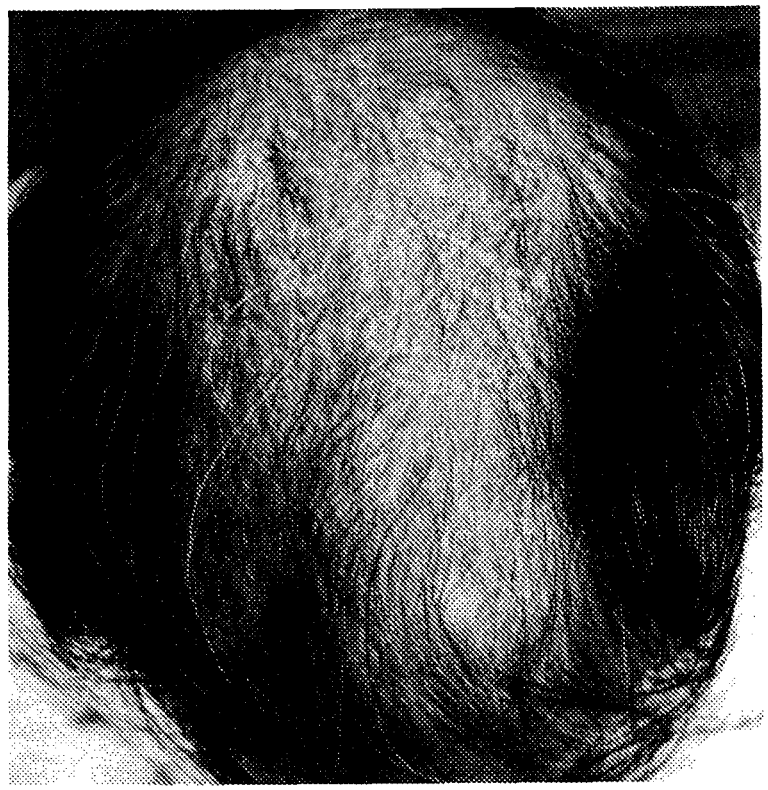
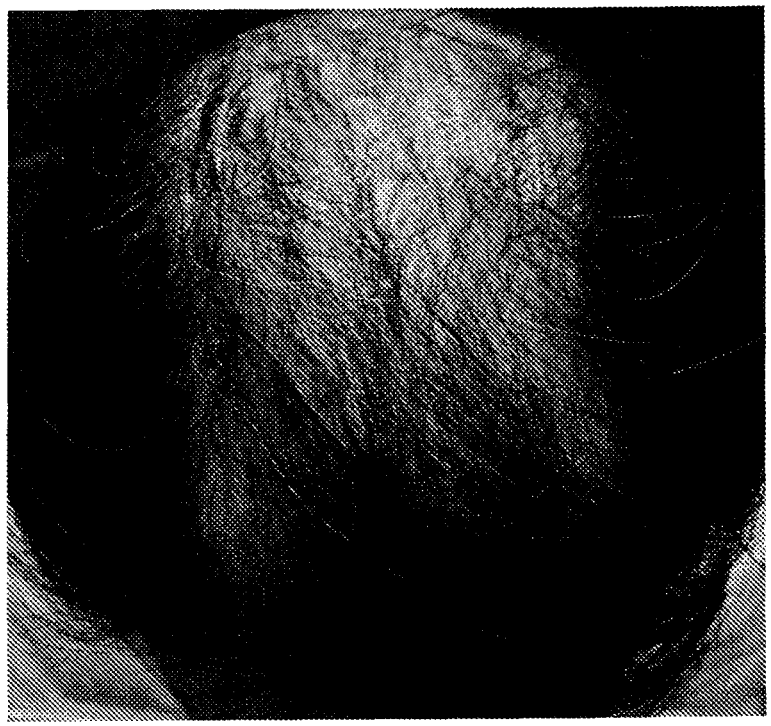

[Fig. 54]
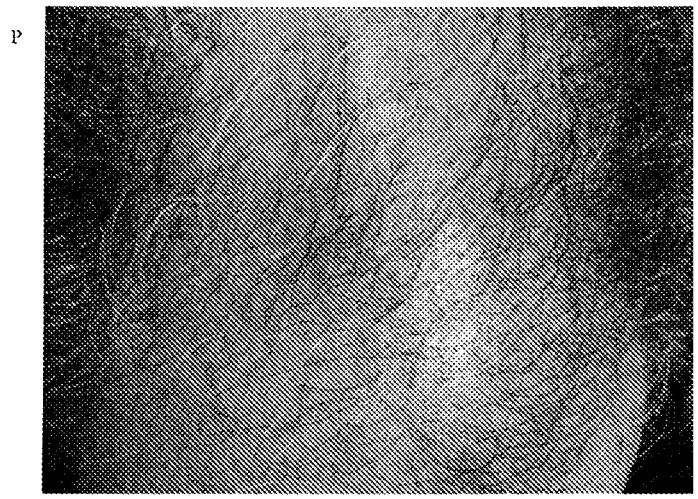
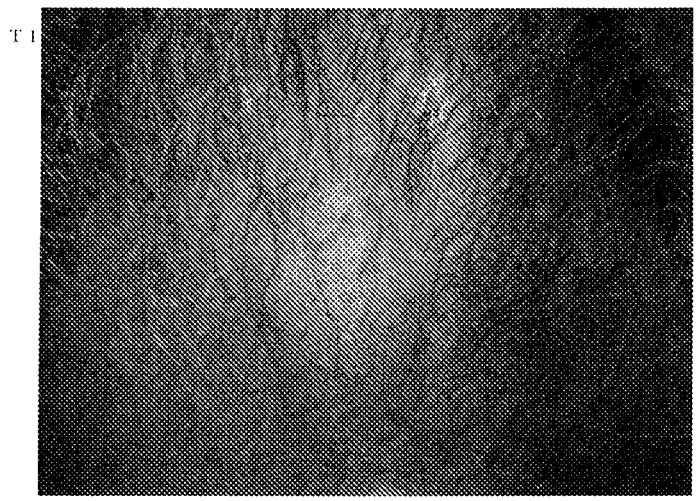
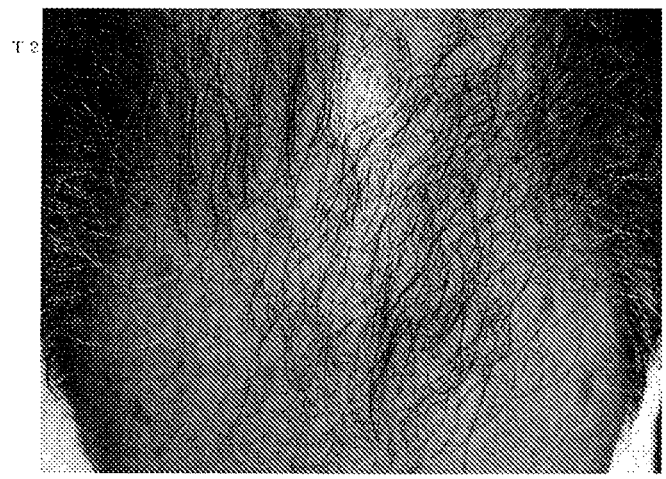

[Fig. 55]
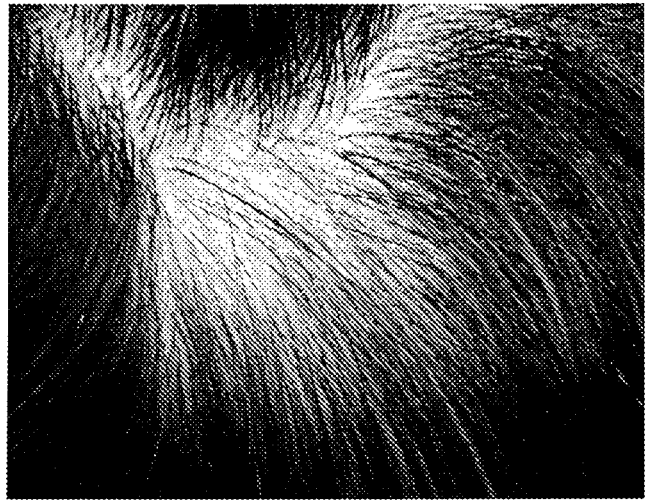

[Fig. 56-1]
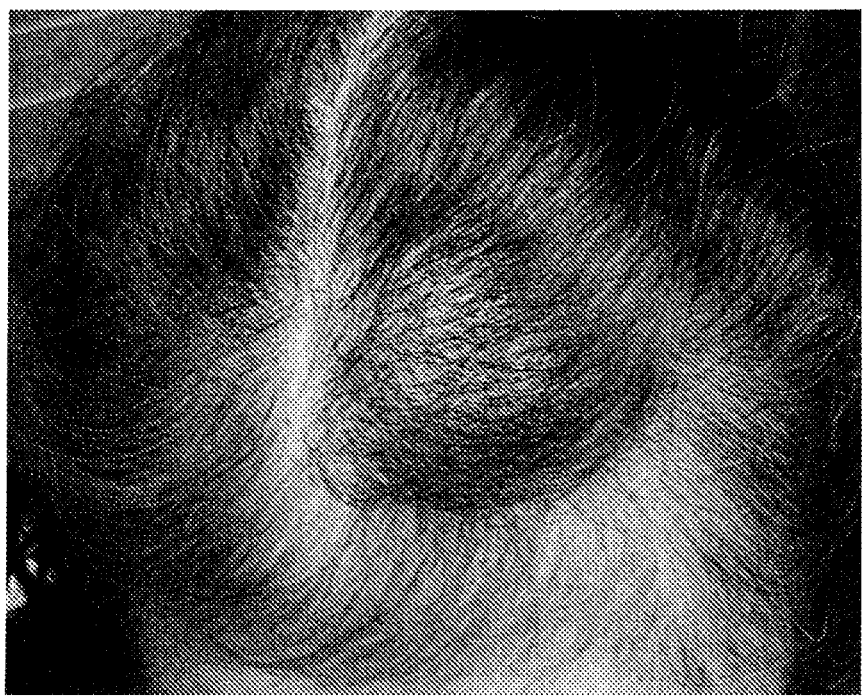
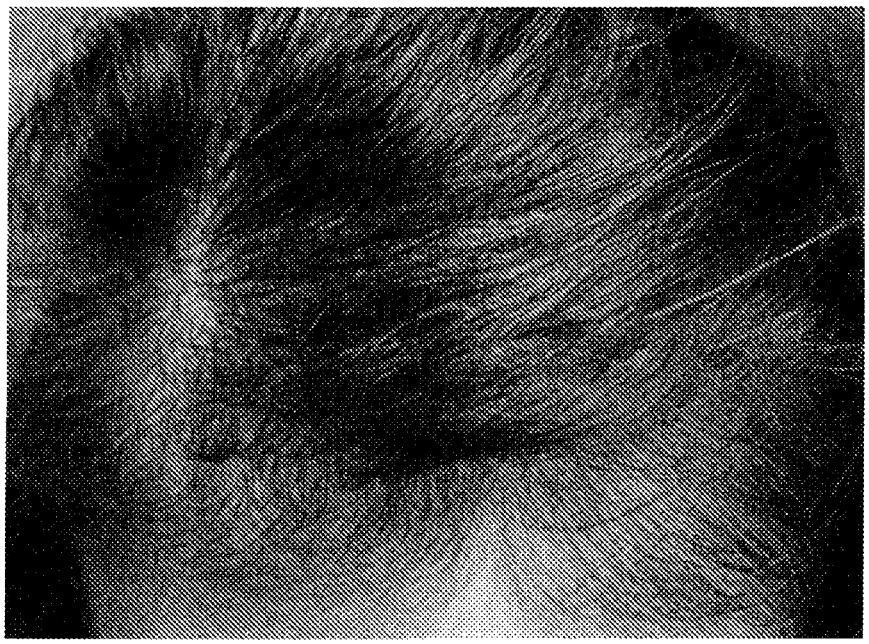

[Fig. 56-2]
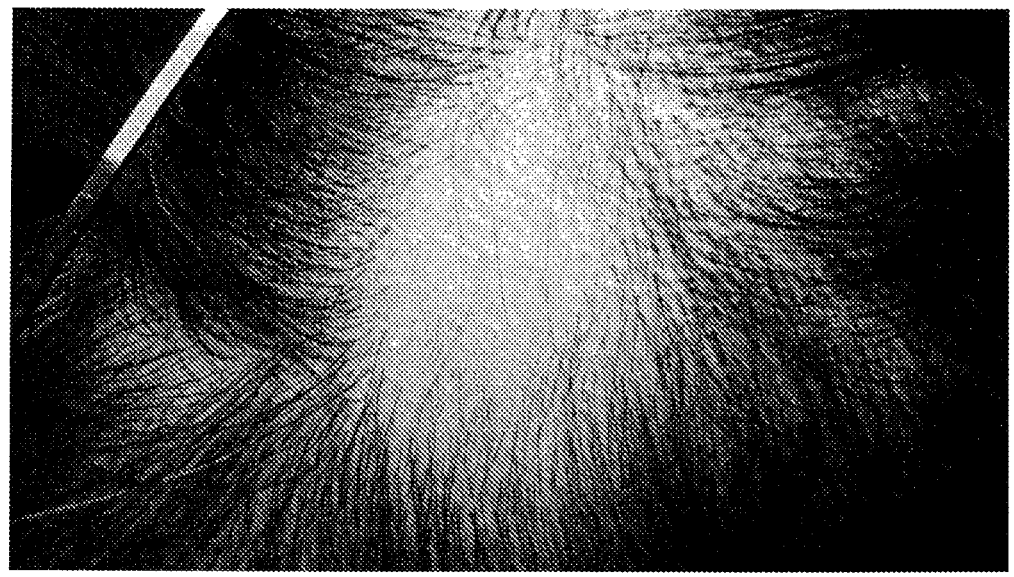
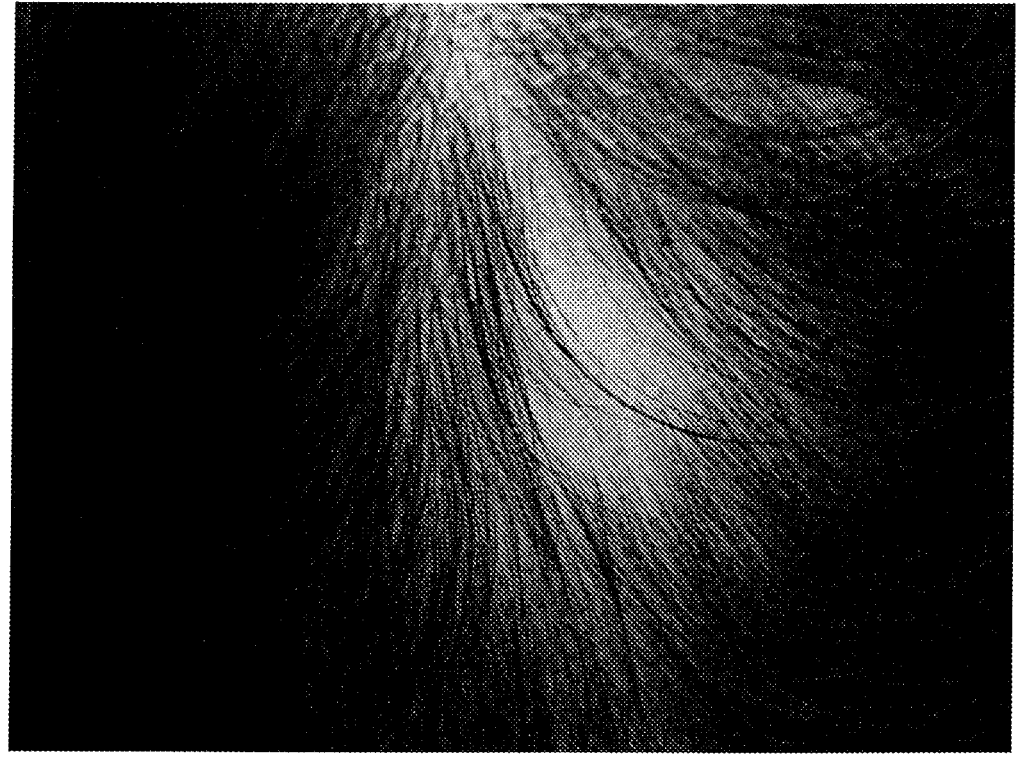

[Fig. 57]
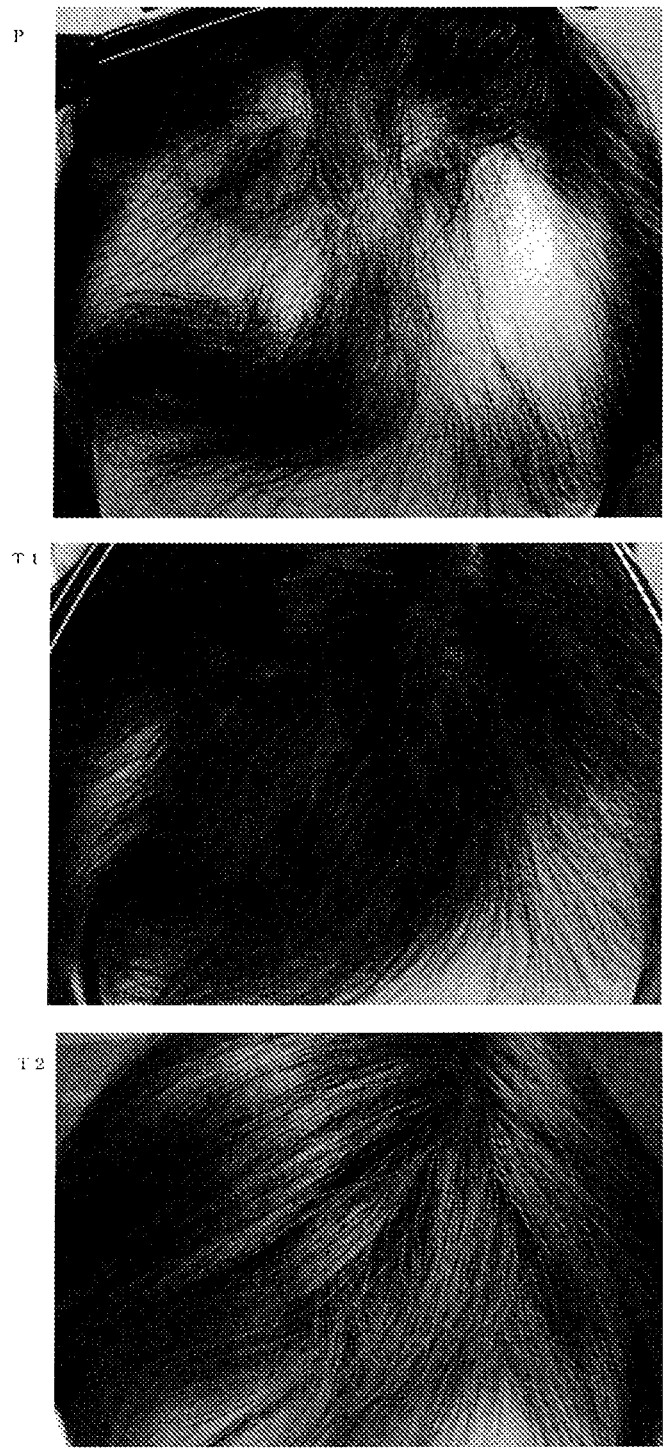

METHOD FOR TREATING ALOPECIA WITH B-TYPE NATRIURETIC PEPTIDE

RELATED APPLICATIONS

This application is a continuation of U.S. patent application Ser. No. 14/254,938, filed Apr. 17, 2014, now issued as U.S. Pat. No. 9,480,728, which is a continuation of U.S. patent application Ser. No. 13/355,484, filed Jan. 21, 2012, which claims the benefit under 35 U.S.C. §119(e) of U.S. provisional application Ser. No. 61/437,032, filed Jan. 28, 2011, the entire disclosures of which are incorporated herein by reference.

TECHNICAL FIELD

The present invention relates to an agent for the treatment and/or prevention of alopecia, dandruff, white hair, and seborrheic scalp, the agent containing as an active ingredient an A-type natriuretic peptide (ANP), a B-type natriuretic peptide (BNP), a C-type natriuretic peptide (CNP), a derivative of these natriuretic peptides (NPs), a chimeric peptide of 2 or more NPs selected from the above NPs, or a derivative of a chimeric peptide of the above NPs (hereinafter, they are collectively called 'natriuretic peptides (NPs)').

In particular, the present invention relates to an agent for the treatment and/or prevention of alopecia, dandruff, white hair, and seborrheic scalp, the agent containing as an active ingredient BNP, CNP, a derivative of BNP, a derivative of CNP, a chimeric peptide of CNP or BNP, or a derivative thereof.

The agent for the treatment and/or prevention is expressed simply as an agent for the treatment below.

BACKGROUND ART

1. Alopecia

Alopecia is a disease in which hair is lost. The loss of hair in alopecia is not limited just to head hair but can happen anywhere on the body. Although not usually life-threatening, since it is accompanied by serious emotional distress due to issues related to appearance, there is a desire for an excellent agent for the treatment and an excellent agent for the prevention of alopecia. Furthermore, since alopecia is often accompanied by fading of hair color, there is a desire for an agent for the prevention and an agent for the treatment of fading of hair color accompanying alopecia. Moreover, since alopecia is often accompanied by deterioration of hair quality such as hair becoming finer or hair becoming shorter, there is a desire for an agent for the prevention and an agent for the treatment of deterioration of hair quality accompanying alopecia.

With regard to types of alopecia, there are alopecia areata, androgenetic alopecia, postmenopausal alopecia, female pattern alopecia, seborrheic alopecia, alopecia pityroides, senile alopecia, cancer chemotherapy drug-induced alopecia, alopecia due to radiation exposure, trichotillomania, postpartum alopecia, etc.

These types of alopecia have the same symptoms of hair loss, but are based on different causes, and therapies therefor are different from each other. In particular, androgenetic alopecia, which is based on the action of male hormone, and alopecia areata, which is suspected to be an immune disease, are very different diseases. Furthermore, it is thought that postpartum alopecia, female pattern alopecia, seborrheic alopecia, alopecia pityroides, senile alopecia, cancer chemotherapy drug-induced alopecia, and alopecia due to radiation exposure have different causes from each other, and there are hardly any effective therapies.

Alopecia areata is alopecia in which coin-sized circular to patchy bald area(s) with a clear outline suddenly occur, without any subjective symptoms or prodromal symptoms, etc. in many cases, and subsequently when spontaneous recovery does not occur they gradually increase in area and become intractable. Alopecia areata is suspected to be an autoimmune disease, but the cause thereof has not yet been discovered, and there is no known definite treatment method.

Alopecia areata is known to be associated with an autoimmune disease such as a thyroid disease represented by Hashimoto's disease, vitiligo, systemic lupus erythematosus, rheumatoid arthritis, or myasthenia gravis or an atopic disease such as bronchial asthma, atopic dermatitis, or allergic rhinitis.

Androgenetic alopecia (AGA) is alopecia in which male hormone acts on male hormone-sensitive hair follicles to form vellus hair, and occurs in about half of males and 10% to 20% of females. It is thought that genetic predisposition is a large factor in androgenetic alopecia; in androgenetic alopecia in males, the head hair on the frontal region and crown becomes fine and short and turns into vellus hair, the hair line on the forehead finally retreats, and head hair on the crown is lost. On the other hand, in androgenetic alopecia in females, in general the hairline does not change but hair of the entire head, in particular the crown and the frontal region, becomes fine. Finasteride improves only about ¼ of patients for androgenetic alopecia in males, and since administration of finasteride to females is contraindicated, finasteride cannot be used for androgenetic alopecia in females.

Postpartum alopecia is alopecia in which hair whose growth phase has been maintained by estrogen enters the resting phase all at once due to childbirth, and hair loss increases. The hair loss of postpartum alopecia usually starts approximately 2 months after childbirth and continues until about 6 months after childbirth; since it usually recovers within 1 year unless there is late childbearing, in most cases a treatment is not particularly required, but there are cases in which hair does not recover spontaneously.

Female pattern alopecia is alopecia that is thought to occur due to a decrease in the amount of the female hormone estrogen relative to the amount of androgen in the bloodstream. It often occurs after the menopause, and in this case it is also called postmenopausal alopecia. Female pattern alopecia might be improved by hormone replacement therapy but is intractable in many cases.

Seborrheic alopecia is alopecia that is caused by excessive sebum secretion on the scalp, pores are blocked thereby causing inflammation around the pores or in the hair root, and the hair falls out. Seborrheic alopecia is improved to some extent by removing sebum by washing the hair, but it easily reoccurs and exhibits intractability.

Alopecia pityroides is alopecia that is caused by dandruff blocking pores to thus cause inflammation. Alopecia pityroides is often caused by excessive hair washing; remission is achieved by reducing the number of times of hair washing or using a shampoo having a weak washing power, but it easily reoccurs and is intractable.

Trichotillomania is alopecia due to a hair-pulling disorder. Trichotillomania is a symptom resulting from pathological anxiety and can be treated by behavioral therapy or psychological therapy.

Senile alopecia is alopecia in which, due to aging regardless of gender, body hair of the entire body, including all of the head hair, gradually becomes thinner. It is thought that this is a natural phenomenon that appears in many people due to aging, and this is not particularly a target for treatment at the present. However, there is a desire for improvement since there is an increased social requirement for improving the quality of life of elderly people accompanying a rise in the average lifespan.

Cancer chemotherapy drug-induced alopecia is alopecia that is a side effect of anticancer treatment with a cancer chemotherapy drug. The shock to the patient caused by loss of hair in all areas including not only the head but also the eyebrows, eyelashes, nasal hair, underarm hair, and pubic hair is profound even if it is explained in advance. Since this also hinders the carrying out of cancer chemotherapy, there is a high need for a treatment for this. Similarly, alopecia accompanying radiation exposure is also alopecia that occurs based on the same mechanism as that for cancer chemotherapy drug-induced alopecia in terms of cancer cells being selectively killed by inhibiting cell division. Therefore, a drug that can treat alopecia accompanying cancer chemotherapy can also treat alopecia accompanying radiation exposure.

In addition, alopecia due to an adverse reaction to a drug such as an antithyroid drug, an anticoagulant, thallium, a psychotropic drug, or a β-blocker, alopecia due to a fungus, alopecia due to an endocrine disorder such as dyspituitarism, hypothyroidism, or hyperthyroidism, alopecia due to a metabolic disorder such as a nutritional disorder, hypoalbuminemia, cachexia, iron-deficiency anemia, zinc deficiency, homocystinuria, or cirrhosis of the liver, toxic alopecia, alopecia due to high temperature, childbirth, major surgery, sudden body weight loss, or serious illness, etc. are known, and they can be tackled by removing the respective causes thereof.

Among these types of alopecia, female pattern alopecia, seborrheic alopecia, and alopecia pityroides can be tackled to some extent by removing the respective causes thereof, but they easily reoccur, and are intractable. Furthermore, although it is thought that the cause of female pattern alopecia is related to hormone balance, hormone replacement therapy is indicated for menopausal disorders, osteoporosis, and hyperlipidemia but is not indicated for female pattern alopecia; since there is a possibility of cancer being caused by hormone replacement therapy, hormone replacement therapy is not carried out for the purpose of treating female pattern alopecia. Furthermore, with regard to androgenetic alopecia, there is no adequate therapy yet, and with regard to alopecia areata, even the cause thereof is little understood.

As described above, among the types of alopecia, the types of alopecia that are difficult to treat are alopecia areata and androgenetic alopecia, and for alopecia areata in particular there are hardly any effective treatment methods. Moreover, there are hardly any therapies for postpartum alopecia, female pattern alopecia, alopecia pityroides, senile alopecia, and cancer chemotherapy drug-induced alopecia.

2. Androgenetic Alopecia and Methods for its Treatment

The frequency of occurrence of androgenetic alopecia increases with age, and in the case of Japanese people, about 10% of people develop it in their twenties, 20% in their thirties, 30% in their forties, and about 40% in their fifties onward (Non-Patent Document 1). In male hormone-sensitive hair follicles such as in the frontal region, the crown, etc., in contrast to hair in other areas, the phenomenon of turning into vellus hair is caused by male hormone to thus cause the head hair to become thin. Although it is a physiological phenomenon, its social effect is large due to the impression of the appearance being greatly affected. Recently, a minoxidil external medicine and a finasteride internal medicine, which are effective for androgenetic alopecia, have been developed and have also been actively used in a dermatological treatment, but it cannot yet be said that sufficient therapeutic effects are obtained.

With regard to medicinal agents that can be used in the treatment of androgenetic alopecia, there are vasodilators such as minoxidil, carpronium chloride, and various extracts, male hormone activity inhibitors such as finasteride, female hormone drugs such as estrogen, estradiol, and progesterone, and antifungal drugs such as ketoconazole, pentadecane, cytopurine (6-benzylaminopurine), t-flavanone, and adenosine.

In 'Androgenetic alopecia diagnosis and treatment guidelines, 2010 edition' (Non-Patent Document 2) by the Japanese Dermatological Association, the above-mentioned medicinal agents are evaluated using five grades, that is, recommendation A (strongly recommended for use), recommendation B (recommended for use), recommendation C1 (can be considered for use, but there is insufficient evidence), recommendation C2 (not recommended because there is no evidence), and recommendation D (recommended not to use). In accordance with the above, as a therapy of recommendation A, minoxidil, which is a vasodilator, and finasteride, which is a testosterone 5α-reductase inhibitor, are cited; for minoxidil it is stated that '5% minoxidil external solution should be used as the drug of choice in external therapy for a male case, and 1% minoxidil external solution should be used as the drug of choice in treatment for a female case', and for finasteride internal medicine it is stated that 'it should be used as the drug of choice in internal therapy for a male case, whereas it should not be used for a female case'. The same guidelines classify carpronium chloride, pentadecane, cytopurine, t-flavanone, adenosine, and ketoconazole as recommendation C1, which is 'can be considered for use, but there is insufficient evidence', and classify cepharanthin as recommendation C2 with a written recommendation saying 'better not used'.

Furthermore, minoxidil has side effects such as drug-induced contact alopecia, hair hyperplasia, decrease of blood pressure, and decrease in heart rate, and there is the problem that when its use is stopped the symptoms recur. With female hormone drugs there is the possibility of thrombosis. Furthermore, finasteride has side effects such as prostate hyperplasia, erectile dysfunction, and ejaculatory disorder, when its use is stopped the symptoms recur, and it is contraindicated for pregnant women.

Furthermore, in accordance with the Drug Interview Form for finasteride (Non-Patent Document 3), the clinical effect of finasteride is confirmed based on evaluation of photographs of the crown. That is, although a hair thickening effect of finasteride on the crown or O-shaped site of androgenetic alopecia has been confirmed, there is no known evidence for a hair thickening effect on hair loss in the frontal region or M-shaped site. Therefore, there is a desire for a new treatment agent that exhibits a clear therapeutic effect toward androgenetic alopecia that continues for a certain period after its use is stopped, exhibits clear effectiveness toward hair loss in areas other than on the crown, and has fewer side effects.

3. Alopecia Areata and Methods for its Treatment

Alopecia areata is a disease that has the highest frequency among acquired alopecias; it occurs in about 0.1% to 0.2% of the population in America, and it seems to be at the same level in Japan. Alopecia areata develops in a person at any age. A quarter of alopecia areata patients develop it at an age of no older than 15 years old, and it is seen relatively often among children. Serious types of alopecia areata such as alopecia totalis or alopecia universalis are relatively often seen among children. There is no gender difference for alopecia areata. About a quarter of alopecia areata patients show characteristic symptoms on the nails, such as a small dent or a horizontal line. With regard to alopecia areata, basically, the wider the hair loss area, the more intractable it is, and classification of severity based on the hair loss area has also been considered (Non-Patent Document 4). Many patients with alopecia areata do not have a physical disorder other than hair loss, but the patients are deeply worried, and the psychological damage and degradation of QOL are great. Because of this, it is considered to be a skin disease that must be treated using any possible method, but there are hardly any effective treatment methods in the current situation.

With regard to the clinical classification of alopecia areata, it is classified according to the number of bald areas, the area, and the configuration as follows.

[1]. Standard alopecia areata
  Alopecia areata monolocularis: single bald area
  Alopecia areata multilocularis: a plurality of bald areas are observed
[2]. Alopecia totalis: bald patch enlarges to the entire head
[3]. Alopecia universalis: hair loss enlarges to the entire body
[4]. Alopecia ophiasis: band-shaped hair loss occurs at the head hairline Furthermore, as an index representing severity, USA alopecia areata evaluation guidelines determine severity using the proportion (S) of bald patch area occupying the entire head area and the degree (B) of hair loss other than on the head. Here, they are defined as follows.
  S0: No hair loss
  S1: Bald patch is less than 25% of the entire head
  S2: Bald patch is 25% to 49%
  S3: Bald patch is 50% to 74%
  S4: Bald patch is 75% to 99%
  S5: 100% hair loss
  B0: No hair loss in region other than the head
  B1: Partial hair loss is seen in region other than the head
  B2: Complete hair loss over whole body The wider the bald patch area in alopecia areata, the more serious the case is, and the more intractable it is.

In recent years, the cause of alopecia areata has been thought to be an autoimmune disease of hair follicle tissue (Non-Patent Document 5). There is also a report that the rate of coexistence of alopecia areata with an atopic disease is relatively high (Non-Patent Document 6). When alopecia is caused by exacerbation of atopic dermatitis it is called atopic alopecia. In particular, atopic alopecia patients having a filaggrin gene abnormality tend to suffer from coexisting serious alopecia areata (Non-Patent Document 7). Histopathologically also, in a group having an atopic predisposition, lymphocyte infiltration into an area around the hair follicle is often seen, and eosinophils and mast cells also infiltrate. Of the infiltrating lymphocytes, CD4-positive T lymphocytes occupy 60% to 80%, CD8-positive T lymphocytes occupy 20% to 40%, and there are a large number of HLA-DR-positive cells and INF-γ-positive cells (Non-Patent Document 8).

However, on the other hand, there is a report that the frequency of an atopic or autoimmune disease in alopecia areata patients is not different from that in healthy people (Non-Patent Document 9). Furthermore, although some relationship between alopecia areata and immune abnormality has been suggested, the specific causal relationship is not at all clear.

As medicinal agents that can be used for the treatment of alopecia areata, there are steroid drugs such as diflorasone, betamethasone, dexamethasone, clobetasol, prednisolone, mometasone, methylprednisolone, Deprodone, difluprednate, fluocinonide, amcinonide, triamcinolone, difluprednate, and hydrocortisone, second-generation antihistamine drugs such as azelastine, Glycyron (registered trademark), which is a complex of glycyrrhizin, methionine, and glycine, carpronium chloride, cepharanthin, minoxidil, cyclosporin A, Cassia Twig plus Dragon's Bone and Oyster Shell Decoction (Keishikaryukotsuboreito), Pinellia and Magnolia Decoction (Hangekobokuto), biotin, Anthralin (Dithranol), tricyclic antidepressants, etc.

Furthermore, as treatments for alopecia areata there are local immunotherapy in which a synthetic reagent called SADBE (squalic acid dibutyl ester) or DPCP (diphenylcyclopropenone) is contacted with a hair loss area to thus form a rash in the hair loss area and modulate immunity, a cooling therapy in which carbon dioxide snow or liquid nitrogen is used, a linearly polarized near-infrared ray irradiation therapy (Super Lizer therapy), a PUVA therapy, which is a photochemical therapy employing in combination Psoralen and long wavelength UV rays (UVA), stellate ganglion block, hypnotherapy, and acupuncture and moxibustion treatments.

With regard to these medicinal agents and therapies, an evaluation was carried out in 'Japanese Dermatological Association Alopecia Areata Diagnosis and Treatment Guidelines 2010 edition' (Non-Patent Document 10) using five categories, that is, recommendation A (strongly recommended for use), recommendation B (recommended for use), recommendation C1 (can be considered for use, but there is insufficient evidence), recommendation C2 (not recommended because there is no evidence), and recommendation D (recommended not to use).

In accordance with the above, no therapy is evaluated as recommendation A; as therapies with recommendation B steroid local injection and local immunotherapy are cited, the steroid local injection 'should be used for monolocularis and multilocularis adult cases where the state of the disease is fixed at S1 or below', and the local immunotherapy 'should be carried out as the first choice for multilocularis, totalis, and universalis cases regardless of age where the state of the disease is fixed at S2 or above'. As therapies with recommendation C1, a steroid pulse therapy by intravenous drip infusion is for 'adult cases of S2 or above rapidly progressing within 6 months after onset', orally administered steroid or orally administered steroid pulse therapy is for 'adult cases of S2 or above in which hair loss is rapidly progressing', and the second-generation antihistamine drug is 'one of the combined therapies for monolocularis and multilocularis cases having an atopic predisposition', all being recommended for use with recommendation C1. The same guidelines classify cepharanthin, Glycyron, steroid external preparation, carpronium chloride external preparation, minoxidil external preparation, cooling therapy, linearly polarized near-infrared ray irradiation therapy, and PUVA therapy as recommendation C1 'while taking the actual results of diagnosis and treatment into consideration' even though the 'benefit is not sufficiently proved at the present stage'.

On the other hand, cyclosporin A and Keishikaryukotsuboreito are classified as recommendation C2 with a written recommendation of 'cannot be recommended at the current time'. Furthermore, Anthralin, a tricyclic antidepressant, stellate ganglion block, and hypnotherapy are classified as recommendation C2 with a written recommendation of 'better not used' or 'better to withhold'. The acupuncture and moxibustion treatments are classified as recommendation D since they have 'not reached a standard for medical evaluation'.

With regard to the prognosis for alopecia areata, in a case where the duration of the bald patch is long or a case where there is a history of an atopic disease or an autoimmune endocrine disease, the possibility of a cure is low (Non-Patent Document 11). In accordance with reports from a number of European and American institutions, of all patients, 34% to 50% shift to the totalis type or the universalis type, and in these cases the recovery rate becomes as low as no greater than 10% (Non-Patent Document 12). In adult cases where the hair loss area is less than 50%, 56% thereof recovered, but for alopecia areata with a hair loss area of 50% or greater the recovery rate was only 3.7% (Non-Patent Document 13). Furthermore, the recovery rate is also low for cases in which it developed at the age of 15 or younger or for alopecia ophiasis (Non-Patent Document 12), and there is no recommendable therapy. Therefore, there is a strong desire for development of a new therapy for serious cases of alopecia, in particular S2 or above.

4. Female Pattern Alopecia and Methods for its Treatment

In female pattern alopecia, loss of hormone balance causes a shorter hair growth phase and a longer resting phase. Because of this, the number of hairs emerging from one pore decreases, the hair itself becomes half or less the width of the healthy state, or the hair color becomes pale. As a result, a state in which the scalp is seen through hairs around the center of the crown, that is, a pattern in which it becomes thinner overall, is observed.

Olsen E. et al. 2003 (Non-Patent Document 25) state that the manner of widening of the hair parting from the crown toward the frontal region resembling the manner of spreading of the branches of a Christmas tree is an important initial symptom for female pattern alopecia. Female pattern alopecia usually has an older age of onset than that of androgenetic alopecia, and is often confirmed from the 40s to 50s or after menopause. Since oral administration of finasteride, which suppresses activation of testosterone into dihydrotestosterone, is not effective for menopausal females, it is now generally thought that female thinning hair is not the same as androgenetic alopecia. As herein described, female pattern alopecia is diagnosed, clearly separately from androgenetic alopecia, from gender, age, and a diffuse alopecia state.

With regard to the causes of female pattern alopecia, it is caused by a decrease in estrogen due to the menopause as well as a decrease in female hormone due to severe diet, stress, or suspension of oral contraceptive use.

With regard to treatment for female pattern alopecia, finasteride is contraindicated in practice since it cannot be used for female pattern alopecia of a female who might be pregnant or a female who is breast-feeding. Minoxidil and cepharanthin both have a weak effect on female pattern alopecia. There is no known effect of female hormone replacement therapy on female pattern alopecia. As described above, there are hardly any effective treatment methods for female pattern alopecia.

5. Postpartum Alopecia and Methods for its Treatment

Many females experience the hair becoming thick during pregnancy and hair loss occurring when breast-feeding after childbirth. Since the cause of postpartum alopecia is clear, its diagnosis is easy and it cures spontaneously in many cases, it is not particularly treated. However, it is said that about 40% of postnatal females experience postpartum alopecia, so there are a considerable number of patients. Furthermore, there are variations among individuals for the degree of hair loss of postpartum alopecia and the extent of recovery, and there are rare cases in which hair loss does not stop if postpartum stress continues. In these cases, if a steroid is used for a long period, it often becomes difficult for hair to grow, and this requires attention.

As described above, when postpartum alopecia does not spontaneously recover, a steroid cannot be used for the treatment thereof, and there are no other effective therapies.

6. Seborrheic Alopecia and Methods for its Treatment

In the case of seborrheic alopecia, a large amount of sebum is continuously secreted from the pores, and the pores are blocked to such a degree that it can be seen by the naked eye. Because of this, if sebum is removed, the pores are seen to be red due to inflammation, this inflammation causes hair to be lost, and diagnosis is therefore relatively easy.

With regard to the cause of seborrheic alopecia, it is thought that inflammation is caused by abnormal growth of indigenous bacteria on the scalp due to excessive secretion of sebum; a certain therapeutic effect can be anticipated by appropriately removing sebum in the pores using a less irritating shampoo, but it is difficult to maintain an appropriate level of sebum. It is also said that proliferation of *Malassezia globosa*, which is a type of fungus, is one factor; there are cases in which external application of an antifungal agent shows a therapeutic effect, but since constitutional secretion of excess sebum is the ultimate factor, it is difficult to improve, and there are hardly any treatments for seborrheic alopecia.

7. Alopecia Pityroides and Methods for its Treatment

Alopecia pityroides is a disease in which a large amount of dandruff is generated abnormally such that dandruff becomes scab-like and blocks the pores to thus cause inflammation, and the diagnosis thereof is relatively easy. With regard to the cause thereof, it is said that indigenous bacteria on the scalp proliferate abnormally due to an abnormal hormone balance, and this gives rise to hair loss.

As a treatment therefor, a steroid treatment exhibits the highest effect among present therapies, but since this method might take a long time to achieve a complete cure or might easily result in a case in which the symptoms become chronic and the treatment becomes rather difficult, it is not a therapy that can be recommended. However, since there is no other therapy in the current situation, in general, the shampoo is changed to one having a weaker washing power, the number of times of hair washing is decreased, or a moisturizer is applied to thus prevent the scalp from becoming dry, with the expectation that the symptoms will be alleviated.

8. Senile Alopecia and Methods for its Treatment

Senile alopecia is alopecia in which, regardless of difference in gender, hair falling out and thinning occur for body hair of the entire body, including the entire head, accompanying aging. As symptoms of senile alopecia, the characteristics of the scalp becoming dry and blood vessels being visible through the skin are often observed. The cause of senile alopecia is due to deterioration in the ability to produce new cells in the body caused by aging, and it is therefore difficult to treat. As a current treatment for senile alopecia, hair papilla are activated by massaging the scalp, etc. to thus improve the possibility of hair growth, and there are hardly any therapies.

9. Cancer Chemotherapy Drug-Induced Alopecia and Methods for its Treatment

Cancer chemotherapy drug-induced alopecia is alopecia that occurs due to a cancer chemotherapy drug inhibiting cell division to thus selectively kill cancer cells, which actively undergo cell division, and at the same time inhibiting hair matrix cells, which also actively undergo cell division in the same manner.

It is known that alopecia is caused by chemotherapy agents such as, for example, cyclophosphamide, ifosfamide, doxorubicin, amrubicin, paclitaxel, docetaxel, irinotecan, epirubicin, etoposide, actinomycin D, bleomycin, vincristine, vinorelbine, carboplatin, methotrexate, cisplatin, melphalan, fluorouracil, gemcitabine, capecitabine, tegafur-gimeracil-oteracil potassium, vinblastine, and ixabepilone, which are generic names.

In general, with regard to cancer chemotherapy drug-induced alopecia, taking the initial administration of a chemotherapy drug as the starting point, hair loss starts after 10 days, hair loss becomes conspicuous after 20 days, and all body hair is lost after 30 to 60 days. With regard to recovery of body hair after completion of cancer chemotherapy, taking completion of administration of the chemotherapy drug as the starting point, hair growth normally starts 3 to 6 months later, and body hair has almost recovered in about 8 to 12 months.

However, since cancer chemotherapy drug-induced alopecia is caused by hair matrix cells within the hair follicle being inhibited by the cancer chemotherapy drug, recovery of body hair after completion of the cancer chemotherapy varies depending on the degree of inhibition of hair matrix cells. Because of this, although there seems to be recovery, even in a mild case the quality of the hair might be degraded and the color or thickness of the hair might change, and in serious cases recovery might be only to the growth of downy hair. Furthermore, even if body hair recovers, since a state in which there is no body hair continues for half a year to one and a half years, the appearance changes greatly during this period and this, coupled with anxiety with respect to the cancer itself, causes considerable distress to the patient.

Objective evaluation of cancer chemotherapy drug-induced alopecia is generally carried out as part of a skin disorder and hair loss evaluation based on Common Terminology Criteria for Adverse Events (CTCAE). Specifically, evaluation by CTCAE of cancer chemotherapy drug-induced alopecia is carried out such that a case without hair loss is evaluated as grade 0, a case with light hair loss is grade 1, and a case with conspicuous hair loss is grade 2.

There is no method for preventing or treating cancer chemotherapy drug-induced alopecia. Therefore, until cancer chemotherapy drug-induced alopecia spontaneously recovers, countermeasures such as a wig being used in place of head hair, eyebrows being drawn by an eyebrow pencil, and artificial eyelashes being used are taken to give a natural appearance.

As described above, alopecia areata, androgenetic alopecia, female pattern alopecia, postpartum alopecia, seborrheic alopecia, alopecia pityroides, senile alopecia, and cancer chemotherapy drug-induced alopecia not only have different causes from each other, but the therapies therefor are also very limited. For example, there are hardly any therapies for female pattern alopecia, postpartum alopecia, alopecia pityroides, senile alopecia, and cancer chemotherapy drug-induced alopecia. Moreover, with regard to androgenetic alopecia, a treatment using minoxidil or finasteride is recommended, but the effects thereof are weak.

Furthermore, for alopecia areata, steroid local injection or local immunotherapy are recommended, and although there are cases in which some effects can be seen, there are many cases in which no effects can be seen at all, and there are cases in which hair grows temporarily but when treatment is stopped the situation deteriorates due to steroid rebound. There is therefore a strong desire for the development of new therapies therefor.

4. Natriuretic Peptides

As natriuretic peptides (NPs), a family of 3 types of natriuretic peptides is known; specifically there are atrial natriuretic peptide (ANP; atrial natriuretic peptide), B-type natriuretic peptide (BNP; B-type natriuretic peptide), and C-type natriuretic peptide (CNP; C-type natriuretic peptide), those formed from 28, 32, and 22 amino acid residues respectively being the ones that are best known.

(1) ANP and BNP

ANP is mainly synthesized in the atrium and BNP is mainly synthesized in the ventricle, and they are then secreted from the heart to the whole body. Substantially 100% of ANP and BNP circulating in the blood is said to be heart-derived. It is reported that ANP and BNP are deeply involved in clinical conditions such as high blood pressure, cardiomegaly, heart failure, myocardial infarction, valvular disease, arrhythmia, and pulmonary hypertension.

Human ANP is a peptide formed from 28 amino acids produced in and secreted from the atrial cells, and forms a cyclic structure due to an intramolecular disulfide bond between cysteine residue 7 and cysteine residue 23. ANP exhibits a diuretic action in the kidney, and it relaxes and expands vascular smooth muscle in blood vessels. On the other hand, human BNP is a peptide formed from 32 amino acids produced in and secreted from the ventricular cells, and forms a cyclic structure due to an intramolecular disulfide bond between cysteine residue 10 and cysteine residue 26. BNP also has a diuretic action and a vasodilating action. BNP is a peptide that was isolated from pig brain in 1988 and identified, and is also called brain natriuretic peptide.

Both ANP and BNP bind to an NPR-A receptor having a guanylate cyclase domain (also called GC-A), promote the production of cGMP, and exhibit the above-mentioned action. In reality, secretion of ANP is promoted accompanying an increase in atrial inflation pressure in congestive heart failure, etc., and it functions to alleviate the symptoms of congestive heart failure, etc. by virtue of the above-mentioned action. Secretion of BNP is also promoted in myocardial infarction, etc., and it functions to alleviate various symptoms accompanying myocardial infarction, etc. by virtue of the above-mentioned action (Non-Patent Document 14). Most BNP in the blood is derived from the ventricle, but some is also secreted from the atrium. Expression of both ANP and BNP is increased to 100 times the normal level in a heart failure state, but it is also reported that the increase of BNP is larger and faster than that of ANP. ANP (hANP) is commercially available in Japan as an acute heart failure treatment drug, and in the USA BNP is commercially available as a congestive heart failure treatment drug.

(2) CNP

Because CNP was first discovered in the brain, it was thought that it functioned as a cranial nerve peptide, but it was later found that it also exists in the periphery. In particular, since in the blood vessel wall there are many CNP-specific receptors in smooth muscle cells, monocyte/macrophage cells and endothelial cells produce CNP, etc., it is thought that CNP is involved in the suppression of growth of smooth muscle cells as a local factor in the blood vessel wall. Because of this, the possibility of administration of CNP being able to prevent intravascular restenosis, which occurs with a certain frequency among patients with an ischemic heart disease after receiving percutaneous transluminal coronary angioplasty (PTCA) and is a clinical problem, is currently being examined in terms of clinical application.

Furthermore, an animal experiment has recently been reported in which intravenous administration of CNP clearly improves enlargement of the heart and fibrosis after myocardial infarction and improves the cardiac function. Fibrosis of the heart is known to cause diastolic heart failure or arrhythmia, and since CNP has the action of strongly suppressing the growth of fibroblasts, research has been carried out into its use as a drug for the treatment of fibrosis of the heart. Since CNP is a hormone present in the body, there are no concerns about side effects, and its application as a clinical treatment drug for arteriosclerotic disease or cardiac disease is anticipated. As CNP, CNP-22 having 22 amino acids, CNP-53 having 53 amino acids in which amino acid residues are added to the N terminal of the above, etc. are known.

(3) Natriuretic Peptide Receptors

As receptors for NPs, three types are known, that is, an NPR-A receptor having a guanylate cyclase domain (also called GC-A), an NPR-B receptor having a guanylate cyclase domain (also called GC-B), and an NPR-C receptor having no guanylate cyclase domain, and it is known that ANP binds to the NPR-A receptor and the NPR-C receptor, BNP binds to the NPR-A receptor and the NPR-C receptor, and CNP binds to the NPR-B receptor and the NPR-C receptor.

It is said that activation of the NPR-A receptor brings about vasodilatory action, diuretic action, and cytostatic action. On the other hand, NPR-B receptors are present in large numbers in vascular smooth muscle cells, and are thought to bring about growth-inhibition action for vascular smooth muscle cells. The NPR-C receptor is also called a clearance receptor and is though to remove NPs in blood and regulate the concentration of NPs in tissue.

(4) Relationship Between Natriuretic Peptides and the Immune System

With regard to natriuretic peptides, historically ANP was first discovered as a peptide secreted by the atrium, and its vasodilatory action and diuretic action have received attention. Following this, BNP and CNP were found as peptides analogous to ANP. Due to such historical reasons, with regard to the relationship between natriuretic peptides and immunity, those related to the cardiovascular system have attracted attention.

Furthermore, following this, because of poor growth of the cartilage it has been found that a CNP knockout mouse exhibits a microsomia-like phenotype (Non-Patent Document 15), and since CNP is anticipated to promote regeneration of articular cartilage, the relationship between arthritis and natriuretic peptides is also attracting attention. However, there is no mention in this publication of a relationship between CNP and alopecia.

It has been suggested that ANP has a role in arthritis or septicemia since it suppresses secretion by macrophages of tumor necrosis factor α (INF-α) and interleukin 1β (IL1β), which are inflammatory cytokines (Non-Patent Document 16). However, there is no mention in this publication of a relationship between ANP and alopecia.

Furthermore, since it has been reported that the concentration of BNP in blood increases in parallel to heart transplant rejection, it has been suggested that it is involved in immune modulation in the cardiovascular system (Non-Patent Document 17). However, there is no mention in this publication of a relationship between BNP and alopecia.

Kuroski de Bold et al. have examined the immunomodulating action of natriuretic peptides while noting an increase in the concentration of BNP in blood at the time of heart transplant rejection and have found that ANP and BNP both suppress lymphocyte proliferation (Non-Patent Document 18). However, there is no mention in this publication of a relationship between NP and alopecia.

On the other hand, Chiurchiu et al. have examined the immunomodulating action of BNP while noting the relationship with cardiac disease and septicemia and have reported that since BNP promotes the release by macrophages of arachidonic acid, prostaglandin E2 (PGE2), and leucotriene B4 (LTB4), which are inflammatory cytokines, and interleukin 10 (IL10), which is an anti-inflammatory cytokine, it has some type of action in modulating inflammation, but they could not conclude whether or not it functions to suppress or promote inflammation overall (Non-Patent Document 19). There is no mention in this publication either of a relationship between BNP and alopecia.

It has been reported that CNP is secreted from macrophages (Non-Patent Document 20). Furthermore, Scotland et al. have reported that CNP suppressed platelet aggregation and leucocyte migration during the course of examining the role of CNP in myocardial damage after cardiac ischemia and reperfusion (Non-Patent Document 21). However, there is no mention in these publications of a relationship between CNP and alopecia.

Similarly, Obata et al. have examined the action of CNP in myocarditis and have reported that when pig myosin was injected into a rat myocarditis model and CNP was administered continuously for 1 week following this, necrosis and inflammation of the heart tissue were suppressed, angiogenesis was promoted, and deterioration of cardiac function was suppressed (Non-Patent Document 22). However, there is no mention in this publication of a relationship between CNP and alopecia.

Furthermore, since CNP knockout mice show a microsomia-like phenotype, CNP is attracting attention in terms of the relationship with the growth of cartilage. Agoston et al. have found that, in primary culture of cartilage cells separated from mouse embryo neckbone, dexamethasone increases expression of the CNP gene (Non-Patent Document 23). However, there is no mention in this publication of a relationship between CNP and alopecia.

As hereinbefore described, in recent years, the relationship between immunity and natriuretic peptides has been attracting attention, but it is only the relationship between cardiovascular inflammation and natriuretic peptides or between arthritis and natriuretic peptides that is attracting attention, and there is no report of a relationship between alopecia and natriuretic peptides.

(5) Reports on Applications Related to Natriuretic Peptides

There are a large number of reports on the application of ANP, BNP, and CNP as described below in addition to the above. However, none of these publications refer to a relationship between natriuretic peptides and specific types of alopecia such as alopecia areata, androgenetic alopecia, alopecia pityroides, postpartum alopecia, female pattern alopecia, seborrheic alopecia, trichotillomania, and senile alopecia. Furthermore, none of these publications demonstrate that CNP or BNP is useful for the treatment of alopecia.

Shoji Tanaka et al. have proposed C-type natriuretic peptides exhibiting growth-inhibitory action for vascular smooth muscle cells and a vascular smooth muscle growth inhibitor containing these peptides as an active ingredient (Patent Document 1).

However, this means the use of CNP as an agent for the inhibition of smooth muscle cells and does not suggest the application of CNP or BNP to an agent for the treatment of alopecia.

Katsuhiko Nakata et al. have proposed an eye dropper for the promotion of lacrimal secretion or the treatment of keratoconjunctival disorder that contains a natriuretic peptide as an active ingredient, and ANP, BNP, and CNP are cited as natriuretic peptides that can be used (Patent Document 2).

However, this concerns utilization of the action of ANP, BNP, and CNP in promotion of lacrimal secretion as an eye dropper for the treatment of keratoconjunctival disorder, and does not suggest the application of CNP or BNP to an agent for the treatment of alopecia.

Kazuwa Nakao et al. have proposed a composition for increasing height that is administered to an individual having no FGFR3 abnormality and contains a guanyl cyclase B (GC-B) activator such as CNP as an active ingredient (Patent Document 3).

However, the intention was to utilize CNP as a composition for increasing height based on the knowledge that the length between the nose and the anus is larger for a transgenic mouse overexpressing CNP than for a normal littermate, and does not suggest any application of CNP or BNP to an agent for the treatment of alopecia.

Similarly, Kazuwa Nakao et al. have proposed an agent for the treatment or prevention of arthritis, the agent containing a guanyl cyclase B (GC-B) activator such as CNP as an active ingredient (Patent Document 4).

However, this is only a finding that in a transgenic mouse overexpressing CNP, the thickness of the articular cartilage is large compared with a normal littermate, and when CNP is continuously administered to an arthritis model animal, the arthritis is suppressed, the intention being to utilize CNP as an agent for the treatment or prevention of arthritis, and does not suggest the application of CNP or BNP to an agent for the treatment of alopecia.

Similarly, Kazuwa Nakao et al. have proposed an agent for the prevention or treatment of fatty liver that contains a GC-A receptor agonist as an active ingredient since in a BNP transgenic mouse overexpressing BNP there is resistance to fat increasing with a high-fat diet load and the glucose tolerance and insulin sensitivity are improved, and a hetero knockout mouse with respect to a gene for GC-A receptor, which is a receptor for ANP and BNP, easily becomes fat with a high-fat diet load, and the glucose tolerance and insulin sensitivity are impaired (Patent Document 6).

However, this does not suggest the application of a natriuretic peptide to an agent for the treatment of alopecia and does not mention CNP at all.

Isao Sakaida et al. have proposed an agent for suppressing hepatic fibrosis that contains a natriuretic peptide as an active ingredient based on the finding that when ANP or CNP was continuously administered to rats together with N-diethylnitrosoamine, hepatic fibrosis due to N-diethylnitrosoamine was suppressed (Patent Document 7).

However, the intention was to use a natriuretic peptide for prevention of cirrhosis of the liver or liver cancer, and there was no suggestion of the application of a natriuretic peptide to an agent for the treatment of alopecia.

Yasuhiko Ito et al. have proposed an agent for suppressing peritoneal fibrosis that contains a natriuretic peptide as an active ingredient based on the finding that when ANP was continuously administered to a rat abrasion-induced peritoneal fibrosis model, the peritoneal fibrosis was suppressed (Patent Document 8).

However, the intention was to use a natriuretic peptide for suppression of peritoneal fibrosis at the time of peritoneal dialysis and there was no suggestion of the application of a natriuretic peptide to an agent for the treatment of alopecia.

Chen et al. have proposed a peritoneal dialysis solution containing ANP based on the finding that when a peritoneal dialysis solution containing ANP was injected into a rat, net ultrafiltration and sodium clearance increased (Patent Document 9).

However, the intention was to add ANP to a peritoneal dialysis solution and apply it to the treatment of a patient with kidney damage, and there was no suggestion of the application of a natriuretic peptide to an agent for the treatment of alopecia.

Toshiyuki Hori et al. have proposed an agent for the prevention or treatment of a Th1 immune disease that contains a GC-A receptor agonist as an active ingredient based on the finding that when LPS is added to a medium the proliferation of naive T cells induced by dendritic cells was suppressed by the simultaneous addition of ANP (Patent Document 10).

However, the intention was to apply ANP to the prevention or treatment of a Th1 immune disease such as Crohn's disease, and there was no suggestion of the application of a natriuretic peptide to an agent for the treatment of alopecia.

Hisako Koide et al. have proposed a preparation for repair and regeneration of tissue and organ that contains as an active component ANP, BNP, CNP, Urodilatin (P-Uro), a precursor thereof, a derivative thereof, or a combination thereof, and which may contain a pharmaceutically acceptable diluent, excipient, filler, or adjuvant, and have cited, as one example of the repair and regeneration of tissue and organ, hair restoration, hair growth, and hair thickening (Patent Document 5). Furthermore, in Example 3 of the same publication, it was reported that when ANP was applied twice a day after hair washing to the scalp of '54 year old and 89 year old males with thin head hair', 'downy hair-like hair growth was observed on the frontal region with 1 week of ANP administration, and sites started to appear where black hair papilla appeared after hair had fallen out', 'after 2-3 weeks, resilience and rigidity increased for the entire head hair', and 'after 1 month the scalp, which could been seen before use, was obviously difficult to see'.

However, Patent Document 5 describes only hair growth due to ANP and does not demonstrate any of hair restoration, hair growth, and hair thickening by CNP or BNP. Furthermore, with regard to alopecia, there are various types of alopecia in terms of the cause, and their therapies are very different from each other, but the mere description of '54 year old and 89 year old males with thin head hair' cannot clarify for which type of alopecia an effect was exhibited; since the characteristic that 'the foremost line of retreating head hair moved forward' is a characteristic that can be seen in various types of alopecia, it is not clear what kind of cause or disease the 'thin hair' is derived from. Furthermore, said publication only considers a 'drug for hair growth, hair restoration, and hair thickening' as a very broad concept; it is unclear whether it is a treatment agent or a preventive agent, and it does not suggest a treatment or preventive agent for a specific alopecia and does not suggest a treatment or preventive agent for dandruff, white hair, and seborrheic scalp. It is therefore clear that this publication does not suggest an agent for the treatment or prevention of alopecia areata, androgenetic alopecia, postpartum alopecia, female pattern alopecia, seborrheic alopecia, alopecia pityroides, senile alopecia, cancer chemotherapy drug-induced alopecia, alopecia due to radiation exposure, dandruff, white hair, and seborrheic scalp.

Shoji Tanaka et al. have announced as described below that CNP has a completely different structure and effect from those of ANP and BNP (Patent Document 1).

'It is currently thought that ANP and BNP both function as a hormone secreted from the heart into the blood, also function as a neurotransmitter, and play an important role in maintaining homeostasis in the fluid volume and blood pressure of a living body . . . there are many unclear points regarding the physiological role of CNP as an NP. That is, the amino acid primary sequence of CNP is similar to those of ANP and BNP; furthermore, it exhibits natriuretic action and hypotensive action by in vivo administration, and it is therefore classed as belonging to the NP family. However, since the natriuretic action and hypotensive action of CNP are much weaker than those of ANP and BNP ($\frac{1}{50}$ to $\frac{1}{100}$) . . . CNP occupies a specific position within the NP family, and it is assumed that with regard to its physiological role, it might play a role other than maintenance of homeostasis in the fluid volume and blood pressure . . . when the structure of CNP is compared with those of ANP and BNP, it can be seen that CNP is different from ANP or BNP in terms of the points described below . . . . That is, it can be seen that the amino acid primary sequence of CNP is completely different from that of ANP or BNP for the exocyclic N-terminal domain, and within 17 amino acid residues in the endocyclic domain it is different from ANP by 5 residues and from BNP by 4 residues. Furthermore, the structure of the exocyclic C-terminal domain of CNP is very different from those of ANP and BNP, CNP does not have a tail structure, which is present in ANP and BNP (in the case of ANP and BNP, there are 5 amino acid residues added to the C-terminal of the cyclic structure for ANP and 6 amino acid residues for BNP, and these structures are called tail structures for convenience). It is clear that the above-mentioned difference in structure between CNP and ANP or BNP is involved in exhibition of the above-mentioned characteristic pharmacological action of CNP.'

In reality, as shown in FIG. 1 also, ANP, BNP, and CNP have very different structures and are thought to carry out different roles from each other.

RELATED ART DOCUMENTS

Patent Documents

[Patent Document 1] JP, A, 6-9688
[Patent Document 2] JP, A, 2000-169387
[Patent Document 3] WO2005/094890
[Patent Document 4] WO2005/094889
[Patent Document 5] JP, A, 2008-162987
[Patent Document 6] Republished Japanese translation 2008-032450 of a PCT application
[Patent Document 7] JP, A, 2010-168283
[Patent Document 8] Republished Japanese translation 2008-140125 of a PCT application
[Patent Document 9] Published Japanese translation 2000-516836 of a PCT application
[Patent Document 10] Republished Japanese translation 2004-110489 of a PCT application Non-Patent Documents

[Non-Patent Document 1] Satoshi Itami: Hair survey (male pattern hair loss) Japanese adult males, The Japan Medical Journal: No. 4209, 27-29, 2004
[Non-Patent Document 2] Androgenetic alopecia diagnosis and treatment guidelines (2010 edition) (The Japanese Journal of Dermatology: 120(5), 977-986, 2010)
[Non-Patent Document 3] Drug Interview Form Propecia tablets, revised July 2011, MSD
[Non-Patent Document 4] Olsen E et al.: Alopecia areata investigational assessment guidelines, J Am Acad Dermatol 40: 242-246, 1999
[Non-Patent Document 5] Gilhar A et al.: Autoimmune hair loss (alopecia areata) transferred by T lymphocytes to human scalp explants on SCID mice, J Clin Invest. 101: 62-67, 1998
[Non-Patent Document 6] Shellow W V et al.: Profile of alopecia areata: a questionnaire analysis of patient and family, Int J dermatol 31: 186-189, 1992.
[Non-Patent Document 7] Betz R C et al., Loss-of-function mutations in the filaggrin gene and alopecia areata: strong risk factor for a severe course of disease in patients comorbid for atopic disease, J Invest Dermatol. 127, 2539-2543, 2007.
[Non-Patent Document 8] Kensei Katsuoka: Atopic disease and alopecia areata—atopic alopecia areata—, Derma 23, 9-12, 1999
[Non-Patent Document 9] Serarslan G et al., Is atopy and autoimmunity more prevalent in patients with alopecia areata? A comparative study, J Eur Acad Dermatol Venereol. doi: 10.1111/j.1468-3083.2011.
[Non-Patent Document 10] Japanese Dermatological Association alopecia areata diagnosis and treatment guidelines 2010 (The Japanese Journal of Dermatology: 120(9), 1841-1859, 2010)
[Non-Patent Document 11] Ikeda T.: A new classification of alopecia areata, Dermatologica 131: 421-445, 1965.
[Non-Patent Document 12] MacDonald Hull S P et al.: Guidelines for the management of alopecia areata, Br J Dermatol 149: 692-699, 2003
[Non-Patent Document 13] Tosti A et al.: Alopecia areata: A long term follow-up study of 191 patients, J Am Acad Dermatol 55: 438-441, 2006
[Non-Patent Document 14] Yoshibayashi M. et al., Brain natriuretic peptide versus atrial natriuretic peptide—physiological and pathophysiological significance in children and adults: a review, Eur J Endocrinol. 135(3): 265-8, 1996
[Non-Patent Document 15] Chusho H. et al., Dwarfism and early death in mice lacking C-type natriuretic peptide, Proceedings of the National Academy of Sciences of the United States of America, 98(7): 4016-21, 2001
[Non-Patent Document 16] Kiemer A. K., Vollmar A. M., Annals of the Rheumatic Disease, The atrial natriuretic peptide regulates the production of inflammatory mediators in macrophages, 60: iii68-iii70. 2001
[Non-Patent Document 17] Meirovich Y. F. et al., Relationship between natriuretic peptides and inflammation: proteomic evidence obtained during acute cellular cardiac allograft rejection in humans, the Journal of Heart and Lung Transplantation, 27(1): 31-7, 2008
[Non-Patent Document 18] de Bold M L et al., Cardiac hormones ANF and BNP modulate proliferation in the unidirectional mixed lymphocyte reaction, the Journal of Heart and Lung Transplantation, 29(3): 323-6, 2010
[Non-Patent Document 19] Chiurchiù V. et al., Brain Natriuretic Peptide (BNP) regulates the production of inflammatory mediators in human THP-1 macrophages, Regulatory Peptides, 148(1-3): 26-32, 2008
[Non-Patent Document 20] Kubo A et al, C-type natriuretic peptide is synthesized and secreted from leukemia cell lines, peripheral blood cells, and peritoneal macrophages, Experimental Hematology, 29(5): 609-15, 2001

[Non-Patent Document 21] Scotland R. S. et al., C-type natriuretic peptide inhibits leukocyte recruitment and platelet-leukocyte interactions via suppression of P-selectin expression, Proceedings of the National Academy of Sciences, 102(40): 14452-7, 2005

[Non-Patent Document 22] Obata H. et al., CNP infusion attenuates cardiac dysfunction and inflammation in myocarditis, Biochemical and Biophysical Research Communications, 356(1): 60-6, 2007

[Non-Patent Document 23] Agoston H. et al., Dexamethasone stimulates expression of C-type Natriuretic Peptide in chondrocytes, BMC Musculoskeletal Disorders, 7: 87, 2006

[Non-Patent Document 24] Norwood O T. Male pattern baldness: Classification and incidence, South Med. J. 68: 1359-70, 1975

[Non-Patent Document 25] Olsen E A.: Current and novel methods for assessing efficacy of hair growth promotors in pattern hair loss, J Am Acad Dermatol; 48: 253-62, 2003

SUMMARY OF THE INVENTION

Problems to be Solved by the Invention

In spite of the fact that alopecia causes serious emotional distress due to problems related to appearance, no definite therapy has yet been found. With regard to androgenetic alopecia in particular, even minoxidil or finasteride cannot give a sufficient therapeutic effect in many cases, and with regard to alopecia areata, there are hardly any effective treatment methods. Furthermore, since alopecia areata is a recurring disease and also an intractable disease, greatly degrades the appearance, and might cause depression, it is therefore necessary for it to be treated.

With regard to postpartum alopecia, after childbirth, since a large amount of body hair is lost in a short period, coupled with postpartum depression the emotional burden on the patient is large, but there are hardly any therapies. Female pattern alopecia, seborrheic alopecia, alopecia pityroides, and senile alopecia are not widely recognized and there are hardly any therapies. With regard to cancer chemotherapy drug-induced alopecia, since body hair is rapidly lost over the whole body, and this state continues for a long period, a large shock is given to the patient, but there are hardly any therapies therefor, and there is a strong desire for the development of a therapy for cancer treatment. The same applies to alopecia due to radiation exposure as for cancer chemotherapy drug-induced alopecia.

Therefore, it is an object of the present invention to provide a novel agent for the treatment of alopecia for patients with alopecia, in particular alopecia areata, androgenetic alopecia, postpartum alopecia, female pattern alopecia, seborrheic alopecia, alopecia pityroides, senile alopecia, cancer chemotherapy drug-induced alopecia, and alopecia due to radiation exposure, the agent being not only effective and safe but also free from side effects such as an itching sensation, irritation, or feminization, not being contraindicated, and there being no recurrence when the use thereof is stopped.

Furthermore, it is an object of the present invention to provide a new agent for the treatment and/or prevention of alopecia, the agent having hair growth, hair restoration, and hair thickening effects, a white hair therapeutic effect, and a terminal hair growth effect, regardless of the cause of the alopecia, that is, any cause such as male hormone, female hormone, the balance thereof, any immune abnormality, inflammation, aging, or cancer chemotherapy drug, and to provide an agent for the treatment and/or prevention of dandruff, white hair, and seborrheic scalp.

Means for Solving the Problems

As a result of an intensive investigation by the present inventors in light of the above-mentioned circumstances, it has been found that an A-type natriuretic peptide (ANP) known as an acute heart failure treatment drug, a B-type natriuretic peptide (BNP) known as a congestive heart failure treatment drug, and a C-type natriuretic peptide (CNP) conventionally known as a vascular smooth muscle growth inhibitor, etc. have excellent effectiveness and safety as agents for the treatment and/or prevention of alopecia, dandruff, white hair, and seborrheic scalp.

The agent for the treatment of alopecia of the present invention has excellent effectiveness and safety for in particular alopecia areata, androgenetic alopecia, postpartum alopecia, female pattern alopecia, seborrheic alopecia, alopecia pityroides, senile alopecia, cancer chemotherapy drug-induced alopecia, and alopecia due to radiation exposure. Moreover, the agent for the treatment of alopecia of the present invention exhibits a clear therapeutic effect toward alopecia having resistance to treatment with a steroid agent, an antihistamine drug, Glycyron (registered trademark), carpronium chloride, cepharanthin, minoxidil, finasteride, cyclosporin A, Keishikaryukotsuboreito, Hangekobokuto, biotin, Anthralin, local immunotherapy, cooling therapy, linearly polarized near-infrared ray irradiation therapy, or PUVA therapy, which are conventional treatment methods, and does not have side effects such as an itching sensation, irritation, or feminization, and it has been confirmed that even if the use thereof is stopped there is no immediate recurrence, thus completing the present invention.

Furthermore, in multilayer application such as with a combination of CNP or BNP with betamethasone valerate and gentamicin sulfate, a combination of CNP or BNP with clobetasol propionate, a combination of CNP with carpronium chloride, or a combination of CNP or BNP with minoxidil, it has been confirmed that black terminal hair grows for alopecia other than alopecia areata, that is, androgenetic alopecia, postpartum alopecia, female pattern alopecia, seborrheic alopecia, alopecia pityroides, senile alopecia, cancer chemotherapy drug-induced alopecia, and alopecia due to radiation exposure, thus completing the present invention.

The present invention is specifically as follows.

[1] An agent for the treatment or prevention of alopecia, dandruff, itching, white hair, and seborrheic scalp, or a hair growth agent, a hair restoration agent, a hair loss progression preventive agent, a hair thinning progression preventive agent, a hair development promotion agent, a hair growth promotion agent, a hair cultivating agent, or an agent for the treatment or prevention of hair loss after childbirth or after a disease, the agent containing a natriuretic peptide (NP) as an active ingredient.

[2] The treatment or prevention agent according to [1], wherein the alopecia is alopecia areata, androgenetic alopecia, postpartum alopecia, female pattern alopecia, seborrheic alopecia, alopecia pityroides, trichotillomania, cancer chemotherapy drug-induced alopecia, senile alopecia, or drug-induced alopecia.

[3] The treatment or prevention agent according to [1], wherein the natriuretic peptide (NP) is any of a CNP derivative, a BNP derivative, and an ANP derivative.

[4] The treatment or prevention agent according to [1], wherein the natriuretic peptide (NP) is any of a C-type natriuretic peptide (CNP), a B-type natriuretic peptide (BNP), and an A-type natriuretic peptide (ANP).

[5] The treatment or prevention agent according to [1], wherein the natriuretic peptide (NP) is any of CNP-22, CNP-53, and a CNP derivative having CNP activity in which any amino acid in the amino acid sequence of CNP-22 or CNP-53 has been deleted, substituted, or added.

[6] The treatment or prevention agent according to [1], wherein the natriuretic peptide (NP) is CNP-22.

[7] The treatment or prevention agent according to [1], wherein the natriuretic peptide (NP) is any of BNP-26, BNP-32, BNP-45, and a BNP derivative having BNP activity in which any amino acid in the amino acid sequence of BNP-26, BNP-32, or BNP-45 has been deleted, substituted, or added.

[8] The treatment or prevention agent according to [1], wherein the natriuretic peptide (NP) is BNP-32.

[9] The treatment or prevention agent according to [1], wherein the natriuretic peptide (NP) is an A-type natriuretic peptide (ANP), ANP28, or a BNP derivative having BNP activity in which any amino acid in the ANP28 amino acid sequence has been deleted, substituted, or added.

[10] The treatment or prevention agent according to [1], wherein the natriuretic peptide (NP) is a chimeric peptide of two or more natriuretic peptides (NPs) selected from ANP, BNP, and CNP, the chimeric peptide forming a cyclic structure by an intramolecular disulfide bond, the CNP is a peptide selected from the group consisting of CNP-22, CNP-53, a peptide containing any amino acid sequence having 5 or more contiguous amino acids from the CNP-22 amino acid sequence in which any 1 to 5 amino acids have been deleted, substituted, or added, and a peptide containing any amino acid sequence having 5 or more contiguous amino acids from the CNP-53 amino acid sequence in which any 1 to 5 amino acids have been deleted, substituted, or added, the BNP is a peptide selected from the group consisting of BNP-26, BNP-32, BNP-45, a peptide containing any amino acid sequence having 5 or more contiguous amino acids from the BNP-26 amino acid sequence in which any 1 to 5 amino acids have been deleted, substituted, or added, a peptide containing any amino acid sequence having 5 or more contiguous amino acids from the BNP-32 amino acid sequence in which any 1 to 5 amino acids have been deleted, substituted, or added, and a peptide containing any amino acid sequence having 5 or more contiguous amino acids from the BNP-45 amino acid sequence in which any 1 to 5 amino acids have been deleted, substituted, or added, the ANP is ANP or a peptide containing any amino acid sequence having 5 or more contiguous amino acids from the ANP amino acid sequence in which any 1 to 5 amino acids have been deleted, substituted, or added, and said chimeric peptide has CNP activity, BNP activity, or ANP activity, or the natriuretic peptide (NP) is a derivative of the chimeric peptide of NPs.

[11] The treatment or prevention agent according to [1], wherein it further comprises at least one medicinal agent selected from the group consisting of a steroid drug, an antihistamine drug, a vasodilator, a male hormone activity inhibitor, a female hormone drug, an antibiotic, an antifungal agent, pentadecane, cytopurine (6-benzylaminopurine), t-flavanone, adenosine, cepharanthin, Glycyron (registered trademark), which is a complex of glycyrrhizin, methionine, and glycine, cyclosporin A, Keishikaryukotsuboreito, Hangekobokuto, biotin, Anthralin, tacrolimus, and a tricyclic antidepressant.

[12] The treatment or prevention agent according to [1], wherein it further contains at least one steroid drug selected from the group consisting of diflorasone, betamethasone, dexamethasone, clobetasol, prednisolone, mometasone, methylprednisolone, Deprodone, difluprednate, fluocinonide, amcinonide, triamcinolone, difluprednate, and hydrocortisone.

[13] The treatment or prevention agent according to [1], wherein it further contains at least one antihistamine drug selected from the group consisting of azelastine, oxatomide, fexofenadine, emedastine, ebastine, cetirizine, bepotastine, olopatadine, and loratadine.

[14] The treatment or prevention agent according to [1], wherein it further contains at least one vasodilator selected from the group consisting of minoxidil and carpronium chloride.

[15] The treatment or prevention agent according to [1], wherein it further contains finasteride.

[16] The treatment or prevention agent according to [1], wherein it further contains at least one female hormone drug selected from the group consisting of estrogen, estradiol, and progesterone.

[17] The treatment or prevention agent according to [1], wherein it further contains at least one antibiotic or antifungal agent selected from the group consisting of gentamicin, amphotericin B, nystatin, ketoconazole, terbinafine, flucytosine, fluconazole, itoraconazole, griseofulvin, and micafungin.

[18] The treatment or prevention agent according to [1], wherein it further contains at least one medicinal agent selected from the group consisting of betamethasone, clobetasol, gentamicin, carpronium chloride, and minoxidil.

[19] The treatment or prevention agent according to [1], wherein it recovers hair growth with original hair color from a state in which hair has grown with a paler color than the original hair color accompanying alopecia.

[20] The treatment or prevention agent according to [1], wherein it grows black hair.

[21] The treatment or prevention agent according to [1], wherein it changes the hair quality to terminal hair.

[22] The treatment or prevention agent according to [1], wherein it suppresses the occurrence of dandruff or the scalp becoming seborrheic.

[23] The treatment or prevention agent according to [2], wherein the androgenetic alopecia is androgenetic alopecia in a male or androgenetic alopecia in a female.

[24] The treatment or prevention agent according to [2], wherein the androgenetic alopecia is androgenetic alopecia coexisting with seborrheic alopecia or alopecia pityroides.

[25] The treatment or prevention agent according to [2], wherein the female pattern alopecia is female pattern alopecia coexisting with seborrheic alopecia or alopecia pityroides.

[26] The treatment or prevention agent according to [1] or [23], wherein the hair loss site is the frontal region or the crown.

[27] The treatment or prevention agent according to [2], wherein the androgenetic alopecia is type Va, VI, or VII on the Hamilton-Norwood scale.

[28] The treatment or prevention agent according to [1], wherein the alopecia areata is normal alopecia areata, alopecia totalis, alopecia universalis, or alopecia ophiasis.

[29] The treatment or prevention agent according to [1], wherein the alopecia is alopecia of a target having a history of, or coexisting, allergic disease or autoimmune disease.

[30] The treatment or prevention agent according to [29], wherein the autoimmune disease is any of chronic discoid lupus erythematosus, localized scleroderma, pemphigus, pemphigoid, herpes gestationis, linear IgA bullous dermatosis, acquired epidermolysis bullosa, vitiligo, or Sutton's nevus.

[31] The treatment or prevention agent according to [1], wherein the alopecia is alopecia of a target having a history of, or coexisting, allergic disease.

[32] The treatment or prevention agent according to [1], wherein the alopecia is alopecia of a target having a history of, or coexisting, atopic disease.

[33] The treatment or prevention agent according to [1], wherein the alopecia is alopecia of a target having a history of, or coexisting, autoimmune thyroid disease, vitiligo, systemic lupus erythematosus, rheumatoid arthritis, or myasthenia gravis.

[34] The treatment or prevention agent according to [1], wherein the alopecia is alopecia accompanied by erythema, scale, or crust.

[35] The treatment or prevention agent according to [1], wherein the alopecia is alopecia of a target having a history of, or coexisting, atopic dermatitis or allergic rhinitis.

[36] The treatment or prevention agent according to [1], wherein the alopecia is alopecia of a target having a filaggrin gene abnormality and having a history of, or coexisting, atopic dermatitis.

[37] The treatment or prevention agent according to [1], wherein the alopecia is alopecia of a target showing an allergic reaction toward at least one allergen selected from the group consisting of house dust, mite, cedar, Dactylis, ragweed, and cat fur.

[38] The treatment or prevention agent according to [1], wherein the alopecia is alopecia of a target showing an allergic reaction toward at least one allergen selected from the group consisting of house dust, mite, cedar, Dactylis, ragweed, and cat fur in an allergen test by any of a scratch test, an intradermal test, a patch test, and a specific IgE antibody in vitro assay.

[39] The treatment or prevention agent according to [1] or [2], wherein the alopecia is alopecia exhibiting resistance to treatment with a steroid drug, an antihistamine drug, Glycyron (registered trademark), carpronium chloride, cepharanthin, minoxidil, finasteride, cyclosporin A, Keishikaryukotsuboreito, Hangekobokuto, biotin, Anthralin, local immunotherapy, cooling therapy, linearly polarized near-infrared ray irradiation therapy, PUVA therapy, or tacrolimus.

[40] The treatment or prevention agent according to [1], wherein the alopecia is alopecia exhibiting resistance to treatment with a steroid treatment agent.

[41] The treatment or prevention agent according to [1], wherein the alopecia is alopecia of a target that has attained a steroid-dependent state.

[42] The treatment or prevention agent according to [1], wherein the alopecia is alopecia of a target for which a steroid treatment agent cannot be used.

[43] The treatment or prevention agent according to [1], wherein the alopecia is alopecia exhibiting resistance to treatment with carpronium chloride.

[44] The treatment or prevention agent according to [1], wherein the alopecia is alopecia exhibiting resistance to treatment with cepharanthin.

[45] The treatment or prevention agent according to [1], wherein the alopecia is alopecia of a target for which a 5α-reductase type 2 inhibitor cannot be used.

[46] The treatment or prevention agent according to [1], wherein the alopecia is alopecia exhibiting resistance to treatment with an antiallergy drug.

[47] The treatment or prevention agent according to [1], wherein the alopecia is alopecia exhibiting resistance to treatment with an antihistamine drug.

[48] The treatment or prevention agent according to [1], wherein the alopecia is alopecia exhibiting resistance to treatment by stimulation therapy using liquid nitrogen.

[49] The treatment or prevention agent according to [1], wherein the alopecia is alopecia exhibiting resistance to treatment with minoxidil.

[50] The treatment or prevention agent according to [1], wherein the alopecia is alopecia exhibiting resistance to treatment with a 5α-reductase type 2 inhibitor.

[51] The treatment or prevention agent according to [50], wherein the 5α-reductase type 2 inhibitor is finasteride.

[52] The treatment or prevention agent according to [1], wherein the alopecia is alopecia exhibiting resistance to treatment with an antifungal agent.

[53] The treatment or prevention agent according to [2], wherein the alopecia areata is S1 or B0 alopecia or above.

[54] The treatment or prevention agent according to [2], wherein the alopecia areata is S2 alopecia or above.

[55] The treatment or prevention agent according to [2], wherein the alopecia areata is S3 alopecia or above.

[56] The treatment or prevention agent according to [2], wherein the alopecia areata is S4 alopecia or above.

[57] The treatment or prevention agent according to [2], wherein the alopecia areata is S5 alopecia or above.

[58] The treatment or prevention agent according to [2], wherein the alopecia areata is B0 alopecia.

[59] The treatment or prevention agent according to [2], wherein the alopecia areata is B1 alopecia.

[60] The treatment or prevention agent according to [2], wherein the alopecia areata is B2 alopecia.

[61] The treatment or prevention agent according to [1], wherein a therapeutic effect is obtained by application for 3 weeks or longer.

[62] The treatment or prevention agent according to [1], wherein a therapeutic effect is obtained by application for 2 weeks or longer.

[63] The treatment or prevention agent according to [1], wherein a therapeutic effect is obtained by application for 1 week or longer.

[64] The treatment or prevention agent according to [1], wherein there is no recurrence for a period of 1 month or longer even when application is stopped.

[65] The treatment or prevention agent according to [1], wherein there is no recurrence for a period of 2 months or longer even when application is stopped.

[66] The treatment or prevention agent according to [1], wherein there is no recurrence for a period of 6 months or longer even when application is stopped.

[67] The treatment or prevention agent according to [1], wherein the dosage form is an ointment, a gel, a cream, a lotion, a liquid, a wax, a powder, a spray, a gel spray, a foam, a shampoo, a treatment, a scalp treatment, or a tonic.

[68] The treatment or prevention agent according to [1], wherein the dosage form is an ointment or a gel.

[69] The treatment or prevention agent according to [1], wherein the content of the natriuretic peptide (NP) is 1 to 1000 μg/g.

[70] The treatment or prevention agent according to [1], wherein the content of the natriuretic peptide (NP) is 10 to 500 µg/g.

[71] The treatment or prevention agent according to [1], wherein the content of the natriuretic peptide (NP) is 20 to 300 µg/g.

[72] The treatment or prevention agent according to [1], wherein the content of the natriuretic peptide (NP) is 30 to 200 µg/g.

[73] The treatment or prevention agent according to [1], wherein the content of the natriuretic peptide (NP) is 50 to 100 µg/g.

[74] The treatment or prevention agent according to [1], wherein the alopecia is alopecia due to an endocrine disorder such as dyspituitarism, hypothyroidism, or hyperthyroidism, or a metabolic disorder such as a nutritional disorder, hypoalbuminemia, cachexia, iron-deficiency anemia, zinc deficiency, homocystinuria, or cirrhosis of the liver, is telogenic alopecia due to high fever, childbirth, major surgery, etc., or is drug-induced alopecia due to an antithyroid drug, an anticoagulant, an antitumor drug, thallium, a psychotropic drug, a β-blocker, etc.

Effects of the Invention

As is clear from the case tests described below, the treatment agent of the present invention containing a natriuretic peptide (NP) as an active ingredient can outstandingly improve alopecia areata, androgenetic alopecia, female pattern alopecia, seborrheic alopecia, alopecia pityroides, postpartum alopecia, senile alopecia, and cancer chemotherapy drug-induced alopecia. Furthermore, the treatment agent of the present invention can restore white hair to black hair or its original color. Moreover, in accordance with use of the treatment agent of the present invention, dandruff is decreased. Furthermore, the treatment agent of the present invention does not have side effects such as an itching sensation, irritation, and feminization, and there is no recurrence of alopecia areata and cancer chemotherapy drug-induced alopecia for at least half a year even if its use is stopped.

The treatment agent of the present invention can be anticipated to be useful as a very effective treatment drug for androgenetic alopecia, for which sufficient therapeutic effects cannot be obtained by the conventional minoxidil or finasteride, and alopecia areata, for which there are hardly any effective treatment methods. Furthermore, the treatment agent of the present invention has marked hair growth, hair restoration, and hair thickening effects for female pattern alopecia, seborrheic alopecia, alopecia pityroides, postpartum alopecia, senile alopecia, cancer chemotherapy drug-induced alopecia, and alopecia due to radiation exposure, for which there are hardly any therapies, can dramatically decrease the amount of hair falling out, and can prevent the progress of hair loss.

Moreover, the treatment agent of the present invention can convert miniaturized hair root into large hair root that grows terminal hair and can change the hair quality so that it is harder and thicker. Furthermore, the treatment agent of the present invention promotes hair growth of terminal hair, prolongs the growth phase, and increases long hair. Moreover, the treatment agent of the present invention promotes hair restoration and hair lengthening and speeds up the hair lengthening rate.

Furthermore, the treatment agent of the present invention can increase the number of hairs per hair follicle. The treatment agent of the present invention promotes hair growth and hair restoration in the frontal region or M-shaped site, which is intractable, and has a hair growth effect, hair restoration effect, and hair thickening effect for alopecia that is classified as Va, VI, or VII on the Hamilton-Norwood scale, which is wide area, severe androgenetic alopecia. The treatment agent of the present invention restores hair for alopecia areata and has the effect of preventing restored hair from falling out such that newly grown hair does not fall out after its application is stopped.

The treatment agent of the present invention can in particular dramatically improve severe alopecia on the adult head that has been difficult to treat and causes problems in social life, without any side effects at all. The treatment agent of the present invention is not only effective for intractable alopecia but also exhibits the same effects for both males and females and for both adults and younger people.

In the case of minoxidil and finasteride, which are conventionally used, there is the serious problem that when their use is stopped, the severity prior to use immediately returns, but in the present invention, this defect is not seen for alopecia areata, postpartum alopecia, cancer chemotherapy drug-induced alopecia, and alopecia due to radiation exposure. Furthermore, with regard to androgenetic alopecia, not only for the crown, for which a hair thickening effect by finasteride was confirmed, but also for the frontal region and the front temporal region the same hair growth, hair restoration, and hair thickening effects as for the crown are confirmed.

Moreover, there is an excellent effect in improving seborrheic and pityriatic state of the scalp and preventing dandruff from occurring. The target of a treatment plan using minoxidil and finasteride by European and American specialists is only Hamilton-Norwood scale Classes II-V (Non-Patent Document 24); no effect is expected for Hamilton-Norwood scale Classes Va, VI, and VII, and a hair follicle transplant or a wig is recommended. However, in accordance with the present invention, improvement effects such as the amount of hair falling out dramatically decreasing, a longer growth phase, increase in long hair, terminal hair growth, hair thickening and darkening, hair restoration, promotion of hair lengthening, faster lengthening rate, black hair thickening, hair growing, and improvement of white hair are observed 1 week to 3 weeks after application even for Hamilton-Norwood scale Classes Va, VI, and VII.

Furthermore, steroid local injection, which is conventionally used for alopecia areata, has the difficulty that skin atrophy occurs at the local injection site and a substantial number of times of injection and total amount injected are required when the hair loss has spread to a wide area, and local immunotherapy for alopecia areata has the problem that there is the adverse event that it is associated with systemic contact alopecia, local lymphadenopathy, and mechanical urticaria. However, in the present invention this defect is not only not seen at all, but the excellent effects that hair is newly grown, the therapeutic effect for alopecia is not lost for a long period after its use is stopped, and restored hair is prevented from falling out have been confirmed. Even when application is stopped the effects from the treatment agent of the present invention are maintained as a good skin state for over half a year with respect to alopecia areata and cancer chemotherapy drug-induced alopecia.

Furthermore, the treatment agent of the present invention containing as an active ingredient ANP, BNP, CNP, a derivative of these NPs, a chimeric peptide of 2 or more NPs selected from these NPs, or a derivative of a chimeric peptide of these NPs exhibits therapeutic effects toward alopecia areata, which shows resistance to treatment with steroid drugs, cooling therapy, antiallergy drugs, carpronium chloride, and cepharanthin. In particular, the treatment agent of the present invention containing as an active ingredient BNP, CNP, a derivative of these NPs, a chimeric peptide of these NPs, or a derivative of a chimeric peptide of these NPs is also effective for alopecia areata that has a large hair loss area and is intractable, and alopecia ophiasis, which is said to have a poor prognosis, and also exhibits marked effects on female pattern alopecia, postpartum alopecia, seborrheic alopecia, alopecia pityroides, senile alopecia, cancer chemotherapy drug-induced alopecia, and minoxidil treatment-resistant androgenetic alopecia.

Furthermore, when the treatment agent of the present invention contains CNP or BNP as an active ingredient, the amount of hair falling out decreases dramatically about 3 days after application, hair grows with application once or twice a day for 1 week to 2 weeks, and in many cases the skin becomes difficult to see after application for 4 weeks. Following this, the hair continues to grow without continuous application, it becomes terminal hair, and there is a cure. The effect of the treatment agent of the present invention containing CNP or BNP as an active ingredient is strong, and even for alopecia ophiasis type alopecia areata, which is very intractable, hair growth recovers markedly.

In particular, the treatment agent of the present invention containing CNP as an active ingredient can more reliably suppress inflammation in a hair loss site than when BNP is an active ingredient, and symptoms such as erythema, scale, and crust can be improved in a short period. Furthermore, the treatment agent of the present invention containing CNP as an active ingredient has a stronger effect in decreasing the amount of hair falling out, suppressing itchiness, and giving earlier hair growth than when BNP is an active ingredient.

Furthermore, when the treatment agent of the present invention containing CNP as an active ingredient is applied only for 1 week to 2 weeks, the hair growth effect is sustained for a longer period after the application is stopped, and hair continues to thicken. Therefore, when inflammatory symptoms such as erythema or scale are seen in the hair loss site on the scalp, CNP is most recommended. This is a surprising finding even for the present inventors, who are dermatologists. Furthermore, when the treatment agent of the present invention contains ANP as an active ingredient, it is effective only for alopecia in which there is no erythema, scale, seborrheic desquamation, etc. on the scalp and for which erythema, scale, seborrheic desquamation, etc. on the scalp that are induced by ANP application do not occur. In this case, hair grows with application twice a day for 1 week to 2 weeks.

Furthermore, the treatment agent of the present invention can suppress inflammation of seborrheic alopecia and alopecia pityroides and make hair grow. The treatment agent of the present invention can also promote restoration of hair, dramatically decrease the amount of hair falling out, make terminal hair grow, make hair thick and dark, restore hair, promote lengthening of hair, give a faster lengthening rate, and increase long hair for female pattern alopecia, postpartum alopecia, senile alopecia, cancer chemotherapy drug-induced alopecia, and alopecia due to radiation exposure.

Since the treatment agent of the present invention suppress skin inflammation, it can make hair grow on a hair loss site of a target having a history of, or coexisting, autoimmune disease accompanied by skin symptoms such as chronic discoid lupus erythematosus, localized scleroderma, pemphigus, pemphigoid, herpes gestationis, linear IgA bullous dermatosis, acquired epidermolysis bullosa, vitiligo, or Sutton's nevus.

It is known that alopecia areata might be comorbid with an autoimmune disease, and the treatment agent of the present invention can make hair grow in a hair loss site of a target having a history of, or coexisting, autoimmune disease such as autoimmune thyroid disease, vitiligo, systemic lupus erythematosus, rheumatoid arthritis, or myasthenia gravis.

Furthermore, since the treatment agent of the present invention suppresses inflammation and improves the state of scalp skin, it is also effective for alopecia due to an endocrine disorder such as dyspituitarism, hypothyroidism, or hyperthyroidism or a metabolic disorder such as a nutritional disorder, hypoalbuminemia, cachexia, iron-deficiency anemia, zinc deficiency, homocystinuria, or cirrhosis of the liver, telogenic alopecia due to high fever, childbirth, or major surgery, and alopecia medicamentosa due to an antithyroid drug, an anticoagulant, an antitumor drug, thallium, a psychotropic drug, or a β-blocker.

In addition, an NPR-C receptor, which is common to NPs, is though to be a clearance receptor that does not mediate pharmacological action. It is said that ANP and BNP bring about vasodilatory action, diuretic action, and cytostatic action by activation of an NPR-A receptor, it is thought that CNP brings about vascular smooth muscle cell growth-inhibition by activation of an NPR-B receptor, and it is therefore expected that the action of CNP is different from that of BNP and ANP.

However, the present inventors actually carried out testing on patients with alopecia, in particular patients with androgenetic alopecia and alopecia areata, and surprisingly it has been found that the treatment agent of the present invention containing CNP or BNP as an active ingredient clearly shows higher therapeutic effects than when ANP is an active ingredient, and among them the therapeutic effect was even higher when CNP was an active ingredient. On the other hand, the treatment agent of the present invention containing BNP as an active ingredient is characterized in that black terminal hair often grows.

Natriuretic peptides (NPs), which are the active ingredients of the present invention, are hormones originally present in the body; there are no concerns about side effects when applied to the skin, it is thought that there is only a slight effect on hemodynamics as long as the dosage is appropriate, they can be used safely for a patient having low or unstable blood pressure, and it is therefore possible to administer them for a long period to a patient with chronic alopecia.

Furthermore, they are effective for a patient exhibiting resistance to treatment with a steroid drug, carpronium chloride, an antifungal agent, cepharanthin, or minoxidil, hair grows with application twice a day for 3 days to 2 weeks and, moreover, in the case of alopecia areata and cancer chemotherapy drug-induced alopecia, after administration is stopped alopecia symptoms do not recur at the application site. In addition, the treatment agent of the present invention is an unprecedented and outstanding treatment agent having the advantage that it can be used for children and females.

BRIEF DESCRIPTION OF DRAWINGS

FIG. 1 A diagram comparing the amino acid sequence of human CNP peptide, the amino acid sequence of human BNP peptide, and the amino acid sequence of human ANP peptide. Each character denotes the type of amino acid as a one letter code. The line connecting C (cysteine) and C (cysteine) denotes an intramolecular disulfide bond. The amino acid sequence of human CNP peptide and the amino acid sequences of human BNP peptide and human ANP peptide have three common regions, that is, an amino acid sequence represented by 'CFG', an amino acid sequence represented by 'DRI', and an amino acid sequence represented by 'SGLGC', and four mutually different sequences separated by these three common sequences.

FIG. 2 A diagram showing the therapeutic effects on alopecia areata from an ANP gel. The severity of the alopecia areata was evaluated in terms of the proportion of bald patch area relative to the entire head in accordance with the USA alopecia areata evaluation guidelines, and a comparison was made for each case between that before application of the ANP gel and that after the application thereof. Each point on the left-hand side denotes the severity before application and each point on the right-hand side denotes the severity after application. The point for the severity before application and the point for the severity after application from the same test subject are connected by a straight line. The ANP gel rarely exhibited a fixed effect in the treatment of alopecia areata in those cases where no symptoms of irritation occurred, but in many cases there was no change in the proportion of the bald patch area, and itchiness occurred in many cases. Furthermore, the ANP gel rather aggravated erythema, scale, itchiness, and dandruff and increased the amount of hair falling out, and its use was stopped in most cases; this tendency was particularly marked for androgenetic alopecia.

FIG. 3 A diagram showing the therapeutic effects on alopecia areata from a BNP gel. The severity of alopecia areata was evaluated in terms of the proportion of bald patch area relative to the entire head in accordance with the USA alopecia areata evaluation guidelines, and a comparison was made for each case between that before application of the BNP gel and that after application thereof. Each point on the left-hand side denotes the severity before application and each point on the right-hand side denotes the severity after application. The point for the severity before application and the point for the severity after application from the same test subject are connected by a straight line. It was found that the BNP gel was effective in the treatment of alopecia areata in all cases.

FIG. 4 A diagram showing the therapeutic effects on alopecia areata from a BNP ointment. The severity of alopecia areata was evaluated in terms of the proportion of bald patch area relative to the entire head in accordance with the USA alopecia areata evaluation guidelines, and a comparison was made for each case between that before application of the BNP ointment and that after application thereof. Each point on the left-hand side denotes the severity before application and each point on the right-hand side denotes the severity after application. The point for the severity before application and the point for the severity after application from the same test subject are connected by a straight line. It was found that the BNP ointment was effective in the treatment of alopecia areata in all cases.

FIG. 5 A diagram showing the therapeutic effects on alopecia areata from a CNP gel. The severity of alopecia areata was evaluated in terms of the proportion of bald patch area relative to the entire head in accordance with the USA alopecia areata evaluation guidelines, and a comparison was made for each case between that before application of the CNP gel and that after application thereof. Each point on the left-hand side denotes the severity before application and each point on the right-hand side denotes the severity after application. The point for the severity before application and the point for the severity after application from the same test subject are connected by a straight line. It was found that the CNP gel was effective in the treatment of alopecia areata. In case C1, because it was the $7^{th}$ day of CNP gel application the presence or absence of a therapeutic effect could not be confirmed clearly.

FIG. 6 A diagram showing the therapeutic effects on alopecia areata from a CNP ointment. The severity of alopecia areata was evaluated in terms of the proportion of bald patch area relative to the entire head in accordance with the USA alopecia areata evaluation guidelines, and a comparison was made for each case between that before application of the CNP ointment and that after application thereof. Each point on the left-hand side denotes the severity before application and each point on the right-hand side denotes the severity after application. The point for the severity before application and the point for the severity after application from the same test subject are connected by a straight line. It was found that the CNP ointment exhibited clear effects in the treatment of alopecia areata except in one case, that of case C14. In case C14, insofar as the bald patch area could be evaluated there was no hair growth that covered the entire bald patch, but clear growth of terminal hair was confirmed.

FIG. 7 A photographic diagram showing the therapeutic effect when an ANP gel was applied to the back of the head of alopecia areata case A2 test subject. P denotes a bald patch before application and T denotes the bald patch of the same site after 100 μg/g ANP gel was applied twice a day for 5 weeks. Clear hair growth was observed.

FIG. 8-1 A photographic diagram showing the therapeutic effect when an ANP gel was applied to the right temporal region of alopecia areata case A3 test subject (case C15 test subject). The test subject faced toward the right in the photograph. P denotes a bald patch before application and T1 denotes the bald patch of the same site after 100 μg/g CNP ointment was applied twice a day for 2 weeks and from the next day after that 100 μg/g ANP gel was applied twice a day for 2 weeks. Strong hair growth was observed.

FIG. 8-2 A photographic diagram showing the therapeutic effect when an ANP gel was applied to the right temporal region of alopecia areata case A3 test subject (case C15 test subject). The test subject faced toward the right in the photograph. T2 denotes the bald patch of the same site after 100 μg/g CNP ointment was applied twice a day for 2 weeks and from the next day after that 100 μg/g ANP gel was applied twice a day for 5 weeks. Compared with that before application and that of T1 in FIG. 8-1, stronger hair growth was observed.

FIG. 9 A photographic diagram showing the therapeutic effect when an ANP gel was applied to alopecia areata case A4 test subject. P denotes a bald patch before application and T denotes the bald patch of the same site after 100 μg/g ANP gel was applied twice a day for 4 weeks. It can be seen that the bald patch was cured.

FIG. 10 A photographic diagram showing the therapeutic effect when an ANP gel and a BNP gel were applied to alopecia areata case A5 test subject (case B3 test subject). The test subject faced toward the right in the photograph. P denotes a bald patch before application, T1 denotes the bald patch of the same site after 100 μg/g ANP gel was applied twice a day for 3 weeks, and T2 denotes the bald patch of the same site after application of the ANP gel was stopped at 3 weeks and from the next day after that 100 μg/g BNP gel was applied twice a day for 2 weeks. Although the ANP gel enlarged the hair loss range somewhat, marked hair growth was observed with the BNP gel.

FIG. 11 A photographic diagram showing the therapeutic effect when an ANP gel was applied to the crown of alopecia areata case A6 test subject (case C3 and C4 test subject). The test subject faced upward in the photograph. P denotes a bald patch before application, and T denotes the bald patch of the same site after 100 μg/g ANP gel was applied twice a day for 2 weeks. In the case of this test subject, there was no effect, and the hair loss range was somewhat enlarged.

FIG. 12-1 A photographic diagram showing the therapeutic effect when a BNP gel was applied to the right temporal region of alopecia areata case B1 test subject (case C12 test subject). The test subject faced toward the right in the photograph. P denotes a bald patch before application and T1 denotes the bald patch of the same site after 100 μg/g BNP gel was applied twice a day for 7 days. Clear hair growth was observed.

FIG. 12-2 A photographic diagram showing the therapeutic effect when a BNP gel was applied to the right temporal region of alopecia areata case B1 test subject (case C12 test subject). The test subject faced toward the right in the photograph. T2 denotes the bald patch of the same site after 100 μg/g BNP gel was applied twice a day for 23 days, and T3 denotes the bald patch of the same site after application of 100 μg/g BNP gel was stopped at 24 days and 5 months had elapsed. Hair growth was observed to such an extent that the location of the bald patch was substantially lost, and the hair growth continued after application was stopped.

FIG. 13 A photographic diagram showing the therapeutic effect when a BNP gel was applied to alopecia areata case B2 test subject. P denotes a bald patch before application and T1 denotes the bald patch of the same site after 50 μg/g BNP gel was applied twice a day for 7 days. Clear hair growth was observed and there was a cure.

FIG. 14 A photographic diagram showing the therapeutic effect when a BNP gel was applied to the left frontal region of alopecia areata case B4 test subject (test subject of test subject C9). The test subject faced downward in the photograph. P denotes a bald patch before application, T1 denotes the bald patch of the same site after 100 μg/g BNP gel was applied twice a day for 2 weeks, T2 denotes the bald patch of the same site after 100 μg/g BNP gel was applied twice a day for 3 weeks, and T3 denotes the bald patch of the same site after application of 100 μg/g BNP gel was stopped at 3 weeks and 3 weeks had elapsed. Marked hair growth and hair thickening were observed.

FIG. 15-1 A photographic diagram showing the therapeutic effect when a BNP ointment was applied to a bald area of the crown of alopecia areata case B5 test subject. The test subject faced upward in the photograph. P denotes the bald patch before application, and T1 denotes the bald patch of the same site after 50 μg/g BNP ointment was applied twice a day for 2 weeks and from the next day after that 30 μg/g BNP ointment was applied twice a day for 1 week. Clear hair growth was observed.

FIG. 15-2 A photographic diagram showing the therapeutic effect when a BNP ointment was applied to the bald area of the crown of alopecia areata case B5 test subject. The test subject faced upward in the photograph. T2 denotes the bald patch of the same site after 50 μg/g BNP ointment was applied twice a day for 2 weeks, from the next day after that 30 μg/g BNP ointment was applied twice a day for 1 week, and after that a further 50 μg/g BNP ointment was applied twice a day for 2 weeks. Compared with T1 in FIG. 15-1, further marked hair growth and hair thickening were observed.

FIG. 16 A photographic diagram showing the therapeutic effect when a BNP ointment was applied to a bald area of the right temporal region of alopecia areata case B5 test subject. The test subject faced toward the right in the photograph. P denotes the bald patch before application, and T1 denotes the bald patch of the same site after 50 μg/g BNP ointment was applied twice a day for 2 weeks, from the next day after that 30 μg/g BNP ointment was applied twice a day for 1 week, and after that a further 50 μg/g BNP ointment was applied twice a day for 2 weeks. Marked hair growth that covered the entire bald patch was observed.

FIG. 17 A photographic diagram showing the therapeutic effect when a CNP gel was applied to the crown of alopecia areata case C1 test subject. P denotes a bald patch before application, and T denotes the bald patch of the same site after 100 μg/g CNP gel was applied twice a day for 1 week. Clear hair growth was observed.

FIG. 18-1 A photographic diagram showing the therapeutic effect when a CNP ointment was applied to a bald patch of the crown of alopecia areata case C2 test subject (case C11 test subject). P denotes a bald patch before application, and T1 denotes the bald patch of the same site after 100 μg/g CNP ointment was applied twice a day for 1 week. Clear hair growth was observed.

FIG. 18-2 A photographic diagram showing the therapeutic effect when a CNP ointment and a CNP gel were applied to the bald patch of the crown of alopecia areata case C2 test subject (case C11 test subject). T2 denotes the bald patch of the same site after 100 μg/g CNP ointment was applied twice a day for 1 week and from the next day after that 100 μg/g CNP gel was applied twice a day for 1 week, and T3 denotes the bald patch of the same site after 100 μg/g CNP ointment was applied twice a day for 1 week and from the next day after that 100 μg/g CNP gel was applied twice a day for 3 weeks. Clear hair growth and enlargement of the hair growth region were observed.

FIG. 19-1 A photographic diagram showing the therapeutic effect when a CNP ointment was applied to a bald patch of the frontal region of alopecia areata case C2 test subject (case C11 test subject). The test subject faced downward in the photograph. P denotes the bald patch before application, and T1 denotes the bald patch of the same site after 100 μg/g CNP ointment was applied twice a day for 1 week. Clear hair growth was observed.

FIG. 19-2 A photographic diagram showing the therapeutic effect when a CNP ointment and a CNP gel were applied to the bald patch of the frontal region of alopecia areata case C2 test subject (case C11 test subject). The test subject faced downward in the photograph. T2 denotes the bald patch of the same site after 100 μg/g CNP ointment was applied twice a day for 1 week and from the next day after that 100 μg/g CNP gel was applied twice a day for 3 weeks. Compared with T1 in FIG. 19-1, clear hair growth and enlargement of the hair growth region were observed.

FIG. 20 A photographic diagram showing the therapeutic effect when a CNP gel was applied to a bald patch of the left temporal region of alopecia areata case C3 test subject (case A6 and C4 test subject). The test subject faced toward the left in the photograph. P denotes the bald patch before application, T1 denotes the bald patch of the same site after 100 μg/g CNP gel was applied twice a day for 2 weeks, and T2 denotes the bald patch of the same site after 100 μg/g CNP gel was applied twice a day for 3 weeks and after that application of CNP gel was stopped and 6 months had elapsed. Clear hair growth and enlargement of the hair growth region were observed.

FIG. 21 A photographic diagram showing the therapeutic effect when a CNP ointment was applied to a bald patch of the left temporal region of alopecia areata case C5 test subject (case A1 test subject). The test subject faced downward in the photograph. P denotes the bald patch before application, T1 denotes the bald patch of the same site after 100 μg/g CNP ointment was applied twice a day for 3 weeks, and T2 denotes the bald patch of the same site after 100 μg/g CNP gel was applied twice a day for 3 weeks and after that application of CNP ointment was stopped and 6 months had elapsed. Clear hair growth and enlargement of the hair growth region were observed.

FIG. 22 A photographic diagram showing the therapeutic effect when a CNP ointment was applied to a bald patch of the right frontal region of alopecia areata case C6 test subject (case A7 test subject). The test subject faced toward the right in the photograph. P denotes the bald patch before application, and T denotes the bald patch of the same site after 50 μg/g CNP ointment was applied twice a day for 3 weeks. Clear growth of terminal hair was observed.

FIG. 23 A photographic diagram showing the therapeutic effect when a CNP ointment was applied to alopecia areata case C7 test subject. P denotes a bald patch before application, and T denotes the bald patch of the same site after 100 μg/g CNP ointment was applied twice a day for 2 weeks. Clear hair growth was observed.

FIG. 24-1 A photographic diagram showing the therapeutic effect when a CNP ointment was applied to alopecia areata case C10 test subject (case B6 test subject). P denotes a bald patch before application, and T1 denotes the bald patch of the same site after 100 μg/g CNP ointment was applied twice a day for 2 weeks. Clear hair growth was observed.

FIG. 24-2 A photographic diagram showing the therapeutic effect when a CNP ointment was applied to alopecia areata case C10 test subject (case B6 test subject). T2 denotes the bald patch of the same site after 100 μg/g CNP ointment was applied twice a day for 3 weeks. Compared with T1 in FIG. 24-1, clearer hair growth was observed.

FIG. 25 A photographic diagram showing the therapeutic effect when a CNP ointment was applied to a bald patch of the left temporal region of alopecia areata case C12 test subject (case B1 test subject). The test subject faced toward the left in the photograph. P denotes the bald patch before application, T1 denotes the bald patch of the same site after 100 μg/g CNP ointment was applied twice a day for 3 weeks, and T2 denotes the bald patch of the same site after 100 μg/g CNP ointment was applied twice a day for 5 weeks. Enlargement of the hair growth region over time and formation of terminal hair were clearly observed.

FIG. 26 A photographic diagram showing the therapeutic effect when a CNP ointment was applied to alopecia areata case C13 test subject. P denotes a bald patch before application, and T denotes the bald patch of the same site after 100 μg/g CNP ointment was applied twice a day for 2 weeks. Clear hair growth was observed.

FIG. 27 A photographic diagram showing the therapeutic effect when an ANP gel was applied to the crown of androgenetic alopecia case A8 test subject (case B8 test subject). P denotes a bald patch before application, and T denotes the bald patch of the same site after 100 μg/g ANP gel was applied twice a day for 2 weeks. Hair growth was not observed at all.

FIG. 28-1 A photographic diagram showing the therapeutic effect when a BNP gel was applied to the crown of androgenetic alopecia case B7 test subject. P denotes a bald patch before application, and T1 denotes the bald patch of the same site after 100 μg/g BNP gel was applied twice a day for 10 days. Hair growth and formation of terminal hair were observed.

FIG. 28-2 A photographic diagram showing the therapeutic effect when a BNP gel was applied to the crown of androgenetic alopecia case B7 test subject. T2 denotes the bald patch of the same site after 100 μg/g BNP gel was applied twice a day for 14 days and from the next day after that application of the BNP gel was stopped and 6 months had elapsed. Compared with T1 in FIG. 28-1, formation of terminal hair progressed, the area of thinning hair was reduced, and a substantially normal state was recovered.

FIG. 29 A photographic diagram showing the therapeutic effect when a BNP gel was applied to the crown of androgenetic alopecia case B12 test subject. P denotes a bald patch before application, T1 denotes the bald patch of the same site after 50 μg/g BNP gel was applied twice a day for 3 days, and T2 denotes the bald patch of the same site after 50 μg/g BNP gel was applied twice a day for 21 days. Clear hair growth and formation of terminal hair were observed.

FIG. 30-1 A photographic diagram showing the therapeutic effect when a CNP ointment was applied to the crown and frontal region of androgenetic alopecia case C16 test subject. The test subject faced downward in the photograph. P denotes a bald patch before application, and T1 denotes the bald patch of the same site after 100 μg/g CNP ointment was applied twice a day for 3 weeks. Clear hair growth and formation of terminal hair were observed.

FIG. 30-2 A photographic diagram showing the therapeutic effect when a CNP ointment was applied to the crown and frontal region of androgenetic alopecia case C16 test subject. The test subject faced downward in the photograph. T2 denotes the bald patch of the same site after 100 μg/g CNP ointment was applied twice a day for 4 weeks. Compared with that before application and that of T1 in FIG. 30-1, very marked hair growth over time and formation of terminal hair were observed.

FIG. 31 A photographic diagram showing the therapeutic effect when a CNP ointment was applied to androgenetic alopecia case C17 test subject. The test subject faced downward in the photograph. P denotes a bald patch before application, and T denotes the bald patch of the same site after 100 μg/g CNP ointment was applied twice a day for 1 week. Clear hair growth and formation of terminal hair were observed.

FIG. 32 A photographic diagram showing the therapeutic effect when a CNP gel was applied to postpartum alopecia case C18 test subject. The test subject faced downward in the photograph. P denotes a bald patch before application, and T denotes the bald patch of the same site after 100 μg/g CNP gel was applied twice a day for 1 week. Clear hair growth and formation of terminal hair were observed.

FIG. 33 A photographic diagram showing the therapeutic effect when a CNP gel was applied to female pattern alopecia case C19 test subject. The test subject faced downward in the photograph. P denotes a bald patch before application, and T denotes the bald patch of the same site after 100 μg/g CNP gel was applied twice a day for 4 days. Although it was short, clear hair growth was observed.

FIG. 34 A photographic diagram showing the therapeutic effect when a BNP gel was applied to a circular bald area of the crown of alopecia areata case B13 test subject (case C13 test subject). The test subject faced downward in the photograph. P denotes the bald patch before application, and T denotes the bald patch of the same site after 50 μg/g BNP gel was applied twice a day for 2 weeks. There was no hair on the scalp of the bald area within the range encircled by the dotted line in P, whereas clear hair growth was observed on the scalp of the bald area within the range encircled by the dotted line in T.

FIG. 35 A photographic diagram showing the therapeutic effect when a CNP gel was applied to a circular bald area of the left temporal region of alopecia areata case C20 test subject. The test subject faced downward and toward the left in the photograph in P2, and upward and toward the left in T2. P2 denotes a hair loss site before application, and T2 denotes the same site after 50 μg/g CNP gel was applied twice a day for 2 weeks. The areas photographed in photographs P2 and T2 were substantially identical to each other. There was almost no hair growth on the scalp of the bald area within the range encircled by the dotted line in P2, whereas a large amount of hair growth was observed on the scalp within the range encircled by the dotted line in T2.

FIG. 36 A photographic diagram showing the therapeutic effect when a BNP:betamethasone:gentamicin combination was applied to a circular bald area of the crown of alopecia areata case B14 test subject. The test subject faced upward in the photograph. P denotes the bald patch before application, and T denotes the bald patch of the same site after a 50 μg/g BNP:600 μg/mL betamethasone:500 μg/mL gentamicin combination was applied twice a day for 7 days. There was no hair growth in a central part of the bald area within the range encircled by the dotted line in P, whereas a large amount of hair growth was observed in the middle of the bald area within the range encircled by the dotted line in T.

FIG. 37 A photographic diagram showing the therapeutic effect when a CNP:betamethasone:gentamicin combination was applied to a circular bald area of the right crown of alopecia areata case C21 test subject. The test subject faced rearward in the photograph of P and upward and toward the left in the photograph of T. P denotes the bald patch before application, and T denotes the bald patch of the same site after a 50 μg/g CNP:600 μg/mL betamethasone:500 μg/mL gentamicin combination was applied twice a day for 3 weeks and then stopped for 1 week. In P the skin of the scalp of the bald area within the range encircled by the dotted line could be seen and there was only slight growth of very fine white downy hair, whereas in T black hair grew densely on the scalp of the bald area within the range encircled by the dotted line.

FIG. 38 A photographic diagram showing the therapeutic effect when a CNP:betamethasone:gentamicin combination was applied to a circular bald area of the crown of alopecia areata case C22 test subject. The test subject faced toward the left in the photograph. P denotes the bald patch before application, and T denotes the bald patch after 50 μg/g CNP gel was applied twice a day for 2 weeks and subsequently a 50 μg/g CNP:600 μg/mL betamethasone:500 μg/mL gentamicin combination was applied twice a day for 2 weeks. In P there was no hair growth at all on the scalp of the bald area within the range encircled by the dotted line, whereas in T black hair grew densely on the scalp, at the upper and lower edges of the photograph, of the bald area within the range encircled by the dotted line.

FIG. 39 A photographic diagram showing the therapeutic effect when a CNP gel was applied to a circular bald area of the back of the head of alopecia areata case C23 test subject. The test subject faced rearward in the photograph. P denotes the bald patch before application, and T denotes the bald patch of the same site after 50 μg/g CNP gel was applied twice a day for 2 weeks. In P the hair growth in the bald area within the range encircled by the dotted line was scattered with fine hair, whereas in T the hair growth in the bald area within the range encircled by the dotted line was dense with thick and sturdy hair.

FIG. 40 A photographic diagram showing the therapeutic effect when a BNP gel was applied to a thinning hair site of the frontal region and the crown of androgenetic alopecia case B15 test subject. The test subject faced downward in the photograph. P denotes the thinning hair site before application, and T denotes the hair loss site of the same site after 50 μg/g BNP gel was applied twice a day for 2 weeks. In P the hair growth of the hair loss site was scattered with fine hair, whereas in T the hair growth was dense with thick sturdy hair. In particular, focusing on the skin of the M-shaped site, it could be seen that the hair growth was dense.

FIG. 41 A photographic diagram showing the therapeutic effect when a BNP gel was applied to a hair loss site of the crown and the frontal region of androgenetic alopecia case B16 test subject. The test subject faced downward in the photograph. P denotes the hair loss site before application, T1 denotes the hair loss site of the same site after 100 μg/g BNP gel was applied twice a day for 3 weeks, and T2 denotes the hair loss site of the same site when the application of 100 μg/g BNP gel was stopped after 3 weeks and from the next day 200 μg/g BNP gel was applied twice a day for 2 weeks. In P hair was scattered in the hair loss site within the range encircled by the dotted line, whereas in T1 hair with a feeling of volume grew densely in a central part within the range encircled by the dotted line, and in T2 the hair grew more densely and the so-called M-shaped hair loss site disappeared. In the photograph of T2, the reason why a central part within the range encircled by the dotted line, the so-called O-shaped hair loss site, was conspicuous is because the photograph was taken from a camera angle directly above the crown such that the crown, which was the remaining hair loss site, could be seen well.

FIG. 42 A photographic diagram showing the therapeutic effect when a CNP gel was applied to a hair loss site of the crown of androgenetic alopecia case C24 test subject. The test subject faced downward in the photograph. P denotes the bald patch before application, and T denotes the bald patch of the same site after 50 μg/g CNP gel was applied twice a day for 1 week. In P hair was scattered and the scalp could be seen, whereas in T hair with a feeling of volume grew and it was difficult to see the scalp.

FIG. 43 A photographic diagram showing the therapeutic effect when a CNP:betamethasone:gentamicin combination was applied to a hair loss site of the frontal region of androgenetic alopecia case C25 test subject. The test subject faced forward in the photograph. P1 denotes the hair loss site before application, and T1 denotes the hair loss site of the same site after a 25 μg/g CNP:600 μg/mL betamethasone: 500 μg/mL gentamicin combination was applied twice a day for 12 days. Compared with the photograph of P1, in the photograph of T1 the feeling of volume of the hair increased, and the scalp of the frontal region was more difficult to see.

FIG. 44 A photographic diagram showing the therapeutic effect when a CNP:betamethasone:gentamicin combination was applied to a hair loss site of the frontal region of androgenetic alopecia case C25 test subject. The test subject faced toward the right in the photograph, with the right frontal region visible. P2 denotes the hair loss site before application, and T2 denotes the hair loss site of the same site after a 25 μg/g CNP:600 μg/mL betamethasone:500 μg/mL gentamicin combination was applied twice a day for 12 days. Compared with the photograph of P2, in the photograph of T2 the feeling of volume of the hair increased, and the scalp of the frontal region was more difficult to see.

FIG. 45 A photographic diagram showing the therapeutic effect when a CNP:clobetasol combination was applied to a hair loss site of the frontal region and the crown of androgenetic alopecia case C26 test subject. The test subject faced downward in the photograph. P denotes the hair loss site before application, and T denotes the hair loss site of the same site after a 50 µg/mL CNP:250 µg/g clobetasol combination was applied twice a day for 1 week. Compared with the photograph of P, in the photograph of T the density of the hair increased, each hair thickened, and even black hairs increased.

FIG. 46 A photographic diagram showing the therapeutic effect when a CNP gel was applied to a male pattern hair loss site at the M-shaped hair line of the right frontal region of androgenetic alopecia case C27 test subject. The test subject faced toward the right in the photograph. P denotes the hair loss site before application, and T denotes the same site after 50 µg/g CNP gel was applied twice a day for 2 weeks. In P there was hardly any hair on the scalp of the hair loss site, whereas in T a large amount of hair growth was observed on the scalp of the hair loss site.

FIG. 47 A photographic diagram showing the therapeutic effect when an ANP gel or a BNP gel was applied to a hair loss site of the crown of postpartum alopecia case A10 (B17) test subject. The test subject faced downward in the photograph. P denotes the hair loss site before application, T1 denotes the same site after 100 µg/g ANP gel was applied twice a day for 3 weeks, and T2 denotes the same site when application of the ANP gel was ended after 3 weeks and application was suspended for 6 months, following which 50 µg/g BNP gel was applied to the hair loss site of the crown once every 3 to 4 days for 3 weeks. In photograph (T1) after application of the ANP gel, the hair loss range enlarged, but in photograph (T2) after application of the BNP gel, thinning hair on the crown thickened to such an extent that it was not noticeable to the eye.

FIG. 48 A photographic diagram showing the therapeutic effect when a CNP gel was applied to a hair loss site at the parting on the frontal region of female pattern alopecia case B19 test subject. The test subject faced downward in the photograph. P denotes the hair loss site before application, and T denotes the same site after 50 µg/g BNP gel was applied twice a day for 1 week. Comparing the two, in the photograph of P the scalp had scattered hair growth, but in the photograph of T hair growth could be confirmed on the scalp.

FIG. 49 A photographic diagram showing the therapeutic effect when a BNP gel was applied to a thinning hair part of the crown of female pattern alopecia case B20 test subject. The test subject faced downward in the photograph. P denotes the thinning hair part before application, and T denotes the same site after 50 µg/g BNP gel was applied twice a day for 2 weeks. After the BNP gel was applied for 2 weeks, the thinning hair became inconspicuous.

FIG. 50 A photographic diagram showing the therapeutic effect when a CNP gel was applied to a thinning hair part of the frontal region and the crown of female pattern alopecia case C28 test subject. The test subject faced downward in the photograph. P denotes the thinning hair part before application, and T denotes the same site after 50 µg/g CNP gel was applied once or twice a day for 4 weeks. After the CNP gel was applied for 4 weeks, the hair thickened to such an extent that thinning hair could hardly be seen.

FIG. 51 A photographic diagram showing the therapeutic effect when a BNP gel was applied to a thinning hair part of the frontal region and the crown of case B23 test subject with coexisting senile alopecia and alopecia pityroides. The test subject faced downward in the photograph. P denotes the thinning hair part before application, and T denotes the same site when 50 µg/g BNP gel was applied for 2 weeks, application was then suspended for 1 week, and 200 µg/g BNP gel was applied once a day for 5 days. After the BNP gel was applied, pityriatic desquamation was alleviated, vellus hair turned into terminal hair and became black, and the thinning hair was greatly improved.

FIG. 52 A photographic diagram showing the therapeutic effect when a CNP gel was applied to a thinning hair part of the frontal region and the crown of alopecia pityroides case C31 test subject. The test subject faced downward in the photograph. P denotes the thinning hair part before application, and T denotes the same site after 100 µg/g CNP gel was applied twice a day for 2 weeks. After the CNP gel was applied, a considerable amount of thickly adhering scale was lost, and hair started to thicken on the crown.

FIG. 53 A photographic diagram showing the therapeutic effect when a BNP gel was applied to a thinning hair part of the frontal region and the crown of alopecia pityroides case B28 test subject. The test subject faced downward in the photograph. P denotes the thinning hair part before application, and T denotes the same site after 20 µg/g BNP gel was applied for 1 week. After the BNP gel was applied, thickly accumulated scale disappeared, and fairly clear hair growth and hair thickening were observed from the frontal region to the crown.

FIG. 54 A photographic diagram showing the therapeutic effect when an ANP gel or a BNP gel was applied to a thinning hair part of the frontal region and the crown of senile alopecia case A15 test subject. The test subject faced downward in the photograph. P denotes the thinning hair part before application, T1 denotes the thinning hair part after 100 µg/g ANP gel was applied twice a day for 3 weeks, and T2 denotes the same site when 50 µg/g CNP gel was applied twice a day for 4 weeks from the next day after the ANP gel had been applied for 1 week. After the CNP gel was applied, clear hair thickening was seen in the frontal region, and hair stopped falling out.

FIG. 55 A photographic diagram showing the therapeutic effect when a BNP gel was applied to a bald area of the back of the head of alopecia areata case B26 test subject. The test subject faced rearward in the photograph. P denotes the bald area before application, T1 denotes the same site after 50 µg/g BNP gel was applied twice a day for 2 weeks, and T2 denotes the same site when application of the BNP gel was ended after 2 weeks and 6 weeks had elapsed after that. Marked hair growth was seen in the bald area to which the BNP gel had been applied.

FIG. 56-1 A photographic diagram showing the therapeutic effect when a CNP gel was applied to a bald area of the frontal region and the crown of cancer chemotherapy drug-induced alopecia case C35 test subject. The test subject faced downward in the photograph. P denotes the hair loss site before application, and T denotes the same site after 50 µg/g concentration CNP gel was applied to an area from the frontal region to the crown twice a day for 6 weeks. The number of hairs increased in the hair loss site to which the CNP gel had been applied, considerable hair thickening was observed, and it was confirmed that the hairs had become thick and long.

FIG. 56-2 A photographic diagram showing the therapeutic effect when a 50 µg/g CNP:600 µg/mL betamethasone: 500 µg/mL gentamicin combination was applied to a circular bald area occurring in the left temporal region of cancer chemotherapy drug-induced alopecia case C35 test subject. The test subject faced toward the left in the photograph. P denotes the hair loss site before application, and T denotes the same site after the 50 μg/g CNP:600 μg/mL betamethasone:500 μg/mL gentamicin combination was applied twice a day for 3 weeks. Marked terminal hair growth was confirmed for the bald area to which the CNP gel had been applied.

FIG. 57 A photographic diagram showing the therapeutic effect when a BNP gel was applied to the left frontal region of alopecia areata case B4 (case C9) test subject and a CNP ointment was applied to the right frontal region. The test subject faced forward and slightly downward in the photograph. P denotes the hair loss site before application, T denotes the same site at a time when 100 μg/g BNP gel had been applied for 3 weeks and application had been suspended for 2 weeks for the left frontal region and at a time immediately after 100 μg/g CNP ointment had been applied for 3 weeks to the right frontal region, and T2 denotes the same site when application had subsequently been suspended for 1 year. The alopecia areata multilocularis was completely cured by applying the BNP gel or the CNP ointment for 3 weeks, and there was no recurrence for over 1 year.

MODES FOR CARRYING OUT THE INVENTION

The present invention is an agent for the treatment or prevention of alopecia, dandruff, white hair, and seborrheic scalp, the agent containing a natriuretic peptide (NP) as an active ingredient, and the agent being for the treatment of alopecia areata, androgenetic alopecia, seborrheic alopecia, alopecia pityroides, female pattern alopecia, postpartum alopecia, senile alopecia, cancer chemotherapy drug-induced alopecia, and alopecia due to radiation exposure.

The alopecia areata referred to in the present specification is not particularly limited and means alopecia that is generally clinically diagnosed as alopecia areata, in particular alopecia that occurs suddenly without a clear cause in a target having a history of, or coexisting, immune disease or a target having a genetic background of immune disease. Alopecia areata in the present specification includes alopecia that is generally clinically diagnosed as alopecia areata, but is not limited thereto, and includes all types of alopecia in a target having an overreaction or abnormality in the immune system, the cause being unclear other than there being an overreaction or immune abnormality in the immune system.

The alopecia that is generally clinically diagnosed as alopecia areata is alopecia in which a coin-sized circular to patchy bald area with a clear outline suddenly occurs without any subjective symptoms, prodromal symptoms, etc., gradually increases in area if it does not spontaneously cure, and becomes intractable. With regard to the alopecia that is generally clinically diagnosed as alopecia areata, during its active stage broken hair, dead hair (black spot within hair follicle), and diseased hair that easily falls out are observed within and outside the lesion, the configuration of these hair root parts being similar to the shape of an exclamation mark being conclusive for the diagnosis.

The immune disease referred to in the present specification means a disease caused by an overreaction or immune abnormality in the immune system, and includes an allergic disease and an autoimmune disease. The overreaction or immune abnormality in the immune system means an excessive immunoreaction or an abnormal immunoreaction that will damage normal cells of the target itself, and specifically includes an allergic disease and an autoimmune disease. The overreaction or immune abnormality in the immune system can be recognized as a history of, or coexisting, immune disease. The target having an overreaction or immune abnormality in the immune system referred to in the present specification has the same meaning as alopecia having a history of, or coexisting, immune disease.

The target having a genetic background of an immune disease means a target for whom there is one having an overreaction or immune abnormality in the immune system among the genetically-related family. Since it is known that alopecia areata occurs with high frequency when there is one having an immune disease among the genetically-related family, alopecia of unknown cause in a target having a genetic background of immune disease can be considered to be alopecia areata.

In the present specification, when there is one having a history of, or coexisting, allergic disease or autoimmune disease at least among the biological parents, biological brothers and sisters, biological grandparents, biological children, and biological grandchildren, it is determined that it is a target having a genetic background of immune disease. Furthermore, in the present specification, when there is one having a history of, or coexisting, alopecia areata at least among the biological parents, brothers and sisters, and grandparents, it is determined that it is a target having a genetic background of alopecia areata.

Here, examples of the allergic disease include atopic disease, pollen allergy, food allergy, latex allergy, metal allergy, sick house syndrome, allergic granulomatous angiitis, food-dependent exercise-induced anaphylaxy, and celiac disease.

The atopic disease includes bronchial asthma, atopic dermatitis, allergic rhinitis, and atopic alopecia. Atopic alopecia means a state in which alopecia is caused by exacerbation of atopic dermatitis. The target having an atopic predisposition referred to in the present specification means a target for whom at last one of themselves, biological parents, biological brothers and sisters, biological grandparents, biological children, and biological grandchildren has a history of bronchial asthma, atopic dermatitis, allergic rhinitis, or atopic alopecia.

Examples of allergens causing an allergic reaction include house dust, mite, cedar, Dactylis, ragweed, and cat fur. The cedar, Dactylis, and ragweed referred to here mean cedar pollen, Dactylis pollen, and ragweed pollen respectively. A target that shows an allergic reaction toward at least one allergen among house dust, mite, cedar, Dactylis, ragweed, and cat fur in an allergen test such as any of a scratch test, an intradermal test, a patch test, and a specific IgE antibody in vitro assay is a target having a genetic background of an immune disease.

Examples of the autoimmune disease include an autoimmune thyroid disease such as Hashimoto's disease, Basedow's disease, or primary hypothyroidism, vitiligo, systemic lupus erythematosus, rheumatoid arthritis, myasthenia gravis, chronic discoid lupus erythematosus, localized scleroderma, pemphigus, pemphigoid, herpes gestationis, linear IgA bullous dermatosis, acquired epidermolysis bullosa, Sutton's nevus, Guillain Barré syndrome, chronic atrophic gastritis, autoimmune hepatitis, primary biliary cirrhosis, primary sclerosing cholangitis, autoimmune pancreatitis, aortitis, Goodpasture's syndrome, rapidly progressive glomerulonephritis, megaloblastic anemia, autoimmune hemolytic anemia, autoimmune neutropenia, idiopathic thrombocytopenic purpura, idiopathic Addison's disease, insulin-dependent diabetes mellitus, systemic scleroderma, alopecia areata, Vogt-Koyanagi-Harada disease, autoimmune optic neuropathy, idiopathic azoospermia, habitual abortion, antiphospholipid antibody syndrome, polymyositis, dermatomyositis, systemic dermatosclerosis, Sjogren syndrome, IgG4-related disease, polyarteritis nodosa, microscopic polyangiitis, allergic granulomatous angiitis, Wegener's granulomatosis, mixed connective tissue disease, ulcerative colitis, amyotrophic lateral sclerosis, Crohn's disease, collagen disease, relapsing polychondritis, sarcoidosis, stiff person syndrome, adult Still's disease, multiple sclerosis, immune thrombocytopenic purpura, eosinophilic pneumonia, and Behcet's disease.

The autoimmune disease includes an autoimmune disease with skin symptoms. Examples of the autoimmune disease with skin symptoms include chronic discoid lupus erythematosus, localized scleroderma, pemphigus, pemphigoid, herpes gestationis, linear IgA bullous dermatosis, acquired epidermolysis bullosa, vitiligo, and Sutton's nevus. The autoimmune disease with skin symptoms tends to be accompanied by alopecia.

The autoimmune disease includes an autoimmune disease that is liable to be accompanied by alopecia areata. Examples of the autoimmune disease that is particularly liable to be accompanied by alopecia areata include an autoimmune thyroid disease, vitiligo, systemic lupus erythematosus, rheumatoid arthritis, and myasthenia gravis (Non-Patent Document 8).

The androgenetic alopecia referred to in the present specification means symptoms in an adult male or female in which hair on the frontal region and/or crown gradually becomes vellus hair, thinner, and shorter over a few years or longer. As also described in 'Androgenetic alopecia Diagnosis and Treatment Guidelines 2010 edition' (Non-Patent Document 2), regardless of the name 'androgenetic alopecia', it occurs in females as a pattern in which head hair over a relatively wide area of the crown becomes thin. Since androgenetic alopecia occurs as a result of hair papilla cells of the scalp of the frontal region or crown reacting with $5\alpha$ dihydrotestosterone and the hair follicles miniaturizing, if in a target having a genetic background of androgenetic alopecia, hair of the frontal region and/or crown gradually becomes vellus hair, thin, and short over a few years or longer, it is androgenetic alopecia.

Having a genetic background of androgenetic alopecia means having a genetic background of male hormone acting on male hormone-sensitive hair follicles to form vellus hair, and specifically means that it can be genetically diagnosed that hair papilla cells in the scalp of the frontal region or crown react with $5\alpha$ dihydrotestosterone to thus cause hair follicle miniaturization or means that there is a related male in a state in which head hair of the frontal region or crown has fallen out and the scalp can be seen from 20 years old onward at least among biological parents, biological brothers and sisters, biological grandparents, biological children, and biological grandchildren.

The alopecia pityroides referred to in the present specification means alopecia pityroides in terms of the normal medical meaning, and alopecia due to dandruff blocking pores to thus cause inflammation is included in alopecia pityroides.

The female pattern alopecia referred to in the present specification means female pattern alopecia in terms of the normal medical meaning, and alopecia caused by the amount of the female hormone estrogen decreasing relative to the amount of androgen in the blood stream is included in female pattern alopecia.

The postpartum alopecia referred to in the present specification means postpartum alopecia in terms of the normal medical meaning, and alopecia in which hair whose growth phase has been maintained by estrogen enters the resting phase all at once after childbirth and hair loss increases is included in postpartum alopecia.

The target referred to in the present specification means any biological individual, preferably a vertebrate, more preferably a mammal, yet more preferably a rodent such as a mouse, a rat, a Mongolian gerbil, or a guinea pig, a cat family animal such as a cat, a puma, or a tiger, a cervid animal such as a deer or an elk, a rabbit, a dog, a mink, a sheep, a goat, a cow, a horse, a monkey, or a human, and most preferably a human.

The natriuretic peptide (NP) referred to in the present invention means an A-type natriuretic peptide (ANP), a B-type natriuretic peptide (BNP), a C-type natriuretic peptide (CNP), a derivative of these NPs, a chimeric peptide of 2 or more NPs selected from these NPs, or a derivative of a chimeric peptide of the NPs, and is not particularly limited as long as it has ANP activity, BNP activity, or CNP activity. It is particularly preferably ANP, BNP, or CNP.

The ANP referred to here means ANP-28 ($\alpha$-ANP) formed from 28 amino acids, $\alpha$-ANP[4-28] formed from the $4^{th}$ to the $28^{th}$ amino acids of ANP-28, $\alpha$-ANP[5-28] formed from the $5^{th}$ to the $28^{th}$ amino acids of ANP-28, or a derivative thereof, and is not particularly limited as long as it has ANP activity. The ANP derivatives include, as long as they have ANP activity, one in which the C-terminal of ANP has been amidated, one in which the C-terminal of ANP has been methoxylated, one in which polyethylene glycol has been added to ANP, one in which a sugar chain has been added to ANP, one in which an alkyl chain has been added to ANP, and one in which a fatty acid has been added to ANP. The ANP may be $\beta$-ANP, which has a structure that is an antiparallel dimer of ANP-28, or a polymer type $\gamma$-ANP having a molecular weight of 13000 formed by cleaving a signal peptide from an ANP precursor. $\alpha$-ANP and a derivative thereof are particularly preferable. The amino acid sequence of human ANP-28 is shown as the sequence with SEQ ID No: 1 in the present specification.

The ANP derivative referred to here means one having preferably 1 to 5, more preferably 1 to 3, and yet more preferably 1 to 2 amino acids in the ANP-28 amino acid sequence deleted, substituted, or added and having ANP activity, or one having a sequence that is at least 85%, preferably at least 90%, and yet more preferably at least 95% homologous to the ANP-28 amino acid sequence and having ANP activity. The ANP derivative includes, as long as it has ANP activity, one in which the C-terminal of ANP has been amidated, one in which the C-terminal of ANP has been methoxylated, one in which polyethylene glycol has been added to ANP, one in which a sugar chain has been added to ANP, one in which an alkyl chain has been added to ANP, and one in which a fatty acid has been added to ANP.

In the present invention, provided that it has ANP activity, any known ANP can be used. Examples thereof include 819 ANP derivates disclosed as AP1 to AP819 in U.S. Pat. No. 5,047,397 or U.S. Pat. No. 4,804,650 and 32 ANP derivatives disclosed as Compound Nos. 1 to 32 in Tables 1 to 3 of U.S. Pat. No. 5,204,328.

Furthermore, the presence or absence of ANP activity may be confirmed easily by known means and, for example, it may be confirmed by testing cGMP production activity in NPR-A receptor-expressing cells.

As an active ingredient of the present invention, any ANP or derivative thereof can be used, but from the viewpoint of efficacy and availability ANP-28 is preferable.

The ANP of the present invention can be prepared by chemical synthesis or genetic engineering using a human ANP gene (e.g. Nature. 1984 Vol. 312 (5990): 152-155), but since ANP is already commercially available, it may be obtained from the market. Furthermore, it may be obtained for example as ANP (Human, 1-28) from the Peptide Institute, Inc.

As hereinbefore described, the ANP that can be used in the present invention includes purified natural ANP, recombinant ANP produced by a known genetic engineering method, and ANP produced by a known chemical synthesis method (e.g. a solid-phase synthesis method using a peptide synthesizer). Basic methods such as a gene-recombination technique, a site-specific mutagenesis method, or a PCR technique are publicly known or well known and are described in, for example, Current Protocols In Molecular Biology; John Wiley & Sons (1998).

The BNP referred to here means BNP-26, BNP-32, or BNP-45, which have 26, 32, and 45 amino acids respectively, or a derivative thereof, and is not particularly limited as long as it has BNP activity. The BNP may be a polymer type γ-BNP formed by cleaving a signal peptide from a BNP precursor and having a molecular weight of about 13000. It is particularly preferably BNP-32 or a derivative thereof. The amino acid sequence of human BNP-32 is shown as the sequence with SEQ ID No: 41 in the present specification. Furthermore, the amino acid sequence of human BNP-26 is shown as the sequence with SEQ ID No: 82 in the present specification.

The BNP derivative referred to here means one having preferably 1 to 5, more preferably 1 to 3, and yet more preferably 1 or 2 amino acids in the amino acid sequence of BNP-26, BNP-32, or BNP-45 deleted, substituted, or added and having BNP activity, or one having a sequence that is at least 85%, preferably at least 90%, and more preferably at least 95% homologous to the BNP-26, BNP-32, or BNP-45 amino acid sequence and having BNP activity. The BNP derivative includes, as long as it has BNP activity, one in which the C-terminal of BNP has been amidated, one in which the C-terminal of BNP has been methoxylated, one in which polyethylene glycol has been added to BNP, one in which a sugar chain has been added to BNP, one in which an alkyl chain has been added to BNP, and one in which a fatty acid has been added to BNP.

In the present invention, provided that it has BNP activity, any known BNP can be used. Examples thereof include a BNP derivative disclosed in published Japanese translation 2007-525213 of a PCT application, 29 BNP derivatives disclosed as SEQ ID No: 1 to 29 in U.S. Pat. No. 6,028,055, a BNP derivative disclosed by the Formula of Claim 1 in U.S. Pat. No. 5,114,923, BD-NP disclosed in U.S. Pat. No. 6,818,619, and a diuretic polypeptide or a natriuretic polypeptide disclosed in published Japanese translation 2010-500032 of a PCT application.

Furthermore, the presence or absence of BNP activity may be confirmed easily by known means and, for example, it may be confirmed by testing cGMP production activity in NPR-A receptor-expressing cells.

As an active ingredient of the present invention, any of BNP-26, BNP-32, BNP-45, and derivatives thereof can be used, but from the viewpoint of efficacy and availability BNP-32 is preferable.

The BNP of the present invention can be prepared by chemical synthesis or genetic engineering using a human BNP gene (e.g. JP, A, 5-207891, published Japanese translation 2007-525957 of a PCT application, published Japanese translation 2007-525213 of a PCT application), but since BNP is already commercially available, it may be obtained from the market. Furthermore, it may be obtained for example as BNP-32 (human) from the Peptide Institute, Inc.

As hereinbefore described, the BNP that can be used in the present invention includes purified natural BNP, recombinant BNP produced by a known genetic engineering method, and BNP produced by a known chemical synthesis method (e.g. a solid-phase synthesis method using a peptide synthesizer). Basic methods such as a gene-recombination technique, a site-specific mutagenesis method, or a PCR technique are publicly known or well known and are described in, for example, Current Protocols In Molecular Biology; John Wiley & Sons (1998), JP, A, 5-207891, etc.

The CNP referred to here means CNP-22 having 22 amino acids, CNP-53 having 53 amino acids formed by adding 31 amino acid residues to the N-terminal of CNP-22, or a derivative thereof, and is not particularly limited as long as it has CNP activity. CNP-22 and a derivative thereof are particularly preferable.

The CNP derivative referred to here means one having preferably 1 to 5, more preferably 1 to 3, and yet more preferably 1 or 2 amino acids in the CNP-22 or CNP-53 amino acid sequence deleted, substituted, or added and having CNP activity, or one having a sequence that is at least 85%, preferably at least 90%, and yet more preferably at least 95% homologous to the CNP-22 or CNP-53 amino acid sequence and having CNP activity. The CNP derivative includes, as long as it has CNP activity, one in which the C-terminal of CNP has been amidated, one in which the C-terminal of CNP has been methoxylated, one in which polyethylene glycol has been added to CNP, one in which a sugar chain has been added to CNP, one in which an alkyl chain has been added to CNP, and one in which a fatty acid has been added to CNP. The amino acid sequence of human CNP-22 is shown as the sequence with SEQ ID No: 81 in the present specification. Furthermore, the amino acid sequence of human CNP-53 is shown as the sequence with SEQ ID No: 83 in the present specification.

In the present invention, provided that it has CNP activity, any known CNP can be used. Examples thereof include a CNP derivative disclosed in JP, A, 6-9688, CNP derivatives disclosed as VNP (SEQ ID No: 4) and SEQ ID No: 9 peptides in U.S. Pat. No. 558,310, and CD-NP disclosed in U.S. Pat. No. 6,818,619. Furthermore, the presence or absence of CNP activity may be confirmed easily by known means and, for example, it may be confirmed by testing the growth-inhibitory action for vascular smooth muscle cells or cGMP production activity in NPR-B receptor-expressing cells.

As an active ingredient of the present invention, any of CNP-22, CNP-53, and derivatives thereof can be used, but from the viewpoint of absorbability CNP-22, which has a low molecular weight, is preferable. CNP-22 may be prepared by chemical synthesis or genetic engineering using a human CNP gene, but may be obtained for example from the Peptide Institute, Inc. as CNP-22 (human).

The CNP that can be used in the present invention includes purified natural CNP, recombinant CNP produced by a known genetic engineering method, and CNP produced by a known chemical synthesis method (e.g. a solid-phase synthesis method using a peptide synthesizer). Basic methods such as a gene-recombination technique, a site-specific mutagenesis method, or a PCR technique are publicly known or well known and are described in, for example, Current Protocols In Molecular Biology; John Wiley & Sons (1998), JP, A, 5-207891, etc.

The origin of a natriuretic peptide is not particularly limited as long as it has CNP activity, BNP activity, or ANP activity, but it is preferably mammal (including human)- or bird-derived NP, more preferably human-, monkey-, mouse-, rat-, or pig-derived NP, and particularly preferably human-derived NP.

With regard to amino acids that can be substituted in the ANP derivatives, BNP derivatives, and CNP derivatives, it is desirable to carry out conservative amino acid substitution. Conservative amino acids are classified according to polarity or type of electric charge. For example, nonpolar uncharged type amino acids include glycine, alanine, valine, leucine, isoleucine, proline, etc., aromatic amino acids include phenylalanine, tyrosine, and tryptophan, polar uncharged type amino acids include serine, threonine, cysteine, methionine, asparagine, glutamine, etc., negatively charged amino acids include aspartic acid and glutamic acid, and positively charged amino acids include lysine, arginine, and histidine. As described above, amino acid substitution is desirably carried out such that conservative amino acids belonging to the same class are substituted for each other. However, when another nonpolar uncharged type amino acid is substituted for proline or when proline is substituted for a nonpolar uncharged type amino acid other than proline, it is necessary to note that proline does not have a sterically flexible structure. Furthermore, when another polar uncharged type amino acid is substituted for cysteine or when cysteine is substituted for a polar uncharged type amino acid other than cysteine, it is necessary to note that cysteine can form a disulfide bond with another cysteine.

Moreover, when a natriuretic peptide (NP) is referred to in the present specification, a chimeric peptide of two or more natriuretic peptides (NPs) selected from ANP, BNP, and CNP is also included. That is, when an NP is referred to in the present specification, it also means a chimeric peptide of 2 or more natriuretic peptides (NPs) selected from ANP, BNP, and CNP, the chimeric peptide forming a cyclic structure via an intramolecular disulfide bond, the CNP being a peptide selected from the group consisting of CNP-22, CNP-53, a peptide containing any amino acid sequence having 5 or more contiguous amino acids from the CNP-22 amino acid sequence in which any 1 to 5 amino acids have been deleted, substituted, or added, and a peptide containing any amino acid sequence having 5 or more contiguous amino acids from the CNP-53 amino acid sequence in which any 1 to 5 amino acids have been deleted, substituted, or added, the BNP being a peptide selected from the group consisting of BNP-26, BNP-32, BNP-45, a peptide containing any amino acid sequence having 5 or more contiguous amino acids from the BNP-26 amino acid sequence in which any 1 to 5 amino acids have been deleted, substituted, or added, a peptide containing any amino acid sequence having 5 or more contiguous amino acids from the BNP-32 amino acid sequence in which any 1 to 5 amino acids have been deleted, substituted, or added, and a peptide containing any amino acid sequence having 5 or more contiguous amino acids from the BNP-45 amino acid sequence in which any 1 to 5 amino acids have been deleted, substituted, or added, the ANP being ANP-28 or a peptide containing any amino acid sequence having 5 or more contiguous amino acids from the ANP amino acid sequence in which any 1 to 5 amino acids have been deleted, substituted, or added, and the chimeric peptide having CNP activity, BNP activity, or ANP activity, or a derivative thereof.

A preferred chimeric peptide of the natriuretic peptides (NPs) in the present invention is a chimeric peptide of CNP and BNP. That is, it is preferable to use a chimeric peptide of CNP and BNP, the chimeric peptide forming a cyclic structure via an intramolecular disulfide bond, the CNP being a peptide selected from the group consisting of CNP-22, CNP-53, a peptide containing any amino acid sequence having 5 or more contiguous amino acids from the CNP-22 amino acid sequence in which any 1 to 5 amino acids have been deleted, substituted, or added, and a peptide containing any amino acid sequence having 5 or more contiguous amino acids from the CNP-53 amino acid sequence in which any 1 to 5 amino acids have been deleted, substituted, or added, the BNP being a peptide selected from the group consisting of BNP-26, BNP-32, BNP-45, a peptide containing any amino acid sequence having 5 or more contiguous amino acids from the BNP-26 amino acid sequence in which any 1 to 5 amino acids have been deleted, substituted, or added, a peptide containing any amino acid sequence having 5 or more contiguous amino acids from the BNP-32 amino acid sequence in which any 1 to 5 amino acids have been deleted, substituted, or added, and a peptide containing any amino acid sequence having 5 or more contiguous amino acids from the BNP-45 amino acid sequence in which any 1 to 5 amino acids have been deleted, substituted, or added, and the chimeric peptide having CNP activity or BNP activity, or a derivative thereof.

When CNP or BNP is referred to in the present specification, this means either one of CNP or BNP and also means a chimeric peptide of CNP and BNP.

The origin of CNP-22 and CNP-53 is not particularly limited as long as it has CNP activity, but it is preferably mammal (including human)- or bird-derived CNP, more preferably human-, monkey-, mouse-, rat-, or pig-derived CNP, and particularly preferably human-derived CNP. Similarly, the origin of BNP-26, BNP-32, and BNP-45 is not particularly limited as long as it has BNP activity, but it is preferably mammal (including human)- or bird-derived BNP, more preferably human-, monkey-, mouse-, rat-, or pig-derived BNP, and particularly preferably human-derived BNP. Similarly, the origin of ANP-28 is not particularly limited as long as it has ANP activity, but it is preferably mammal (including human)- or bird-derived ANP, more preferably human-, monkey-, mouse-, rat-, or pig-derived ANP, and particularly preferably human-derived ANP.

Furthermore, the derivative of a chimeric peptide of 2 or more NPs selected from ANP, BNP, and CNP referred to here means one having preferably 1 to 5, more preferably 1 to 3, and yet more preferably 1 or 2, amino acids in the NP chimeric peptide amino acid sequence deleted, substituted or added and having CNP activity or BNP activity.

The amino acids that can be substituted in a derivative of a chimeric peptide of natriuretic peptide (NP) derivatives are the same as the amino acids that can be substituted with respect to the ANP derivative, BNP derivative, and CNP derivative.

Furthermore, the derivative of the chimeric peptide of the natriuretic peptide (NP) derivatives includes, as long as it has CNP activity, BNP activity, or ANP activity, one in which the C-terminal of the chimeric peptide of the NPs has been amidated, one in which the C-terminal of the chimeric peptide of the NPs has been methoxylated, one in which polyethylene glycol has been added to the chimeric peptide of the NPs, one in which a sugar chain has been added to the chimeric peptide of the NPs, one in which an alkyl chain has been added to the chimeric peptide of the NPs, and one in which a fatty acid has been added to the chimeric peptide of the NPs.

Furthermore, the amino acid sequence of human ANP peptide represented by SEQ ID No: 1, the amino acid sequence of human BNP peptide represented by SEQ ID No: 41, and the amino acid sequence of human CNP peptide represented by SEQ ID No: 81 have, as shown in FIG. 1, four mutually different sequences separated by three common sequences represented by 'CFG', 'DRI', and 'SGLGC' amino acid sequences respectively. Therefore, as chimeric peptides of 2 or more NPs selected from ANP, BNP, and CNP, in accordance with combinations of these four mutually different sequences, at least 78 types of chimeric peptides represented by SEQ ID No: 2 to 40 and SEQ ID No: 42 to 80 can be cited as examples. It can be expected that these chimeric peptides and derivatives thereof will have properties in common with ANP, BNP, and CNP. That is, these chimeric peptides and derivatives thereof may be used as an active ingredient of the agent for the treatment of alopecia of the present invention.

As described above, in the present invention, a chimeric peptide of any known natriuretic peptides (NPs) or a derivative thereof can be used provided that it has ANP activity, BNP activity, or CNP activity. For example, it may be an aquaretic polypeptide or a natriuretic polypeptide disclosed as ABC-NP, ABC-NP1, BC-NP, etc. in published Japanese translation 2010-502231 of a PCT application, or a chimeric peptide disclosed as BD-NP (SEQ ID No: 1) or CD-NP (SEQ ID No: 2) in U.S. Pat. No. 6,818,619.

The presence or absence of ANP activity, BNP activity, or CNP activity can be easily confirmed by known means, and it can be confirmed by, for example, testing cGMP production activity in NPR-A receptor-expressing cells or NPR-B expressing cells.

All of ANP, BNP, CNP, derivatives of these NPs, and chimeric peptides of 2 or more NPs selected from these NPs are known and may be prepared by chemical synthesis or genetic engineering.

The disease to which the agent for the treatment of alopecia of the present invention is applied is not particularly limited as long as it is so-called alopecia in which hair thins or falls out. The agent for the treatment of alopecia of the present invention may be applied to various types of alopecia.

Examples of alopecia to which the agent for the treatment of alopecia of the present invention can be applied include alopecia areata, androgenetic alopecia, postpartum alopecia, female pattern alopecia, seborrheic alopecia, alopecia pityroides, and senile alopecia; from the viewpoint of the curing effect, alopecia areata, androgenetic alopecia, postpartum alopecia, and female pattern alopecia are preferable, and alopecia areata is particularly preferable.

Androgenetic alopecia may be either androgenetic alopecia in a male or androgenetic alopecia in a female. In accordance with use of the agent for the treatment of alopecia of the present invention, it is possible to regenerate effectively head hair on the frontal region or the crown.

With regard to alopecia areata, it may be any of standard alopecia areata monolocularis, standard alopecia areata multilocularis, alopecia totalis, alopecia universalis, and alopecia ophiasis, and the severity thereof may be any of S1 to S5 and B0 to B2.

The agent for the treatment of alopecia of the present invention exhibits excellent effectiveness and safety as a drug for the treatment of intractable alopecia ophiasis, which is considered to be difficult to cure or put into remission for a long time, and is effective.

The meaning of the terminology and characteristics of the symptoms of these various types of alopecia are as described in the Background Art section above.

The agent for the treatment of alopecia of the present invention contains as an active ingredient an A-type natriuretic peptide (ANP), a B-type natriuretic peptide (BNP), a C-type natriuretic peptide (CNP), a derivative of these natriuretic peptides (NPs), a chimeric peptide of 2 or more NPs selected from these NPs, or a derivative of a chimeric peptide of 2 or more NPs selected from these NPs, and its route of administration and dosage form are not particularly limited.

The agent for the treatment of alopecia of the present invention may, in addition to ANP, BNP, CNP, a derivative of these NPs, a chimeric peptide of 2 or more NPs selected from these NPs, or a derivative thereof, further contain as a combination a steroid drug, an antihistamine drug, a vasodilator, a male hormone activity inhibitor, a female hormone drug, an antibiotic, an antifungal agent, pentadecane, cytopurine (6-benzylaminopurine), t-flavanone, adenosine, cepharanthin, Glycyron (registered trademark), which is a complex of glycyrrhizin, methionine, and glycine, cyclosporin A, Keishikaryukotsuboreito, Hangekobokuto, biotin, Anthralin, or a tricyclic antidepressant, or may be used at the same time as these.

As the steroid drug, diflorasone, betamethasone, dexamethasone, clobetasol, prednisolone, mometasone, methylprednisolone, Deprodone, difluprednate, fluocinonide, amcinonide, triamcinolone, difluprednate, or hydrocortisone is preferable, and betamethasone or clobetasol is particularly preferable.

As the antihistamine drug, azelastine, oxatomide, fexofenadine, emedastine, ebastine, cetirizine, bepotastine, olopatadine, or loratadine is preferable.

As the vasodilator, minoxidil or carpronium chloride is preferable. As the male hormone activity inhibitor, finasteride is preferable.

As the female hormone drug, estrogen, estradiol, or progesterone is preferable.

As the antibiotic, gentamicin is preferable. As the antifungal agent, amphotericin B, nystatin, ketoconazole, terbinafine, flucytosine, fluconazole, itoraconazole, griseofulvin, or micafungin is preferable.

The agent for the treatment of alopecia of the present invention can be made into a preparation by generally used techniques. Examples of the preparation configuration include an external preparation.

The dosage form of the agent for the treatment of alopecia of the present invention is preferably an external preparation (percutaneous absorbent) such as a gel, an ointment, or a liquid.

The external preparation is not particularly limited and the present agent may be directly applied, sprayed, or put as a patch onto a required site (affected part) of the skin. The configuration of the agent for the treatment of alopecia of the present invention is preferably an external preparation such as an ointment, gel, cream, lotion, liquid, spray, gel spray, foam, patch, shampoo, treatment, scalp treatment, or tonic, it is particularly preferably an ointment, gel, cream, or liquid from the viewpoint of simplicity of application, and it is yet more preferably a gel, ointment, or liquid.

These external preparations may be easily obtained in accordance with publicly or well known methods by formulating a natriuretic peptide (NP) as an active ingredient or principal agent, a pharmaceutically acceptable base, and various types of additives as necessary.

The gel (suspension base) may be any of a hydrogel, an anhydrous gel, or a gel formed from a swellable gel-forming material and having a low water content. Furthermore, either a hydrogel base or a lyogel base may be used, but a transparent hydrogel having an inorganic or organic macromolecular base is preferable. In the same way as for a preparation containing an oil or a fat, the gel itself is not absorbed by the skin.

A hydrogel base is free from fat, has a consistency similar to that of an ointment, and aims to increase the percutaneous absorbability of the medicinal agent, and a lyogel base is formed by suspending stearyl alcohol, etc. in propylene glycol to form a gel and has excellent percutaneous absorbability and hygroscopicity. The gel may be used as a gel spray by charging a spray container therewith.

The gel of the present invention may be a gel in which a natriuretic peptide (NP) as an active ingredient is uniformly dispersed in a hydrophilic gel base containing a carboxyvinyl polymer, sodium polyacrylate, sodium polyacrylate, a (vinyl methyl ether/ethyl maleate) copolymer, polymethacrylate, propylene glycol, etc. Examples of such a gel include a gel formed by uniformly dispersing in a commercially available long-lasting water retention agent such as Lubrajel NP, Lubrajel CG, Lubrajel DV, Lubrajel MS, Lubrajel OIL, Lubrajel TW, or Lubrajel DS, which are commercial products from ISP Japan Ltd.

One specific example of the 'gel' of the present invention is a gel preparation prepared in accordance with Example 2.

The liquid of the present invention is one in which a natriuretic peptide (NP) as an active ingredient is dissolved in alcohol, propylene glycol, polyethylene glycol, water, etc. as a base, and is preferably a liquid formed from an aqueous solution in which a natriuretic peptide is dissolved in physiological saline. The aqueous solution may contain a small amount of organic base such as alcohol, propylene glycol, or polyethylene glycol in addition to physiological saline.

In this case, in order to ensure the biological utilization rate and provide a more effective liquid preparation, a natriuretic peptide is used as an active ingredient, an acidic solution may be formed by combining it with one type or two or more types from the group consisting of butyric acid, lactic acid, phosphoric acid, glycine, citric acid, hydrochloric acid, propionic acid, butyric acid, benzoic acid, and salts thereof, or a polar organic solution may be formed by combining it with one type or two or more types from the group consisting of an alcohol and/or N-methyl-2-pyrrolidine, dimethylformamide, dimethylsulfoxide, and methylparaben, and the pH may be adjusted to 3.0-7.0.

The ointment preparation of the present invention may be either an oleaginous base or a water-soluble base, and both may easily be obtained in accordance with a known method. An oleaginous base such as Vaseline causes little irritation, has no odor, and is excellent in terms of skin protecting action, softening action, crust removing action, granulation, and epithelization promoting action. The water-soluble base is an ointment mainly containing a Macrogol base and has a strong effect in absorbing and removing aqueous secretions.

One specific example of the 'ointment' of the present invention is an ointment prepared in accordance with Example 2.

The cream (emulsion base) may be an oil-in-water base (O/W) (vanishing cream) or a water-in-oil base (W/O) (cold cream). The oil-in-water base has a smaller amount of oil-soluble component than water-soluble component, and has the advantage that when applied the whiteness of the cream seems to disappear. It also spreads well, has a good feeling when used, even on sweaty skin, and has excellent cosmetic aspects. Furthermore, since it has excellent absorbability toward the skin, application to a chronic hypertrophic lesion is good. The water-in-oil base contains a smaller amount of water-soluble component than oil-soluble component and is also called a cold cream since when applied to and spread on the skin it exhibits a cooling action.

The lotion means a liquid external preparation in which a natriuretic peptide is dissolved or uniformly dispersed in a liquid. Since an ointment or a cream sticks to the hair, a lotion is suitable for use on head hair, etc. The configuration of the lotion may be any of a suspension lotion base, an emulsion lotion, and a solution lotion base.

The patch promotes absorption of a medicinal agent by making a component containing a natriuretic peptide adhere to the patch and utilizing the airtightness of the patch. Applying a patch enables scratching to be prevented.

The spray is used by making a solution of a natriuretic peptide and spraying by means of gas pressure or a hand pushing operation. It is convenient when used over a wide area.

The foam is a spray that is released in the form of a foam by making a solution of a natriuretic peptide and adding a surfactant. The foam is excellent in terms of adhesion to the scalp.

The shampoo is a dosage form that has a natriuretic peptide mixed or dissolved in a shampoo and that can apply the medicinal agent at the same time as washing the hair. Since a shampoo is a surfactant, it has an effect in making a natriuretic peptide penetrate into the scalp. In seborrheic alopecia in particular, a shampoo is advantageous since it can also remove excessive sebum.

The treatment is a dosage form that has a natriuretic peptide mixed or dissolved in a treatment used when washing hair and that can apply the medicinal agent at the same time as treatment being carried out. The treatment can supplement moisture and oil content in the scalp at the same time as application of the medicinal agent. In alopecia pityroides in particular, a treatment is advantageous since it can also moisturize and supplement the oil content in the scalp at the same time as application of the medicinal agent.

The scalp treatment is a treatment agent in which a component designed to moisturize or supplement the oil content in the scalp is particularly formulated. A scalp treatment often contains various plant extract components such as rosemary extract, soapberry extract, or coconut extract.

The tonic may be prepared by adding a natriuretic peptide to 50% to 70% alcohol and water as a substrate, a component having an action of keeping head hair and the scalp healthy such as hinokitiol, panthenol, or Swertia Japonica extract, and dipotassium glycyrrhizinate, which exhibits a female hormone-like action, together with a microbicidal agent, a moisturizing component such as glycerol, salicylic acid, which makes it easy to remove dandruff, menthol, which prevents itchiness and gives a refreshing feel, a fragrance, etc. A tonic is advantageous as a dosage form of an agent for the treatment of alopecia that is often accompanied by itchiness since it is a dosage form that is used after washing hair in order to prevent dandruff and head odor, maintain the cleanliness of head hair, prevent itchiness and perspiration damage, and remove unpleasant symptoms related to head hair.

As described above, the agent for the treatment of alopecia of the present invention is a percutaneous external preparation formed by formulating appropriate amounts of a natriuretic peptide, various types of base, and additives as necessary. In order to exhibit efficacy as an external preparation, the way in which the natriuretic peptide as an active ingredient applied to the skin surface reaches a lesion area at an effective concentration and is maintained is important. Therefore, the dosage form and the base may be selected appropriately according to the symptoms or the patient.

Furthermore, an additive may be used as appropriate according to the intended application. As the additive, those below can be used.

Vaseline: may be used as a base of an ointment preparation. Its viscosity and consistency changes depending on temperature and the hardness varies between winter and summer, but it is one of the safest bases. There are yellow Vaseline and white Vaseline, which has a high degree of purification, and either may be used.

Propylene glycol: may be used as a solvent for a drug, a solution adjuvant, or a base.

Paraffin: may be used when the consistency of an ointment is adjusted. Since it is comparatively easy to emulsify, it may be used as an oleaginous agent in production of a cream.

Beeswax (white beeswax): processed beehive wax, and may be used as a Japanese Pharmacopoeia simple ointment by formulating with a plant oil. White beeswax is formed by bleaching beeswax so as to improve color and odor.

Macrogol: a mixture of polyethylene glycols having different molecular weights. It has excellent solubility and miscibility for a medicinal agent, absorbs water well, and is therefore suitable when absorbing and removing a liquid leached out from the mucous membrane or the affected lesion area.

Stearyl alcohol: may be used in an emulsion lotion.

Isopropanol: may be used as a solvent, a solution adjuvant, etc.

Benzyl alcohol: may be used as a solution adjuvant, a preservative, etc.

Parahydroxybenzoic acid esters (parabens): may be used as an antiseptic, a preservative, or a stabilizer.

Gelled hydrocarbon: generally called a 'Plastibase' and formed by gelling (semi-solidifying) liquid paraffin using polyethylene.

Citric acid and sodium citrate: may be used as a buffer or a pH adjusting agent.

Squalene: used as a base and has a slightly less oily feel and less stickiness than liquid paraffin. It can be used widely in emulsion lotions as well as in creams.

Lanolins: fats obtained from sheep wool, useful for improvement of skin suppleness although they have a problem with color and odor.

Glycerol: may be formulated into a cream, etc. as a moisturizing agent.

Polyoxyethylene hardened castor oil: may be used as an emulsifying agent, a solubilizing agent, etc.

Sorbitan fatty acid ester and glycerol fatty acid ester: may be used as an emulsifying agent, etc.

The agent for the treatment of alopecia of the present invention may further contain a moisturizing agent (skin softening agent), a symptom-relieving agent, etc., which are described below.

Moisturizing agent (skin softening agent): a moisturizing agent provides moisture and oil to the skin. A moisturizing agent is most effective if it is used when the skin is already wet, as is the case immediately after a bath or shower. Components contained in the moisturizing agent are glycerol, mineral oil, Vaseline, etc. With regard to the form and type of the moisturizing agent, there is a lotion, a cream, an ointment, a bath oil, etc. One containing urea, lactic acid, or glycolic acid is excellent in terms of moisturizing effect.

Symptom-relieving agent: many skin diseases are accompanied by itchiness. Itchiness and a slight degree of pain can be relieved by formulating a sedative, specific examples thereof including chamomile, eucalyptus, camphor, menthol, zinc oxide, talc, glycerol, and Calamine. In order to suppress itchiness due to allergy, an antihistamine agent such as diphenhydramine may be added.

As hereinbefore described, when producing the agent for the treatment of alopecia of the present invention, various types of base, moisturizing agent, UV absorbing agent, alcohol, chelate, pH adjusting agent, antiseptic, thickener, colorant, fragrance, filler, excipient, disintegrant, extending agent, binder, film-forming agent, solubilizing agent, suspending agent, buffer, stabilizer, preservative, surfactant, antioxidant, dispersant, emulsifying agent, solvent, solution adjuvant, etc. may be formulated in any combination. Furthermore, in addition to a natriuretic peptide, which is the main medicinal component, various types of medicinal agents such as an anti-inflammatory and analgesic agent, a microbicidal agent, a vitamin, and a skin softening agent may be appropriately formulated as necessary.

When the skin external preparation composition of the present invention is used as a skin texture improvement agent, it may be used as a skin care cosmetic or a quasi-drug, and specific examples of the application form include a cream, a foam, a cosmetic lotion, a pack, a skin softener, an emulsion, a foundation, a makeup base, an essence, a soap, a liquid washing agent, a bath agent, a sunscreen cream, a sun oil, and a spray type liquid. All thereof may be produced easily by applying a publicly or well known preparation technique.

As representative preparation examples of the present agent for the treatment of alopecia, production of a gel, an ointment, and a liquid is now explained.

A gel may be obtained, in accordance with a publicly or well known method, by dissolving an appropriate amount of natriuretic peptide in distilled water or physiological saline to give an aqueous solution, and mixing and stirring this with a publicly or well known gel base. When the concentration of the natriuretic peptide is no greater than 1 µg/g, the effect is not sufficient, and a sufficient effect can be obtained without formulating it over 1000 µg/g. Preparation is carried out such that the final concentration of the natriuretic peptide in the gel is preferably 1 to 1000 µg/g, more preferably 10 to 500 µg/g, yet more preferably 20 to 300 µg/g, even more preferably 30 to 200 µg/g, and particularly preferably 50 to 100 µg/g.

Examples of a gel base formed from a macromolecular inorganic component include hydrated or water-absorbing silicates such as aluminum silicate, for example bentonite, magnesium aluminum silicate, and colloidal silica. As a gel base formed from a macromolecular organic material, a natural, semi-synthetic, or synthetic polymer may be used. Examples of the natural and semi-synthetic polymers include polysaccharides such as cellulose, starch, tragacanth, gum arabic, xanthan gum, agar-agar, gelatin, alginic acid, a salt thereof such as sodium alginate, and a derivative thereof, a lower alkyl cellulose such as methylcellulose or ethylcellulose, and a carboxy- or hydroxy-lower-alkyl cellulose such as carboxymethylcellulose or hydroxypropylcellulose. Examples of the synthetic gel base include polyvinyl alcohol, polyvinylpyrrolidone, polyacrylic acid, and polymethacrylic acid. Furthermore, a gel base formed by carrying out uniform dispersion in a commercially available long-lasting water retention agent such as Lubrajel NP, Lubrajel CG, Lubrajel DV, Lubrajel MS, Lubrajel OIL, Lubrajel TW, or Lubrajel DS, which are commercial products from ISP Japan Ltd., may be used. With regard to these gel bases, one type thereof or a gel base mixture of two or more types thereof may be used.

The ointment (Vaseline preparation) may be obtained, in accordance with a publicly or well known method, by dissolving an appropriate amount of natriuretic peptide in distilled water or physiological saline to give an aqueous solution, and mixing and stirring this with a publicly or well known Vaseline. When the concentration of the natriuretic peptide is no greater than 1 μg/g, the effect is not sufficient, and a sufficient effect can be obtained without formulating it over 1000 μg/g. Preparation is carried out so that the final concentration of the natriuretic peptide in the ointment is preferably 1 to 1000 μg/g, more preferably 10 to 500 μg/g, yet more preferably 20 to 300 μg/g, even more preferably 30 to 200 μg/g, and particularly preferably 50 to 100 μg/g.

The liquid may be prepared by, for example, dissolving as a main agent 0.01 mg to 10 mg of human ANP (1-28) (Peptide Institute, Inc.), human BNP-32 (Peptide Institute, Inc.), or human CNP-22 (Peptide Institute, Inc.) in 10 mL of physiological saline, thus giving a liquid having a natriuretic peptide concentration of 1 to 1000 μg/g. Since the specific gravity of water is 1, in this case the ANP concentration, the BNP concentration, and the CNP concentration are 1 to 1000 μg/g ratio by weight. When the concentration of the natriuretic peptide is no greater than 1 μg/g, the effect is not sufficient, and a sufficient effect can be obtained without formulating it over 1000 μg/g. The concentration of the natriuretic peptide in the aqueous solution preparation is preferably 1 to 1000 μg/g, more preferably 10 to 500 μg/g, yet more preferably 20 to 300 μg/g, even more preferably 30 to 200 μg/g, and particularly preferably 50 to 100 μg/g.

A percutaneous absorption adjuvant may be added as desired. Examples of the percutaneous absorption adjuvant include acetic acid, sodium acetate, limonene, menthol, salicylic acid, hyaluronic acid, oleic acid, N,N-diethyl-m-toluamide, n-butyl stearate, benzyl alcohol, isopropyl myristate, isopropyl palmitate, polypropylene glycol, crotamiton, diethyl sebacate, N-methylpyrrolidone, N-ethylpyrrolidone, and lauryl alcohol. Furthermore, an antiseptic, an antioxidant, etc. may be added as desired.

The concentration of the natriuretic peptide in the present agent for the treatment of alopecia may be selected as appropriate while taking into consideration symptoms, age, dosage form, etc. The concentration of the natriuretic peptide is preferably 1 to 1000 μg/g relative to the external preparation such as a liquid, a gel, an ointment, or a lotion, more preferably 10 to 500 μg/g, yet more preferably 20 to 300 μg/g, even more preferably 30 to 200 μg/g, and particularly preferably 50 to 100 μg/g. It is preferable to use one with a concentration of 20 to 100 μg/g for a young patient or a patient with weak skin. Since the solution used in the liquid of the present invention has a specific gravity of substantially 1, when the concentration of ANP, BNP, or CNP in the liquid is expressed using units of μg/g, it has the same meaning as that when the concentration of the natriuretic peptide is expressed using units of μg/mL.

Administration of the present agent for the treatment of alopecia depends on symptoms, age, agent form, etc., but it is typically twice a day and the period of administration is from 7 days to 28 days. In the case of alopecia in the chronic stage where symptoms are fixed, it is desirable to carry out administration for about 28 days, but in the acute stage administration for about 7 days is sufficient. In general, it is desirable to carry out administration for at least 14 days for an adult but administration for about 7 days is sufficient for a minor.

The present invention is explained below by reference to Examples, but the present invention is in no way limited to these Examples, etc.

EXAMPLES

Example 1

Diagnosis and Evaluation of Test Subjects

First, prior to administration of a natriuretic peptide preparation, diagnosis and evaluation of test subjects were carried out. Methods for the diagnosis and evaluation of test subjects were as follows.

1. Diagnosis of Test Subject;

The test subjects were patients with alopecia areata, androgenetic alopecia, postpartum alopecia, female pattern alopecia, alopecia pityroides, and senile alopecia. Diagnosis and treatment of these test subjects were carried out by the present inventors as physicians.

2. Evaluation of Symptoms;

Clinical classification of alopecia was carried out in accordance with the Classification of the Japanese Dermatological Association, and evaluation of the severity of alopecia areata was carried out in accordance with the above-mentioned 'USA Alopecia Areata Evaluation Guidelines', the area of hair loss being classified using 6 grades of S0 to S5 and the hair loss site being classified using 3 grades of B0 to B2.

3. Test Method;

In general, in order to confirm the effect of an external medicine in an individual case, a method involving separate left and right applications is desirable. The separate left and right application method is a method in which, for example, an external medicine containing an active ingredient to be tested is applied to the left-hand side of an affected site, and an external medicine not containing the active ingredient is applied to the right-hand side, thus enabling a therapeutic effect to be confirmed. With regard to the test of the preparation of the present invention, a preparatory test was carried out in accordance with the separate left and right applications method. However, taking into consideration medical ethics, the preparatory test in accordance with the separate left and right applications method was minimized, and when a preparatory test was not carried out, a therapeutic effect was evaluated by comparison between that before application and that after application.

Example 2

1. Production of Gel

Preparation of a gel containing an NP as an active ingredient was carried out by weighing, as a main agent, 3 mg of any one of human ANP(1-28) (Peptide Institute, Inc.), human BNP-32 (Peptide Institute, Inc.), and human CNP-22 (Peptide Institute, Inc.), dissolving this in 3 mL of purified water to give an NP solution having a concentration of 1000 μg/mL, and mixing 1 mL of this solution with 9 g of Lubrajel NP (ISP Japan Ltd.) by uniform stirring, thus giving an ANP gel, a BNP gel, and a CNP gel having a concentration of 100 μg/g.

Similarly, 500 μL of the NP solution having a concentration of 1000 μg/mL obtained above was diluted with 500 μL of physiological saline to thus adjust the concentration to 500 μg/mL, and 1 mL of this solution was mixed with 9 g of Lubrajel NP (ISP Japan Ltd.) by uniformly stirring, thus giving an ANP gel, a BNP gel, and a CNP gel having a concentration of 50 μg/g.

2. Production of Ointment (Vaseline Preparation)

Preparation of an ointment (Vaseline preparation) containing an NP as an active ingredient was carried out by weighing, as a main agent, 3 mg of any one of human ANP(1-28) (Peptide Institute, Inc.), human BNP-32 (Peptide Institute, Inc.), and human CNP-22 (Peptide Institute, Inc.), dissolving this in 3 mL of physiological saline to give an NP solution having a concentration of 1000 μg/mL, and mixing 1 mL of this solution with 9 g of Japanese pharmacopoeia white Vaseline by uniform stirring at high speed, thus giving an ANP ointment, a BNP ointment, and a CNP ointment having a concentration of 100 μg/g.

Similarly, 500 μL of the NP solution having a concentration of 1000 μg/mL obtained above was diluted with 500 μL of physiological saline to thus adjust the concentration to 500 μg/mL, and 1 mL of this solution was mixed with 9 g of Japanese pharmacopoeia white Vaseline by uniformly stirring at high speed, thus giving an ANP ointment, a BNP ointment, and a CNP ointment having a concentration of 50 μg/g.

Similarly, 300 μL of the BNP solution having a concentration of 1000 μg/mL obtained above was diluted with 700 μL of physiological saline to thus adjust the concentration to 300 μg/mL, and 1 mL of this solution was mixed with 9 g of Japanese pharmacopoeia white Vaseline by uniformly stirring at high speed, thus giving a BNP ointment having a concentration of 30 μg/g.

3. Production of BNP:Betamethasone:Gentamicin Combination

Preparation of a BNP, betamethasone, and gentamicin combination was carried out by mixing Dermosol (trademark) G lotion (Dermosol-G Lotion) manufactured by Iwaki Seiyaku Co., Ltd. with the BNP gel obtained in '1. Production of gel' above at equal volumes. In the present specification, this is called a BNP:betamethasone:gentamicin combination. Since Dermosol G lotion contains betamethasone valerate at a concentration of 1200 μg/mL and gentamicin sulfate at a concentration of 1000 μg/mL, mixing the CNP gel having a concentration of 100 μg/g and Dermosol G lotion at a 1:1 ratio by volume gave a combination containing CNP at a concentration of 50 μg/g, betamethasone valerate at a concentration of 600 μg/mL, and gentamicin sulfate at a concentration of 500 μg/mL. In the present specification, this is called a 50 μg/g BNP:600 μg/mL betamethasone:500 μg/mL gentamicin combination.

4. Production of CNP:Betamethasone:Gentamicin Combination

Preparation of a CNP, betamethasone, and gentamicin combination was carried out by mixing Dermosol (trademark) G lotion (Dermosol-G Lotion) manufactured by Iwaki Seiyaku Co., Ltd. with the CNP gel obtained in '1. Production of gel' above at equal volumes. In the present specification, this is called a CNP:betamethasone:gentamicin combination. Since Dermosol G lotion contains betamethasone valerate at a concentration of 1200 μg/mL and gentamicin sulfate at a concentration of 1000 μg/mL, mixing the CNP gel having a concentration of 100 μg/g and Dermosol G lotion at a 1:1 ratio by volume gave a combination containing CNP at a concentration of 50 μg/g, betamethasone valerate at a concentration of 600 μg/mL, and gentamicin sulfate at a concentration of 500 μg/mL. In the present specification, this is called a 50 μg/g CNP:600 μg/mL betamethasone:500 μg/mL gentamicin combination Similarly, mixing the CNP gel having a concentration of 50 μg/g and Dermosol G lotion at a 1:1 ratio by volume gave a combination containing CNP at a concentration of 25 μg/g, betamethasone valerate at a concentration of 600 μg/mL, and gentamicin sulfate at a concentration of 500 μg/mL. In the present specification, this is called a 25 μg/g CNP:600 μg/mL betamethasone:500 μg/mL gentamicin combination.

5. Production of BNP:Clobetasol Combination

A combination of BNP and clobetasol propionate was prepared by mixing Dermovate (trademark) Scalp Lotion 0.05% (Dermovate Scalp Lotion 0.05%) manufactured by GlaxoSmithKline plc and the BNP gel obtained in '1. Production of gel' above at equal volumes. In the present specification, this is called a BNP:clobetasol combination. Since Dermovate Scalp Lotion 0.05% contains clobetasol propionate at a concentration of 500 μg/g, mixing the BNP gel having a concentration of 100 μg/mL and Dermovate Scalp Lotion 0.05% at a 1:1 ratio by volume gave a combination containing BNP at a concentration of 50 μg/mL and clobetasol propionate at a concentration of 250 μg/g. In the present specification, this is called a 50 μg/mL BNP:250 μg/g clobetasol combination.

6. Production of CNP:Clobetasol Combination

A combination of CNP and clobetasol propionate was prepared by mixing Dermovate (trademark) Scalp Lotion 0.05% (Dermovate Scalp Lotion 0.05%) manufactured by GlaxoSmithKline plc and the CNP gel obtained in '1. Production of gel' above at equal volumes. In the present specification, this is called a CNP:clobetasol combination. Since Dermovate Scalp Lotion 0.05% contains clobetasol propionate at a concentration of 500 μg/g, mixing the CNP gel having a concentration of 100 μg/mL and Dermovate Scalp Lotion 0.05% at a 1:1 ratio by volume gave a combination containing CNP at a concentration of 50 μg/mL and clobetasol propionate at a concentration of 250 μg/g. In the present specification, this is called a 50 μg/mL CNP:250 μg/g clobetasol combination.

7. Production of CNP:Carpronium Chloride Combination

A combination of CNP and carpronium chloride was prepared by mixing Calpranin (trademark) solution 5% (Calpranin) manufactured by Taiyo Pharmaceutical Industry Co., Ltd. with the CNP gel obtained in '1. Production of gel' above at equal volumes. In the present specification, this is called a CNP:carpronium chloride combination. Since the Calpranin solution 5% contains carpronium chloride at a concentration of 50 mg/mL, mixing the CNP gel having a concentration of 100 μg/mL and the Calpranin solution 5% at a 1:1 ratio by volume gave a combination containing CNP at a concentration of 50 μg/mL and carpronium chloride at a concentration of 50 mg/mL. In the present specification, this is called a 50 μg/mL CNP gel:50 mg/mL carpronium chloride combination.

Example 3

1. Diagnosis and Treatment of Test Subjects

Prior to administration of the ANP gel, BNP gel, CNP gel, BNP ointment, and CNP ointment of the present invention, as is routine for dermatological diagnosis and treatment, the test subjects were interviewed regarding age, gender, history of disease, and family history of disease; when an allergic predisposition was suspected, a scratch test against the main allergens and an evaluation thereof were carried out. In dermatological diagnosis and treatment, since there are a relatively large number of patients who have strong immunoreactivity toward a specific allergen, or a disease such as atopic dermatitis that is suspected to be related to having an allergic predisposition, in order to assist diagnosis, an interview with respect to family history and previous history of allergic disease in addition to gender and age, and a scratch test toward the main allergens, are widely carried out as simple supplemental test methods.

With regard to evaluation of the results of the scratch test, when a reactivity of 1+ or above is exhibited toward any allergen, there can be said to be a more or less allergic predisposition. In the case of patients who come to the dermatology department, many show a reactivity of 1+ or 2+ toward some allergens in the scratch test, and there are only few patients who do not show any reactivity toward any of the allergens. Since the scratch test is a simple test for estimating the presence or absence of an allergic predisposition, it cannot precisely evaluate whether or not there is allergic predisposition but, empirically, if a reactivity of 2+ is shown for a specific allergen, the relationship with an immune disease should be noted when carrying out diagnosis.

Table 1 to Table 23 show the results of interviews with the test subjects and the results of the scratch test together with evaluation of the diagnostic findings and symptoms of the test subjects carried out in [Example 1] above.

The therapeutic effects of the agent for the treatment of alopecia of the present invention on each alopecia are summarized in the Tables as follows.

Therapeutic Effect on Alopecia Areata:
    ANP: Table 1, Table 2
    BNP: Table 3-1, Table 3-2
    CNP: Table 4, Table 5, Table 6, Table 7-1
    BNP:betamethasone:gentamicin combination: Table 7-2
    CNP:betamethasone:gentamicin combination: Table 7-3

Therapeutic Effect on Androgenetic Alopecia:
    ANP: Table 8
    BNP: Table 9-1, Table 9-2
    CNP: Table 10-1, Table 10-2
    CNP:betamethasone:gentamicin combination: Table 10-3
    CNP:clobetasol combination: Table 10-4
    CNP:carpronium chloride combination: Table 10-5
    Multilayer application of CNP gel and minoxidil: Table 10-6
    Multilayer application of BNP gel and minoxidil: Table 10-7

Therapeutic Effect on Postpartum Alopecia:
    ANP: Table 10-8
    BNP: Table 10-9
    CNP: Table 11-1

Therapeutic Effect on Female Pattern Alopecia:
    BNP: Table 11-2
    CNP: Table 12

Therapeutic Effect on Seborrheic Alopecia:
    ANP: Table 13
    BNP: Table 14

Therapeutic Effect on Alopecia Pityroides:
    ANP: Table 15
    BNP: Table 16
    CNP: Table 17, Table 18

Therapeutic Effect on Senile Alopecia:
    ANP: Table 19
    BNP: Table 20
    CNP: Table 21

Therapeutic Effect on Cancer Chemotherapy Drug-Induced Alopecia:
    BNP: Table 22
    CNP: Table 23

The 'non-recurrence period' referred to here means the period during which the symptoms did not recur even when treatment with the preparation of the present invention was discontinued after the symptoms had been relieved. In order to carry out evaluation objectively, photographs before and after application of the NP preparation were recorded in all cases. Photographs of some of these cases are shown in the drawings.

Example 4

2. Therapeutic Effect of ANP Gel on Alopecia Areata

The therapeutic effects of the ANP gel on alopecia areata are shown in Table 1 (cases A1 to A5) and Table 2 (cases A6 and A7).

TABLE 1

| | Case | | | | |
|---|---|---|---|---|---|
| | A1 (=C5) | A2 | A3 (=C15) | A4 | A5 (=B3) |
| Figure | | FIG. 7 | FIG. 8-1 FIG. 8-2 | FIG. 9 | FIG. 10 |
| Gender | Female | Female | Female | Male | Male |
| Age | 33 years old | 33 years old | 52 years old | 32 years old | 16 years old |
| When developed | 13 years old | 31 years old | 51 years old | 1 month earlier | 7 years old |
| Hair loss range | S3 | S3 | S3 | S1 | S3 |
| Treatment site | Right temporal region | Right temporal region, back of the head, crown | Right temporal region | Left temporal region, crown, right temporal region | Right temporal region |
| Hair loss site other than head | Eyebrows (B1) | None (B0) | None (B0) | None (B0) | Eyebrows, lower limbs (B1) |
| Family history of alopecia | None | None | None | None | None |
| Family history of immune disease | Mother: atopic dermatitis Older sister: atopic dermatitis, allergic rhinitis | None | None | None | None |
| Previous history | Atopic dermatitis, atopic alopecia | None | Allergic rhinitis | Atopic dermatitis, allergic rhinitis | Atopic dermatitis |

TABLE 1-continued

| | Case | | | | |
|---|---|---|---|---|---|
| | A1 (=C5) | A2 | A3 (=C15) | A4 | A5 (=B3) |
| Scratch Test | House dust: 2+<br>Mite: 1+<br>Cedar: —<br>Dactylis: 2+<br>Ragweed: 2+ | House dust: 2+<br>Mite: 3+<br>Cedar: 3+<br>Dactylis: 2+<br>Ragweed: 2+ | House dust: 1+<br>Mite: —<br>Cedar: 3+<br>Dactylis: 2+<br>Ragweed: 2+ | House dust: 2+<br>Mite: 3+<br>Cedar: 2−<br>Dactylis: 1+<br>Ragweed: 1+ | House dust: 3+<br>Mite: 3+<br>Cedar: —<br>Dactylis: 2+<br>Ragweed: 1+ |
| Effect of minoxidil | Not applied | Not applied | Not applied | Not applied | Not applied |
| Effect of steroid drug | No effect | No effect | Unknown | Not applied | No effect |
| Effect of cooling therapy | No effect | Not applied | Not applied | Not applied | Not applied |
| Antiallergic drug | Not applied | Not applied | Not applied | Not applied | Not applied |
| Effect of carpronium chloride | Not applied | No effect | No effect | Not applied | Not applied |
| Effect of cepharanthin | Not applied | No effect | Not applied | Not applied | Not applied |
| Dosage form | ANP gel | ANP gel | ANP gel (changed to ANP gel after 2 weeks' application of CNP ointment) | ANP gel | ANP gel |
| Dose | 100 µg/g | 100 µg/g | 100 µg/g | 100 µg/g | 100 µg/g |
| Number of days used | 21 days | 5 weeks | 5 weeks | 4 weeks | 21 days |
| Degree of improvement in symptoms | S3→S3 | S3→S3 | S3→S2 | S1→S0 | S3→S3 |
| Non-recurrence period | Insufficient effect | Insufficient effect | Treatment continuing | 2 weeks | No effect |

Case A1

The test subject was a 33 year old female and was a patient with severe alopecia areata for which the hair loss range was S3 and which, other than the head, was accompanied by B1 hair loss of the eyebrows. There was a previous history of atopic dermatitis, and coexisting alopecia due to exacerbation of atopic dermatitis. The results of the scratch test were house dust 2+, mite 1+, Dactylis 2+, and ragweed 2+. This test subject showed erythema and pityriatic scale accompanied by itching in the scalp of the hair loss site, and there was coexisting alopecia pityroides. For this test subject, a circular bald area had appeared at the age of 13 and also in the crown at the age of 14, and it had then become alopecia totalis in half a month. Following this, the symptoms of the test subject had fluctuated, and alopecia had extended to the entire body at the age of 15. External and orally administered steroid had not given any therapeutic effect at all with this test subject. This test subject had continued to receive stimulation therapy with liquid nitrogen, but there had been hardly any therapeutic effect. This test subject was the same test subject as that of case C5.

When 100 µg/g ANP gel was applied to the entire bald area on the right temporal region of this test subject twice a day for 3 weeks, growth of vellus hair was observed, but erythema and pityriatic desquamation of the scalp were not relieved and there was itching.

Case A2

The test subject was a 33 year old female and was a patient with severe alopecia areata having a hair loss range of S3. The results of the scratch test were house dust 2+, mite 3+, cedar 3+, Dactylis 2+, and ragweed 2+. This test subject had been affected by alopecia areata 2 years earlier and had two bald patches, which had cured spontaneously. This time, after stress in the workplace had continued for about 1 month half a year earlier, a bald area had appeared on the right temporal region, the back of the head, and the crown. This test subject had for 6 months been subjected to external steroid treatment, application of carpronium chloride, and orally administered cepharanthin, but there had been no change at all.

When 100 µg/g ANP gel was applied to the bald area on the right temporal region, the back of the head, and the crown of this test subject twice a day, hair growth was clearly confirmed in 1 week, and growth of short black hair was observed over a wider area in 2 weeks, but in terms of subjective symptoms felt by the test subject there was still a large amount of hair falling out. The rate of growth of hair after the ANP gel was applied to this test subject was slow, and there was no formation of terminal hair. A photograph of the bald area before application and a photograph of the bald area after 100 µg/g ANP gel was applied twice a day for 5 weeks are shown in FIG. 7. In the case of this test subject, although vellus hair growth was observed, formation of terminal hair was not seen, and the hair did not become long.

Case A3

The test subject was a 52 year old female and was a patient with severe alopecia areata having a hair loss range of S3. There was a previous history of allergic rhinitis. The results of the scratch test were house dust 1+, cedar 2+, Dactylis 1+, and ragweed 1+. A bald patch had appeared on the frontal region of this test subject about 1 year earlier when doing continuous night shifts, following this there had been a tendency for enlargement, and multiple bald areas had appeared over the entire scalp. Application of carpronium chloride to the bald patch had continued for 8 months, but the hair loss range had only enlarged and there had been no therapeutic effect. This test subject was a case in which there were no inflammatory symptoms such as erythema, crust, or scale on the scalp of the hair loss area. This test subject was the same test subject as the test subject of case C15.

When 100 µg/g CNP ointment was applied to the entire bald area of the right temporal region of this test subject twice a day, hair growth was confirmed in 1 week, further marked hair growth was observed in 2 weeks, and enlargement of the bald area stopped completely. Application of the CNP ointment was stopped after 14 days, from the next day after that 100 µg/g ANP gel was applied twice a day with the expectation of further effects, and the therapeutic effect of the CNP ointment continued as it was; currently, with 5 weeks elapsed after the treatment with CNP ointment started, although application of the ANP gel is continuing, thickening of terminal hair and enlargement of the hair growth area can be seen (Ref. FIG. 8-1 and FIG. 8-2). This test subject could not be subjected to continuing treatment thereafter, and the bald area remained.

Case A4

The test subject was a 32 year old male and was a patient with alopecia areata having a hair loss range of S1. There was a previous history of atopic dermatitis and allergic rhinitis. The results of the scratch test were house dust 2+, mite 3+, cedar 2+, Dactylis 2+, and ragweed 2+. A bald area, triggered by mental stress, had appeared in the left temporal region of this test subject 1 month earlier, and following this bald areas had been observed in the crown and the right temporal region. This was accompanied by itching.

When 100 μg/g ANP gel was applied to the entire bald area of this test subject twice a day, hair growth was confirmed in 1 week on all of the left temporal region, the crown, and the right temporal region. Following this, there was a cure 4 weeks after starting application. Currently, with 2 weeks elapsed after application of the ANP gel was stopped after 4 weeks, there is no recurrence of the bald patch (Ref. FIG. 9). However, application of the ANP gel to this test subject did not grow hair at the hair line on the back of the head.

Case A5

The test subject was a 16 year old male and was a patient with alopecia ophiasis type alopecia areata having a hair loss range of S3, which was said to be intractable. This test subject was also affected by atopic dermatitis. The results of the scratch test were house dust 3+, mite 3+, Dactylis 2+, and ragweed 1+. This test subject had been subjected to surgical removal of the adenoids and palatine tonsils at the age of 6, alopecia areata had occurred from the age of 7, and hair loss was also observed in the eyebrows and lower limbs in addition to the head. This test subject had not been cured by internal or external use of a steroid. Invasive erythema and scale accompanied by itching were observed on the scalp of the hair loss site of this test subject. This test subject was the same test subject as the test subject of case B3.

When 100 μg/g ANP gel was applied to the entire bald area of the right temporal region of this test subject twice a day for 3 weeks, the erythema seemed to be relieved slightly, but short terminal hair remaining around the hair loss area fell out and the hair loss range was somewhat enlarged (Ref. T1 of FIG. 10).

TABLE 2

| | Case | |
|---|---|---|
| | A6 (=C3, C4) | A7 (=C6) |
| Figure | FIG. 11 | |
| Gender | Female | Female |
| Age | 50 years old | 22 years old |
| When developed | 40 years old | >1.5 years earlier |
| Hair loss range | S2 | S3 |
| Treatment site | Crown | Frontal region, temporal region ophiasic loss area |
| Hair loss site other than head | None (B0) | Eyebrows (B1) |
| Family history of alopecia | Mother: alopecia areata | None |
| Family history of immune disease | Child: allergic rhinitis, chronic urticaria | Grandfather: atopic dermatitis Mother, older brother, older sister: allergic rhinitis |

TABLE 2-continued

| | Case | |
|---|---|---|
| | A6 (=C3, C4) | A7 (=C6) |
| Previous history | Atopic dermatitis, allergic rhinitis | Atopic dermatitis, allergic rhinitis |
| Scratch Test | House dust: 1+ Mite: 1+ Cedar: — Dactylis: 2+ Ragweed: 1+ | House dust: 2+ Mite: 3+ Cedar: — Dactylis: 1+ Ragweed: — |
| Effect of minoxidil | Not applied | Not applied |
| Effect of steroid drug | No effect | No effect |
| Effect of cooling therapy | Not applied | Not applied |
| Antiallergic drug | No effect | No effect |
| Effect of carpronium chloride | No effect | Not applied |
| Effect of cepharanthin | Not applied | Not applied |
| Dosage form | ANP gel | ANP gel |
| Dose | 100 μg/g | 50 μg/g |
| Number of days used | 14 days | 3 days |
| Degree of improvement in symptoms | S2→S2 | S3→S3 |
| Non-recurrence period | No effect | No effect |

Case A6

The test subject was a 50 year old female and was a patient with severe alopecia areata multilocularis having a hair loss range of S2. There was a previous history of atopic dermatitis and allergic rhinitis. The mother of the subject had a history of alopecia areata, and a child was affected by allergic rhinitis and chronic urticaria. The results of the scratch test were house dust 1+, mite 1+, Dactylis 2+, and ragweed 1+. Erythema and pityriatic scale accompanied by itching were observed on the scalp of the hair loss site of this test subject, and there was coexisting alopecia pityroides. This test subject had been affected by alopecia areata multilocularis 10 years earlier, and there had been repeated partial remission and recurrence of alopecia areata. When this test subject became busy at work, the symptoms of alopecia tended to deteriorate. There had been no effect from the external use of steroid and carpronium chloride and an orally administered antiallergy drug for 6 months. This test subject was the same test subject as the test subject of case C3 and case C4.

100 μg/g ANP gel was applied to the multiple bald areas on the crown of this test subject for 2 weeks, but there was no effect, rough scale increased, erythema appeared, itchiness occurred, the amount of hair falling out increased, and the hair loss range enlarged somewhat (Ref. FIG. 11).

Case A7

The test subject was a 22 year old female and was a patient with severe alopecia ophiasis type alopecia areata having a hair loss range of S3, which was said to be intractable. This test subject had a previous history of atopic dermatitis and allergic rhinitis. A grandfather of this test subject was affected by atopic dermatitis, and the father, the mother, and the brother were affected by allergic rhinitis. The results of the scratch test were house dust 2+, mite 3+, and Dactylis 1+. This test subject had been affected by a bald area more than one and half years earlier, and a band-shaped bald area in a state in which hair did not grow at all was observed with a clear border along the outside edge of the part where hair was growing. Erythema, scale, crust, and inflammatory symptoms that seemed to be due to atopic alopecia were observed on the hair loss site of this test subject, and were accompanied by itching. This test subject had hair loss on the eyebrows in addition to the head. The skin of this test subject was in an erythrodermic state, which seemed to be due to steroid rebound, and redness and infiltration were observed on the skin of the entire body including the scalp. There had been no therapeutic effect at all on this test subject from treatment with a steroid and an antiallergy drug. This test subject was the same test subject as the test subject of case C6.

50 µg/g ANP gel was applied to the entire bald area of this test subject twice a day for 3 days, but there was no improvement in redness or itching, redness appeared on the scalp somewhat, and there was no sign of hair growth.

3. Therapeutic Effect of BNP Gel on Alopecia Areata

The therapeutic effects of BNP gel are shown in Table 3-1 (cases B1 to B4 and B13) and Table 3-2 (case B26).

months, but there had been no effect, and no hair growth had been observed. This test subject was the same test subject as the test subject of case C12.

When 100 µg/g BNP gel was applied to the entire bald area of the right temporal region of this test subject twice a day morning and evening, clear hair growth was observed in 2 weeks. After the application of BNP gel was stopped after 24 days, there was no recurrence of hair loss at the application site even after 8 months had elapsed (Ref. FIG. 12-1 and FIG. 12-2).

Case B2

The test subject was a 13 year old male with alopecia areata monolocularis having a hair loss range of S1. This test subject was not subjected to a scratch test.

TABLE 3-1

| | Case | | | | |
|---|---|---|---|---|---|
| | B1 (=C12) | B2 | B3 | B4 (C9) | B13 (C13) |
| Figure | FIG. 12-1 FIG. 12-2 | FIG. 13 | FIG. 10 | FIG. 14 FIG. 57 | FIG. 34 |
| Gender | Female | Male | Male | Female | Male |
| Age | 63 years old | 13 years old | 16 years old | 24 years old | 39 years old |
| When developed | 62 years old (1.5 years earlier) | 1 month earlier | 7 years old | As a junior high school student | 2 months earlier |
| Hair loss range | S2 | S1 | S3 | S2 | S1 |
| Treatment site | Right temporal region | Crown | Right temporal region | Left frontal region, right frontal region | Right temporal region, back of the head |
| Hair loss site other than head | None (B0) | None (B0) | Eyebrows, lower limbs (B1) | None (B0) | None (B0) |
| Family history of alopecia | None | None | None | None | None |
| Family history of immune disease | None | None | None | Mother: bronchial asthma | None |
| Previous history | Allergic rhinitis, atopic dermatitis | None | Atopic dermatitis | Allergic rhinitis | None |
| Scratch Test | House dust: 2+ Mite: 1+ Cedar: — Dactylis: 2+ Ragweed: 1+ | Not tested | House dust: 3+ Mite: 3+ Cedar: — Dactylis: 2+ Ragweed: 1+ | House dust: 2+ Mite: 2+ Cedar: 2+ Dactylis: 1+ Ragweed: 1+ | House dust: 1+ Mite: 1+ Cedar: 1+ Dactylis: — Ragweed: 1+ |
| Effect of minoxidil | Not applied | Not applied | Not applied | Not applied | Not applied |
| Effect of steroid drug | No effect | Not applied | No effect | No effect | Not applied |
| Effect of cooling therapy | Not applied | Not applied | Not applied | Not applied | Not applied |
| Antiallergic drug | Not applied | Not applied | Not applied | No effect | Not applied |
| Effect of carpronium chloride | No effect | Not applied | Not applied | No effect | No effect |
| Effect of cepharanthin | Not applied | Not applied | Not applied | Not applied | Not applied |
| Dosage form | BNP gel | BNP gel | BNP gel | BNP gel (left frontal region) | BNP gel |
| Dose | 100 µg/g | 50 µg/g | 100 µg/g | 100 µg/g | 50 µg/g |
| Number of days used | 24 days | 7 days | 14 days | 21 days | 14 days |
| Degree of improvement in symptoms | S2→S0 | S1→S0 | (Note) | S2→S0 | S1→S0 |
| Non-recurrence period | 8 months | 9 months | 4 months | 1 year | 1 year |

(Note):
applied only to right temporal region and not to entire region, degree of improvement could not be evaluated by proportion (S) of bald patch area occupying entire head area.

Case B1

The test subject was a 63 year old female and was a patient with severe alopecia areata multilocularis having a hair loss range of S2. This test subject had a history of allergic rhinitis, and there was coexisting atopic dermatitis. The results of the scratch test were house dust 2+, mite 1+, Dactylis 2+, and ragweed 1+. The alopecia areata of this test subject had continued for over one and a half years. This test subject had previously received application of a steroid and carpronium chloride to the bald area continuously for 10

When 50 µg/g BNP gel was applied to the entire bald area of this test subject twice a day for 1 week, hair growth was clearly confirmed and there was a cure. After application of the BNP gel was stopped after 7 days, there was no recurrence even after 9 months had elapsed (Ref. FIG. 13).

Case B3

The test subject was a 16 year old male and was a patient with ophiasis type alopecia areata having a hair loss range of S3, which was said to be intractable. There was coexisting atopic dermatitis. The results of the scratch test were house dust 3+, mite 3+, Dactylis 2+, and ragweed 1+. This test subject had been subjected to surgical removal of the adenoids and palatine tonsils at the age of 6, alopecia areata had occurred from the age of 7, and hair loss was also observed in the eyebrows and lower limbs in addition to the head. This test subject had not been cured by internal or external use of a steroid. Invasive erythema and scale accompanied by itching were observed on the scalp of the hair loss site of this test subject. This test subject was the same test subject as the test subject of case A5.

When 100 µg/g ANP gel was applied to the bald area of the right temporal region of this test subject twice a day for 3 weeks, erythema seemed to be relieved slightly, but short terminal hair remaining around the hair loss area fell out and the hair loss range enlarged somewhat. When 100 µg/g BNP gel was then applied to the hair loss area of the right temporal region twice a day from 2 days after the ANP gel was stopped, marked hair growth was observed in 2 weeks (Ref. T2 of FIG. 10). There was no hair growth at all in the left temporal region, to which the BNP was not applied. After application of the BNP gel was stopped after 14 days, there was no recurrence for 4 months, but a new bald area occurred in another place at the time of a school entrance examination when 4 months had elapsed.

This test subject did not come to the clinic thereafter, and the progress thereafter is not known.

Case B4

The test subject was a 24 year old female and was a patient with severe alopecia areata multilocularis having a hair loss range of S2. There was a history of allergic rhinitis. The mother was affected by bronchial asthma. The results of the scratch test were house dust 2+, mite 2+, cedar 2+, Dactylis 1+, and ragweed 1+. There had been repeated partial remission and recurrence of the alopecia areata of this test subject since junior high school. A slight degree of itching sensation had started to appear on and around the frontal region half a year earlier, and following this the multiple bald areas enlarged. Even when a steroid or carpronium chloride had been applied to the hair loss site of this test subject for 3 months or an antiallergy drug had been orally administered to the test subject, hair growth had not been observed, and the susceptibility to hair loss could not be improved. This test subject was the same test subject as the test subject of case C9.

In accordance with the separate left and right application method, 100 µg/g BNP gel was applied to the left frontal region of this test subject, and only Lubrajel NP (ISP Japan Ltd.), which is a gel base, was applied to the right frontal region twice a day; hair growth was observed after 1 week only on the site of the left frontal region to which the BNP gel was applied, and after 2 weeks hair growth became more marked on the site of the left frontal region to which the BNP gel had been applied. On the other hand, no hair growth was observed on the right frontal region to which only the gel base had been applied. Therefore, it was determined that the hair growth was due to the hair growth effect of the BNP gel. Application of 100 µg/g BNP gel to the left frontal region was continued, application of 100 µg/g CNP ointment to the right frontal region was started, hair growth was also observed on the right frontal region after 1 week, and marked hair growth and hair thickening were observed on the entire hair loss site of the right frontal region after 3 weeks. Before starting the treatment two handfuls of hair had fallen out each time it was shampooed, but the amount of hair falling out decreased dramatically, and only 5 to 6 hairs fell out per shampooing. External application was stopped after the BNP gel had been applied to the left frontal region for 3 weeks and the CNP ointment to the right frontal region for 3 weeks, but following that hair continued to grow on the left frontal region and the right frontal region, the alopecia was substantially cured by the second week after application was stopped, and subsequently there was a complete cure. For this test subject, there has been no recurrence up to the present, that is, after a further 1 year has elapsed (FIG. 14 and FIG. 57).

Case B13

The test subject was a 39 year old male and is the same test subject as the test subject of case C13 described later. When 100 µg/g CNP ointment was applied twice a day to a circular bald area of the temporal region and the back of the head of this test subject, hair grew after 1 week's application, and it spontaneously cured after the application was stopped at 1 week. However, a new circular bald area occurred on the crown after 10 months had elapsed since application of the CNP ointment had stopped.

When 50 µg/g BNP gel was applied twice a day to the circular bald area of the crown of this test subject, growth of black terminal hair was observed on the entire bald area of the crown after 2 weeks' application (FIG. 34).

Progress was examined after application of the BNP gel was stopped at 2 weeks, but since hair growth was not observed in a central area, a 50 µg/g BNP:600 µg/mL betamethasone:500 µg/mL gentamicin combination was applied once a day for 2 weeks starting 3 weeks after the BNP gel was stopped, and black terminal hair grew at a higher hair growth rate.

4. Therapeutic Effect of BNP Ointment on Alopecia Areata

The therapeutic effects of BNP ointment are shown in Table 3-2 (test subjects B5 and B6).

TABLE 3-2

| | Case | | |
|---|---|---|---|
| | B5 | B6 (C10) | B26 (C7) |
| Figure | FIG. 15-1<br>FIG. 15-2<br>FIG. 16 | | FIG. 55 |
| Gender | Female | Female | Female |
| Age | 50 years old | 33 years old | 38 years old |
| When developed | 4 months earlier | 5 months earlier | 1 month earlier |
| Hair loss range | S3 | S1 | S1 |
| Treatment site | Crown, Temporal region | Left temporal region, crown, back of the head | Back of the head |
| Hair loss site other than head | None (B0) | None (B0) | None (B0) |
| Family history of alopecia | None | None | Relative: alopecia areata |

TABLE 3-2-continued

| | Case | | |
|---|---|---|---|
| | B5 | B6 (C10) | B26 (C7) |
| Family history of immune disease | None | Child: atopic dermatitis | Child: atopic dermatitis |
| Previous history | Allergic rhinitis, atopic dermatitis | None | None |
| Scratch Test | House dust: 3+<br>Mite: 3+<br>Cedar: 3+<br>Dactylis: 2+<br>Ragweed: 2+ | House dust: 2+<br>Mite: 2+<br>Cedar: —<br>Dactylis: 2+<br>Ragweed: 2+ | Not tested |
| Effect of minoxidil | Not applied | Not applied | Not applied |
| Effect of steroid drug | No effect | No effect | No effect |
| Effect of cooling therapy | Not applied | Not applied | Not applied |
| Antiallergic drug | Not applied | No effect | No effect |
| Effect of carpronium chloride | No effect | No effect | No effect |
| Effect of cepharanthin | Not applied | Not applied | Not applied |
| Dosage form | BNP ointment | BNP ointment | BNP gel |
| Dose | 30 μg/g<br>50 μg/g | 100 μg/g | 50 μg/g |
| Number of days used | 35 days | 7 days | 14 days |
| Degree of improvement in symptoms | S3→S0 | S1→S0 | S1→S0 |
| Non-recurrence period | Immediately after end of treatment | 1 month | 3 weeks |

Case B5

The test subject was a 50 year old female and was a patient with severe alopecia areata multilocularis having a hair loss range of S3. There was a history of allergic rhinitis, and there was coexisting atopic dermatitis. The results of the scratch test were house dust 3+, mite 3+, cedar 3+, Dactylis 2+, and ragweed 2+. Alopecia areata of this test subject had developed 4 months earlier due to stress caused by relationships in the workplace, and 2 months after the onset multilocularis started. Steroid lotion and carpronium chloride had been applied to the hair loss site of this test subject continuously for 10 months, but no hair growth had been observed, susceptibility to hair loss had not been suppressed, and there had been no therapeutic effects.

When 50 μg/g BNP ointment was applied to the entire bald area of the crown and temporal region of this test subject twice a day morning and evening, hair completely stopped falling out after starting the application. When application of the BNP ointment to the entire hair loss site was continued for 2 weeks, hair growth could be clearly confirmed. Application of 50 μg/g BNP ointment twice a day was ended after 2 weeks, and when from the next day after that 30 μg/g BNP ointment was applied twice a day for 1 week, and from the next day after that 50 μg/g BNP ointment was applied twice a day for 2 weeks, hair thickening continued to progress. The hair growth had a characteristic pattern, hair started to grow in double rings and recovered so as to give complete coverage in 20 days (Ref. FIG. 15-1, FIG. 15-2, and FIG. 16). However, since this test subject was affected by the Great East Japan Earthquake on 11 Mar. 2011, treatment with the BNP ointment was stopped. According to this test subject, the hair grew to some extent, but it stopped growing after application of the BNP ointment was stopped.

Case B6

The test subject was a 33 year old female and was a patient with alopecia areata having a hair loss range of S1. A child of this test subject was affected by atopic dermatitis. The mother of this test subject had alopecia areata and a history of allergic rhinitis. The results of the scratch test were house dust 2+, mite 2+, Dactylis 2+, and ragweed 2+, which were those of a case with an atopic predisposition. This test subject had developed a circular bald area 5 months earlier, treatments involving external use of a steroid, application of carpronium chloride, and an orally administered antiallergy drug had been continued for 7 weeks, but not only had hair continued to fall out but the hair loss range had also enlarged and multilocularis was seen; orally administered steroid had been given in combination, but there had been no therapeutic effect. This test subject showed bald areas on the left temporal region, the crown, and the back of the head, with a hair loss range of S1. This test subject was the same test subject as the test subject of case C10.

Among the bald areas of this test subject, when 100 μg/g BNP ointment was applied to the left temporal region and the crown twice a day, growth of mainly white hair was observed on the 7$^{th}$ day after the application of BNP ointment was started. On the other hand, hair growth was not observed on the bald area of the back of the head, to which the BNP ointment had not been applied. However, since there was still a large amount of hair falling out, application of the BNP ointment was stopped after 7 days, and 100 μg/g CNP ointment was applied twice a day to all the bald areas of the left temporal region, the crown, and the back of the head from the 8$^{th}$ day. As a result, hair stopped falling out, marked hair growth was confirmed on all the bald areas including the back of the head after 3 weeks, and there was a cure.

Case B26

The test subject was a 38 year old female and was a patient with alopecia areata monolocularis having a hair loss range of S1. A child of this test subject was affected by atopic dermatitis. A cousin, a niece, an aunt, and a child of this test subject were affected by alopecia areata multilocularis. This test subject was not subjected to a scratch test.

When 100 μg/g CNP ointment was applied twice a day for 2 weeks to the entire circular bald area of the crown of this test subject, clear hair growth was observed (Ref. FIG. 23). There was no recurrence of the bald area in the site that had been cured by the CNP ointment even when 1 year had elapsed since application of the CNP ointment was stopped after 2 weeks.

However, one year after the circular bald area on the crown had been cured by the CNP ointment a new circular bald area appeared, this time on the back of the head.

When 50 μg/g BNP gel was applied twice a day for 2 weeks, hair grew markedly and became terminal hair, and there was almost a cure (FIG. 55). Application of the BNP gel was stopped after 2 weeks, and there was a complete cure and no recurrence even when 6 weeks had subsequently elapsed (FIG. 55).

This test subject was the same test subject as the test subject of case C7.

5. Therapeutic Effect of CNP Gel on Alopecia Areata

The therapeutic effects of CNP gel on alopecia areata are shown in Table 4 (test subjects C1, C3, C20, and C23).

the entire scalp had been seen 5 months after onset. For this test subject, a change of workplace had triggered the onset of alopecia areata. This test subject had not shown any therapeutic effect from the application of carpronium chloride.

When 100 μg/g CNP gel was applied twice a day to the entire bald area of the crown of this test subject, marked hair growth was observed after 1 week (Ref. FIG. 17).

Case C2

The test subject was a 47 year old female and was a patient with alopecia areata having a hair loss range of S1. This test subject had a previous history of glaucoma. A child of this test subject was affected by atopic dermatitis and allergic rhinitis. The results of the scratch test were house dust 3+, mite 3+, cedar 2+, Dactylis 2+, and ragweed 2+. A bald patch had appeared on the crown of this test subject 1 month earlier, and following this bald areas had been

TABLE 4

| | Case | | | |
|---|---|---|---|---|
| | C1 | C2 (=C11) | C3 (=A6, C4) | C20 |
| Figure | FIG. 17 | FIG. 18-1<br>FIG. 18-2<br>FIG. 19-1<br>FIG. 19-2 | FIG. 20 | FIG. 35 |
| Gender | Female | Female | Female | Male |
| Age | 32 years old | 47 years old | 50 years old | 32 years old |
| When developed | Half year earlier | 1 month earlier | 40 years old | About 30 years old |
| Hair loss range | S2 | S1 | S2 | Frontal region |
| Treatment site | Crown | Crown, frontal region, left temporal region | Left temporal region | Hairline of the frontal region became thin. Circular bald area seen in left temporal region. |
| Hair loss site other than head | None (B0) | None (B0) | None (B0) | None |
| Family history of alopecia | None | None | Mother: alopecia areata | None |
| Family history of immune disease | None | Child: allergic rhinitis | Child: allergic rhinitis, chronic urticaria | None |
| Previous history | None | Glaucoma | Atopic dermatitis, allergic rhinitis | Not tested |
| Scratch Test | House dust: 2+<br>Mite: 3+<br>Cedar: 2+<br>Dactylis: 3+<br>Ragweed: 2+ | House dust: 3+<br>Mite: 3+<br>Cedar: 2+<br>Dactylis: 2+<br>Ragweed: 2+ | House dust: 1+<br>Mite: 1+<br>Cedar: —<br>Dactylis: 2+<br>Ragweed: 1+ | Not applied |
| Effect of minoxidil | Not applied | Not applied | Not applied | Not applied |
| Effect of steroid drug | Not applied | Unable to use | No effect | Not applied |
| Effect of cooling therapy | Not applied | Not applied | Not applied | Not applied |
| Antiallergic drug | Not applied | Not applied | No effect | Not applied |
| Effect of carpronium chloride | No effect | Not applied | No effect | Not applied |
| Effect of cepharanthin | Not applied | Not applied | Not applied | Not applied |
| Dosage form | CNP gel | CNP ointment | CNP gel | CNP gel |
| Dose | 100 μg/g | 100 μg/g | 100 μg/g | 50 μg/ml |
| Number of days used | 7 days | 28 days | 21 days | 14 days |
| Degree of improvement in symptoms | S2→S2 | S1→S0 | S2→S0 | S1→S0 |
| Non-recurrence period | Unknown | 3 weeks | 8 months | 5 weeks |

Case C1

The test subject was a 32 year old female and was a patient with a serious case of alopecia areata multilocularis having a hair loss range of S3. There was a history of allergic rhinitis. The results of the scratch test were house dust 2+, mite 3+, cedar 2+, Dactylis 3+, and ragweed 2+. With regard to the alopecia areata of this test subject, alopecia had developed half a year earlier, it had enlarged, and there were multiple occurrences, and a tendency for hair to be lost over observed on the frontal region and left temporal region. Since this test subject had a history of glaucoma, this was a case in which use of a steroid should be avoided. This test subject had been affected by thyroid cancer 7 years earlier and had received surgical removal. This test subject was the same test subject as the test subject of case C11.

When 100 μg/g CNP ointment was applied to the crown and the frontal region of this test subject twice a day, hair growth was confirmed after 1 week of application (Ref. FIG.

18-1, FIG. 19-1, and FIG. 19-2). From the following day, that is, the 8th day, the dosage form was changed on request from the test subject, 100 μg/g CNP gel continued to be applied twice a day for a further 1 week, further marked hair growth was observed, and the amount of hair falling out decreased (Ref. FIG. 18-1, FIG. 18-2, FIG. 19-1, and FIG. 19-2). However, in the left temporal region of this test subject, to which external CNP ointment had not been applied, there was no hair growth. Since an effect had been confirmed, from the 8th day after application of the CNP ointment to the crown and the frontal region was started, application of 100 μg/g CNP gel to the left temporal region twice a day was started, and 2 weeks after the start of application marked hair growth was confirmed for the left temporal region in the same way as for the crown and the frontal region. There was no recurrence even when 3 weeks had elapsed after application of the CNP gel was stopped after 28 days.

Case C3

The test subject was a 50 year old female and was a patient with a serious case of alopecia areata multilocularis having a hair loss range of S2. This test subject had a previous history of atopic dermatitis and allergic rhinitis. The mother of this test subject had a history of alopecia areata, and a child was affected by allergic rhinitis and chronic urticaria. The results of the scratch test were house dust 1+, mite 1+, Dactylis 2+, and ragweed 1+. This test subject showed erythema and pityriatic scale accompanied by itching on the scalp of the hair loss site, and there was coexisting alopecia pityroides. This test subject had been affected by alopecia areata multilocularis 10 years earlier, and there had been repeated partial remission and recurrence. When work became busy, in the case of this test subject the alopecia areata tended to deteriorate. There had been no effect from external use of a steroid, external use of carpronium chloride, and an orally administered antiallergy drug for 6 months. This test subject was the same test subject as the test subject of case A6 and case C4.

When 100 μg/g CNP gel was applied to the entire bald area of the left temporal region of this test subject twice a day, the amount of hair falling out decreased from the next day, hair growth was clearly confirmed after 2 weeks, and application was stopped after 3 weeks' application, but recovery progressed well after the application was stopped, and there was no recurrence on the application site after 8 months had elapsed since stopping the application (Ref. FIG. 20). There was no subsequent recurrence for this test subject even when a further 1 year had elapsed.

Case C20

The test subject was a 32 year old male with androgenetic alopecia. For this test subject, at the age of 30 the hair line of the M-shaped part in the frontal region had rapidly become thin and retreated. Alopecia areata monolocularis had also developed in the left temporal region 6 weeks before visiting the clinic. This test subject had no family history of alopecia patient. This test subject had so-called M-shaped androgenetic alopecia that was classified as type III on the Hamilton-Norwood scale. This test subject was the same test subject as the test subject of case C27.

When 50 μg/g CNP gel was applied twice a day to the androgenetic alopecia area of the frontal region and the circular bald area of the left temporal region of this test subject, growth of black terminal hair was observed 2 weeks later both in the M-shaped hair line area (FIG. 46) and the circular bald area (FIG. 35).

Furthermore, when 50 μg/mL CNP gel:50 mg/mL carpronium chloride combination was applied twice a day for 1 week to the androgenetic alopecia area of the frontal region and the circular bald area of the left temporal region of this test subject, the same degree of hair growth effect as that from the application of 50 μg/g CNP gel was maintained.

Subsequently, when the 50 μg/g CNP:600 μg/mL betamethasone:500 μg/mL gentamicin combination was applied for 1 week after the application of 50 μg/g CNP gel was suspended for 3 weeks, further marked hair growth was observed, and following this even though application was stopped hair growth continued and there was a cure.

6. Therapeutic Effect of CNP Ointment on Alopecia Areata

The therapeutic effects of CNP ointment on alopecia areata are shown in Table 4 (case C2), Table 5 (test subjects C4 to C7), Table 6 (test subjects C8 to C12), and Table 7-1 (test subjects C13 to C15, and C36).

TABLE 5

| | Case | | | |
|---|---|---|---|---|
| | C4 (=A6, C3) | C5 (=A1) | C6 (=A7) | C7 |
| Figure | | FIG. 21 | FIG. 22 | FIG. 23 |
| Gender | Female | Female | Female | Female |
| Age | 50 years old | 33 years old | 22 years old | 38 years old |
| When developed | 40 years old | 13 years old | >1.5 years earlier | About 1 year earlier |
| Hair loss range | S2 | S3 | S3 | S1 |
| Treatment site | Right frontal region | Left temporal region | Frontal region, temporal region | Crown |
| Hair loss site other than head | None (B0) | Eyebrows (B1) | Eyebrows (B1) | None (B0) |
| Family history of alopecia | Mother: alopecia areata | None | None | Relative: alopecia areata |
| Family history of immune disease | Child: allergic rhinitis, chronic urticaria | Mother: atopic dermatitis Older sister: atopic dermatitis, allergic rhinitis | Grandfather: atopic dermatitis Mother, older brother, older sister: allergic rhinitis | Child: atopic dermatitis, alopecia areata multilocularis |
| Previous history | Atopic dermatitis, allergic rhinitis | Atopic dermatitis | Atopic dermatitis, allergic rhinitis | None |
| Scratch Test | House dust: 1+ Mite: 1+ Cedar: — Dactylis: 2+ Ragweed: 1+ | House dust: 2+ Mite: 1+ Cedar: — Dactylis: 2+ Ragweed: 2+ | House dust: 2+ Mite: 3+ Cedar: — Dactylis: 1+ Ragweed: — | Not tested |

TABLE 5-continued

| | Case | | | |
|---|---|---|---|---|
| | C4 (=A6, C3) | C5 (=A1) | C6 (=A7) | C7 |
| Effect of minoxidil | Not applied | Not applied | Not applied | Not applied |
| Effect of steroid drug | No effect | No effect | No effect | No effect |
| Effect of cooling therapy | Not applied | No effect | Not applied | Not applied |
| Antiallergic drug | No effect | No effect | No effect | No effect |
| Effect of carpronium chloride | No effect | Not applied | Not applied | No effect |
| Effect of cepharanthin | Not applied | Not applied | Not applied | Not applied |
| Dosage form | CNP ointment | CNP ointment | CNP ointment | CNP ointment |
| Dose | 100 μg/g | 100 μg/g | 50 μg/g | 100 μg/g |
| Number of days used | 14 days | 21 days | 28 days | 14 days |
| Degree of improvement in symptoms | S2→S1 | S3→S1 | S3→S0 | S1→S0 |
| Non-recurrence period | Treatment continuing | At least 5 months | 9 months | 1 year |

Case C4

The test subject was a 50 year old female and was a patient with severe alopecia areata multilocularis having a hair loss range of S2. This test subject had a previous history of atopic dermatitis and allergic rhinitis. The mother of this test subject had a history of alopecia areata, and a child was affected by allergic rhinitis and chronic urticaria. The results of the scratch test were house dust 1+, mite 1+, Dactylis 2+, and ragweed 1+. Erythema and pityriatic scale accompanied by itching were observed on the scalp of the hair loss site of this test subject, and there was coexisting alopecia pityroides. This test subject had been affected by alopecia areata multilocularis 10 years earlier, and there had been repeated partial remission and recurrence. When work became busy, in the case of this test subject the alopecia areata tended to deteriorate. There had been no effect from external use of a steroid, external use of carpronium chloride, and an orally administered antiallergy drug for 6 months. This test subject was the same test subject as the test subject of case A6 and case C3.

When 100 μg/g CNP gel was applied to the entire bald area of the left temporal region of this test subject twice a day, the amount of hair falling out decreased from the next day, hair growth was clearly confirmed after 2 weeks, and application was stopped after 3 weeks' application, but recovery progressed well after the application was stopped, and there was no recurrence on the application site after 8 months had elapsed since stopping the application (Ref. FIG. 20).

However, half a year after stopping the application a new bald area appeared, this time on the right frontal region; 100 μg/g CNP ointment was applied twice a day, hair growth was clearly observed in 2 weeks, and erythema and scale of the scalp disappeared. The application to the bald area of the right frontal region was stopped after 2 weeks, but the hair continued to recover even after the application was stopped, and there was a complete cure. There was no recurrence in the bald area of the right frontal region even when over 1 year had elapsed since the application was stopped.

100 μg/g ANP gel was applied for 2 weeks to new multiple bald areas on the crown, which appeared around the same time as the bald area on the right frontal region, but there was no effect, rough scale increased, there was itching, and the hair loss range enlarged somewhat.

Case C5

The test subject was a 33 year old female and was a patient with severe alopecia areata for which the hair loss range was S3 and which, other than the head, was accompanied by B1 hair loss of the eyebrows. There was a previous history of atopic dermatitis, and coexisting alopecia due to exacerbation of atopic dermatitis. The results of the scratch test were house dust 2+, mite 1+, Dactylis 2+, and ragweed 2+. This test subject showed erythema and pityriatic scale accompanied by itching in the scalp of the hair loss site, and there was coexisting alopecia pityroides. For this test subject, a circular bald area had appeared at the age of 13 and also in the crown at the age of 14, and it had then become alopecia totalis in half a month. Following this, the symptoms of the test subject had fluctuated, and alopecia had extended to the entire body at the age of 15. External and orally administered steroid had not given any therapeutic effect at all with this test subject. This test subject had continued to receive stimulation therapy with liquid nitrogen, but there had been hardly any therapeutic effect. This test subject was the same test subject as that of case A1.

When 100 μg/g ANP gel was applied to the bald area on the left temporal region twice a day for 3 weeks, growth of vellus hair was observed, but erythema and pityriatic desquamation of the scalp were not relieved and there was itching. Therefore, 100 μg/g CNP ointment was applied to the entire bald area of the left temporal region twice a day for 1 week starting 2 weeks after stopping the ANP gel, erythema, pityriatic desquamation, and the itching sensation of the scalp disappeared, hair restoration and hair growth were promoted, and terminal hair covered the scalp. Following this, the CNP ointment was applied for another week, and as a result the terminal hair grew and there was almost a cure. 7 months have elapsed since application of the CNP ointment was stopped after 21 days, but there has been no recurrence of the alopecia (Ref. FIG. 21). This test subject had been subjected to orally administered steroid, liquid nitrogen cooling therapy, etc. since her teens, and this was the first time that there had been such hair growth.

Case C6

The test subject was a 22 year old female and was a patient with severe ophiasis type alopecia areata having a hair loss range of S3, which was said to be intractable. This test subject had a previous history of atopic dermatitis and allergic rhinitis. A grandfather of this test subject was affected by atopic dermatitis, and the father, the mother, and the brother were affected by allergic rhinitis. The results of the scratch test were house dust 2+, mite 3+, and Dactylis 1+. This test subject had been affected by a bald area more than one and half years earlier, and a band-shaped bald area in a state in which hair did not grow at all was observed with a clear border along the outside edge of the part where hair was growing. Erythema, scale, crust, and inflammatory symptoms that seemed to be due to atopic alopecia were observed on the hair loss site of this test subject, and were accompanied by itching. This test subject had hair loss on the eyebrows in addition to the head. This test subject was a case of coexisting atopic dermatitis and allergic rhinitis. The skin of this test subject was in an erythrodermic state, which seemed to be due to steroid rebound, and redness and infiltration were observed on the skin of the entire body including the scalp. There had been no therapeutic effect at all on this test subject from treatment with a steroid and an antiallergy drug. This test subject was the same test subject as the test subject of case A7.

Although 50 μg/g ANP gel was applied twice a day for 3 days to the entire bald area of this test subject, there was no improvement in either redness or itching, and there was no sign of hair growth.

When it was changed to application of 50 μg/g CNP ointment twice a day to the entire bald area of the frontal region and the temporal region of this test subject, erythema was relieved on the second day, and the itching sensation disappeared. Marked growth of terminal hair was observed after 3 weeks' application, and once terminal hair grew, the hair thickened while vellus hair became dark and grew even without external application, terminal hair also grew, and there was a cure (Ref. FIG. 22). The hair continued to grow even after application of the CNP ointment was stopped after 4 weeks and there was a complete cure. There was no recurrence for this test subject even after 9 months had elapsed, and the alopecia areata ophiasis was completely cured without any marking.

Case C7

The test subject was a 38 year old female and was a patient with alopecia areata monolocularis having a hair loss range of S1. A child of this test subject was affected by atopic dermatitis. A cousin, a niece, an aunt, and a child of this test subject were affected by alopecia areata multilocularis. This test subject was not subjected to a scratch test.

When 100 μg/g CNP ointment was applied to the entire circular bald area of the crown of this test subject twice a day for 2 weeks, clear hair growth was observed (Ref. FIG. 23). After application of the CNP ointment was stopped after 2 weeks, even after 1 year had elapsed there was no recurrence in the site that had been cured by the CNP ointment.

However, 1 year after the circular bald area of the crown was cured by the CNP ointment, a new circular bald area appeared, this time on the back of the head.

When 50 μg/g BNP gel was applied twice a day for 2 weeks, there was a marked hair growth and terminal hair formed, and the bald area was almost cured.

This test subject was the same test subject as the test subject of case B26.

TABLE 6

| | Case | | | | |
|---|---|---|---|---|---|
| | C8 | C9 (=B4) | C10 (=B6) | C11 (=C2) | C12 (=B1) |
| Figure | | | FIG. 24-1 FIG. 24-2 | FIG. 18 | FIG. 25 |
| Gender | Female | Female | Female | Female | Female |
| Age | 32 years old | 24 years old | 33 years old | 47 years old | 63 years old |
| When developed | 1.5 years earlier | As a junior high school student | 5 months earlier | 1 month earlier | 64 years old (1.5 years earlier) |
| Hair loss range | S1 | S2 | S1 | S1 | S2 |
| Treatment site | Right temporal region | Right frontal region | Left temporal region, crown, back of the head | Crown, frontal region | Left temporal region |
| Hair loss site other than head | None (B0) | None (B0) | None (B0) | None (B0) | None (B0) |
| Family history of alopecia | None | None | None | None | None |
| Family history of immune disease | Child: allergic rhinitis | Mother: bronchial asthma | Child: atopic dermatitis | Child: allergic rhinitis | None? |
| Previous history | Allergic rhinitis | Allergic rhinitis, | None | Glaucoma | Allergic rhinitis, atopic dermatitis |
| Scratch Test | House dust: — Mite: 1+ Cedar: 2+ Dactylis: 2+ Ragweed: 2+ | House dust: 2+ Mite: 2+ Cedar: 2+ Dactylis: 1+ Ragweed: 1+ | House dust: 2+ Mite: 2+ Cedar: — Dactylis: 2+ Ragweed: 2+ | House dust: 3+ Mite: 3+ Cedar: 2+ Dactylis: 2+ Ragweed: 2+ | House dust: 2+ Mite: 1+ Cedar: — Dactylis: 2+ Ragweed: 1+ |
| Effect of minoxidil | Not applied | Not applied | Not applied | Not applied | Not applied |
| Effect of steroid drug | No effect | No effect | No effect | Unable to use | No effect |
| Effect of cooling therapy | Not applied | Not applied | Not applied | Not applied | Not applied |
| Antiallergic drug | No effect | No effect | No effect | Not applied | Not applied |
| Effect of carpronium chloride | No effect | No effect | No effect | Not applied | No effect |
| Effect of cepharanthin | Not applied | Not applied | Not applied | Not applied | Not applied |
| Dosage form | CNP ointment | CNP ointment (right frontal region) | CNP ointment | CNP ointment | CNP ointment |

TABLE 6-continued

| | | Case | | | |
|---|---|---|---|---|---|
| | C8 | C9 (=B4) | C10 (=B6) | C11 (=C2) | C12 (=B1) |
| Dose | 100 µg/g | 100 µg/g | 100 µg/g | 100 µg/g | 100 µg/g |
| Number of days used | 7 days | 21 days | 21 days | 28 days | 20 days |
| Degree of improvement in symptoms | S1→S0 | S2→S0 | S1→S0 | S1→S0 | S2→S0 |
| Non-recurrence period | 1 month | 1 year | 1 month | 3 weeks | 11 months |

Case C8

The test subject was a 32 year old female and was a patient with alopecia areata multilocularis having a hair loss range of S1. The results of the scratch test were house dust −, mite 1+, cedar 2+, Dactylis 2+, and ragweed 2+. This test subject had been affected by alopecia multilocularis one and a half years earlier, and had received treatment involving external use of a steroid, application of carpronium chloride, and an orally administered antiallergy drug for one and a half years, but a satisfactory effect could not be obtained. A slight degree of erythema was observed on a hair loss area of this test subject, and was accompanied by an itching sensation. In the case of this test subject, multiple bald areas were observed on the right temporal region and the left temporal region.

When 100 µg/g CNP ointment was applied to the entire bald area of this test subject twice a day, erythema and the itching sensation disappeared after 3 days' application, the amount of hair falling out decreased after 10 days' application, and clear hair growth was observed. There was no recurrence even when 1 month had elapsed after application of the CNP ointment was stopped after 7 days.

Case C9

The test subject was a 24 year old female and was a patient with severe alopecia areata multilocularis having a hair loss range of S2. There was a history of allergic rhinitis. The mother was affected by bronchial asthma. The results of the scratch test were house dust 2+, mite 2+, cedar 2+, Dactylis 1+, and ragweed 1+. There had been repeated partial remission and recurrence of the alopecia areata of this test subject since junior high school. A slight degree of itching sensation had started to appear on and around the frontal region half a year earlier, and following this multiple bald areas enlarged. Even when a steroid or carpronium chloride had been applied to the hair loss site of this test subject for 3 months or an antiallergy drug had been orally administered to the test subject, hair growth had not been observed, and the susceptibility to hair loss could not be improved. This test subject was the same test subject as the test subject of case B4.

In accordance with the separate left and right application method, 100 µg/g BNP gel was applied to the left frontal region of this test subject, and only Lubrajel NP (ISP Japan Ltd.), which is a gel base, was applied to the right frontal region twice a day; hair growth was observed after 1 week only on the site of the left-hand side to which the BNP gel had been applied, and after 2 weeks hair growth became more marked on the site of the left-hand side to which the BNP gel had been applied. On the other hand, no hair growth was observed on the right-hand side to which only the gel base had been applied. Therefore, it was determined that the hair growth was due to the hair growth effect of the BNP gel.

Application of 100 µg/g BNP gel to the left frontal region was continued, and application of 100 µg/g CNP ointment to the right frontal region was started, hair growth was observed after 1 week, and marked hair growth and hair thickening were observed on the entire hair loss site after 3 weeks. Before starting the treatment two handfuls of hair had fallen out each time it was shampooed, but the amount of hair falling out decreased dramatically, and only 5 to 6 hairs fell out per shampooing. External application was stopped after the BNP gel had been applied to the left frontal region for 3 weeks and the CNP ointment to the right frontal region for 3 weeks, but following this hair continued to grow, the alopecia was substantially cured by the second week after application was stopped, and there has been no recurrence up to the present, that is, after 1 year has elapsed.

Case C10

The test subject was a 33 year old female and was a patient with alopecia areata having a hair loss range of S1. A child of this test subject was affected by atopic dermatitis. The mother of this test subject had alopecia areata and a history of allergic rhinitis. The results of the scratch test were house dust 2+, mite 2+, Dactylis 2+, and ragweed 2+, which were those of a case with an atopic predisposition. This test subject had developed a circular bald area 5 months earlier, treatments involving the external use of a steroid, application of carpronium chloride, and an orally administered antiallergy drug had been continued for 7 weeks, but not only had hair continued to fall out but the hair loss range had also enlarged and multilocularis was seen; orally administered steroid had been given in combination, but there had been no therapeutic effect. This test subject showed bald areas on the left temporal region, the crown, and the back of the head, with a hair loss range of S1. This test subject was the same test subject as the test subject of case B6.

Among the bald areas of this test subject, when 100 µg/g BNP ointment was applied to the left temporal region and the crown twice a day, growth of mainly white hair was observed on the 7$^{th}$ day after application of the BNP ointment was started. On the other hand, hair growth was not observed on the bald area of the back of the head, to which the BNP ointment had not been applied. However, since there was still a large amount of hair falling out, application of the BNP ointment was stopped after 7 days, and 100 µg/g CNP ointment was applied twice a day to all the bald areas of the left temporal region, the crown, and the back of the head from the 8$^{th}$ day. As a result, hair stopped falling out, and marked hair growth was observed on all of the left temporal region, the crown, and the back of the head on the 3rd week after application of the CNP ointment was started (Ref. FIG. 24-1 and FIG. 24-2). The test subject was surprised with the rate of hair growth compared with conventional therapy. There was no recurrence in this test subject even when 1 month had elapsed after application of the CNP ointment was stopped after 21 days.

Case C11

The test subject was a 47 year old female and was a patient with alopecia areata having a hair loss range of S1. This test subject had a previous history of glaucoma. A child of this test subject was affected by atopic dermatitis and allergic rhinitis. The results of the scratch test were house dust 3+, mite 3+, cedar 2+, Dactylis 2+, and ragweed 2+. A bald patch had appeared on the crown of this test subject 1 month earlier, and following this bald areas had been observed on the frontal region and left temporal region. Since this test subject had a history of glaucoma, this was a case in which use of a steroid should be avoided. This test subject had been affected by thyroid cancer 7 years earlier and had received surgical removal. This test subject was the same test subject as the test subject of case C2.

When 100 μg/g CNP ointment was applied to the crown and the frontal region of this test subject twice a day, hair growth was confirmed after 1 week of application (Ref. FIG. 18-1, FIG. 18-2, FIG. 19-1 and FIG. 19-2).

Case C12

The test subject was a 63 year old female and was a patient with severe alopecia areata multilocularis having a hair loss range of S2. There was a history of allergic rhinitis, and there was coexisting atopic dermatitis. The results of the scratch test were house dust 2+, mite 1+, Dactylis 2+, and ragweed 1+. The alopecia areata of this test subject had continued for over one and a half years. This test subject had received application of a steroid and carpronium chloride to the bald area continuously for 10 months, but there had been no effect, and no hair growth had been observed. This test subject was the same test subject as the test subject of case B1.

When 100 μg/g BNP gel was applied to the entire bald area of the right temporal region of this test subject twice a day morning and evening, clear hair growth was observed in 2 weeks. There was no recurrence of hair loss on the application site even when 8 months had elapsed after the application of BNP gel was stopped after 24 days.

However, new multiple bald areas appeared on the left temporal region; 100 μg/g CNP ointment was applied twice a day morning and evening, growth of vellus hair was

TABLE 7-1

| | Case | | | | |
|---|---|---|---|---|---|
| | C13 | C14 | C15 (=A3) | C36 | C23 |
| Figure | FIG. 26 | | FIG. 8 | | FIG. 39 |
| Gender | Male | Female | Female | Male | Female |
| Age | 38 years old | 35 years old | 52 years old | 57 years old | 26 years old |
| When developed | 2 months earlier | 3 months earlier | 51 years old | 55 years old | 26 years old |
| Hair loss range | S1 | S2 | S3 | S2 | S1 |
| Treatment site | Temporal region, back of the head | Back of the head | Whole of scalp | Temporal region, back of the head, frontal region | Back of the head |
| Hair loss site other than head | None (B0) | None (B0) | None (B0) | Eyebrows (B1) | None |
| Family history of alopecia | None | None | None | None | None |
| Family history of immune disease | None | Mother: allergic rhinitis | None | None | None |
| Previous history | None | Allergic rhinitis | Allergic rhinitis | Atopic dermatitis | None |
| Scratch Test | House dust: 1+ Mite: 1+ Cedar: 1+ Dactylis: — Ragweed: 1+ | House dust: 2+ Mite: 2+ Cedar: 2+ Dactylis: 2+ Ragweed: 1+ | House dust: 1+ Mite: — Cedar: 2+ Dactylis: 1+ Ragweed: 1+ | House dust: 1+ Mite: 3+ Cedar: 2+ Dactylis: 1+ Ragweed: 1+ | Not tested |
| Effect of minoxidil | Not applied | Not applied | Not applied | Not applied | Not applied |
| Effect of steroid drug | Not applied | Hair loss range enlarged | Unknown | No effect from external application and oral administration | Small amount of hair growth, but bald area enlarged |
| Effect of cooling therapy | Not applied | Not applied | Not applied | No effect | Not applied |
| Antiallergic drug | Not applied | Not applied | Not applied | No effect | Not applied |
| Effect of carpronium chloride | No effect | Not applied | No effect | No effect | Not applied |
| Effect of cepharanthin | Not applied | Not applied | Not applied | Not applied | Not applied |
| Dosage form | CNP ointment | CNP ointment | CNP ointment | CNP ointment | CNP gel |
| Dose | 100 μg/g | 50 μg/g | 100 μg/g | 100 μg/g | 50 μg/g |
| Number of days used | 28 days | 28 days | 2 weeks | 6 weeks | 2 weeks |
| Degree of improvement in symptoms | S1→S0 | S1→S1 Bald area remained at 1 position at hairline | S3→S2 | S2→S0 | S1→S0 |
| Non-recurrence period | 12 months | Treatment suspended | Treatment continuing | 9 months | 2 months | observed after 1 week of application, and clear growth of terminal hair was observed 3 weeks after the application was started. 50 µg/g CNP ointment was applied twice a day morning and evening for 20 days, the hair thickened so as to cover the entire hair loss area, and there was a cure without subsequent application (Ref. FIG. 25). There was no recurrence even when 1 month had elapsed.

Case C13

The test subject was a 38 year old male and was a patient with alopecia areata multilocularis having a hair loss range of S1. A bald patch had appeared on the temporal region 2 months earlier, and following this a bald area had been observed on the back of the head. There was no previous history or family history of immune disease. The results of the scratch test of this test subject were house dust 2+, mite 2+, cedar 2+, Dactylis 2+, and ragweed 1+. This test subject had received orally administered cepharanthin, but there had been no therapeutic effect.

When 100 µg/g CNP ointment was applied to the entire alopecia of the temporal region and the back of the head of this test subject twice a day, growth of white hair was confirmed on the entire bald patch after 1 week's application, and black hair growth was observed on the peripheral area (Ref. FIG. 26). This test subject was in a state in which mainly white hair had grown and thickened. With regard to this test subject, the hair continued to thicken even when application of the CNP ointment was stopped after 1 week, and there was a spontaneous cure. With regard to this test subject, there was no recurrence on the temporal region or the back of the head even when 1 year had elapsed after application of the CNP ointment was stopped.

However, a circular bald area appeared, this time on the crown, 10 months after application of the CNP ointment was stopped, and when 50 µg/g BNP gel was applied twice a day for 2 weeks, growth of black terminal hair was observed. However, extensive hair growth was not observed even when 50 µg/g BNP gel was applied for 3 weeks; when a 50 µg/g BCNP:600 µg/mL betamethasone:500 µg/mL gentamicin combination was applied once a day for 2 weeks, hair growth was observed earlier than had been the case with use of a single agent, the rate of hair lengthening increased, and terminal hair grew extensively.

Case C14

The test subject was a 35 year old female and was a patient with alopecia areata having a hair loss range of S1. This test subject had a history of allergic rhinitis, the mother of this test subject was also affected by allergic rhinitis, and this test subject was a case with an atopic predisposition. The results of the scratch test of this test subject were house dust 2+, mite 2+, cedar 2+, Dactylis 2+, and ragweed 1+. A bald patch had appeared on the back of the head of this test subject 3 months earlier, it subsequently showed a tendency to enlarge, and the entire back of the head had become thin, accompanied by itching. In the case of this test subject, application of a steroid drug had caused itchiness, and the hair loss range had enlarged somewhat.

When 100 µg/g CNP ointment was applied to the entire bald patch of the back of the head of this test subject twice a day, growth of white hair and vellus hair was observed after 1 week of application, and growth of black terminal hair was clearly observed after 3 weeks. However, although growth of vellus hair was observed in part of the bald area at the hair growth line of the left back of the head, it did not recover so as to cover the entire bald patch.

Case C15

The test subject was a 52 year old female and was a patient with severe alopecia areata having a hair loss range of S3. There was a previous history of allergic rhinitis. The results of the scratch test were house dust 1+, cedar 2+, Dactylis 1+, and ragweed 1+. A bald patch had appeared on the frontal region of this test subject about 1 year earlier when doing continuous night shifts, following this there had been a tendency for enlargement, and multiple bald areas had appeared over the entire scalp. Application of carpronium chloride to the bald patch had been continued for 8 months, but the hair loss range had only enlarged and there had been no therapeutic effect. This was a case in which there were no inflammatory symptoms such as erythema, crust, or scale on the scalp of the hair loss area of the test subject. This test subject was the same test subject as the test subject of case A3.

When 100 µg/g CNP ointment was applied to the entire bald area of the right temporal region of this test subject twice a day, hair growth was confirmed in 1 week, further marked hair growth was observed in 2 weeks, and enlargement of the bald area was completely stopped. Application of the CNP ointment was stopped after 14 days, from the next day after that 100 µg/g ANP gel was applied twice a day with the expectation of further effects, and the therapeutic effect of the CNP ointment continued as it was; after 5 weeks had elapsed, although application of the ANP gel was continuing, thickening of terminal hair and enlargement of the hair growth area were seen. However, since this test subject lived far away from the clinic of the present inventor, she could not visit frequently, and the treatment was suspended. Because of this, the bald area of this test subject remained, and is currently not cured.

Case C36

The test subject was a 57 year old male and was a patient with a serious case of alopecia areata having a hair loss range of S2 with coexisting eyebrow hair loss. This test subject had a previous history of atopic dermatitis. The results of the scratch test were house dust 1+, mite 3+, cedar 2+, Dactylis 1+, and ragweed 1+. With regard to this test subject, multiple bald patches had developed about 5 years earlier due to stress at work. This test subject had received liquid nitrogen therapy, but the hair loss range had only spread, and there had been no therapeutic effect at all. Subsequently, this test subject had been subjected to oral administration and external application of steroid and external application of carpronium chloride for 3 years, but there had not been any effect.

When 100 µg/g CNP ointment was applied twice a day to the entire bald area of the right temporal region of this test subject, hair growth mainly of white hair was observed after 3 weeks. Although application of the CNP ointment was stopped after 6 weeks, the therapeutic effect of the CNP ointment continued thereafter, the hair continued to grow, and there was a cure. 9 months later, there was no recurrence in this test subject.

Case C23

The test subject was a 26 year old female and was a patient with alopecia areata monolocularis having a hair loss range of S1. This test subject had no previous history of alopecia, and none of the family of this test subject was a patient with alopecia areata. This test subject had developed alopecia areata monolocularis on the back of the head, had visited another clinic, and had received application of Rinderon (trademark)-V ointment (Shionogi & Co., Ltd.), which contains 1.2 mg/g betamethasone valerate, for 6 weeks; there had been a little hair growth, but the size of the bald area had increased.

Application of the betamethasone valerate ointment was stopped, and after being suspended for 4 weeks, when 50

μg/g CNP gel was applied twice a day for 2 weeks to a circular bald area of the back of the head of this test subject, marked growth of black terminal hair was observed, and vellus hair became thick and long (FIG. 39).

7. Therapeutic Effect of BNP:Betamethasone:Gentamicin Combination on Alopecia Areata The therapeutic effects of a BNP:betamethasone:gentamicin combination on alopecia areata are shown in Table 7-2 (case B14).

TABLE 7-2

|  | Case B14 |
| --- | --- |
| Figure | FIG. 36 |
| Gender | Female |
| Age | 31 years old |
| When developed | 31 years old |
| Hair loss range | S1 |
| Treatment site | Crown |
| Hair loss site other than head | None |
| Family history of alopecia | None |
| Family history of immune disease | None |
| Previous history | Affected by alopecia areata multilocularis 10 years earlier. |
| Scratch Test | House dust: — |
|  | Mite: 1+ |
|  | Cedar: 1+ |
|  | Dactylis: 1+ |
|  | Ragweed: 2+ |
| Effect of minoxidil | Not applied |
| Effect of steroid drug | Not applied |
| Effect of cooling therapy | Not applied |
| Antiallergic drug | Not applied |
| Effect of carpronium chloride | Not applied |

TABLE 7-2-continued

|  | Case B14 |
| --- | --- |
| Effect of cepharanthin | Not applied |
| Dosage form | BNP: betamethasone: gentamicin combination |
| Dose | BNP: 50 μg/g betamethasone: 600 μg/ml gentamicin: 500 μg/ml |
| Number of days used | 7 days |
| Degree of improvement in symptoms | S1→S0 |
| Non-recurrence period | 6 weeks |

Case B14

The test subject was a 31 year old female and was a patient with alopecia areata monolocularis having a hair loss range of S1. This test subject had no family members with alopecia areata. The results of the scratch test of this test subject were house dust –, mite 1+, cedar 1+, Dactylis 1+, and ragweed 2+. She had been affected by alopecia areata multilocularis 10 years earlier. This time, alopecia areata monolocularis developed on the crown when work became busy.

When 50 μg/g BNP:600 μg/mL betamethasone:500 μg/mL gentamicin combination was applied to a bald area of the crown of this test subject for 1 week, marked hair growth was confirmed (FIG. 36).

8. Therapeutic Effect of CNP:Betamethasone:Gentamicin Combination on Alopecia Areata The therapeutic effects of a CNP:betamethasone:gentamicin combination on alopecia areata are shown in Table 7-3 (cases C21 and C22).

TABLE 7-3

|  | Case | |
| --- | --- | --- |
|  | C21 | C22 |
| Figure | FIG. 37 | FIG. 38 |
| Gender | Male | Female |
| Age | 51 years old | 33 years old |
| When developed | 51 years old | 33 years old |
| Hair loss range | S1 | S1 |
| Treatment site | Crown | Crown |
| Hair loss site other than head | None | None |
| Family history of alopecia | None | None |
| Family history of immune disease | None | None |
| Previous history | None | Affected by alopecia areata when at primary school and junior high school. |
| Scratch Test | Not tested | House dust: 2+ |
|  |  | Mite: 1+ |
|  |  | Cedar: 3+ |
|  |  | Dactylis: 2+ |
|  |  | Ragweed: 2+ |
| Effect of minoxidil | Not applied | Not applied |
| Effect of steroid drug | No effect | No effect |
| Effect of cooling therapy | Not applied | Not applied |
| Antiallergic drug | Not applied | Not applied |
| Effect of carpronium chloride | No effect | No effect |
| Effect of cepharanthin | Not applied | Not applied |
| Dosage form | CNP:betamethasone:gentamicin combination | CNP:betamethasone:gentamicin combination |
| Dose | CNP: 50 μg/g betamethasone: 600 μg/ml gentamicin: 500 μg/ml | CNP: 50 μg/g betamethasone: 600 μg/ml gentamicin: 500 μg/ml |

TABLE 7-3-continued

| | Case | |
|---|---|---|
| | C21 | C22 |
| Number of days used | 21 days | 14 days |
| Degree of Improvement in symptoms | S1→S0 | S1→S0 |
| Non-recurrence period | 2 weeks | 7 weeks |

Case C21

The test subject was a 51 year old male and was a patient with alopecia areata monolocularis having a hair loss range of S1. This test subject had not been affected by alopecia areata in the past, and none of the family of this test subject was a patient with alopecia areata. This test subject had developed a single circular bald area on the right crown about 2 months before visiting the clinic.

'Dermosol-G Lotion' (Iwaki Seiyaku Co., Ltd.), which contains 1200 µg/mL betamethasone valerate and 1000 µg/mL gentamicin sulfate and 'Calpranin solution 5%' (Taiyo Pharmaceutical Industry Co., Ltd.), which contains 50 mg/mL carpronium chloride, were applied to the circular bald area of the right crown of this test subject twice a day for 2 months, but only vellus hair grew, and there was no further hair growth.

The application of Dermosol-G lotion and Calpranin solution 5% was stopped after 2 months, and when from 3 weeks after that a 50 µg/g CNP:600 µg/mL betamethasone:500 µg/mL gentamicin combination was applied twice a day to the circular bald area of the right crown of this test subject, hair growth was observed after 2 weeks' application, and marked hair growth was observed after 3 weeks' application. Although application of the CNP:betamethasone:gentamicin combination was stopped after 3 weeks, the hair continued to grow even when 1 week had elapsed thereafter, and the skin was hidden (FIG. 37).

Case C22

The test subject was a 33 year old female and visited the clinic when a single circular bald area appeared on the crown. This test subject was a patient with alopecia areata monolocularis having a hair loss range of S1. None of the family of this test subject was a patient with alopecia areata. The results of the scratch test of this test subject were house dust 2+, mite 1+, cedar 3+, Dactylis 2+, and ragweed 2+. This test subject had been affected by alopecia areata when she was in primary school and junior high school.

When 50 µg/g CNP gel was applied twice a day for 2 weeks to the circular bald area of the crown of this test subject, the amount of hair falling out decreased, the hair became thick, and growth of black terminal hair was observed.

When application of the CNP gel was stopped after 2 weeks, and from 1 week thereafter a 50 µg/g CNP:600 µg/mL betamethasone:500 µg/mL gentamicin combination was applied twice a day for 2 weeks to the circular bald area of the same site, the amount of hair falling out continued to decrease and thick terminal hair continued to grow (FIG. 38).

9. Therapeutic Effect of ANP Gel on Androgenetic Alopecia

The therapeutic effects of ANP gel on androgenetic alopecia are shown in Table 8 (cases A8 and A9).

TABLE 8

| | Case | |
|---|---|---|
| | A8 (=B8) | A9 (=B11) |
| Figure | FIG. 27 | |
| Gender | Male | Male |
| Age | 45 years old | 75 years old |
| When developed | From 44 years old | About 40 years old to 50 years old |
| Treatment site | Crown | Crown |
| Hair loss state | Hair thinning confined to crown, erythema accompanied by itching and seborrheic scale seen on scalp at hair loss site. | Erythema accompanied by itching and seborrheic scale seen on scalp at hair loss site. |
| Family history of androgenetic alopecia | Father: androgenetic alopecia | Father: androgenetic alopecia |
| Family history of immune disease | None | None |
| Previous history | Atopic dermatitis, allergic rhinitis | Allergic rhinitis |
| Scratch Test | House dust: 2+ | House dust: 2+ |
| | Mite: 3+ | Mite: 2+ |
| | Cedar: — | Cedar: 3+ |
| | Dactylis: 1+ | Dactylis: 2+ |
| | Ragweed: 1+ | Ragweed: 2+ |
| Effect of minoxidil | Not applied | No effect |
| Effect of finasteride | Not applied | Not applied |
| Effect of glycyrrhetinic acid | Not applied | No effect |
| Effect of steroid drug | No effect | No effect |
| Effect of carpronium chloride | Not applied | Not applied |
| Effect of cepharanthin | Not applied | Not applied |
| Dosage form | ANP gel | ANP gel |
| Dose | 100 µg/g | 100 µg/g |

TABLE 8-continued

| | Case | |
|---|---|---|
| | A8 (=B8) | A9 (=B11) |
| Number of days used | 2 weeks | 4 days |
| Degree of Improvement in symptoms | Erythema aggravated and became seborrheic, itching occurred, hair loss range enlarged, no improvement in seborrheic scale. | No Improvement in erythema and seborrheic scale, no improvement in hair thinning. |
| Non-recurrence period | No Improvement | No Improvement |

Case A8

The test subject was a 45 year old male and had suffered from thinning hair confined to the crown since about the age of 44. This test subject had coexisting seborrheic alopecia with erythema accompanied by itching and seborrheic scale on the scalp of the hair loss site. It was classified as type II vertex on the Hamilton-Norwood scale. The father of this test subject had androgenetic alopecia confined to the crown. The scratch test of this test subject was house dust 2+, mite 3+, Dactylis 1+, and ragweed 1+. This test subject was the same test subject as the test subject of case B8.

When 100 µg/g ANP gel was applied twice a day morning and evening for 2 weeks to the entire hair loss site of the crown of this test subject, the erythema was only slightly improved, hair growth was not observed at all, and in addition itching occurred, erythema appeared, and the hair loss range enlarged. The seborrheic scalp was not markedly improved (Ref. FIG. 27).

Case A9

The test subject was a 75 year old male, and hair on the crown had become thin at around 40 to 50 years old. This test subject showed erythema accompanied by itching and seborrheic scale on the scalp of a hair loss site, and had androgenetic alopecia with coexisting seborrheic alopecia. This was classified as type VI on the Hamilton-Norwood scale. The father of this test subject had androgenetic alopecia. The results of the scratch test of this test subject were house dust 2+, mite 2+, cedar 3+, Dactylis 2+, and ragweed 2+, and there was a history of allergic rhinitis. Minoxidil had been applied to this test subject for one year, but there had been no effect. This test subject had also being using glycyrrhetinic acid for 2 years, but said that there had been no effect. This test subject was the same test subject as the test subject of case B11.

100 µg/g ANP gel was applied to the hair loss site of the crown of this test subject twice a day morning and evening for 4 days, but improvement in the erythema and seborrheic scale was not observed, and no effect in improving the alopecia was observed.

10. Therapeutic Effect of BNP Gel on Androgenetic Alopecia

The therapeutic effects of BNP gel on androgenetic alopecia are shown in Table 9-1 (cases B7 to B10) and Table 9-2 (cases B11 to B16).

TABLE 9-1

| | Case | | | |
|---|---|---|---|---|
| | B7 | B8 (=A8) | B9 | B10 |
| Figure | FIG. 28-1<br>FIG. 28-2 | | | |
| Gender | Male | Male | Male | Male |
| Age | 39 years old | 45 years old | 42 years old | 65 years old |
| When developed | From 38 years old | From 44 years old | From 40 years old | 30s to 40s |
| Treatment site | Crown | Crown | Crown | Right frontal region (right M-shaped part) |
| Hair loss state | Tingling of crown, erythema and scale appeared, hair thinning on crown. | Hair thinning confined to crown, erythema accompanied by itching and seborrheic scale seen on scalp at hair loss site. | Hair thinning confined to crown, slight degree of erythema and scale seen on scalp at hair loss site. | Hairline in frontal region and forehead corners retreated and there was hair thinning, wide range of crown was in hair thinning state. |
| Family history of androgenetic alopecia | Paternal grandfather: androgenetic alopecia | Father: androgenetic alopecia | Father, maternal grandfather: androgenetic alopecia | Father: androgenetic alopecia |
| Family history of immune disease | Mother: atopic dermatitis | None | None | None |
| Previous history | Atopic dermatitis | Atopic dermatitis, allergic rhinitis | Atopic dermatitis | Atopic dermatitis |
| Scratch Test | House dust: 3+<br>Mite: 3+<br>Cedar: 1+<br>Dactylis: 2+<br>Ragweed: 1+ | House dust: 2+<br>Mite: 3+<br>Cedar: —<br>Dactylis: 1+<br>Ragweed: 1+ | Not tested | House dust: 2+<br>Mite: 2+<br>Cedar: 1+<br>Dactylis: 1+<br>Ragweed: 1+ |

TABLE 9-1-continued

| | Case | | | |
|---|---|---|---|---|
| | B7 | B8 (=A8) | B9 | B10 |
| Effect of minoxidil | Not applied | Not applied | No effect | Not applied |
| Effect of finasteride | Not applied | Not applied | Not applied | Not applied |
| Effect of glycyrrhetinic acid | Not applied | Not applied | Not applied | Not applied |
| Effect of steroid drug | Not applied? | No effect | Not applied | Not applied |
| Effect of carpronium chloride | Not applied | Not applied | Not applied | Not applied |
| Effect of cepharanthin | Not applied | Not applied | Not applied | Not applied |
| Dosage form | BNP gel | BNP gel | BNP gel | BNP gel |
| Dose | 100 μg/g | 50 μg/g | 50 μg/g | Started with 50 μg/g, increased to 100 μg/g |
| Number of days used | 10 days | 3 weeks | 3 weeks | 50 μg/g for 3 weeks, then 100 μg/g for 3 weeks |
| Degree of improvement in symptoms | Terminal hair grew, hair was restored, and hair extension promoted. Dandruff disappeared, hair thinning range decreased, almost normal state recovered. | Erythema, seborrheic scale, and itching of hair loss site markedly improved, hair falling out decreased. Terminal hair grew, hair was restored, and hair thinning clearly improved. | Hair falling out decreased, vellus hair became dark, and growth of terminal hair observed. | Only for right-hand side to which BNP gel had been applied, vellus hair became terminal hair and grew in length compared with before application. |
| Non-recurrence period | 8 months | Treatment continuing | Treatment suspended | Treatment continuing |

Case B7

The test subject was a 39 year old male; the crown had become irritated at the age of 38, erythema and scale had appeared, the hair of the crown had become thin, and androgenetic alopecia had developed. This was classified as type II vertex on the Hamilton-Norwood scale. The paternal grandfather of this test subject had androgenetic alopecia. The results of the scratch test of this test subject were house dust 3+, mite 3+, cedar 1+, Dactylis 2+, and ragweed 1+.

When 100 μg/g BNP gel was applied to the hair loss site of the crown of this test subject twice a day morning and evening, the irritation started to disappear after about 1 week, the amount of hair falling out decreased, after 10 days' application the terminal hair became dark, the area of thinning hair decreased, and there was recovery to a substantially normal state. There was no recurrence even when 8 months had elapsed after application of the BNP gel was stopped after 10 days (Ref. FIG. 28-1 and FIG. 28-2).

Case B8

The test subject was a 45 year old male and had suffered from thinning hair confined to the crown from about 44 years old. This test subject showed erythema accompanied by itching and seborrheic scale on the scalp at the hair loss site, and had androgenetic alopecia with coexisting seborrheic alopecia. This was classified as type II vertex on the Hamilton-Norwood scale. The father of this test subject had androgenetic alopecia confined to the crown. The results of the scratch test of this test subject were house dust 2+, mite 3+, Dactylis 1+, and ragweed 1+. This test subject was the same test subject as the test subject of case A8.

When 100 μg/g ANP gel was applied to the entire hair loss site of the crown of this test subject twice a day morning and evening for 2 weeks, although the erythema seemed to be slightly improved, the amount of hair falling out remained large, the seborrheic scalp was not improved, and the hair loss range enlarged somewhat. Furthermore, itching occurred about 1 hour after application of the ANP gel, and strong itching appeared on the $2^{nd}$ day.

When 50 μg/g BNP gel was applied twice a day morning and evening to the entire hair loss site of the crown of this test subject, erythema, seborrheic scale, and itching on the hair loss site were markedly improved on the $1^{st}$ week after application of the BNP gel was started, the amount of hair falling out decreased to an unnoticeable level, the hair clearly thickened objectively, and the thinning hair was improved.

When external application of the BNP gel was stopped, with regard to this test subject, the effect continued for 2 months after the external application was stopped, and a good state in which the amount of hair falling out was small and there was no itching continued. Furthermore, with regard to this test subject, about 3 months after the external application of the BNP gel was stopped, the volume of hair on the crown decreased, the thinning hair became conspicuous, the amount of hair falling out increased, and itchiness occurred.

When, this time, 50 μg/g CNP gel was applied twice a day, this test subject noticed that blood circulation improved, the amount of hair falling out started to decrease on about the $5^{th}$ day, and the itching disappeared. With regard to this test subject, the hair started to thicken in about the $3^{rd}$ week after application of the CNP gel was started, and the hair thickened to a substantially normal state after 7 weeks of application. However, for this test subject, if application of the CNP gel was stopped for 2 to 3 months, the amount of hair falling out increased and thinning hair occurred on the crown; the treatment is being continued at the present time.

Case B9

The test subject was a 42 year old male and had suffered from thinning hair confined to the crown from about 40 years old. This test subject had a slight degree of erythema and scale on the scalp of the hair loss site. This was classified as type V on the Hamilton-Norwood scale. The father and the maternal grandfather of this test subject had androgenetic alopecia. This test subject was not subjected to a scratch test.

When 50 µg/g BNP gel was applied twice a day morning and evening to the entire thinning hair site of the crown of this test subject, by the $1^{st}$ week after application was started, the amount of hair falling out decreased, vellus hair darkened, and growth of terminal hair was observed, compared with the state before application in which there was only vellus hair. The hair became darker after 3 weeks, and hair thickening could be confirmed objectively.

Case B10

The test subject was a 65 year old male and the hair had thinned when the hair line of the frontal region and the corners of the forehead retreated during his 30s to 40s. The father also had androgenetic alopecia. This was classified as type VI on the Hamilton-Norwood scale. The results of the scratch test of this test subject were house dust 2+, mite 2+, cedar 1+, Dactylis 1+, and ragweed 1+, and there was a history of atopic dermatitis and allergic conjunctivitis.

Since the thinning hair had left-and-right symmetry, in order to evaluate the effects, 50 µg/g BNP gel was applied twice a day morning and evening to the right front temporal region, that is, the so-called M-shaped part, and only a gel base was applied to the left-hand side. By the $2^{nd}$ week thickening of vellus hair was observed only on the right-hand side, to which the BNP had been applied, compared with that before application; the concentration of the BNP gel was changed to 100 µg/g, it was applied to the right front temporal region for 2 weeks, and vellus hair in the M-shaped part clearly became terminal hair and thick and long compared with that when 50 µg/g BNP gel was applied.

Case B11

The test subject was a 75 year old male and hair on the crown had thinned from around 40 years old to 50 years old. This test subject had androgenetic alopecia with coexisting seborrheic alopecia, in which there was erythema accompanied by itching and seborrheic scale on the scalp of the hair loss site. This was classified as type VI on the Hamilton-Norwood scale. The father of this test subject had androgenetic alopecia. The results of the scratch test of this test subject were house dust 2+, mite 3+, Dactylis 1+, and ragweed 1+. There had been no effect on this test subject when minoxidil had been applied for 1 year. This test subject had been also using glycyrrhetinic acid for 2 years, but said that there had been no effect. This test subject was the same test subject as the test subject of case A9.

When 100 µg/g ANP gel was applied to the hair loss site of the crown of this test subject twice a day morning and evening for 4 days, there was no improvement in the erythema or the seborrheic scale.

When 50 µg/g BNP gel was applied to the hair loss site of the crown of this test subject twice a day morning and evening, on the $3^{rd}$ day after application was started erythema, seborrheic scale, and itching on the hair loss site were markedly improved and the amount of hair falling out become unnoticeable. The hair quality was improved after 2 weeks, the hair became black and thick and darkened, and there was hair thickening. When the BNP gel was also applied to the M-shaped part of this test subject twice a day for 20 days, terminal hair grew, and it was confirmed that growth of hair in the M-shaped part was also promoted. This test subject is still being treated with the BNP gel at present.

Case B12

The test subject was a 62 year old male who had developed thinning hair on the crown at around 50 years old, and had pityriatic scale and erythema accompanied by itching on the scalp of the hair loss site. This test subject had androgenetic alopecia with coexisting alopecia pityroides. This was classified as type III vertex on the Hamilton-Norwood scale. The father and a younger brother of this test subject had androgenetic alopecia. The results of the scratch test of this test subject were house dust 2+, mite 3+, cedar 2+, Dactylis 1+, and ragweed 2+, and there was atopic dermatitis and bronchial asthma. The brother had a history of atopic dermatitis and a child had a history of allergic rhinitis.

When 50 µg/g BNP gel was applied to the entire hair loss site of the crown of this test subject twice a day morning and evening for 3 weeks, the amount of hair falling out decreased markedly on the $3^{rd}$ day after application of the BNP gel started, and the erythema and seborrheic scale were improved. In the $3^{rd}$ week the hair became dark, there was hair thickening, and the thinning hair was improved objectively (Ref. FIG. 29).

When application of the BNP gel was stopped after 3 weeks, and from the following day 50 µg/g ANP gel was applied twice a day, this test subject exhibited seborrheic scale, erythema, and itching, the application was stopped after 1 week.

When from the following day 50 µg/g BNP gel was applied again twice a day, it was as if the seborrheic scale, erythema, and itching due to the ANP gel had never happened, the amount of hair falling out decreased, the itching and the seborrheic scale were also improved, the hair became thick, dark, and long, and there was hair thickening. Since this test subject had coexisting atopic dermatitis, the body was itchy, but there was no itchiness on the scalp. With regard to this test subject, even when application of the BNP gel was stopped after 2 weeks, the amount of hair falling out remained low for 2 months, and only 1 or 2 hairs became attached to a towel when washing the hair. However, when 2 months had elapsed after application of the BNP gel was stopped after 2 weeks, the amount of hair falling out started to increase again; when this time 50 µg/g CNP gel was applied twice a day, the amount of hair falling out decreased markedly, the erythema and seborrheic scale were also improved, and the itchiness disappeared. By the $3^{rd}$ week after application of the CNP gel was started, the hair had become thick, dark, and long, and there was hair thickening.

TABLE 9-2

| | Case | | | |
|---|---|---|---|---|
| | B11 (=A9) | B12 | B15 | B16 |
| Figure | | FIG. 29 | FIG. 40 | FIG. 41 |
| Gender | Male | Male | Male | Male |
| Age | 75 years old | 62 years old | 44 years old | 46 years old |
| When developed | 40s | 50s | Late 30s | Late 30s |

TABLE 9-2-continued

| | Case | | | |
|---|---|---|---|---|
| | B11 (=A9) | B12 | B15 | B16 |
| Treatment site | Crown, frontal region (M-shaped part) | Crown | Frontal region | Crown, frontal region |
| Hair loss state | Hair on crown thinned, and erythema accompanied by itching and seborrheic scale seen on scalp at hair loss site. | Hair on crown thinned, and erythema accompanied by itching and pityriatic desquamation seen on scalp at hair loss site. | Hairline retreated in M shape. | Hair in frontal region thinned, and hair on crown thinned after 40 years old. |
| Family history of androgenetic alopecia | Father: androgenetic alopecia | Father, younger brother: androgenetic alopecia | Father had androgenetic alopecia | Maternal grandfather and father had androgenetic alopecia |
| Family history of immune disease | None | Younger brother: atopic dermatitis Child: allergic rhinitis | None | None |
| Previous history | Allergic rhinitis | Atopic dermatitis, bronchial asthma | None | None |
| Scratch Test | House dust: 2+ Mite: 2+ Cedar: 3+ Dactylis: 2+ Ragweed: 2+ | House dust: 2+ Mite: 3+ Cedar: 2+ Dactylis: 1+ Ragweed: 2+ | Not tested | Not tested |
| Effect of minoxidil | No effect | Not applied | Not applied | Not applied |
| Effect of finasteride | Not applied | Not applied | Not applied | Not applied |
| Effect of glycyrrhetinic acid | No effect | Not applied | Not applied | Not applied |
| Effect of steroid drug | No effect | No effect | Not applied | Not applied |
| Effect of carpronium chloride | Not applied | Not applied | Not applied | Not applied |
| Effect of cepharanthin | Not applied | Not applied | Not applied | Not applied |
| Dosage form | BNP gel | BNP gel | BNP gel | BNP gel |
| Dose | 50 μg/g | 50 μg/g | 100 μg/g | 100 μg/g 200 μg/g |
| Number of days used | 3 weeks | 20 days | 3 weeks | 3 weeks + 2 weeks |
| Deree of improvement in symptoms | Erythema, seborrheic scale, and itching of hair loss site markedly improved, hair falling out decreased, and hair quality improved. Hairs became thick, black, and dense. Terminal hair grew in M-shaped part and became dark. | Erythema, pityriatic desquamation, and itching of hair loss site markedly improved, hair falling out decreased markedly, and hair became dark and thickened. | Hair falling out decreased, and hair thickened. Hairs became thick and long, and black terminal hair grew in hair thinning part of M-shaped part. | Hair loss area of crown decreased. Hairs became thick, terminal hair grew and restored, and feeling of volume increased. Hair in frontal region became thick and hair thickening observed. |
| Non-recurrence period | Treatment continuing | Treatment continuing | Treatment continuing | Treatment continuing |

Case B15

The test subject was a 44 year old male who had developed M-shaped androgenetic alopecia in his late 30s. This was classified as type III on the Hamilton-Norwood scale and this was a so-called M-shaped hair loss case. The father of this test subject had androgenetic alopecia.

When 100 μg/g BNP gel was applied to the frontal region of this test subject twice a day for 2 weeks, growth of black terminal hair was observed on the M-shaped thinning hair part after 5 days, and it became more marked in the 2$^{nd}$ week (FIG. 40).

When application of the BNP gel was stopped after 2 weeks, and from the 5$^{th}$ day after that a 50 μg/g BNP:600 μg/mL betamethasone:500 μg/mL gentamicin combination was applied twice a day for 1 week, the amount of hair falling out further decreased, the number of hairs lost during washing decreased to 1 to 2 hairs, and the hair became thicker. Due to this test subject being busy, the application was stopped, and even when 3 weeks had elapsed, the thickened hair state was certainly maintained compared with that before application.

Case B16

The test subject was a 46 year old male; thinning hair had occurred in the frontal region from the late 30s, and thinning hair occurred also on the crown after the age of 40. This test subject was classified as type V on the Hamilton-Norwood scale, and both the father and the maternal grandfather had androgenetic alopecia.

When 100 μg/g BNP gel was applied to the frontal region and the crown of this test subject twice a day for 3 weeks, marked growth of black terminal hair was observed on the crown, the feeling of volume of the hair increased, and the hair loss range on the crown decreased. The hair loss range of the crown at this point was 4 cm×3.4 cm (FIG. 41).

When the application of 100 μg/g BNP gel was stopped after 3 weeks and from the following day 200 μg/g BNP gel was applied twice a day for 2 weeks, the hair further thickened and restored, and the hair loss range decreased to 2.5 cm×2.4 cm. Furthermore, hair on the frontal region, for which clear improvement could not be observed by application of 100 μg/g BNP gel, became thick and dark with 2 weeks' application of 200 μg/g BNP gel, and the number of terminal hairs increased (FIG. 41).

11. Therapeutic Effect of CNP Ointment on Androgenetic Alopecia

The therapeutic effects of CNP ointment on androgenetic alopecia are shown in Table 10 (cases C16 and C17).

scalp of the hair loss site. The father and the paternal grandfather of this test subject had androgenetic alopecia. The results of the scratch test of this test subject were house dust –, mite 1+, cedar –, Dactylis –, and ragweed –.

When 100 μg/g CNP ointment was applied to the entire hair loss site of the crown and the frontal region of this test subject twice a day morning and evening, the amount of hair falling out decreased after 2 weeks of application, apparent improvement effects were observed, vellus hair became dark, and vellus hair clearly grew and became dark after 4 weeks of application (Ref. FIGS. 30-1 and 30-2). With regard to this test subject, when treatment with the CNP ointment was stopped after it had continued for 8 weeks, the therapeutic effect on hair loss was gradually lost after 3 months has elapsed subsequent to stopping application.

When 50 μg/g BNP gel was applied to the entire hair loss site of the crown and the frontal region of this test subject once a day for 1 month, fine hair became dark and thick, and the amount of hair falling out decreased.

TABLE 10-1

|  | Case | |
| --- | --- | --- |
|  | C16 | C17 |
| Figure | FIG. 30-1<br>FIG. 30-2 | FIG. 31 |
| Gender | Male | Male |
| Age | 56 years old | 59 years old |
| When developed | Late 30s | 50s |
| Treatment site | Crown, frontal region | Crown, frontal region |
| Hair loss state | Hair thinning with vellus hair seen from crown to frontal region. | Hair thinning from crown to frontal region. Scalp at hair loss site had erythema, scale, abrasion scars, and strong itching sensation. |
| Family history of androgenetic alopecia | Father, paternal grandfather: androgenetic alopecia | Father, grandfather: androgenetic alopecia |
| Family history of immune disease | None | None |
| Previous history | Atopic dermatitis | Diabetes |
| Scratch Test | House dust: –<br>Mite: 1+<br>Cedar: –<br>Dactylis: –<br>Ragweed: – | House dust: 2+<br>Mite: 3+<br>Cedar: –<br>Dactylis: 2+<br>Ragweed: 2+ |
| Effect of minoxidil | No effect | Not applied |
| Effect of finasteride | Not applied | Not applied |
| Effect of glycyrrhetinic acid | Not applied | Not applied |
| Effect of steroid drug | Not applied | No effect |
| Effect of carpronium chloride | Not applied | Not applied |
| Effect of cepharanthin | Not applied | Not applied |
| Dosage form | CNP ointment | CNP ointment |
| Dose | 100 μg/g | 50 μg/g |
| Number of days used | 28 days | 14 days |
| Degree of improvement in symptoms | Hair falling out decreased, vellus hair turned into terminal hair, thick and dark. | Itching subsided, erythema and abrasion scars on scalp disappeared, and short hair grew in frontal region and crown. |
| Non-recurrence period | Treatment continuing | Treatment continuing |

Case C16

The test subject was a 56 year old male with androgenetic alopecia in which the hair from the crown to the frontal region had become thin and vellus since his 40s. This test subject was classified as type Va on the Hamilton-Norwood scale and was a case in which there was both the so-called M-shaped and O-shaped hair loss sites. 1% minoxidil had previously been applied to this test subject for many years, but there had been no effect, and because recently there had been redness with itchiness, its use had been stopped. In the case of this test subject, the hair had become thin without inflammatory symptoms such as erythema or scale on the After 2 months had elapsed since the application of 50 μg/g BNP gel was started, it was changed to application of 200 μg/g BNP gel once a day, and when the application had continued for 1 week, hair started to rise and the rate of hair lengthening increased compared with the case with 50 μg/g BNP gel. The hair of this test subject had become white 5 years earlier if it was not dyed, but black hair thickened and lengthened in almost all of the frontal region, which was an area to which the BNP gel had been applied.

Case C17

The test subject was a 59 year old male with androgenetic alopecia in which the hair had become thin from the crown to the frontal region. This test subject was classified as type VII on the Hamilton-Norwood scale, and was a case in which there were both M-shaped and O-shaped hair loss sites. In the case of this test subject, there were erythema, scale, and abrasion scars on the scalp at the hair loss site, and the itching sensation was strong. The father and a grandfather of this test subject had androgenetic alopecia. The results of the scratch test of this test subject were house dust 2+, mite 3+, cedar –, Dactylis 2+, and ragweed 2+. This test subject had previously been prescribed a steroid and had continued with its external use for 7 months, but the itching sensation recurred after only about 1 hour, the inflammation did not calm down, and there was no improvement.

When 50 μg/g CNP ointment was applied to the entire hair loss site of this test subject twice a day for 1 week, the itching calmed down, erythema and abrasion scars on the scalp disappeared, and accompanying this there was growth of short hair on the crown and the frontal region (Ref. FIG. 31). This test subject is currently still being treated with the CNP ointment, and the application of CNP ointment had continued for 14 days at the time of filing of this patent application.

12. Therapeutic Effect of CNP Gel on Androgenetic Alopecia

The therapeutic effects of CNP gel on androgenetic alopecia are shown in Table 10-2 (cases C24 and C37 to C39).

TABLE 10-2

| | Case | | | |
|---|---|---|---|---|
| | C24 (=C40) | C37 | C38 | C39 |
| Figure | FIG. 42 | | | |
| Gender | Male | Male | Male | Male |
| Age | 48 years old | 43 years old | 33 years old | 34 years old |
| When developed | 5 year earlier | 40s | 30s | Late 20's |
| Treatment site | Crown | Frontal region, crown | Frontal region | Frontal region |
| Hair loss state | Hairline in frontal region retreated in M shape and became vellus hair, and thinning hair on crown. | Thinning hair in front temporal region and crown. | Thinning hair on crown, and hair loss in front temporal region. | Thinning hair on crown, and hair loss in front temporal region. |
| Family history of androgenetic alopecia | None | None | Father and maternal grandfather: androgenetic alopecia | Father: androgenetic alopecia |
| Family history of immune disease | Older brother: atopic dermatitis and allergic rhinitis | Unknown | Unknown | Unknown |
| Previous history | Allergic rhinitis and allergic conjunctivitis | Unknown | Unknown | Unknown |
| Scratch Test | House dust: 2+ Mite: 3+ Cedar: 2+ Dactylis: 2+ Ragweed: 2+ | Not tested | Not tested | Not tested |
| Effect of minoxidil | Not applied | Not applied | Not applied | Not applied |
| Effect of finasteride | Not applied | Not applied | Not applied | Not applied |
| Effect of glycyrrhetinic acid | Not applied | Not applied | Not applied | Not applied |
| Effect of steroid drug | Not applied | Not applied | Not applied | Not applied |
| Effect of carpronium chloride | Not applied | Not applied | Not applied | Not applied |
| Effect of cepharanthin | Not applied | Not applied | Not applied | Not applied |
| Dosage form | CNP gel | CNP gel | CNP gel | CNP gel |
| Dose | 50 μg/g | 100 μg/g | 50 μg/g | 50 μg/g |
| Number of days used | 1 week | 2 weeks | 2 weeks | 3 weeks |
| Degree of improvement in symptoms | Hair falling out decreased, hair became thick, and the number of hairs increased. | Hair falling out decreased, hair quality became thick, and hair thinning on crown improved. | Hair thickening seen on crown, and vellus hair became thick and dark. In M-shaped hair thinning part, vellus hair became thick and long, and hair falling out decreased. | Hair thickening seen on crown, and hair became thick and dark. In M-shaped part, hair grew and hair was restored at slow pace. |
| Non-recurrence period | Treatment continuing | Treatment continuing | Treatment continuing | Treatment continuing |

Case C24

The test subject was a 48 year old male and had androgenetic alopecia. With regard to this test subject, 5 years earlier, the hair line in the frontal region had retreated in an M-shape and had become vellus hair, and the hair on the crown had become thin. This was classified as type III vertex on the Hamilton-Norwood scale. None of the family of this test subject had thinning hair.

When 50 μg/g CNP gel was applied twice a day to the crown of this test subject for 1 week, the amount of hair falling out decreased, the hair became thick, and the number of hairs increased (FIG. 42).

When application of the CNP gel was stopped after 1 week and a 50 μg/g CNP:600 μg/mL betamethasone:500 μg/mL gentamicin combination was then applied twice a day for 1 week, the amount of hair falling out further decreased, and the hair became thicker. Furthermore, hair growth was observed also in the M-shaped part 2 weeks after application of the CNP:betamethasone:gentamicin combination was started.

After the application was suspended for 3 weeks, when a 5% minoxidil solution was applied and 100 μg/g CNP gel was then applied as a multilayer application, there were no symptoms of irritation, the hair gradually became thick and there was restoration of terminal hair both in the M-shaped part and the crown after 1 week following starting the multilayer application.

Case C37

The test subject was a 43 year old male and had androgenetic alopecia in which thinning hair had appeared on the front temporal region and the crown from his 40s. This test subject was classified as type V on the Hamilton-Norwood scale, and was a case having both so-called M-shaped and O-shaped hair loss sites.

When 100 μg/g CNP gel was applied to the frontal region and the crown of this test subject twice a day for 2 weeks, the amount of hair falling out decreased, the number of hairs falling became about 10 when washing the hair, the quality of the hair changed from being fine to being thick, the hair became long, the thinning hair on the crown was improved, and it became difficult to see through to the skin.

Case C38

The test subject was a 33 year old male whose hair quality had become curly and fine in his late 20s, and androgenetic alopecia had developed in his 30s. This was classified as type III vertex on the Hamilton-Norwood scale, and there was so-called M-shaped alopecia in which the hair on the crown became thin and the front temporal region had hair loss. The father and the maternal grandfather of this test subject had androgenetic alopecia.

When 50 μg/g CNP gel was applied to the frontal region of this test subject twice a day for 1 week, the amount of hair falling out decreased, and hair did not become attached to a pillow. Hair thickening on the crown of this test subject was confirmed by the $2^{nd}$ week, and vellus hair became thick and dark. This test subject said that when he entered a freezer at work, he subjectively did not feel cold air penetrating the scalp. With regard to this test subject, vellus hair in the M-shaped thinning hair part also became thick and long. With regard to this test subject, when application was subsequently continued, the number of terminal hairs on the crown increased considerably and the hair became longer after 2 months had elapsed, there was hair thickening, and thinning hair became inconspicuous. Even in the M-shaped thinning hair part, although the hair was finer than that on the crown, terminal hair rather than vellus hair increased, became longer, and the number of long hairs increased.

Subsequently, when a 50 μg/g CNP:600 μg/mL betamethasone:500 μg/mL gentamicin combination was applied twice a day for 2 weeks, the hair further thickened on the crown and the hair on the M-shaped part became longer and thicker, but there was accompanying folliculitis, which was thought to be a side effect of a steroid.

Case C39

The test subject was a 34 year old male whose hair had become thin in his late 20's and who had androgenetic alopecia. This was classified as type V on the Hamilton-Norwood scale, and there was thinning hair on the crown and so-called M-shaped alopecia in which there was hair loss on the front temporal region. The father of this test subject had androgenetic alopecia. A 1% minoxidil solution had been applied to this test subject for 1 year, but there had been no effect. Furthermore, biotin and a Chinese medicine had been orally administered to this test subject, but there had been no effect.

When 50 μg/g CNP gel was applied to the frontal region of this test subject twice a day for 3 weeks, hair thickening was observed on the crown, and the hair became thick and dark. On the M-shaped part also hair growth and hair restoration were observed at a slow pace.

13. Therapeutic Effect of CNP:Betamethasone:Gentamicin Combination on Androgenetic Alopecia The therapeutic effects of CNP:betamethasone:gentamicin combination on androgenetic alopecia are shown in Table 10-3 (case C25).

TABLE 10-3

| | Case C25 |
|---|---|
| Figure | FIG. 43, FIG. 44 |
| Gender | Male |
| Age | 75 years old |
| When developed | 5 years earlier |
| Treatment site | Frontal region and crown |
| Hair loss state | Hairline in frontal region retreated in M-shape and became vellus hair, and thinning hair on crown. From half a year earlier there had been coexisting alopecia pityroides accompanied by scale, erythema, and itching. |
| Family history of androgenetic alopecia | None |
| Family history of immune disease | Unknown |
| Previous history | Unknown |
| Scratch Test | Unknown |
| Effect of minoxidil | Not applied |
| Effect of finasteride | Not applied |
| Effect of glycyrrhetinic acid | Not applied |
| Effect of steroid drug | No effect |
| Effect of carpronium chloride | Not applied |
| Effect of cepharanthin | Not applied |
| Dosage form | CNP:betamethasone:gentamicin combination |
| Dose | 25 μg/g CNP 600 μg/ml betamethasone 500 μg/ml gentamicin |
| Number of days used | 12 days |
| Degree of improvement in symptoms | Hair falling out decreased, scale and erythema improved, and marked hair thickening in both crown and M-shaped part. Hair became thick and long. |
| Non-recurrence period | Unknown |

Case C25

The test subject was a 75 year old male who had androgenetic alopecia. With regard to this test subject, the hair line in the frontal region had retreated in an M-shape and the crown had started to become thin from 5 years earlier. This test subject had scale and erythema with accompanying itching, and had coexisting alopecia pityroides. This test subject was a case having both the so-called M-shaped and O-shaped hair loss sites, and was classified as type VI on the Hamilton-Norwood scale.

When a 25 μg/g CNP:600 μg/mL betamethasone:500 μg/mL gentamicin combination was applied to the frontal region and the crown of this test subject twice a day for 12 days, there was almost no hair falling out, and the scale and erythema disappeared completely. Application of the CNP: betamethasone:gentamicin combination was stopped after 12 days, and when observation was made 18 days after application had been stopped, the hair quality had improved for both the hair line of the frontal region and the crown, the hair had become thick and long, and there was marked hair thickening (FIG. 43 and FIG. 44).

14. Therapeutic Effect of CNP:Clobetasol Combination on Androgenetic Alopecia

The therapeutic effects of CNP:clobetasol combination on androgenetic alopecia are shown in Table 10-4 (case C26).

TABLE 10-4

| | Case C26 |
|---|---|
| Figure | FIG. 45 |
| Gender | Male |
| Age | 61 years old |
| When developed | Unknown |
| Treatment site | Frontal region and crown |
| Hair loss state | Hair thinning was conspicuous in frontal region and crown. |
| Family history of androgenetic alopecia | Father, paternal grandfather, and maternal grandfather had androgenetic alopecia. |
| Family history of immune disease | Unknown |
| Previous history | Bronchial asthma |
| Scratch Test | — |
| Effect of minoxidil | Not applied |
| Effect of finasteride | Not applied |
| Effect of glycyrrhetinic acid | Not applied |
| Effect of steroid drug | No effect |
| Effect of carpronium chloride | Not applied |
| Effect of cepharanthin | Not applied |
| Dosage form | CNP:clobetasol combination |
| Dose | 50 μg/g CNP 250 μg/g clobetasol |
| Number of days used | 7 days |
| Degree of improvement in symptoms | Marked growth of black terminal hair, itching sensation disappeared, and dandruff stopped. |
| Non-recurrence period | Treatment continuing |

Case C26

The test subject was a 61 year old male who had androgenetic alopecia. This test subject was a case in which the frontal region and the crown had thinning hair mixed with white hair and there was coexisting alopecia pityroides accompanied by itching and scale. The father, the paternal grandfather, and the maternal grandfather of this test subject had androgenetic alopecia. This test subject was affected by bronchial asthma. The test results of the scratch test of this test subject were as given, and this test subject was a case having both the so-called M-shaped and O-shaped hair loss sites, and was classified as type IVa on the Hamilton-Norwood scale. 'Dermovate Scalp Lotion 0.05%' (GlaxoSmithKline plc), which contains 0.05% of clobetasol propionate and 'Fulmeta Lotion' (Shionogi & Co., Ltd.), which contains 0.1% of mometasone furancarboxylate had been applied to the frontal region and the crown of this test subject for 9 months, but there had been no effect at all, and the hair had become somewhat thin.

When a 50 μg/mL CNP:250 μg/g clobetasol combination was applied to the frontal region and the crown of this test subject twice a day for 1 week, marked growth of black terminal hair was observed, the itching sensation disappeared, and dandruff disappeared (FIG. 45).

When the application of 50 μg/mL CNP:250 μg/g clobetasol combination was stopped after 1 week, and from the following day a 50 μg/mL BNP:250 μg/g clobetasol combination was applied twice a day, growth of black terminal hair became more marked after 1 week, the amount of hair falling out decreased markedly after 2 weeks, and black terminal hair lengthened at a very high rate.

15. Therapeutic Effect of CNP:Carpronium Chloride Combination on Androgenetic Alopecia The therapeutic effects of CNP:carpronium chloride combination on androgenetic alopecia are shown in Table 10-5 (case C27).

TABLE 10-5

| | Case C27 |
|---|---|
| Figure | FIG. 46 |
| Gender | Male |
| Age | 32 years old |
| When developed | About 30 years old |
| Treatment site | Frontal region, left temporal region |
| Hair loss state | Hair loss in M-shaped part of frontal region, and circular bald area in left temporal region. |
| Family history of androgenetic alopecia | None |
| Family history of immune disease | None |
| Previous history | None |
| Scratch Test | Not tested |
| Effect of minoxidil | Not applied |
| Effect of finasteride | Not applied |
| Effect of glycyrrhetinic acid | Not applied |
| Effect of steroid drug | Not applied |
| Effect of carpronium chloride | Not applied |
| Effect of cepharanthin | Not applied |
| Dosage form | CNP:carpronium chloride combination |
| Dose | 50 μg/g |
| Number of days used | 14 days |
| Degree of improvement in symptoms | Larger number of black terminal hairs grew than when single agent was applied. |
| Non-recurrence period | Treatment continuing |

Case C27

The test subject was a 32 year old male who had androgenetic alopecia. With regard to this test subject, hair of the M-shaped hair line in the frontal region suddenly thinned at the age of 30 and retreated. Alopecia areata monolocularis had also developed in the left temporal region 6 weeks before visiting the clinic. None of the family of this test subject had alopecia. This test subject was classified as type III on the Hamilton-Norwood scale, and had so-called M-shaped androgenetic alopecia.

When 50 μg/g CNP gel was applied twice a day to an androgenetic alopecia area of the frontal region and a circular bald area of the left temporal region of this test subject, growth of black terminal hair was observed after 2 weeks both in the M-shaped hair line area and the circular bald area (FIG. 46).

When application of the CNP gel was stopped after 2 weeks and from the following day a CNP:carpronium chloride combination was applied twice a day, a larger amount of black terminal hair than with the single agent grew after 1 week.

16. Therapeutic Effect of Multilayer Application of CNP Gel and Minoxidil on Androgenetic Alopecia The therapeutic effects of multilayer application of CNP gel and minoxidil on androgenetic alopecia are shown in Table 10-6 (case C40).

TABLE 10-6

| | Case<br>C40 (=C24) |
|---|---|
| Figure | |
| Gender | Male |
| Age | 48 years old |
| When developed | 5 years earlier |
| Treatment site | Frontal region, crown |
| Hair loss state | Hairline in frontal region retreated in M-shape and became vellus hair, thinning hair on crown. |
| Family history of androgenetic alopecia | None |
| Family history of immune disease | Older brother: atopic dermatitis and allergic rhinitis |
| Previous history | Allergic rhinitis and allergic conjunctivitis |
| Scratch Test | House dust: 2+ |
| | Mite: 3+ |
| | Cedar: 2+ |
| | Dactylis: 2+ |
| | Ragweed: 2+ |
| Effect of minoxidil | Not applied |
| Effect of finasteride | Not applied |
| Effect of glycyrrhetinic acid | Not applied |
| Effect of steroid drug | Not applied |
| Effect of carpronium chloride | Not applied |
| Effect of cepharanthin | Not applied |
| Dosage form | Multilayer application of CNP gel and minoxidil |
| Dose | 100 µg/g CNP gel<br>1% minoxidil |
| Number of days used | 1 week |
| Degree of improvement in symptoms | Restoration of terminal hair seen in M-shaped part and crown. |
| Non-recurrence period | Treatment continuing |

Case C40

Case C40 was the same test subject as C24 and was an androgenetic alopecia case. Details of this case are as described for case C24.

When 5% minoxidil solution was applied to this test subject and after that 100 µg/g CNP gel was applied by multilayer application, there were no symptoms of irritation, and restoration of black terminal hair was observed, although it was gradual, on the M-shaped part and the crown from 1 week after starting the multilayer application.

17. Therapeutic Effect of Multilayer Application of BNP Gel and Minoxidil on Androgenetic Alopecia The therapeutic effects of multilayer application of BNP gel and minoxidil on androgenetic alopecia are shown in Table 10-7 (case B29).

TABLE 10-7

| | Case<br>B29 |
|---|---|
| Figure | |
| Gender | Male |
| Age | 52 years old |
| When developed | About 23 years old |
| Treatment site | Crown |
| Hair loss state | Frontal region and crown had thinning hair. |

TABLE 10-7-continued

| | Case<br>B29 |
|---|---|
| Family history of androgenetic alopecia | None |
| Family history of immune disease | None |
| Previous history | None |
| Scratch Test | Not tested |
| Effect of minoxidil | Not applied |
| Effect of finasteride | Not applied |
| Effect of glycyrrhetinic acid | Not applied |
| Effect of steroid drug | Not applied |
| Effect of carpronium chloride | Not applied |
| Effect of cepharanthin | Not applied |
| Dosage form | Multilayer application of BNP gel and minoxidil |
| Dose | 100 µg/g BNP gel<br>5% minoxidil |
| Number of days used | 1 week |
| Degree of improvement in symptoms | No symptoms of irritation, hair became supple, and hair thinning on crown improved. |
| Non-recurrence period | Treatment continuing |

Case B29

The test subject was a 52 year old male and had androgenetic alopecia that was classified as type IV on the Hamilton-Norwood scale. This test subject had shown thinning hair in the frontal region at around 23 years old, and the crown currently had thinning hair. This test subject had no family members with alopecia. Oral administration of Hangekobokuto had not shown any effect on this test subject.

When 100 µg/g BNP gel was applied twice a day to the androgenetic alopecia area of the crown of this test subject, the amount of hair falling out decreased dramatically 2 weeks later, the hair on the crown became thick and dark, and growth of black terminal hair was observed. However, after that, when application of the BNP gel was suspended for 3 weeks, the hair became less robust and less resilient.

When multilayer application of 5% minoxidil solution and then 100 µg/g BNP gel was carried out for 1 week, there were no symptoms of irritation, the hair became robust, and the thinning hair on the crown was improved.

Case C32

Case C32 was a case of coexisting androgenetic alopecia and seborrheic alopecia, and was the same as cases A9, B11, and B22.

When 100 µg/g BNP gel was applied to thinning hair sites of the crown and the M-shaped part of this test subject twice a day morning and evening, erythema, seborrheic scale, and itching of the hair loss sites markedly improved on the $3^{rd}$ day after application was started, and the amount of hair falling out become unnoticeable. With regard to this test subject, the hair quality was improved after 2 weeks, the hair became thick and dark, and there was hair thickening. With regard to this test subject, on the $2^{nd}$ week of application, in the M-shaped part also, vellus hair became thick, dark, and although it was slow the hair became long.

In order to examine an external preparation that could further reduce the thinning hair range of the crown of this test subject, after 5% minoxidil solution was applied to the crown and the M-shaped part, 100 µg/g BNP gel was applied by multilayer application; the hair on the crown became black and dark compared with application of a single BNP agent when 1 week had elapsed after the multilayer application had started, and there was hair thickening. This test subject is still having multilayer application treatment with 5% minoxidil and 100 µg/g BNP gel at the present.

18. Therapeutic Effect of ANP Gel on Postpartum Alopecia

The therapeutic effects of ANP gel on postpartum alopecia are shown in Table 10-8 (case A10).

TABLE 10-8

| | Case A10 |
|---|---|
| Figure | FIG. 47 |
| Gender | Female |
| Age | 45 years old |
| When developed | 44 years old |
| Treatment site | Crown |
| Hair loss state | Thinning hair on crown was conspicuous. |
| Hair loss site other than head | None |
| Family history of alopecia | Unknown |
| Family history of immune disease | Unknown |
| Previous history | None |
| Scratch Test | Not tested |
| Effect of minoxidil | Not applied |
| Effect of glycyrrhetinic acid | Not applied |
| Effect of steroid drug | Not applied |
| Effect of cooling therapy | Not applied |
| Antiallergic drug | No effect |
| Effect of carpronium chloride | Not applied |
| Effect of cepharanthin | Not applied |
| Dosage form | ANP gel |
| Dose | 100 µg/g |
| Number of days used | 21 days |
| Degree of improvement in symptoms | Hair falling out did not decrease, but hair loss range of crown enlarged. |
| Non-recurrence period | Treatment continuing |

Case A10

This test subject was a 45 year old female and had developed thinning hair on the crown after childbirth.

When 100 µg/g ANP gel was applied to the crown of this test subject twice a day for 3 weeks, the amount of hair falling out did not decrease, but the hair loss range on the crown enlarged somewhat.

When application of the ANP gel was stopped after 3 weeks and suspended for 6 months, and then 50 µg/g BNP gel was applied to the hair loss site of the crown once every 3 to 4 days for 3 weeks, the thinning hair on the crown thickened to a level such that it was visually unnoticeable (FIG. 47).

19. Therapeutic Effect of BNP Gel on Postpartum Alopecia

The therapeutic effects of BNP gel on postpartum alopecia are shown in Table 10-9 (case B17).

TABLE 10-9

| | Case B17 |
|---|---|
| Figure | FIG. 47 |
| Gender | Female |
| Age | 45 years old |
| When developed | 44 years old |
| Treatment site | Crown |
| Hair loss state | Thinning hair on crown was conspicuous. |
| Hair loss site other than head | None |
| Family history of alopecia | Unknown |
| Family history of immune disease | Unknown |
| Previous history | None |
| Scratch Test | Not tested |
| Effect of minoxidil | Not applied |
| Effect of glycyrrhetinic acid | Not applied |
| Effect of steroid drug | Not applied |
| Effect of cooling therapy | Not applied |
| Antiallergic drug | No effect |
| Effect of carpronium chloride | Not applied |
| Effect of cepharanthin | Not applied |

TABLE 10-9-continued

| | Case B17 |
|---|---|
| Dosage form | BNP gel |
| Dose | 50 µg/g |
| Number of days used | 21 days |
| Degree of improvement in symptoms | Hair grew on crown, thinning hair improved to a level such that it was unnoticeable |
| Non-recurrence period | 2 months |

Case B17

Case B17 was the same test subject as case A10.

When, 6 months after application of the ANP gel was stopped, 50 µg/g BNP gel was applied to the crown 3 to 4 times a day for 3 weeks, the terminal hair thickened, the amount of hair falling out decreased, and the thinning hair recovered to the extent that it was unnoticeable (FIG. 47).

20. Therapeutic Effect of CNP Gel on Postpartum Alopecia

The therapeutic effects of CNP gel on postpartum alopecia are shown in Table 11-1 (case C18).

TABLE 11-1

| | Case C18 | |
|---|---|---|
| Figure | FIG. 32 | |
| Gender | Female | |
| Age | 27 years old | |
| When developed | 27 years old | |
| Treatment site | Crown | |
| Hair loss state | Thinning hair from crown to frontal region was conspicuous. | |
| Hair loss site other than head | None | |
| Family history of alopecia | Mother: androgenetic alopecia in female with thinning on crown | |
| Family history of immune disease | Mother: allergic rhinitis | |
| Previous history | Atopic dermatitis | |
| Scratch Test | House dust: | 3+ |
| | Mite: | 2+ |
| | Cedar: | 2+ |
| | Dactylis: | 2+ |
| | Ragweed: | 2+ |
| Effect of minoxidil | Not applied | |
| Effect of steroid drug | No effect | |
| Effect of cooling therapy | Not applied | |
| Antiallergic drug | Not applied | |
| Effect of carpronium chloride | No effect | |
| Effect of cepharanthin | Not applied | |
| Dosage form | CNP gel | |
| Dose | 100 µg/g | |
| Number of days used | 7 days | |
| Degree of improvement in symptoms | Hair parting was wide and conspicuous, but short sturdy terminal hair grew, and bald area along hair parting improved. | |
| Non-recurrence period | 6 months | |

Case C18

The test subject was a 27 year old female and was a patient with postpartum alopecia. This was a case with a history of atopic dermatitis and with an atopic predisposition. The mother of this test subject was affected by allergic rhinitis, and the mother of this test subject also had female pattern alopecia with a thin crown. The results of the scratch test were house dust 3+, mite 3+, cedar 2+, Dactylis 2+, and ragweed 2+. This test subject had rapidly lost hair due to childbirth 7 months earlier. Thinning hair on the crown and the frontal region was conspicuous for this test subject. This test subject had received application of a steroid and carpronium chloride for 5 months, but there was still a large amount of hair falling out, and thinning hair on the crown had not improved.

When 100 μg/g CNP gel was applied to the entire crown of this test subject twice a day, the amount of hair falling out decreased dramatically after 7 days of application, it improved such that only 5 to 6 hairs fell out per day, and the seborrheic scalp was also improved (Ref. FIG. 32). A large amount of short terminal hair grew from the frontal region to the crown, the thinning hair of the crown became inconspicuous objectively, and a substantially normal state was recovered. However, the amount of hair falling out increased around the summer when half a year had elapsed since application of the CNP gel was stopped after 7 days, and the crown showed thinning hair.

When this time 100 μg/g BNP gel was applied twice a day to the entire crown, the amount of hair falling out decreased dramatically after 7 days' application, and a large amount of short terminal hair grew. Application of the BNP gel was stopped after 7 days, but there was no recurrence for half a year thereafter.

21. Therapeutic Effect of BNP Gel on Female Pattern Alopecia

The therapeutic effects of BNP gel on female pattern alopecia are shown in Table 11-2 (cases B18 to B20 and B27).

TABLE 11-2

|  | Case | | | |
| --- | --- | --- | --- | --- |
|  | B18 | B19 | B20 | B27 |
| Figure | None | FIG. 48 | FIG. 49 |  |
| Gender | Female | Female | Female | Female |
| Age | 46 years old | 59 years old | 50 years old | 66 years old |
| When developed | 46 years old | 59 years old | About 47 years old | 65 years old |
| Treatment site | Crown | Frontal region | Crown | Crown, frontal region, left M-shaped part |
| Hair loss state | Diffuse hair loss on and around the mid line. | Thinning hair in hair parting in frontal region was conspicuous. | Hair thinning on crown and its periphery, large amount of hair falling out. | Thinning hair in wide range from crown to frontal region and left M-shaped part, the skin showed through. Seborrheic scale was conspicuous. The amount of hair falling out was very large. |
| Hair loss site other than head | None | None | None | None |
| Family history of alopecia | Father, grandfather, and older brother had androgenetic alopecia | None | Mother had female pattern alopecia and father had androgenetic alopecia | 65 years old |
| Family history of immune disease | Grandfather, Older brother: asthma | None | None | None |
| Previous history | Atopic dermatitis bronchial asthma allergic rhinitis | None | None | None |
| Scratch Test | House dust: 2+ Mite: 2+ Cedar: — Dactylis: — Ragweed: — | Not tested | Not tested | Not tested |
| Effect of minoxidil | Not tested | Not tested | Not tested | Not tested |
| Effect of steroid drug | Not applied | Not applied | No effect | No effect |
| Effect of cooling therapy | Not applied | Not applied | Not applied | Not applied |
| Antiallergic drug | Not applied | Not applied | Not applied | No effect |
| Effect of carpronium chloride | Not applied | Not applied | Not applied | Not applied |
| Effect of cepharanthin | Not applied | Not applied | Not applied | Not applied |
| Dosage form | BNP gel | BNP gel | BNP gel | BNP gel |
| Dose | 50 μg/g | 100 μg/g | 50 μg/g | 50 μg/g |
| Number of days used | 28 days | 14 days | 14 days | 21 days |
| Degree of improvement in symptoms | After BNP gel was applied for 2 weeks, marked hair growth and restoration was observed, and hair thickened so that no skin could be seen. The number of hairs falling out during shampooing decreased to about 10. | Hair thinning in frontal region improved, and slight degree of erythema disappeared. | Hair falling out decreased to one third, and hair thinning became inconspicuous. | By 10$^{th}$ day after application twice a day for 5 days, black terminal hair grew on hairline and crown, seborrheic scale on scalp was markedly improved, and hair falling out decreased. |
| Non-recurrence period | >4 months | 1 month | 1 month | 2 weeks |

Case B18

The test subject was a 56 year old female and was a patient with female pattern alopecia. This test subject had a large amount of broken hair and hair falling out, and diffuse hair loss was observed centered on the mid line. The father, a grandfather, and an older brother of this test subject had androgenetic alopecia.

When 50 µg/g BNP gel was applied to the crown of this test subject, marked hair growth and hair restoration were observed about 2 weeks after the application was started, and during application the amount of hair falling out and sticking to the hands when shampooing decreased to about 10 hairs. With regard to this test subject, the hair thickened to an extent such that eventually the skin could not be seen. There was no subsequent external application for 4 months, the terminal hair remained, and a state with a small amount of hair falling out could be maintained.

Case B19

The test subject was a 59 year old female and was a patient with female pattern alopecia. This test subject had developed conspicuous thinning hair at the hair parting in the frontal region in her 50s.

When 100 µg/g BNP gel was applied twice a day for 2 weeks, the thinning hair thickened and became inconspicuous to a degree that could be said to be normal, and the application was therefore stopped.

However, half a year later, thinning hair at the hair parting in the frontal region became conspicuous again, and when this time 50 µg/g CNP gel was applied twice a day for 1 week, the thinning hair thickened to an extent such that it was unnoticeable (FIG. 48).

When a 50 µg/g CNP:600 µg/mL betamethasone:500 µg/mL gentamicin combination was further applied twice a day, during the 1$^{st}$ week a state in which the amount of hair falling out was unchanged was maintained and there was no itching, but during the 2$^{nd}$ week a slight degree of erythema occurred and it became possible to see through to the scalp slightly. The application of 50 µg/g CNP:600 µg/mL betamethasone:500 µg/mL gentamicin combination was therefore stopped after 10 days, and when from the following day it was changed to 100 µg/g CNP gel, the hair thickened again with application twice a day for 1 week.

However, when the application of 100 µg/g CNP gel was stopped after 1 week and 100 µg/g ANP gel was applied twice a day for 1 week, a slight degree of erythema appeared, it was possible to see through to the scalp, and the hair became thinner than it had been before application.

Case B20

The test subject was a 50 year old female and was a patient with female pattern alopecia. The hair of this test subject had thinned from the crown to the frontal region a few years earlier, and the hair parting had enlarged. The mother of this test subject had female pattern alopecia, and the father had androgenetic alopecia.

When 'Dermosol-G Lotion' (Iwaki Seiyaku Co., Ltd.), which contains 1200 µg/mL of betamethasone valerate and 1000 µg/mL of gentamicin sulfate, was applied to the crown of this test subject continuously for 8 weeks, the thinning hair was not improved at all.

When 50 µg/g BNP gel was applied to the crown of this test subject twice a day for 1 week, the amount of hair falling out decreased to one third after 1 week, and the thinning hair became inconspicuous after 2 weeks (FIG. 49). After application of the BNP gel was stopped after 2 weeks, a state in which the amount of hair falling out was small was maintained for about 1 month, but the amount of hair falling out increased again after about 1 month.

When 50 µg/g CNP gel was applied twice a day for 2 weeks, in the same way as for the BNP gel the amount of hair falling out decreased to about one third, and the thinning hair became inconspicuous after 2 weeks.

Moreover, when application of the CNP gel was stopped after 2 weeks and 2 weeks after that a 50 µg/g CNP:600 µg/mL betamethasone:500 µg/mL gentamicin combination was applied twice a day for 2 weeks, the state in which the amount of hair falling out decreased was maintained. Even when 2 weeks had elapsed after application of the 50 µg/g CNP:600 µg/mL betamethasone:500 µg/mL gentamicin combination was stopped after 2 weeks, a state in which the thinning hair was inconspicuous and it could be said to be normal was maintained.

Case B27

The test subject was a 66 year old female whose hair had thinned at about 65 years old. This was female pattern alopecia having coexisting seborrheic alopecia with conspicuous seborrheic scale on the scalp. This test subject had thinning hair from the crown to the frontal region and the left-hand side M-shaped part with the skin being quite visible. With regard to this test subject, the amount of hair falling out was very large, and the hair fell out immediately simply by touching it. The father and an older brother of this test subject had androgenetic alopecia.

When 50 µg/g BNP gel was applied to the crown of this test subject twice a day, hair growth and hair restoration were observed about 4 to 5 days after the application was started, and the seborrheic scale on the scalp was markedly improved. The amount of hair falling out for this test subject, for whom a large amount had fallen out simply by touching it before the application, decreased. With regard to this test subject, the thinning hair became inconspicuous to a degree such that the skin could not be seen 21 days after application of 50 µg/g BNP gel had been started.

22. Therapeutic Effect of CNP Gel on Female Pattern Alopecia

The therapeutic effects of CNP gel on female pattern alopecia are shown in Table 12 (cases C19, C28, and C29).

TABLE 12

|  | Case | | |
| --- | --- | --- | --- |
|  | C19 | C28 | C29 |
| Figure | FIG. 33 | FIG. 50 | — |
| Gender | Female | Female | Female |
| Age | 46 years old | 62 years old | 60 years old |
| When developed | About 46 years old | 62 years old | 59 years old |
| Treatment site | Crown | Frontal region and crown | Frontal region |
| Hair loss state | Diffuse hair thinning was conspicuous from crown to frontal region. | Hair thinning occurred from frontal region to crown. Large amount of dandruff on scalp, there was erythema, large amount of hair falling out. | Hair thinning occurred on hairline of frontal region, accompanied by scale. |

TABLE 12-continued

| | Case | | |
|---|---|---|---|
| | C19 | C28 | C29 |
| Hair loss site other than head | None | None | None |
| Family history of alopecia | Grandfather, older brother: androgenetic alopecia | Father had androgenetic alopecia at around 35 years old | Unknown |
| Family history of immune disease | Mother: allergic rhinitis | Unknown | Unknown |
| Previous history | Atopic dermatitis | Unknown | Unknown |
| Scratch Test | Not tested | Not tested | Unknown |
| Effect of minoxidil | Not tested | Not tested | Unknown |
| Effect of steroid drug | No effect | Not applied | Not applied |
| Effect of cooling therapy | Not applied | Not applied | Not applied |
| Antiallergic drug | Not applied | Not applied | Not applied |
| Effect of carpronium chloride | No effect | Not applied | Not applied |
| Effect of cepharanthin | Not applied | Not applied | Not applied |
| Dosage form | CNP gel | CNP gel | CNP gel |
| Dose | 100 µg/g | 50 µg/g | 50 µg/g |
| Number of days used | 4 weeks | 28 days | 14 days |
| Degree of improvement in symptoms | Thinning hair part recovered to almost normal state, and hair falling out decreased. | After 2 weeks' application, hair falling out decreased, and hair thickened from frontal region to crown. 1 month after starting application, hair thinning improved to unnoticeable level. | Hair thinning at hairline of frontal region improved to normal state. Scale also disappeared. |
| Non-recurrence period | 1 month | 3 months | 6 weeks |

Case C19

The test subject was a 56 year old female and was a patient with female pattern alopecia. There was a history of atopic dermatitis, the mother of this test subject was affected by allergic rhinitis, and this was a case with an atopic predisposition. The father of this test subject had androgenetic alopecia, and the mother of this test subject had female pattern alopecia. The results of the scratch test were house dust 2+, mite 2+, cedar 1+, Dactylis 1+, and ragweed 1+. The hair on the crown of this test subject had become thin 10 years earlier. This test subject had been externally applying a steroid and carpronium chloride, but there had been no effect.

When 100 µg/g CNP gel was applied to the crown and the thinning hair part on the crown of this test subject twice a day, the amount of hair falling out decreased after 4 days of application, new terminal hair grew on the frontal region and the crown, and the hair parting on the scalp did not widen (ref. FIG. 33). However, when application of the CNP gel was stopped after 2 weeks, about 2 weeks after the application was stopped a slight degree of erythema and scale reappeared on the scalp of the frontal region and the crown, and there was thinning hair.

When this time 50 µg/g BNP gel was applied twice a day for 3 weeks, vellus hair became thick, hair growth was observed, and the thinning hair improved. However, when application of the BNP gel was stopped after 3 weeks, about 1 month after the application was stopped a slight degree of erythema and scale on the scalp of the frontal region and the crown reappeared, and there was thinning hair.

When 50 µg/g BNP:600 µg/mL betamethasone:500 µg/mL gentamicin combination was applied twice a day for 1 week, vellus hair became thick, and the thinning hair improved.

Case C28

The test subject was a 62 year old female and was a patient with female pattern alopecia. This test subject had developed a dry rough scalp around the April following the Great East Japan Earthquake of 11 Mar. 2011, and had thinning hair from the frontal region to the crown. The father of this test subject had hair loss on the entire head due to androgenetic alopecia at about 35 years old.

When 50 µg/g CNP gel was applied to the frontal region and the crown of this test subject once to twice a day for 2 weeks, the amount of hair falling out decreased, and marked hair thickening was observed from the frontal region to the crown. When application of the CNP gel was continued for a further 2 weeks, the hair thickened so that thinning hair could hardly be seen (FIG. 50).

1 month after the application was stopped, thinning hair became slightly conspicuous again, but when a 50 µg/g CNP:600 µg/mL betamethasone:500 µg/mL gentamicin combination was applied twice a day for 2 weeks the thickened hair state was maintained.

Case C29

The test subject was a 60 year old female and was a patient with female pattern alopecia. With regard to this test subject, scale and itching had appeared 1 year earlier, and hair at the hair line in the frontal region had become thin.

When 50 µg/g CNP gel was applied to the frontal region of this test subject twice a day for 2 weeks, the hair thickened to such a degree that there was no widening of the hair parting and it was not possible to see through to the scalp. Even after 6 weeks had elapsed since application of the CNP gel was stopped, the effects were maintained, and it was not possible to see through to the scalp.

23. Therapeutic Effect of ANP Gel on Seborrheic Alopecia

The therapeutic effects of ANP gel on seborrheic alopecia are shown in Table 13 (cases A11 and A12).

TABLE 13

| | Case | |
|---|---|---|
| | A11 (=A8, B8) | A12 (=A9, B11) |
| Figure | FIG. 27 | |
| Gender | Male | Male |
| Age | 45 years old | 75 years old |
| When developed | From 44 years old | About 40s to 50s |
| Treatment site | Crown | Crown |
| Hair loss state | Thinning hair occurred only on crown, and erythema accompanied by itching and seborrheic scale were seen on scalp at hair loss site. | Erythema accompanied by itching and seborrheic scale were seen on scalp at hair loss site. |
| Family history of androgenetic alopecia | Father: androgenetic alopecia | Father: androgenetic alopecia |
| Family history of immune disease | None | None |
| Previous history | Atopic dermatitis, allergic rhinitis | Allergic rhinitis |
| Scratch Test | House dust: 2+<br>Mite: 3+<br>Cedar: —<br>Dactylis: 1+<br>Ragweed: 1+ | House dust: 2+<br>Mite: 2+<br>Cedar: 3+<br>Dactylis: 2+<br>Ragweed: 2+ |
| Effect of minoxidil | Not applied | No effect |
| Effect of finasteride | Not applied | Not applied |
| Effect of glycyrrhetinic acid | Not applied | No effect |
| Effect of steroid drug | No effect | No effect |
| Effect of cooling therapy | Not applied | Not applied |
| Antiallergic drug | Not applied | Not applied |
| Effect of carpronium chloride | Not applied | Not applied |
| Effect of cepharanthin | Not applied | Not applied |
| Dosage form | ANP gel | ANP gel |
| Dose | 100 µg/g | 100 µg/g |
| Number of days used | 2 weeks | 4 days |
| Degree of improvement in symptoms | Intense itchiness occurred, seborrheic scale aggravated, and hair thinning range enlarged. | No improvement in erythema and seborrheic scale. |
| Non-recurrence period | No improvement | No improvement |

Case A11

Case A11 was a case with coexisting androgenetic alopecia and seborrheic alopecia and is the same case as cases A8 and B8. Details of this case are as described for cases A8 and B8; when 100 µg/g ANP gel was applied to the entire hair loss site of the crown twice a day morning and evening, intense itching appeared on the $2^{nd}$ day, the amount of hair falling out increased, the hair loss range enlarged, seborrheic scalp was aggravated, erythema appeared, and no hair growth was observed.

Case A12

Case A12 was a case with coexisting androgenetic alopecia and seborrheic alopecia and is the same case as cases A9 and B11. Details of this case are as described for cases A9 and B11; when 100 µg/g ANP gel was applied to the hair loss site of the crown twice a day morning and evening for 4 days, there was no improvement in erythema and seborrheic scale, and there was no improvement effect for alopecia either.

24. Therapeutic Effect of BNP Gel on Seborrheic Alopecia

The therapeutic effects of BNP gel on seborrheic alopecia are shown in Table 14 (cases B21 and B22).

TABLE 14

| | Case | |
|---|---|---|
| | B21 (=A8, B8) | B22 (=A9, B11) |
| Figure | | |
| Gender | Male | Male |
| Age | 45 years old | 75 years old |
| When developed | From 44 years old | 40s |
| Treatment site | Crown | Crown |
| Hair loss state | Hair thinning occurred only on crown, and erythema accompanied by itching and seborrheic scale were seen on scalp at hair loss site. | Hair thinning occurred on crown, and erythema accompanied by itching and seborrheic scale were seen on scalp at hair loss site. |
| Family history of androgenetic alopecia | Father: androgenetic alopecia | Father: androgenetic alopecia |
| Family history of immune disease | None | None |
| Previous history | Atopic dermatitis, allergic rhinitis | Allergic rhinitis |
| Scratch Test | House dust: 2+<br>Mite: 3+<br>Cedar: —<br>Dactylis: 1+<br>Ragweed: 1+ | House dust: 2+<br>Mite: 2+<br>Cedar: 3+<br>Dactylis: 2+<br>Ragweed: 2+ |
| Effect of minoxidil | Not applied | No effect |
| Effect of finasteride | Not applied | Not applied |
| Effect of glycyrrhetinic acid | Not applied | No effect |
| Effect of steroid drug | No effect | No effect |
| Effect of cooling therapy | Not applied | Not applied |
| Antiallergic drug | No effect | No effect |
| Effect of carpronium chloride | No effect | Not applied |
| Effect of cepharanthin | Not applied | Not applied |
| Dosage form | BNP gel | BNP gel |
| Dose | 50 µg/g | 100 µg/g |
| Number of days used | 5 weeks | 3 weeks |
| Degree of improvement in symptoms | Erythema, seborrheic scale, and itching at hair loss site markedly improved and hair thinning improved. | Erythema, seborrheic scale, and itching at hair loss site markedly improved, hair falling out decreased, and hair quality improved and became dark. |
| Non-recurrence period | Treatment continuing | Treatment continuing |

Case B21

Case B21 was a case with coexisting androgenetic alopecia and seborrheic alopecia and is the same case as cases A8 and B8. Details of this case are as described for cases A8 and B8.

When 50 µg/g BNP gel was applied to the entire hair loss site of the crown of this test subject twice a day morning and evening, on the $1^{st}$ week after application of the BNP gel was started erythema, seborrheic scale, and itching on the hair loss site markedly improved, the amount of hair falling out decreased to an unnoticeable level, hair became thick on the crown objectively, the number of terminal hairs increased, and the thinning hair improved.

When application of the BNP gel to this test subject was stopped after 3 weeks, the feeling of volume on the crown decreased after 2 months, and itching started.

When multilayer application to the crown was carried out with 5% minoxidil solution and then with 100 µg/g BNP gel, there were no symptoms of irritation as there had been when the ANP gel was applied, when 1 week had elapsed after the multilayer application was started the amount of hair falling out decreased, the itchiness disappeared, and hair growth effects were observed. This test subject is still continuing to receive multilayer application with 5% minoxidil solution and 100 μg/g BNP gel at the present.

Case B22

Case B22 was a case with coexisting androgenetic alopecia and seborrheic alopecia and is the same as cases A9 and B11. Details of this case are as described for cases A9 and B11.

When 100 μg/g BNP gel was applied to thinning hair sites of the crown and the M-shaped part of this test subject twice a day morning and evening, on the $3^{rd}$ day after the application was started erythema, seborrheic scale, and itching in the hair loss sites markedly improved, and the amount of hair falling out become unnoticeable. With regard to this test subject, 2 weeks after, the hair quality improved, the hair became thick and dark, and there was hair thickening. With regard to this test subject, even in the M-shaped part, in the $2^{nd}$ week of application vellus hair became thick and dark, and the hair became long, albeit slowly.

In order to examine an external preparation that could further reduce the thinning hair range of the crown of this test subject, after a 5% minoxidil solution was applied to the crown and the M-shaped part, 100 μg/g BNP gel was applied by multilayer application, compared with application of a single BNP agent, the hair on the crown became black and dark when 1 week had elapsed since the multilayer application had started, and there was hair thickening. This test subject is still having multilayer application treatment with 5% minoxidil and 100 μg/g BNP gel at the present.

25. Therapeutic Effect of ANP Gel on Alopecia Pityroides

The therapeutic effects of ANP gel on alopecia pityroides are shown in Table 15 (case A13).

TABLE 15

| | Case | |
|---|---|---|
| | A13 (=A6, C3, C4) | A14 (=A1, C5) |
| Figure | | FIG. 21 |
| Gender | Female | Female |
| Age | 50 years old | 33 years old |
| When developed | 40 years old | 13 years old |
| Hair loss range | S2 | S3 |
| Treatment site | Crown | Right temporal region |
| Hair loss site other than head | None (B0) | Eyebrows (B1) |
| Family history of alopecia | Mother: alopecia areata | None |
| Family history of immune disease | Child: allergic rhinitis, chronic urticaria | Mother: atopic dermatitis Older Sister: atopic dermatitis, allergic rhinitis |
| Previous history | Atopic dermatitis, allergic rhinitis | Atopic dermatitis |
| Scratch Test | House dust: 1+ Mite: 1+ Cedar: — Dactylis: 2+ Ragweed: 1+ | House dust: 2+ Mite: 1+ Cedar: — Dactylis: 2+ Ragweed: 2+ |
| Effect of minoxidil | Not applied | Not applied |
| Effect of finasteride | Contraindicated | Contraindicated |
| Effect of glycyrrhetinic acid | Not applied | Not applied |
| Effect of steroid drug | No effect | No effect |
| Effect of cooling therapy | Not applied | No effect |
| Antiallergic drug | No effect | No effect |
| Effect of carpronium chloride | No effect | Not applied |
| Effect of cepharanthin | Not applied | Not applied |
| Dosage form | ANP gel | ANP ointment |
| Dose | 100 μg/g | 100 μg/g |
| Number of days used | 14 days | 21 days |

TABLE 15-continued

| | Case | |
|---|---|---|
| | A13 (=A6, C3, C4) | A14 (=A1, C5) |
| Degree of improvement in symptoms | S2→S2 | S3→S3 |
| Non-recurrence period | — | — |

Case A13

Case A13 was a case with coexisting alopecia areata and alopecia pityroides and is the same case as cases A6, C3, C4, and C30. CNP ointment was applied to the crown. Details of this case are as described for cases A6, C3, and C4; there was no effect from application of 100 μg/g ANP gel for 2 weeks, dry rough scale increased, there was itching, and the hair loss range enlarged somewhat.

26. Therapeutic Effect of ANP Ointment on Alopecia Pityroides

The therapeutic effects of ANP ointment on alopecia pityroides are shown in Table 15 (case A14).

Case A14

Case A14 was a case with coexisting alopecia areata and alopecia pityroides and is the same case as cases A1 and C5. It should be noted that CNP ointment was applied after a 2 week period of drug suspension. Details of this case are as described for cases A1 and C5; when 100 μg/g ANP gel was applied twice a day for 3 weeks, there was growth of vellus hair, but erythema and pityriatic desquamation on the scalp were not alleviated, and there was itching.

27. Therapeutic Effect of BNP Gel on Alopecia Pityroides

The therapeutic effects of BNP gel on alopecia pityroides are shown in Table 16 (cases B23 and B28).

TABLE 16

| | Case | |
|---|---|---|
| | B23 | B28 |
| Figure | FIG. 51 | FIG. 53 |
| Gender | Male | Male |
| Age | 81 years old | 59 years old |
| When developed | About 78 years old | 57 years old |
| Treatment site | Frontal region and crown | Frontal region and crown |
| Hair loss state | Hair thinning was conspicuous all over | Frontal region and crown |
| Hair loss site other than head | None | None (B0) |
| Family history of alopecia | None | None |
| Family history of immune disease | None | None |
| Previous history | None | None |
| Scratch Test | Not tested | Negative |
| Effect of minoxidil | Not applied | No effect |
| Effect of finasteride | Not applied | Not applied |
| Effect of glycyrrhetinic acid | Not applied | Not applied |
| Effect of steroid drug | Not applied | Not applied |
| Effect of cooling therapy | Not applied | Not applied |
| Antiallergic drug | Not applied | Not applied |
| Effect of carpronium chloride | Not applied | Not applied |
| Effect of cepharanthin | Not applied | Not applied |
| Dosage form | BNP gel | BNP gel |
| Dose | 50 μg/g, 200 μg/g | 20 μg/g |

TABLE 16-continued

| | Case | |
|---|---|---|
| | B23 | B28 |
| Number of days used | 14 days + 5 days | 7 days |
| Degree of improvement in symptoms | Pityriatic scale improved, vellus hair turned into terminal hair and became thick and black, and thinning hair improved. | Dandruff, scale, and itching disappeared, and hair falling out decreased. Hair growth and hair thickening were observed. |
| Non-recurrence period | — | Treatment continuing |

Case B23

The test subject was a 81 year old male who had developed thinning hair from the frontal region to the crown 3 years earlier. This was a case with coexisting senile alopecia and alopecia pityroides in which pityriatic scale was seen on the scalp.

After 50 μg/g BNP gel was applied to the frontal region and the crown of this test subject for 2 weeks and suspended for 1 week, when 200 μg/g BNP gel was applied once a day for 5 days, pityriatic desquamation was alleviated, vellus hair became terminal hair and black, and thinning hair was greatly improved (FIG. 51).

Case B28

The test subject was a 59 year old male and had alopecia pityroides. This test subject was in a thinning hair state in which there was hardly any hair from the frontal region to the crown. Thinning hair had occurred 2 years earlier, RiUP X5 (trademark), which contains 0.05 g/mL minoxidil, had been applied twice a day for one and a half years, but dandruff had became worse, itchiness had occurred, and the amount of hair falling out and the thinning hair had rapidly become aggravated 4 months earlier. This test subject was in a state in which a large amount of hair became attached to scale on the scalp and fell out when washing the hair.

When 20 μg/g BNP gel was applied to the frontal region and the crown of this test subject twice a day for 7 days, the effect was very good; there was no itching, dandruff stopped occurring, and the amount of hair falling out when washing the hair decreased to a few hairs. In accordance with application of the BNP gel, scale thickly deposited on the frontal region and the crown disappeared, and quite clear hair growth and hair thickening were observed from the frontal region to the crown (FIG. 53).

28. Therapeutic Effect of CNP Gel on Alopecia Pityroides

The therapeutic effects of CNP gel on alopecia pityroides are shown in Table 17 (cases C30 and C31).

TABLE 17

| | Case | |
|---|---|---|
| | C30 (=A6, A13, C3, C4, C33) | C31 |
| Figure | | FIG. 52 |
| Gender | Female | Male |
| Age | 50 years old | 42 years old |
| When developed | 40 years old | Late 30s |
| Hair loss range | S2 | Frontal region and crown |
| Treatment site | Left temporal region | Frontal region and crown |
| Hair loss site other than head | None (B0) | None (B0) |

TABLE 17-continued

| | Case | |
|---|---|---|
| | C30 (=A6, A13, C3, C4, C33) | C31 |
| Family history of alopecia | Mother: alopecia areata | Father: androgenetic alopecia |
| Family history of immune disease | Child: allergic rhinitis, chronic urticaria | Younger brother: atopic dermatitis |
| Previous history | Atopic dermatitis, allergic rhinitis | None |
| Scratch Test | House dust: 1+ Mite: 1+ Cedar: — Dactylis: 2+ Ragweed: 1+ | House dust: 3+ Mite: 3+ Cedar: 2+ Dactylis: 2+ Ragweed: 1+ |
| Effect of minoxidil | Not applied | Not applied |
| Effect of finasteride | Contraindicated | Not applied |
| Effect of glycyrrhetinic acid | Not applied | Not applied |
| Effect of steroid drug | No effect | No effect on hair falling out or dandruff after 2 years' external application. |
| Effect of cooling therapy | Not applied | Not applied |
| Antiallergic drug | No effect | Not applied |
| Effect of carpronium chloride | No effect | Not applied |
| Effect of cepharanthin | Not applied | Not applied |
| Dosage form | CNP gel | CNP gel |
| Dose | 100 μg/g | 100 μg/g |
| Number of days used | 21 days | 14 days |
| Degree of improvement in symptoms | S2→S0 | Thick scale markedly improved and hair thickened. |
| Non-recurrence period | 8 months | Treatment continuing |

Case C30

Case C30 was a case with coexisting alopecia areata and alopecia pityroides and is the same case as cases A6, C3, C4, and A13. It should be noted that CNP ointment was applied to the right frontal region. The details of this case are as described for cases A6, C3, and C4; with application of 100 μg/g CNP gel twice a day for 3 weeks, there was good progress even after application was stopped, and there was no recurrence at the application site even when 8 months had elapsed after the application was stopped.

Case C31

The test subject was a 42 year old male and was a patient with alopecia pityroides. From the late 30s the hair of the frontal region and the crown had become thin. From 2 years earlier, 'Nitrazen Cream 2% for external application' (Iwaki Seiyaku Co., Ltd.), which contains 2% ketoconazole, which is an antifungal agent, and 'Betnoval G Ointment Cream' (Sato Pharmaceutical Co., Ltd.), which contains 1.2 mg/g betamethasone valerate, which is a synthetic adrenal cortex hormone, and 1 mg/g of gentamicin, which is an antibiotic, had been applied continuously, but not only were there no effects at all, but also dandruff had adhered thickly and the thinning hair had become aggravated from 1 year earlier.

When 100 μg/g CNP gel was applied to the frontal region and the crown of this test subject twice a day for 2 weeks, scale that had been thickly adhering disappeared considerably, and hair started to thicken on the crown (FIG. 52).

29. Therapeutic Effect of CNP Ointment on Alopecia Pityroides

The therapeutic effects of CNP ointment on alopecia pityroides are shown in Table 18 (case C33).

TABLE 18

| | Case<br>C33 (=A6, A13, C3, C4, C30) |
|---|---|
| Figure | |
| Gender | Female |
| Age | 50 years old |
| When developed | 40 years old |
| Hair loss range | S2 |
| Treatment site | Right frontal region |
| Hair loss site other than head | None (B0) |
| Family history of alopecia | Mother: alopecia areata |
| Family history of immune disease | Child: allergic rhinitis, chronic urticaria |
| Previous history | Atopic dermatitis, allergic rhinitis |
| Scratch Test | House dust: 1+<br>Mite: 1+<br>Cedar: —<br>Dactylis: 2+<br>Ragweed: 1+ |
| Effect of minoxidil | Not applied |
| Effect of finasteride | Contraindicated |
| Effect of glycyrrhetinic acid | Not applied |
| Effect of steroid drug | No effect |
| Effect of cooling therapy | Not applied |
| Antiallergic drug | No effect |
| Effect of carpronium chloride | No effect |
| Effect of cepharanthin | Not applied |
| Dosage form | CNP ointment |
| Dose | 100 μg/g |
| Number of days used | 14 days |
| Degree of improvement in symptoms | S2→S1 |
| Non-recurrence period | 1 year |

Case C33

Case C33 was a case with coexisting alopecia areata and alopecia pityroides and is the same case as cases A6, C3, C4, A13, and C30. It should be noted that CNP ointment was applied to the right frontal region. The details of this case are as described for cases A6, C3, and C4, and by applying 100 μg/g CNP ointment twice a day for 2 weeks clear hair growth was observed and the erythema and scale on the scalp disappeared.

30. Therapeutic Effect of ANP Gel on Senile Alopecia

The therapeutic effects of ANP gel on senile alopecia are shown in Table 19 (case A15).

TABLE 19

| Case | A15 |
|---|---|
| Figure | FIG. 54 |
| Gender | Male |
| Age | 74 years old |
| When developed | Unknown |
| Treatment site | Frontal region and crown |
| Hair loss state | Hair thinning was conspicuous all over. |
| Hair loss site other than head | None |
| Family history of alopecia | None |
| Family history of immune disease | None |
| Previous history | None |
| Scratch Test | Not tested |
| Effect of minoxidil | Not applied |
| Effect of finasteride | Not applied |
| Effect of glycyrrhetinic acid | Not applied |
| Effect of steroid drug | Not applied |
| Effect of cooling therapy | Not applied |
| Antiallergic drug | Not applied |
| Effect of carpronium chloride | Not applied |
| Effect of cepharanthin | Not applied |
| Dosage form | ANP gel (CNP gel) |
| Dose | ANP gel: 100 μg/g (CNP gel: 50 μg/g) |
| Number of days used | 1 week |
| Degree of improvement in symptoms | Erythema, scale, and itching aggravated, no hair thickening effect, and hair loss increased somewhat. |
| Non-recurrence period | Treatment continuing |

Case A15

The test subject was a 74 year old male who had senile alopecia in which there was dandruff, there was a large amount of hair falling out, there was thinning hair over the entire head part, and white hair was conspicuous. This test subject had intense itchiness on the scalp, the amount of dandruff was large, and the amount of hair falling out was large.

When 100 μg/g ANP gel was applied to the crown of this test subject twice a day for 1 week, erythema, scale, and itching were aggravated, there was no hair thickening effect, and the hair loss increased somewhat (FIG. 54).

When ANP gel was stopped after 1 week and from the following day 50 μg/g CNP gel was applied twice a day for 2 days, erythema, scale, and itching were alleviated. For a further 4 weeks after that, 50 μg/g CNP gel continued to be applied twice a day, clear hair thickening was observed in the frontal region in particular, and hair stopped falling out (FIG. 54). Hair that had grown was black terminal hair and did not fall out even when rubbed strongly. It was surprising to observe the hair thickening effect of the CNP gel for such an old age of 74.

31. Therapeutic Effect of BNP Gel on Senile Alopecia

The therapeutic effects of BNP gel on senile alopecia are shown in Table 20 (B24).

TABLE 20

| Case | B24 |
|---|---|
| Figure | FIG. 51 |
| Gender | Male |
| Age | 81 years old |
| When developed | About 78 years old |
| Treatment site | Frontal region and crown |
| Hair loss state | Hair thinning was conspicuous all over. |
| Hair loss site other than head | None |
| Family history of alopecia | None |
| Family history of immune disease | None |
| Previous history | None |
| Scratch Test | Not tested |
| Effect of minoxidil | Not applied |
| Effect of finasteride | Not applied |
| Effect of glycyrrhetinic acid | Not applied |
| Effect of steroid drug | Not applied |
| Effect of cooling therapy | Not applied |
| Antiallergic drug | Not applied |
| Effect of carpronium chloride | Not applied |
| Effect of cepharanthin | Not applied |
| Dosage form | BNP gel |
| Dose | 50 μg/g, 200 μg/g |
| Number of days used | 14 days + 5 days |
| Degree of improvement in symptoms | Pityriatic scale improved, vellus hair turned into terminal hair and became thick and black, and hair thinning improved. |
| Non-recurrence period | Treatment continuing |

Case B24

Case B24 was a case with coexisting senile alopecia and alopecia pityroides, and is the same case as case B23. Details of this case are as described for case B23.

When 200 µg/g BNP gel was applied to the frontal region and the crown of this test subject once a day for 5 days, pityriatic desquamation was alleviated, rich black terminal hair grew, and the thinning hair was greatly improved (FIG. 51). Most of the hair was white before the application, but hair that grew after the application was black.

32. Therapeutic Effect of CNP Gel on Senile Alopecia

The therapeutic effects of CNP gel on senile alopecia are shown in Table 21 (case C34).

TABLE 21

| | Case C34 |
|---|---|
| Figure | |
| Gender | Female |
| Age | 70 years old |
| When developed | About 68 years old |
| Treatment site | Crown |
| Hair loss state | Hair thinning was conspicuous from frontal region to crown. |
| Hair loss site other than head | None |
| Family history of alopecia | None |
| Family history of immune disease | None |
| Previous history | None |
| Scratch Test | Not tested |
| Effect of minoxidil | Not applied |
| Effect of finasteride | Not applied |
| Effect of glycyrrhetinic acid | Not applied |
| Effect of steroid drug | No effect |
| Effect of cooling therapy | Not applied |
| Antiallergic drug | Not applied |
| Effect of car premium chloride | Not applied |
| Effect of cepharanthin | Not applied |
| Dosage form | CNP gel |
| Dose | 50 µg/g |
| Number of days used | 7 days |
| Degree of improvement in symptoms | Hair became supple, and thinning hair on crown improved to unnoticeable level. Hair falling out decreased, and there was no pain on scalp during external application. |
| Non-recurrence period | 2 weeks |

Case C34

The test subject was a 70 year old female and had thinning hair on the crown from 68 years old. According to the test subject, the skin of the crown with the thinning hair became atrophic and was too painful to touch. When 50 µg/g CNP gel was applied twice a day for 3 days, the pain of the scalp was alleviated, and the amount of hair falling out decreased. After that, when the application was continued for a further 3 days, erythema of the scalp disappeared, itching and pain became unnoticeable, and there was hair thickening.

When the medication was changed to only 'Dermosol G lotion (Dermosol-G Lotion)' (Iwaki Seiyaku Co., Ltd.), which contains 1200 µg/mL betamethasone valerate and 1000 µg/mL gentamicin sulfate, the skin of the crown started tingling after 3 days, a slight degree of erythema reappeared, and there was thinning hair.

When 100 µg/g BNP gel was applied once a day for 1 week, the erythema on the crown disappeared, the hair thickened, and the thinning hair became inconspicuous.

When a 50 µg/g BNP:600 µg/mL betamethasone:500 µg/mL gentamicin combination was applied for 1 week, the symptoms of erythema on the crown and thinning hair, which were exhibited with application of Dermosol G lotion alone, did not appear, and a state with hair thickening was maintained even when 3 weeks had elapsed after the application was started.

33. Therapeutic Effect of BNP Gel on Cancer Chemotherapy Drug-Induced Alopecia

The therapeutic effects of BNP gel on cancer chemotherapy drug-induced alopecia are shown in Table 22 (case B25).

TABLE 22

| | Case B25 |
|---|---|
| Figure | |
| Gender | Female |
| Age | 54 years old |
| When developed | 54 years old |
| Cancer chemotherapy | R-CHOP therapy |
| Treatment site | Hairline part in frontal region |
| Hair loss state | White hair all over. Left-hand side hairline part retreated and had hair thinning. |
| Hair loss site other than head | Whole body |
| Family history of alopecia | None |
| Family history of immune disease | None |
| Previous history | None |
| Scratch Test | Not tested |
| Effect of minoxidil | Not applied |
| Effect of glycyrrhetinic acid | Not applied |
| Effect of steroid drug | Not used |
| Effect of cooling therapy | Not applied |
| Antiallergic drug | Not applied |
| Effect of carpronium chloride | Not applied |
| Effect of cepharanthin | Not applied |
| Dosage form | BNP gel |
| Dose | 100 µg/g |
| Number of days used | 7 days |
| Degree of improvement in symptoms | Growth and restoration of black terminal hair was observed in left front temporal region, which had white hair and was thin, after 2 weeks. |
| Non-recurrence period | 3 months |

Case B25

The test subject was a 54 year old female. The test subject was diagnosed with malignant lymphoma and had received 6 courses of R-CHOP therapy from April to September 2011. The R-CHOP therapy referred to here is one type of cocktail therapy using a plurality of chemotherapy drugs in which 1 course of the administration schedule consisted of an intravenous drip of rituximab, which is a mouse-human•chimeric monoclonal antibody against CD20, which is a human B cell surface antigen, on the $1^{st}$ day, oral administration, after each meal, of prednisolone tablet, which is a synthetic adrenal cortex hormone drug, intravenous injection of vincristine, which is a microtubule inhibitor, intravenous injection of doxorubicin, which is an inhibitor of DNA and RNA synthesis, and intravenous injection of cyclophosphamide, which is a prodrug of an inhibitor of DNA synthesis, on the $2^{nd}$ day, only oral administration, after each meal, of prednisolone tablet from the $3^{rd}$ day to the $6^{th}$ day, and a drug suspension period from the $7^{th}$ day to the $21^{st}$ day, and this administration cycle is repeated. With regard to the test subject, the hair started to fall out from the $2^{nd}$ week of the first course, and all the hair had fallen out in July when the $4^{th}$ course had ended. When the treatment was completed in September, the hair started to grow gradually; the hair that grew was pure white, and the left-hand side hair line part had retreated and had become very thin.

When 100 µg/g BNP gel was applied to this left-hand side hair line part twice a day for 1 week, black terminal hair started to grow in the thinning hair part with white downy hair after 2 weeks, the hair gradually thickened, and black hair seemed to have grown in a round shape in the hair line part that had retreated in an M-shape. In the site to which the BNP gel had been applied in the left-hand side hair line M-shaped site, all the hair that had grown was black. Although no application was carried out for 3 months after that hair did not fall out again and there was no formation of white hair.

34. Therapeutic Effect of CNP Gel on Cancer Chemotherapy Drug-Induced Alopecia

The therapeutic effects of BNP gel on cancer chemotherapy drug-induced alopecia are shown in Table 23 (case C35).

TABLE 23

|  | Case C35 |
|---|---|
| Figure | FIG. 56-1, FIG. 56-2 |
| Gender | Female |
| Age | 47 years old |
| When developed | 47 years old |
| Cancer chemotherapy | Cisplatin |
| Treatment site | Frontal region, crown |
| Hair loss state | Hair thinning was conspicuous from frontal region to crown, mainly with fine vellus hair. |
| Hair loss site other than head | Whole body |
| Family history of alopecia | Unknown |
| Family history of immune disease | Child: atopic dermatitis |
| Previous history | Cancer of body of uterus, alopecia areata, atopic dermatitis, allergic rhinitis |
| Scratch Test | House dust: 3+ |
|  | Mite: 3+ |
|  | Cedar: — |
|  | Dactylis: — |
|  | Ragweed: 1+ |
| Effect of minoxidil | Not applied |
| Effect of glycyrrhetinic acid | Not applied |
| Effect of steroid drug | No effect |
| Effect of cooling therapy | Not applied |
| Antiallergic drug | No effect |
| Effect of carpronium chloride | No effect |
| Effect of cepharanthin | No effect |
| Dosage form | CNP gel |
| Dose | 50 μg/g |
| Number of days used | 6 weeks |
| Degree of improvement in symptoms | Hair thickened, and hairs became thick and dark, and was restored. |
| Non-recurrence period | Treatment continuing |

Case C35

The test subject was a 47 year old female. The test subject had received an operation to remove cancer of the body of the uterus in November 2009, had 6 courses of treatment with cisplatin, which is a cancer chemotherapy drug, and had completed the cancer chemotherapy in March 2010. The test subject showed hair loss of the entire head accompanying the treatment with cisplatin, and although fine soft short hair grew around May 2011 when almost 1 year had elapsed since the treatment with cisplatin was completed, an area from the frontal region to the crown recovered only to a state with thin hair. There had been no effect on the test subject when carpronium chloride had been applied thereto for 6 months.

The application of carpronium chloride was therefore stopped. When, 2 months after stopping, 50 μg/g CNP gel was applied twice a day for 6 weeks to the area from the frontal region to the crown, the number of hairs increased and the hair thickened considerably from the frontal region to the crown, and the hair became thick and long (FIG. 56-1).

When application of the CNP gel was stopped after 6 weeks, and 3 weeks after that a CNP:betamethasone:gentamicin combination was applied twice a day for 2 weeks, the hair thickened further.

At this point, new alopecia areata occurred in the left temporal region; a 50 μg/g CNP:600 μg/mL betamethasone:500 μg/mL gentamicin combination was applied twice a day, hair growth was confirmed after 2 weeks, and marked growth of terminal hair was confirmed after 3 weeks (FIG. 56-2).

Conclusions from Case Test Results

As is clear from the above-mentioned test cases, the agent for the treatment of alopecia of the present invention had a very high recovery rate for hair loss, and the period taken to express its hair growth promoting effect was short. In most cases, hair growth was confirmed by applying the agent for the treatment of alopecia of the present invention for 1 week to 2 weeks, and clear hair growth was observed during the $3^{rd}$ week. Furthermore, the treatment agent of the present invention restored white hair to black hair, decreased dandruff in an alopecia pityroides patient, and improved seborrheic scalp in a seborrheic alopecia patient.

When the agent for the treatment of alopecia of the present invention contained CNP or BNP as an active ingredient, the therapeutic effects were marked, hair grew almost certainly with application twice a day for 1 week, terminal hair was observed with application for 2 weeks, and it became difficult to see the skin with application for 4 weeks. Worthy of special note is that it was unnecessary to continue application after vellus hair grew; the vellus hair became dark and thick, became terminal hair, and continued to grow.

In particular, when the agent for the treatment of alopecia of the present invention contained CNP as an active ingredient it could more reliably suppress inflammation of a hair loss site than one containing BNP as an active ingredient, the amount of hair falling out decreased dramatically in 1 day to a few days, and hair grew earlier. On the other hand, the agent for the treatment of alopecia of the present invention containing BNP as an active ingredient was characterized by black terminal hair often growing. Furthermore, when the agent for the treatment of alopecia of the present invention contained ANP as an active ingredient, it was effective only for alopecia in which there was no erythema, scale, seborrheic desquamation, etc. on the scalp, but there were many cases in which erythema and itchiness occurred and the state became worse than that before application.

Moreover, the agent for the treatment of alopecia of the present invention exhibited marked effects on alopecia areata and androgenetic alopecia, could suppress inflammation of seborrheic alopecia and alopecia pityroides so that hair could grow, dramatically decreased dandruff, and could suppress itchiness. Furthermore, it promoted restoration of hair in female pattern alopecia, postpartum alopecia, and senile alopecia, and it was also confirmed that it promoted growth of black hair in cancer chemotherapy drug-induced alopecia.

The agent for the treatment of alopecia of the present invention exhibited an improvement effect with long duration for androgenetic alopecia, female pattern alopecia, seborrheic alopecia, alopecia pityroides, and senile alopecia, and there was no recurrence of hair loss at the application site for at least 2 months after the application was stopped.

These therapeutic effects of the present invention in the treatment of androgenetic alopecia were in marked contrast to the fact that in a group that has had orally administered finasteride for 1 year and has then stopped administration, the improvement effect disappears and androgenetic alopecia progresses. That is, the effect of finasteride is seen only while it is being orally administered, whereas with external application of the agent for the treatment of alopecia of the present invention for 1 to 3 weeks, the improved hair growth state could be maintained for about 2 months after its use was stopped. After 3 months had elapsed since application of the agent for the treatment of alopecia of the present invention was stopped, there was a case in which the original hair loss state returned, but even in this case reapplying the agent for the treatment of alopecia of the present invention allowed the same black terminal hair to grow as previously without side effects.

Moreover, with regard to alopecia areata and cancer chemotherapy drug-induced alopecia, with external application of the agent for the treatment of alopecia of the present invention for 1 to 3 weeks, the hair growth state kept improving even after its use was stopped and there was a cure, and there was no recurrence of alopecia at the application site.

Moreover, BNP and CNP did not exhibit any adverse events such as local symptoms of irritation, skin atrophy, or an itching sensation resulting from their application, and there were no systemic side effects.

Since it was confirmed that the agent for the treatment of alopecia of the present invention exhibited marked effects in the treatment of alopecia areata, androgenetic alopecia, seborrheic alopecia, alopecia pityroides, female pattern alopecia, postpartum alopecia, senile alopecia, and cancer chemotherapy drug-induced alopecia, it was substantially proved that it was effective not only for the treatment of the above but also for the treatment of almost all types of alopecia.

That is, since the above-mentioned respective types of alopecia have completely different development mechanisms from each other, being effective for these various different types of alopecia clearly means being useful for the treatment of all types of alopecia.

Furthermore, as is disclosed in the present specification, since the test subjects for whom the effectiveness of the agent for the treatment of alopecia of the present invention had been confirmed include many test subjects both with and without a history of, or coexisting, immune disease, and test subjects having a biological family both with and without a history of, or coexisting, immune disease, the agent for the treatment of alopecia of the present invention is useful for targets both with and without a genetic background or a history of, or coexisting, immune disease. Furthermore, with regard to the relationship between the test subjects and an allergic predisposition, there was no systematic relationship between the effectiveness of the agent for the treatment of alopecia of the present invention and the results of the scratch test of the test subjects for whom the effectiveness was confirmed; the agent for the treatment of alopecia of the present invention is effective for targets both with and without an allergic predisposition, regardless of the presence or absence of an allergic predisposition.

It was confirmed that the agent for the treatment of alopecia of the present invention has a marked effect on the treatment of alopecia areata and androgenetic alopecia. The period taken to confirm hair growth subjectively was short not only for alopecia areata monolocularis but also even for intractable alopecia areata multilocularis, in which the hair loss period is long and the hair loss range is wide, and even for intractable alopecia areata ophiasis; there is no pain accompanying the treatment, it is therefore possible to recover from emotional distress and regain QOL (quality of life) at an early stage, and it can be said to be a completely new therapy that can be highly recommended.

It is clear that the agent for the treatment of alopecia of the present invention is very effective not only for alopecia areata monolocularis but also for S2 or greater alopecia areata multilocularis, which is severe, a case in which hair loss occurs in another place in addition to the head, a case with a coexisting atopic disease, which is said to be intractable, and alopecia ophiasis.

The agent for the treatment of alopecia of the present invention could restore the hair of a patient with postpartum alopecia that did not cure spontaneously even over half a year after childbirth to the same state as that before childbirth, and it became clear that it was effective for a target having resistance to treatment with a steroid or carpronium chloride.

The agent for the treatment of alopecia of the present invention was also effective for female pattern alopecia and could restore the hair to such an extent that it became unnoticeable in appearance with 1 to 2 weeks' application, and it was effective for a patient having resistance to treatment with carpronium chloride, a steroid, and an antifungal agent. It was confirmed that, when the agent for the treatment of alopecia of the present invention was used for female pattern alopecia, there was a case in which thinning hair reoccurred about 1 month after the application was stopped, but re-application thereof could restore the hair in the same manner as that of the previous application, and no side effects were seen.

It became clear that the agent for the treatment of alopecia of the present invention could markedly improve erythema, seborrheic scale, and itching of a hair loss site of seborrheic alopecia and decrease the amount of hair falling out.

It was confirmed that the agent for the treatment of alopecia of the present invention could make erythema and scale of alopecia pityroides disappear, make black terminal hair grow, and prevent recurrence even when 1 month had elapsed after the application was stopped. Furthermore, the agent for the treatment of alopecia of the present invention exhibits marked effects on alopecia pityroides having resistance to treatment with an antifungal agent or a steroid.

It was shown that the agent for the treatment of alopecia of the present invention could relieve pain and itching of the scalp in senile alopecia, alleviate erythema and pityriatic desquamation, and make black terminal hair grow.

It was confirmed that the agent for the treatment of alopecia of the present invention was effective for cancer chemotherapy drug-induced alopecia and could make black hair grow even in an area in which hair had become white and maintain a hair growth state even when 2 months or longer had elapsed after the application was stopped.

The agent for the treatment of alopecia of the present invention exhibited a very marked therapeutic effect for alopecia if either of BNP or CNP was an active ingredient. Furthermore, when there was no erythema, scale, seborrheic erythema, seborrheic desquamation, or pityriatic desquamation on the scalp, one containing ANP as an active ingredient exhibited a hair growth effect.

Therefore, it can be appreciated that a chimeric peptide of 2 or more NPs selected from ANP, BNP, and CNP also exhibits a therapeutic effect for alopecia. Moreover, when taking into consideration that it is generally thought that ANP and BNP activate the NPR-A receptor so as to bring about vasodilatory action, diuretic action, and cytostatic action, and CNP shows a growth-inhibitory action on vascular smooth muscle cells via the NPR-B receptor, it is surprising that the agent for the treatment of alopecia of the present invention containing CNP or BNP as an active ingredient exhibited a particularly marked therapeutic effect for alopecia, and it is sufficient to appreciate that a chimeric peptide of BNP and CNP exhibits the same therapeutic effect for alopecia.

Alopecia areata occurs in young females at the same frequency as in males, and in spite of the appearance being greatly impaired, there are only rough treatment methods involving local injection of a steroid or intentionally irritating the skin in anticipation of producing immune modulation.

Moreover, the therapeutic effects of the above methods are not high, and there might be adverse events such as skin atrophy due to steroid local injection or systemic contact dermatitis from local immunotherapy. On the other hand, the agent for the treatment of alopecia of the present invention exhibits remarkable effects on alopecia areata in particular, there are no side effects from BNP and CNP, the effects are not only seen during application but the improved state is also maintained after application is stopped, and although a new bald area might occur at a site to which no application is made, there was no recurrence in the application sites as far as the cases that have been experienced are concerned, and this is great hope for a patient suffering from alopecia areata.

INDUSTRIAL APPLICABILITY

The agent for the treatment of alopecia of the present invention containing a natriuretic peptide (NP) as an active ingredient promotes hair regeneration, hair growth, and hair thickening on a hair loss site of an alopecia areata patient, an androgenetic alopecia patient, a female pattern alopecia patient, a postpartum alopecia patient, a seborrheic alopecia patient, an alopecia pityroides patient, a senile alopecia patient, a cancer chemotherapy drug-induced alopecia patient, and a patient with alopecia due to radiation exposure, can improve the alopecia outstandingly, does not cause side effects such as an itching sensation, irritation, or feminization, and the therapeutic effects for alopecia are not lost over a long period even when its use is stopped.

Furthermore, it shows therapeutic effects on androgenetic alopecia that exhibits resistance to treatment with minoxidil or finasteride, and shows marked therapeutic effects on alopecia areata that exhibits resistance to treatment with steroid local injection or local immunotherapy.

Therefore, the agent for the treatment of alopecia of the present invention can be anticipated to be useful as a very effective treatment drug for alopecia for which sufficient therapeutic effects cannot be obtained by the conventional minoxidil or finasteride, and alopecia that develops in relation to an immune overreaction or an immune abnormality.

In particular, the agent for the treatment of alopecia of the present invention can dramatically improve severe alopecia on the adult head that has been very difficult to treat and causes problems in social life, without any side effects at all. The agent for the treatment of alopecia of the present invention is not only effective for intractable alopecia but also exhibits the same effects regardless of gender and is not limited to adults but is also effective for patients in their teens.

Therefore, practical use of the agent for the treatment of alopecia of the present invention as a new agent for the treatment of androgenetic alopecia that replaces minoxidil or finasteride can be anticipated, and the practical use thereof as an agent for the treatment of alopecia areata, which has had no effective therapy for a long time, is very promising.
[Sequence Listing]

The invention claimed is:

1. A method of treating alopecia, the method comprising: externally applying a composition that comprises an effective amount of B-type natriuretic peptide (BNP) to a required site of skin of a subject in need of such treatment, wherein the BNP comprises an amino acid sequence selected from the group comprising the human amino acid sequence of BNP-26, BNP-32 or BNP-45, and wherein the alopecia is one or more selected from the group consisting of alopecia areata, androgenetic alopecia, seborrheic alopecia, alopecia pityroides, female pattern alopecia, postpartum alopecia, senile alopecia, cancer chemotherapy drug-induced alopecia and alopecia due to radiation exposure.

2. The method of treating alopecia according to claim 1, wherein the composition further comprises an agent for the treatment of white hair, an agent for the treatment of vellus hair formation, or an agent for inhibiting seborrheic scalp or the occurrence of dandruff.

3. The method of treating alopecia according to claim 1, wherein the androgenetic alopecia is androgenetic alopecia in a male or androgenetic alopecia in a female.

4. The method of treating alopecia according to claim 1, wherein the required site of skin is the frontal region or the crown.

5. The method of treating alopecia according to claim 1, wherein there is coexisting seborrheic alopecia or alopecia pityroides.

6. The method of treating alopecia according to claim 1, wherein the alopecia areata is normal alopecia areata, alopecia totalis, alopecia universalis, or alopecia ophiasis.

7. The method of treating alopecia according to claim 1, wherein the alopecia is alopecia of a subject that has attained a steroid-dependent state or a subject for which a steroid treatment agent cannot be used.

8. The method of treating alopecia according to claim 1, wherein the alopecia areata is S1 or B0 alopecia or above.

9. The method of treating alopecia according to claim 1, wherein a therapeutic effect is obtained by application for 1 week or longer.

10. The method of treating alopecia according to claim 1, wherein there is no recurrence of the alopecia for a period of 1 month or longer even when application is stopped.

11. The method of treating alopecia according to claim 1, wherein the dosage form of the composition is an ointment, a gel, a cream, a lotion, a liquid, a wax, a powder, a spray, a gel spray, a foam, a shampoo, a treatment, a scalp treatment, or a tonic.

12. The method of treating alopecia according to claim 1, wherein the content of the B-type natriuretic peptide (BNP) in the composition is 1 to 1000 μg BNP/g composition.

13. The method of treating alopecia according to claim 1, wherein the B-type natriuretic peptide (BNP) comprises BNP-26 and/or BNP-32 and/or BNP-45.

14. The method of treating alopecia according to claim 1, wherein the alopecia is treated without causing an itching sensation.

15. A method for hair growth, hair restoration, hair development promotion, hair growth promotion, or hair cultivating comprising: externally applying a composition that comprises an effective amount of B-type natriuretic peptide (BNP) to a required site of skin of a subject in need, wherein the BNP comprises an amino acid sequence selected from the group comprising the human amino acid sequence of BNP-26, BNP-32 or BNP-45.

\* \* \* \* \*

```
SEQUENCE LISTING

<160> NUMBER OF SEQ ID NOS: 83

<210> SEQ ID NO 1
<211> LENGTH: 28
<212> TYPE: PRT
<213> ORGANISM: Homo sapiens
<220> FEATURE:
<221> NAME/KEY: MISC_FEATURE
<223> OTHER INFORMATION: Human ANP peptide

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 29
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 2

Ser Leu Arg Arg Ser Ser Cys Phe Gly Gly Arg Met Asp Arg Ile Gly
1               5                   10                  15

Ala Gln Ser Gly Leu Gly Cys Lys Val Leu Arg Arg His
            20                  25
```

<210> SEQ ID NO 3
<211> LENGTH: 23
<212> TYPE: PRT
<213> ORGANISM: Artificial Sequence
<220> FEATURE:
<223> OTHER INFORMATION: A human ANP fragment lacking C-trminal five
     amino acids.

<400> SEQUENCE: 3

Ser Leu Arg Arg Ser Ser Cys Phe Gly Gly Arg Met Asp Arg Ile Gly
1               5                   10                  15

Ala Gln Ser Gly Leu Gly Cys
            20

<210> SEQ ID NO 4
<211> LENGTH: 28
<212> TYPE: PRT
<213> ORGANISM: Artificial Sequence
<220> FEATURE:
<223> OTHER INFORMATION: A chimeric peptide of human ANP peptide and
     human BNP peptide.

<400> SEQUENCE: 4

Ser Leu Arg Arg Ser Ser Cys Phe Gly Gly Arg Met Asp Arg Ile Ser
1               5                   10                  15

Ser Ser Ser Gly Leu Gly Cys Asn Ser Phe Arg Tyr
            20                  25

<210> SEQ ID NO 5
<211> LENGTH: 29
<212> TYPE: PRT
<213> ORGANISM: Artificial Sequence
<220> FEATURE:
<223> OTHER INFORMATION: A chimeric peptide of human ANP peptide and
     human BNP peptide.

<400> SEQUENCE: 5

Ser Leu Arg Arg Ser Ser Cys Phe Gly Gly Arg Met Asp Arg Ile Ser
1               5                   10                  15

Ser Ser Ser Gly Leu Gly Cys Lys Val Leu Arg Arg His
            20                  25

<210> SEQ ID NO 6
<211> LENGTH: 23
<212> TYPE: PRT
<213> ORGANISM: Artificial Sequence
<220> FEATURE:
<223> OTHER INFORMATION: A chimeric peptide of human ANP peptide and
     human BNP peptide.

<400> SEQUENCE: 6

Ser Leu Arg Arg Ser Ser Cys Phe Gly Gly Arg Met Asp Arg Ile Ser
1               5                   10                  15

Ser Ser Ser Gly Leu Gly Cys
            20

<210> SEQ ID NO 7
<211> LENGTH: 28
<212> TYPE: PRT
<213> ORGANISM: Artificial Sequence
<220> FEATURE:
<223> OTHER INFORMATION: A chimeric peptide of human ANP peptide and
     human CNP peptide.

<400> SEQUENCE: 7

Ser Leu Arg Arg Ser Ser Cys Phe Gly Gly Arg Met Asp Arg Ile Gly
1               5                   10                  15

Ser Met Ser Gly Leu Gly Cys Asn Ser Phe Arg Tyr
            20                  25

<210> SEQ ID NO 8
<211> LENGTH: 29
<212> TYPE: PRT
<213> ORGANISM: Artificial Sequence
<220> FEATURE:
<223> OTHER INFORMATION: A chimeric peptide of human ANP peptide, human
      CNP peptide and human CNP peptide.

<400> SEQUENCE: 8

Ser Leu Arg Arg Ser Ser Cys Phe Gly Gly Arg Met Asp Arg Ile Gly
1               5                   10                  15

Ser Met Ser Gly Leu Gly Cys Lys Val Leu Arg Arg His
            20                  25

<210> SEQ ID NO 9
<211> LENGTH: 23
<212> TYPE: PRT
<213> ORGANISM: Artificial Sequence
<220> FEATURE:
<223> OTHER INFORMATION: A chimeric peptide of human ANP peptide and
      human CNP peptide.

<400> SEQUENCE: 9

Ser Leu Arg Arg Ser Ser Cys Phe Gly Gly Arg Met Asp Arg Ile Gly
1               5                   10                  15

Ser Met Ser Gly Leu Gly Cys
            20

<210> SEQ ID NO 10
<211> LENGTH: 28
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 10

Ser Leu Arg Arg Ser Ser Cys Phe Gly Arg Lys Met Asp Arg Ile Gly
1               5                   10                  15

Ala Gln Ser Gly Leu Gly Cys Asn Ser Phe Arg Tyr
            20                  25

<210> SEQ ID NO 11
<211> LENGTH: 29
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 11

Ser Leu Arg Arg Ser Ser Cys Phe Gly Arg Lys Met Asp Arg Ile Gly
1               5                   10                  15

Ala Gln Ser Gly Leu Gly Cys Lys Val Leu Arg Arg His
            20                  25

<210> SEQ ID NO 12
<211> LENGTH: 23
<212> TYPE: PRT
<213> ORGANISM: Artificial Sequence

```
<220> FEATURE:
<223> OTHER INFORMATION: A chimeric peptide of human ANP peptide and
      human BNP peptide.

<400> SEQUENCE: 12

Ser Leu Arg Arg Ser Ser Cys Phe Gly Arg Lys Met Asp Arg Ile Gly
1               5                   10                  15

Ala Gln Ser Gly Leu Gly Cys
            20

<210> SEQ ID NO 13
<211> LENGTH: 28
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 13

Ser Leu Arg Arg Ser Ser Cys Phe Gly Arg Lys Met Asp Arg Ile Ser
1               5                   10                  15

Ser Ser Ser Gly Leu Gly Cys Asn Ser Phe Arg Tyr
            20                  25

<210> SEQ ID NO 14
<211> LENGTH: 29
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 14

Ser Leu Arg Arg Ser Ser Cys Phe Gly Arg Lys Met Asp Arg Ile Ser
1               5                   10                  15

Ser Ser Ser Gly Leu Gly Cys Lys Val Leu Arg Arg His
            20                  25

<210> SEQ ID NO 15
<211> LENGTH: 23
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 15

Ser Leu Arg Arg Ser Ser Cys Phe Gly Arg Lys Met Asp Arg Ile Ser
1               5                   10                  15

Ser Ser Ser Gly Leu Gly Cys
            20

<210> SEQ ID NO 16
<211> LENGTH: 28
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 16

Ser Leu Arg Arg Ser Ser Cys Phe Gly Arg Lys Met Asp Arg Ile Gly
1               5                   10                  15

Ser Met Ser Gly Leu Gly Cys Asn Ser Phe Arg Tyr
            20                  25
```

```
<210> SEQ ID NO 17
<211> LENGTH: 29
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 17

Ser Leu Arg Arg Ser Ser Cys Phe Gly Arg Lys Met Asp Arg Ile Gly
1               5                   10                  15

Ser Met Ser Gly Leu Gly Cys Lys Val Leu Arg Arg His
            20                  25

<210> SEQ ID NO 18
<211> LENGTH: 23
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 18

Ser Leu Arg Arg Ser Ser Cys Phe Gly Arg Lys Met Asp Arg Ile Gly
1               5                   10                  15

Ser Met Ser Gly Leu Gly Cys
            20

<210> SEQ ID NO 19
<211> LENGTH: 28
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 19

Ser Leu Arg Arg Ser Ser Cys Phe Gly Leu Lys Leu Asp Arg Ile Gly
1               5                   10                  15

Ala Gln Ser Gly Leu Gly Cys Asn Ser Phe Arg Tyr
            20                  25

<210> SEQ ID NO 20
<211> LENGTH: 29
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 20

Ser Leu Arg Arg Ser Ser Cys Phe Gly Leu Lys Leu Asp Arg Ile Gly
1               5                   10                  15

Ala Gln Ser Gly Leu Gly Cys Lys Val Leu Arg Arg His
            20                  25

<210> SEQ ID NO 21
<211> LENGTH: 23
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 21
```

Ser Leu Arg Arg Ser Ser Cys Phe Gly Leu Lys Leu Asp Arg Ile Gly
1               5                   10                  15

Ala Gln Ser Gly Leu Gly Cys
            20

<210> SEQ ID NO 22
<211> LENGTH: 28
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 22

Ser Leu Arg Arg Ser Ser Cys Phe Gly Leu Lys Leu Asp Arg Ile Ser
1               5                   10                  15

Ser Ser Ser Gly Leu Gly Cys Asn Ser Phe Arg Tyr
            20                  25

<210> SEQ ID NO 23
<211> LENGTH: 29
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 23

Ser Leu Arg Arg Ser Ser Cys Phe Gly Leu Lys Leu Asp Arg Ile Ser
1               5                   10                  15

Ser Ser Ser Gly Leu Gly Cys Lys Val Leu Arg Arg His
            20                  25

<210> SEQ ID NO 24
<211> LENGTH: 23
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 24

Ser Leu Arg Arg Ser Ser Cys Phe Gly Leu Lys Leu Asp Arg Ile Ser
1               5                   10                  15

Ser Ser Ser Gly Leu Gly Cys
            20

<210> SEQ ID NO 25
<211> LENGTH: 28
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 25

Ser Leu Arg Arg Ser Ser Cys Phe Gly Leu Lys Leu Asp Arg Ile Gly
1               5                   10                  15

Ser Met Ser Gly Leu Gly Cys Asn Ser Phe Arg Tyr
            20                  25

<210> SEQ ID NO 26
<211> LENGTH: 29
<212> TYPE: PRT

```
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 26

Ser Leu Arg Arg Ser Ser Cys Phe Gly Leu Lys Leu Asp Arg Ile Gly
1               5                   10                  15

Ser Met Ser Gly Leu Gly Cys Lys Val Leu Arg Arg His
            20                  25

<210> SEQ ID NO 27
<211> LENGTH: 23
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 27

Ser Leu Arg Arg Ser Ser Cys Phe Gly Leu Lys Leu Asp Arg Ile Gly
1               5                   10                  15

Ser Met Ser Gly Leu Gly Cys
            20

<210> SEQ ID NO 28
<211> LENGTH: 31
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 28

Ser Pro Lys Met Val Gln Gly Ser Gly Cys Phe Gly Gly Arg Met Asp
1               5                   10                  15

Arg Ile Gly Ala Gln Ser Gly Leu Gly Cys Asn Ser Phe Arg Tyr
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 29

Ser Pro Lys Met Val Gln Gly Ser Gly Cys Phe Gly Gly Arg Met Asp
1               5                   10                  15

Arg Ile Gly Ala Gln Ser Gly Leu Gly Cys Lys Val Leu Arg Arg His
            20                  25                  30

<210> SEQ ID NO 30
<211> LENGTH: 26
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 30

Ser Pro Lys Met Val Gln Gly Ser Gly Cys Phe Gly Gly Arg Met Asp
1               5                   10                  15

Arg Ile Gly Ala Gln Ser Gly Leu Gly Cys
            20                  25
```

<210> SEQ ID NO 31
<211> LENGTH: 31
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 31

Ser Pro Lys Met Val Gln Gly Ser Gly Cys Phe Gly Gly Arg Met Asp
1               5                   10                  15

Arg Ile Ser Ser Ser Ser Gly Leu Gly Cys Asn Ser Phe Arg Tyr
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 32

Ser Pro Lys Met Val Gln Gly Ser Gly Cys Phe Gly Gly Arg Met Asp
1               5                   10                  15

Arg Ile Ser Ser Ser Ser Gly Leu Gly Cys Lys Val Leu Arg Arg His
            20                  25                  30

<210> SEQ ID NO 33
<211> LENGTH: 26
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 33

Ser Pro Lys Met Val Gln Gly Ser Gly Cys Phe Gly Gly Arg Met Asp
1               5                   10                  15

Arg Ile Ser Ser Ser Ser Gly Leu Gly Cys
            20                  25

<210> SEQ ID NO 34
<211> LENGTH: 31
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 34

Ser Pro Lys Met Val Gln Gly Ser Gly Cys Phe Gly Gly Arg Met Asp
1               5                   10                  15

Arg Ile Gly Ser Met Ser Gly Leu Gly Cys Asn Ser Phe Arg Tyr
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

```
<400> SEQUENCE: 35

Ser Pro Lys Met Val Gln Gly Ser Gly Cys Phe Gly Gly Arg Met Asp
1               5                   10                  15

Arg Ile Gly Ser Met Ser Gly Leu Gly Cys Lys Val Leu Arg Arg His
            20                  25                  30

<210> SEQ ID NO 36
<211> LENGTH: 26
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 36

Ser Pro Lys Met Val Gln Gly Ser Gly Cys Phe Gly Gly Arg Met Asp
1               5                   10                  15

Arg Ile Gly Ser Met Ser Gly Leu Gly Cys
            20                  25

<210> SEQ ID NO 37
<211> LENGTH: 31
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 37

Ser Pro Lys Met Val Gln Gly Ser Gly Cys Phe Gly Arg Lys Met Asp
1               5                   10                  15

Arg Ile Gly Ala Gln Ser Gly Leu Gly Cys Asn Ser Phe Arg Tyr
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 38

Ser Pro Lys Met Val Gln Gly Ser Gly Cys Phe Gly Arg Lys Met Asp
1               5                   10                  15

Arg Ile Gly Ala Gln Ser Gly Leu Gly Cys Lys Val Leu Arg Arg His
            20                  25                  30

<210> SEQ ID NO 39
<211> LENGTH: 26
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 39

Ser Pro Lys Met Val Gln Gly Ser Gly Cys Phe Gly Arg Lys Met Asp
1               5                   10                  15

Arg Ile Gly Ala Gln Ser Gly Leu Gly Cys
            20                  25

<210> SEQ ID NO 40
<211> LENGTH: 31
```

```
<212> TYPE: PRT
<213> ORGANISM: Artificial Sequence
<220> FEATURE:
<223> OTHER INFORMATION: A chimeric peptide of human ANP peptide and
      human BNP peptide.

<400> SEQUENCE: 40

Ser Pro Lys Met Val Gln Gly Ser Gly Cys Phe Gly Arg Lys Met Asp
1               5                   10                  15

Arg Ile Ser Ser Ser Ser Gly Leu Gly Cys Asn Ser Phe Arg Tyr
            20                  25                  30

<210> SEQ ID NO 41
<211> LENGTH: 32
<212> TYPE: PRT
<213> ORGANISM: Homo sapiens
<220> FEATURE:
<221> NAME/KEY: MISC_FEATURE
<223> OTHER INFORMATION: Human BNP peptide

<400> SEQUENCE: 41

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 42
<211> LENGTH: 26
<212> TYPE: PRT
<213> ORGANISM: Artificial Sequence
<220> FEATURE:
<223> OTHER INFORMATION: A human BNP fragment lacking C-trminal
      six  amino acids.

<400> SEQUENCE: 42

Ser Pro Lys Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 43
<211> LENGTH: 31
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 43

Ser Pro Lys Met Val Gln Gly Ser Gly Cys Phe Gly Arg Lys Met Asp
1               5                   10                  15

Arg Ile Gly Ser Met Ser Gly Leu Gly Cys Asn Ser Phe Arg Tyr
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 44

Ser Pro Lys Met Val Gln Gly Ser Gly Cys Phe Gly Arg Lys Met Asp
1               5                   10                  15
```

```
Arg Ile Gly Ser Met Ser Gly Leu Gly Cys Lys Val Leu Arg Arg His
            20                  25                  30
```

<210> SEQ ID NO 45
<211> LENGTH: 26
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 45

```
Ser Pro Lys Met Val Gln Gly Ser Gly Cys Phe Gly Arg Lys Met Asp
1               5                   10                  15

Arg Ile Gly Ser Met Ser Gly Leu Gly Cys
            20                  25
```

<210> SEQ ID NO 46
<211> LENGTH: 31
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 46

```
Ser Pro Lys Met Val Gln Gly Ser Gly Cys Phe Gly Leu Lys Leu Asp
1               5                   10                  15

Arg Ile Gly Ala Gln Ser Gly Leu Gly Cys Asn Ser Phe Arg Tyr
            20                  25                  30
```

<210> SEQ ID NO 47
<211> LENGTH: 32
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 47

```
Ser Pro Lys Met Val Gln Gly Ser Gly Cys Phe Gly Leu Lys Leu Asp
1               5                   10                  15

Arg Ile Gly Ala Gln Ser Gly Leu Gly Cys Lys Val Leu Arg Arg His
            20                  25                  30
```

<210> SEQ ID NO 48
<211> LENGTH: 26
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 48

```
Ser Pro Lys Met Val Gln Gly Ser Gly Cys Phe Gly Leu Lys Leu Asp
1               5                   10                  15

Arg Ile Gly Ala Gln Ser Gly Leu Gly Cys
            20                  25
```

<210> SEQ ID NO 49
<211> LENGTH: 31
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

```
<400> SEQUENCE: 49

Ser Pro Lys Met Val Gln Gly Ser Gly Cys Phe Gly Leu Lys Leu Asp
1               5                   10                  15

Arg Ile Ser Ser Ser Ser Gly Leu Gly Cys Asn Ser Phe Arg Tyr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 50

Ser Pro Lys Met Val Gln Gly Ser Gly Cys Phe Gly Leu Lys Leu Asp
1               5                   10                  15

Arg Ile Ser Ser Ser Ser Gly Leu Gly Cys Lys Val Leu Arg Arg His
            20                  25                  30

<210> SEQ ID NO 51
<211> LENGTH: 26
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 51

Ser Pro Lys Met Val Gln Gly Ser Gly Cys Phe Gly Leu Lys Leu Asp
1               5                   10                  15

Arg Ile Ser Ser Ser Ser Gly Leu Gly Cys
            20                  25

<210> SEQ ID NO 52
<211> LENGTH: 31
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 52

Ser Pro Lys Met Val Gln Gly Ser Gly Cys Phe Gly Leu Lys Leu Asp
1               5                   10                  15

Arg Ile Gly Ser Met Ser Gly Leu Gly Cys Asn Ser Phe Arg Tyr
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 53

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 54
```

```
<211> LENGTH: 26
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 54

Ser Pro Lys Met Val Gln Gly Ser Gly Cys Phe Gly Leu Lys Leu Asp
1               5                   10                  15

Arg Ile Gly Ser Met Ser Gly Leu Gly Cys
            20                  25

<210> SEQ ID NO 55
<211> LENGTH: 27
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 55

Gly Leu Ser Lys Gly Cys Phe Gly Gly Arg Met Asp Arg Ile Gly Ala
1               5                   10                  15

Gln Ser Gly Leu Gly Cys Asn Ser Phe Arg Tyr
            20                  25

<210> SEQ ID NO 56
<211> LENGTH: 28
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 56

Gly Leu Ser Lys Gly Cys Phe Gly Gly Arg Met Asp Arg Ile Gly Ala
1               5                   10                  15

Gln Ser Gly Leu Gly Cys Lys Val Leu Arg Arg His
            20                  25

<210> SEQ ID NO 57
<211> LENGTH: 22
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 57

Gly Leu Ser Lys Gly Cys Phe Gly Gly Arg Met Asp Arg Ile Gly Ala
1               5                   10                  15

Gln Ser Gly Leu Gly Cys
            20

<210> SEQ ID NO 58
<211> LENGTH: 27
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 58

Gly Leu Ser Lys Gly Cys Phe Gly Gly Arg Met Asp Arg Ile Ser Ser
1               5                   10                  15
```

Ser Ser Gly Leu Gly Cys Asn Ser Phe Arg Tyr
            20                  25

<210> SEQ ID NO 59
<211> LENGTH: 28
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 59

Gly Leu Ser Lys Gly Cys Phe Gly Gly Arg Met Asp Arg Ile Ser Ser
1               5                   10                  15

Ser Ser Gly Leu Gly Cys Lys Val Leu Arg Arg His
            20                  25

<210> SEQ ID NO 60
<211> LENGTH: 22
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 60

Gly Leu Ser Lys Gly Cys Phe Gly Gly Arg Met Asp Arg Ile Ser Ser
1               5                   10                  15

Ser Ser Gly Leu Gly Cys
            20

<210> SEQ ID NO 61
<211> LENGTH: 27
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 61

Gly Leu Ser Lys Gly Cys Phe Gly Gly Arg Met Asp Arg Ile Gly Ser
1               5                   10                  15

Met Ser Gly Leu Gly Cys Asn Ser Phe Arg Tyr
            20                  25

<210> SEQ ID NO 62
<211> LENGTH: 28
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 62

Gly Leu Ser Lys Gly Cys Phe Gly Gly Arg Met Asp Arg Ile Gly Ser
1               5                   10                  15

Met Ser Gly Leu Gly Cys Lys Val Leu Arg Arg His
            20                  25

<210> SEQ ID NO 63
<211> LENGTH: 22
<212> TYPE: PRT
<213> ORGANISM: Artificial Sequence
<220> FEATURE:
<223> OTHER INFORMATION: A chimeric peptide of human ANP peptide and -continued human CNP prptide.

<400> SEQUENCE: 63

Gly Leu Ser Lys Gly Cys Phe Gly Gly Arg Met Asp Arg Ile Gly Ser
1               5                   10                  15

Met Ser Gly Leu Gly Cys
            20

<210> SEQ ID NO 64
<211> LENGTH: 27
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 64

Gly Leu Ser Lys Gly Cys Phe Gly Arg Lys Met Asp Arg Ile Gly Ala
1               5                   10                  15

Gln Ser Gly Leu Gly Cys Asn Ser Phe Arg Tyr
            20                  25

<210> SEQ ID NO 65
<211> LENGTH: 28
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 65

Gly Leu Ser Lys Gly Cys Phe Gly Arg Lys Met Asp Arg Ile Gly Ala
1               5                   10                  15

Gln Ser Gly Leu Gly Cys Lys Val Leu Arg Arg His
            20                  25

<210> SEQ ID NO 66
<211> LENGTH: 22
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 66

Gly Leu Ser Lys Gly Cys Phe Gly Arg Lys Met Asp Arg Ile Gly Ala
1               5                   10                  15

Gln Ser Gly Leu Gly Cys
            20

<210> SEQ ID NO 67
<211> LENGTH: 27
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 67

Gly Leu Ser Lys Gly Cys Phe Gly Arg Lys Met Asp Arg Ile Ser Ser
1               5                   10                  15

Ser Ser Gly Leu Gly Cys Asn Ser Phe Arg Tyr
            20                  25

```
<210> SEQ ID NO 68
<211> LENGTH: 28
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 68

Gly Leu Ser Lys Gly Cys Phe Gly Arg Lys Met Asp Arg Ile Ser Ser
1               5                   10                  15

Ser Ser Gly Leu Gly Cys Lys Val Leu Arg Arg His
            20                  25

<210> SEQ ID NO 69
<211> LENGTH: 22
<212> TYPE: PRT
<213> ORGANISM: Artificial Sequence
<220> FEATURE:
<223> OTHER INFORMATION: A chimeric peptide of human human BNP peptide
      and human CNP prptide.

<400> SEQUENCE: 69

Gly Leu Ser Lys Gly Cys Phe Gly Arg Lys Met Asp Arg Ile Ser Ser
1               5                   10                  15

Ser Ser Gly Leu Gly Cys
            20

<210> SEQ ID NO 70
<211> LENGTH: 27
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 70

Gly Leu Ser Lys Gly Cys Phe Gly Arg Lys Met Asp Arg Ile Gly Ser
1               5                   10                  15

Met Ser Gly Leu Gly Cys Asn Ser Phe Arg Tyr
            20                  25

<210> SEQ ID NO 71
<211> LENGTH: 28
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 71

Gly Leu Ser Lys Gly Cys Phe Gly Arg Lys Met Asp Arg Ile Gly Ser
1               5                   10                  15

Met Ser Gly Leu Gly Cys Lys Val Leu Arg Arg His
            20                  25

<210> SEQ ID NO 72
<211> LENGTH: 22
<212> TYPE: PRT
<213> ORGANISM: Artificial Sequence
<220> FEATURE:
<223> OTHER INFORMATION: A chimeric peptide of human human BNP peptide
      and human CNP prptide.

<400> SEQUENCE: 72

Gly Leu Ser Lys Gly Cys Phe Gly Arg Lys Met Asp Arg Ile Gly Ser
```

```
1               5                   10                  15
Met Ser Gly Leu Gly Cys
                20

<210> SEQ ID NO 73
<211> LENGTH: 27
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 73

Gly Leu Ser Lys Gly Cys Phe Gly Leu Lys Leu Asp Arg Ile Gly Ala
1               5                   10                  15

Gln Ser Gly Leu Gly Cys Asn Ser Phe Arg Tyr
                20                  25

<210> SEQ ID NO 74
<211> LENGTH: 28
<212> TYPE: PRT
<213> ORGANISM: Artificial Sequence
<220> FEATURE:
<223> OTHER INFORMATION: A chimeric peptide of human ANP peptide,
      human BNP peptide and human CNP prptide.

<400> SEQUENCE: 74

Gly Leu Ser Lys Gly Cys Phe Gly Leu Lys Leu Asp Arg Ile Gly Ala
1               5                   10                  15

Gln Ser Gly Leu Gly Cys Lys Val Leu Arg Arg His
                20                  25

<210> SEQ ID NO 75
<211> LENGTH: 22
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 75

Gly Leu Ser Lys Gly Cys Phe Gly Leu Lys Leu Asp Arg Ile Gly Ala
1               5                   10                  15

Gln Ser Gly Leu Gly Cys
                20

<210> SEQ ID NO 76
<211> LENGTH: 27
<212> TYPE: PRT
<213> ORGANISM: Artificial Sequence
<220> FEATURE:
<223> OTHER INFORMATION: A chimeric peptide of human ANP peptide, human
      BNP peptide and human CNP prptide.

<400> SEQUENCE: 76

Gly Leu Ser Lys Gly Cys Phe Gly Leu Lys Leu Asp Arg Ile Ser Ser
1               5                   10                  15

Ser Ser Gly Leu Gly Cys Asn Ser Phe Arg Tyr
                20                  25

<210> SEQ ID NO 77
<211> LENGTH: 28
<212> TYPE: PRT
<213> ORGANISM: Artificial Sequence
<220> FEATURE:
```

```
<223> OTHER INFORMATION: A chimeric peptide of human BNP peptide and
      human CNP prptide.

<400> SEQUENCE: 77

Gly Leu Ser Lys Gly Cys Phe Gly Leu Lys Leu Asp Arg Ile Ser Ser
1               5                   10                  15

Ser Ser Gly Leu Gly Cys Lys Val Leu Arg Arg His
            20                  25

<210> SEQ ID NO 78
<211> LENGTH: 22
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 78

Gly Leu Ser Lys Gly Cys Phe Gly Leu Lys Leu Asp Arg Ile Ser Ser
1               5                   10                  15

Ser Ser Gly Leu Gly Cys
            20

<210> SEQ ID NO 79
<211> LENGTH: 27
<212> TYPE: PRT
<213> ORGANISM: Artificial Sequence
<220> FEATURE:
<223> OTHER INFORMATION: A chimeric peptide of human ANP peptide and
      human CNP prptide.

<400> SEQUENCE: 79

Gly Leu Ser Lys Gly Cys Phe Gly Leu Lys Leu Asp Arg Ile Gly Ser
1               5                   10                  15

Met Ser Gly Leu Gly Cys Asn Ser Phe Arg Tyr
            20                  25

<210> SEQ ID NO 80
<211> LENGTH: 28
<212> TYPE: PRT
<213> ORGANISM: Artificial Sequence
<220> FEATURE:
<223> OTHER INFORMATION: A chimeric peptide of human BNP peptide and
      human CNP prptide.

<400> SEQUENCE: 80

Gly Leu Ser Lys Gly Cys Phe Gly Leu Lys Leu Asp Arg Ile Gly Ser
1               5                   10                  15

Met Ser Gly Leu Gly Cys Lys Val Leu Arg Arg His
            20                  25

<210> SEQ ID NO 81
<211> LENGTH: 22
<212> TYPE: PRT
<213> ORGANISM: Homo sapiens
<220> FEATURE:
<221> NAME/KEY: MISC_FEATURE
<223> OTHER INFORMATION: Human CNP peptide.

<400> SEQUENCE: 81

Gly Leu Ser Lys Gly Cys Phe Gly Leu Lys Leu Asp Arg Ile Gly Ser
1               5                   10                  15

Met Ser Gly Leu Gly Cys
            20
```

```
<210> SEQ ID NO 82
<211> LENGTH: 26
<212> TYPE: PRT
<213> ORGANISM: Homo sapiens
<220> FEATURE:
<221> NAME/KEY: MISC_FEATURE
<223> OTHER INFORMATION: Human BNP peptide, BNP-26

<400> SEQUENCE: 82

Gly Ser Gly Cys Phe Gly Arg Lys Met Asp Arg Ile Ser Ser Ser
1               5                   10                  15

Gly Leu Gly Cys Lys Val Leu Arg Arg His
            20                  25

<210> SEQ ID NO 83
<211> LENGTH: 53
<212> TYPE: PRT
<213> ORGANISM: Homo sapiens
<220> FEATURE:
<221> NAME/KEY: MISC_FEATURE
<223> OTHER INFORMATION: Human CNP peptide, CNP-53.

<400> SEQUENCE: 83

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50
```